US011667701B2

United States Patent
Purcell

(10) Patent No.: US 11,667,701 B2
(45) Date of Patent: Jun. 6, 2023

(54) ANTI-PFRH5 ANTIBODIES AND ANTIGEN-BINDING FRAGMENTS THEREOF

(71) Applicant: Regeneron Pharmaceuticals, Inc., Tarrytown, NY (US)

(72) Inventor: Lisa Purcell, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 144 days.

(21) Appl. No.: 17/041,595

(22) PCT Filed: Mar. 22, 2019

(86) PCT No.: PCT/US2019/023734
§ 371 (c)(1),
(2) Date: Sep. 25, 2020

(87) PCT Pub. No.: WO2019/190931
PCT Pub. Date: Oct. 3, 2019

(65) Prior Publication Data
US 2021/0024625 A1 Jan. 28, 2021

Related U.S. Application Data

(60) Provisional application No. 62/648,259, filed on Mar. 26, 2018.

(51) Int. Cl.
*C07K 16/20* (2006.01)
*A61K 9/00* (2006.01)
*A61K 39/015* (2006.01)

(52) U.S. Cl.
CPC .......... *C07K 16/205* (2013.01); *A61K 9/0019* (2013.01); *A61K 39/015* (2013.01);
(Continued)

(58) Field of Classification Search
CPC ............ A61K 2039/505; A61K 39/015; A61K 9/0019; A61K 31/4706; A61K 2300/00;
(Continued)

(56) References Cited

FOREIGN PATENT DOCUMENTS

WO WO-2012061882 A1 * 5/2012 ........... A61K 39/002
WO WO-2013138712 A1 * 9/2013 ......... A01K 67/0275

OTHER PUBLICATIONS

Bustamante et al., "A full-length recombinant Plasmodium falciparum PfRH5 protein induces inhibitory antibodies that are effective across common PfRH5 genetic variants," Vaccine, vol. 31 (No. 2), pp. 373-379, DOI: 10.1016/j.vaccine.2012.10.106, (2013).
(Continued)

*Primary Examiner* — Jana A Hines
(74) *Attorney, Agent, or Firm* — Schwabe, Williamson & Wyatt PC; Gabe Amodeo

(57) ABSTRACT

The present invention includes antibodies and antigen-binding fragments thereof that specifically bind to *Plasmodium falciparum* reticulocyte binding protein homologue 5 (PfRH5), compositions thereof and methods of making such antibodies, fragments and compositions. Method and compositions for treating, preventing or diagnosing *Plasmodium falciparum* infection and malaria are also part of the present invention.

11 Claims, 12 Drawing Sheets

Specification includes a Sequence Listing.

(52) U.S. Cl.
CPC ...... *C07K 2317/14* (2013.01); *C07K 2317/31* (2013.01); *C07K 2317/565* (2013.01); *C07K 2317/73* (2013.01); *C07K 2317/92* (2013.01)

(58) Field of Classification Search
CPC ............ C07K 2317/76; C07K 2317/31; C07K 2317/565; C07K 2317/33; C07K 16/205; C07K 2317/73; C07K 2317/14; C07K 2317/92; A61P 33/06; Y02A 50/30
See application file for complete search history.

(56) References Cited

OTHER PUBLICATIONS

Douglas et al., "Neutralization of Plasmodium falciparum Merozoites by Antibodies against PfRH5," The Journal Of Immunology, vol. 192 (No. 1), pp. 245-258, DOI: 10.4049/jimmunol.1302045, (2013).
Ord et al., "A malaria vaccine candidate based on an epitope of the Plasmodium falciparum RH5 protein," Malaria Journal, vol. 13 (No. 1), p. 1-9, DOL: 10.1186/1475-2875-13-326, (2014).
WIPO Application No. PCT/US2019/023734, PCT International Search Report dated Jul. 8, 2019.
WIPO Application No. PCT/US2019/023734, PCT International Search Report and Written Opinion of the International Searching Authority dated Aug. 16, 2019.

\* cited by examiner

(PANEL I) Cont. From PANEL G

| | | |
|---|---|---|
| H1H29089P {1} | 1201 | ATGGGTTCCTATATATATGATACAATAAATTTATACAATAAAGAATGAAACATATTTTAACA |
| H1H29089P {2} | 1201 | ATGGGTTCCTATATATATGATACAATAAATTTATACAATAAAGAATGAAACATATTTTAACA |
| H1H29100P {1} | 1201 | ATGGGTTCCTATATATATGATACAATAAATTTATACAATAAAGAATGAAACATATTTTAACA |
| H1H29100P {2} | 1201 | ATGGGTTCCTATATATATGATACAATAAATTTATACAATAAAGAATGAAACATATTTTAACA |
| H1H29147P2 {1} | 1201 | ATGGGTTCCTATATATATGATACAATAAATTTATACAATAAAGAATGAAACATATTTTAACA |
| H1H29147P2 {2} | 1201 | ATGGGTTCCTATATATATGATACAATAAATTTATACAATAAAGAATGAAACATATTTTAACA |
| H1H29187P2 {1} | 1201 | ATGGGTTCCTATATATATGATACAATAAATTTATACAATAAAGAATGAAACATATTTTAACA |
| H1H29187P2 {2} | 1201 | ATGGGTTCCTATATATATGATACAATAAATTTATACAATAAAGAATGAAACATATTTTAACA |
| REGN1932 | 1201 | ATGGGTTCCTATATATATGATACAATAAATTTATACAATAAAGAATGAAACATATTTTAACA |
| e Sequence {3D7} | | ATGGGTTCCTATATATATGATACAATAAATTTATACAATAAAGAATGAAACATATTTTAACA |
| | | |
| H1H29089P {1} | 1351 | CAAAAAGATGAATTATTAAAAAGAATTTTAGACATGTCAAATGAATATTCTTATTCTTATTACTAGTG |
| H1H29089P {2} | 1351 | CAAAAAGATGAATTATTAAAAAGAATTTTAGACATGTCAAATGAATATTCTTATTCTTATTACTAGTG |
| H1H29100P {1} | 1351 | CAAAAAGATGAATTATTAAAAAGAATTTTAGACATGTCAAATGAATATTCTTATTCTTATTACTAGTG |
| H1H29100P {2} | 1351 | CAAAAAGATGAATTATTAAAAAGAATTTTAGACATGTCAAATGAATATTCTTATTCTTATTACTAGTG |
| H1H29147P2 {1} | 1351 | CAAAAAGATGAATTATTAAAAAGAATTTTAGACATGTCAAATGAATATTCTTATTCTTATTACTAGTG |
| H1H29147P2 {2} | 1351 | CAAAAAGATGAATTATTAAAAAGAATTTTAGACATGTCAAATGAATATTCTTATTCTTATTACTAGTG |
| H1H29187P2 {1} | 1351 | CAAAAAGATGAATTATTAAAAAGAATTTTAGACATGTCAAATGAATATTCTTATTCTTATTACTAGTG |
| H1H29187P2 {2} | 1351 | CAAAAAGATGAATTATTAAAAAGAATTTTAGACATGTCAAATGAATATTCTTATTCTTATTACTAGTG |
| REGN1932 | 1351 | CAAAAAGATGAATTATTAAAAAGAATTTTAGACATGTCAAATGAATATTCTTATTCTTATTACTAGTG |
| e Sequence {3D7} | | CAAAAAGATGAATTATTAAAAAGAATTTTAGACATGTCAAATGAATATTCTTATTCTTATTACTAGTG |

Cont. On PANEL J

Cont. On PANEL K

FIG. 1-Cont.

(PANEL K) Cont. From PANEL I

| | | | Cont. On PANEL L |
|---|---|---|---|
| H1H29089P {1} | 1501 | CTACAAATGAAGTTCAATGATGTCCCAATTAAATTAAAATGGAATATTTTCAAACATATAAAAAAATAAAC |
| H1H29089P {2} | 1501 | CTACAAATGAAGTTCAATGATGTCCCAATTAAATTAAAATGGAATATTTTCAAACATATAAAAAAATAAAC |
| H1H29100P {1} | 1501 | CTACAAATGAAGTTCAATGATGTCCCAATTAAATTAAAATGGAATATTTTCAAACATATAAAAAAATAAAC |
| H1H29100P {2} | 1501 | CTACAAATGAAGTTCAATGATGTCCCAATTAAATTAAAATGGAATATTTTCAAACATATAAAAAAATAAAC |
| H1H29147P2 {1} | 1501 | CTACAAATGAAGTTCAATGATGTCCCAATTAAATTAAAATGGAATATTTTCAAACATATAAAAAAATAAAC |
| H1H29147P2 {2} | 1501 | CTACAAATGAAGTTCAATGATGTCCCAATTAAATTAAAATGGAATATTTTCAAACATATAAAAAAATAAAC |
| H1H29187P2 {1} | 1501 | CTACAAATGAAGTTCAATGATGTCCCAATTAAATTAAAATGGAATATTTTCAAACATATAAAAAAATAAAC |
| H1H29187P2 {2} | 1501 | CTACAAATGAAGTTCAATGATGTCCCAATTAAATTAAAATGGAATATTTTCAAACATATAAAAAAATAAAC |
| REGN1932 e Sequence {3D7} | 1501 | CTACAAATGAAGTTCAATGATGTCCCAATTAAATGAATATTTTCAAACATATAAAAAAATAAAC |

FIG. 1-Cont.

| | |
|---|---|
| CACTTACACAATGA | 1581 |
| CACTTACACAATGA | 1581 |
| CACTTACACAATGA | 1581 |
| CACTTACACAATGA | 1581 |
| CACTTACACAATGA | 1581 |
| CACTTACACAATGA | 1581 |
| CACTTACACAATGA | 1581 |
| CACTTACAC | 1576 |
| CACTTACACAATGA | 1581 |
| CACTTACACAATGA | |

(PANEL L) Cont. From PANEL J

Cont. From PANEL K

FIG. 1-Cont.

ANTI-PFRH5 ANTIBODIES AND ANTIGEN-BINDING FRAGMENTS THEREOF

CROSS-REFERENCE TO RELATED APPLICATIONS

This application is a U.S. National Stage Application under 35 U.S.C. § 371 of PCT/US2019/023734, filed Mar. 22, 2019, which claims the benefit under 35 U.S.C § 119(e) of U.S. provisional patent application No. 62/648,259, filed Mar. 26, 2018, each of which is herein incorporated by reference in its entirety.

REFERENCE TO A SEQUENCE LISTING

This application incorporates by reference the sequence listing submitted in computer readable form as file 10437W001-Sequence, created on Mar. 22, 2019 and containing 122,791 bytes.

FIELD OF THE INVENTION

The present invention relates, in part, to antibodies and antigen-binding fragments thereof that bind specifically to PfRH5 as well as methods of use thereof for treating or preventing *Plasmodium falciparum* infections.

BACKGROUND OF THE INVENTION

Invasion of host erythrocytes is an essential step of the *Plasmodium falciparum* life cycle and of malaria pathology. Multiple antimalarial drugs target the asexual blood stages, however, their efficacy is threatened by the appearance of drug resistant strains (Arrow et al., Saving Lives, Buying Time: Economics of Malaria Drugs in an Age of Resistance. National Academies Press (US). 254-266 (2004). PMID: 25009879; and Wright et al., Structure of malaria invasion protein RH5 with erythrocyte basigin and blocking antibodies, Nature: 515: 427-430 (2014). PMID: 25132548). Furthermore, antimalarial drugs display different pharmacokinetic properties. Some antimalarial drugs, such as artemisinin and quinine, are rapidly cleared within one parasite life cycle. On the other hand, hydrophobic and lipophilic antimalarial drugs are eliminated slowly, but they are characterized by different absorption rates depending on the amount of dietary fat consumed (Arrow et al.).

*Plasmodium falciparum* Reticulocyte Binding Protein Homologue 5 (PfRH5) is a member of the super family of erythrocyte ligands referred to as the Reticulocyte Binding Like proteins (RBLs). PfRH5 binds erythrocytes, is likely essential for blood-stage growth of the parasite and is implicated in the species tropism of erythrocyte invasion. Evidence suggests that a receptor for PfRH5 on erythrocytes is the Ok blood group antigen, basigin (BSG; CD147).

SUMMARY OF THE INVENTION

The present invention provides an antigen-binding protein (e.g., antibody or antigen-binding fragment thereof) that (i) specifically binds to the same epitope on *Plasmodium falciparum* Reticulocyte Binding Protein Homologue 5 (PfRH5) as; or (ii) competes for binding to PfRH5 polypeptide with: an antibody or antigen-binding fragment thereof that comprises
(a) a heavy chain immunoglobulin that comprises CDR-H1, CDR-H2 and CDR-H3 of a heavy chain immunoglobulin that comprises the amino acid sequence set forth in SEQ ID NO: 2, 18, 34, 50, 66, 82, 98, 114, 130, 146, 162, 178, 194, 210, 226, 234, 242, 250, 258, 266, 274, 282, 290, 298, 314, 322, 330, 338, 346 or 354; and/or (b) a light chain immunoglobulin that comprises CDR-L1, CDR-L2 and CDR-L3 of a light chain immunoglobulin that comprises the amino acid sequence set forth in SEQ ID NO: 10, 26, 42, 58, 74, 90, 106, 122, 138, 154, 170, 186, 202, 218 or 306. For example, in an embodiment of the invention, the anti-PfRH5 antigen-binding protein (e.g., antibody or antigen-binding fragment thereof) comprises (i) a heavy chain immunoglobulin that comprises CDR-H1, CDR-H2 and CDR-H3 of a heavy chain immunoglobulin that comprises the amino acid sequence set forth in SEQ ID NO: 2, 18, 34, 50, 66, 82, 98, 114, 130, 146, 162, 178, 194, 210, 226, 234, 242, 250, 258, 266, 274, 282, 290, 298, 314, 322, 330, 338, 346 or 354; and/or (ii) a light chain immunoglobulin that comprises CDR-L1, CDR-L2 and CDR-L3 of a light chain immunoglobulin that comprises the amino acid sequence set forth in SEQ ID NO: 10, 26, 42, 58, 74, 90, 106, 122, 138, 154, 170, 186, 202, 218 or 306. For example, in an embodiment of the invention, the antigen-binding protein (e.g., antibody or antigen-binding fragment thereof) comprises: (a) a heavy chain immunoglobulin variable region comprising an amino acid sequence having at least 90% amino acid sequence identity to the amino acid sequence set forth in SEQ ID NO: 2, 18, 34, 50, 66, 82, 98, 114, 130, 146, 162, 178, 194, 210, 226, 234, 242, 250, 258, 266, 274, 282, 290, 298, 314, 322, 330, 338, 346 or 354; and/or (b) a light chain immunoglobulin variable region comprising an amino acid sequence having at least 90% amino acid sequence identity to the amino acid sequence set forth in SEQ ID NO: 10, 26, 42, 58, 74, 90, 106, 122, 138, 154, 170, 186, 202, 218 or 306. In an embodiment of the invention, the antigen-binding protein (e.g., antibody or antigen-binding fragment thereof) comprises (a) a heavy chain immunoglobulin comprising the CDR-H1, CDR-H2 and CDR-H3 of a heavy chain immunoglobulin comprising an amino acid sequence set forth in SEQ ID NO: 2, 18, 34, 50, 66, 82, 98, 114, 130, 146, 162, 178, 194, 210, 226, 234, 242, 250, 258, 266, 274, 282, 290, 298, 314, 322, 330, 338, 346 or 354 and at least 90% amino acid sequence identity to the amino acid sequence set forth in SEQ ID NO: 2, 18, 34, 50, 66, 82, 98, 114, 130, 146, 162, 178, 194, 210, 226, 234, 242, 250, 258, 266, 274, 282, 290, 298, 314, 322, 330, 338, 346 or 354; and/or (b) an light chain immunoglobulin comprising the CDR-L1, CDR-L2 and CDR-L3 of a light chain immunoglobulin comprising an amino acid sequence set forth in SEQ ID NO: 10, 26, 42, 58, 74, 90, 106, 122, 138, 154, 170, 186, 202, 218 or 306 and at least 90% amino acid sequence identity to the amino acid sequence set forth in SEQ ID NO: 10, 26, 42, 58, 74, 90, 106, 122, 138, 154, 170, 186, 202, 218 or 306. The present invention also includes an antigen-binding protein (e.g., antibody or antigen-binding fragment thereof) comprising: a heavy chain immunoglobulin that comprises a CDR-H1 comprising the amino acid sequence: G Y S F T S Y W (SEQ ID NO: 4); a CDR-H2 comprising the amino acid sequence: I Y P G D S D T (SEQ ID NO: 6); and a CDR-H3 comprising the amino acid sequence: A R Q D I T G T T G F D Y (SEQ ID NO: 8); or a CDR-H1 comprising the amino acid sequence: G F T F S S Y A (SEQ ID NO: 20); a CDR-H2 comprising the amino acid sequence: I S Y D G S N K (SEQ ID NO: 22); and a CDR-H3 comprising the amino acid sequence: A K E R L F G V V S Y Y G M D V (SEQ ID NO: 24); or a CDR-H1 comprising the amino acid sequence: G G S I S S S S Y Y (SEQ ID NO: 36); a CDR-H2 comprising the amino acid sequence: I Y Y S G S T (SEQ ID NO: 38); and a CDR-H3 comprising the amino acid sequence: A R Q D R E A L F D Y (SEQ ID NO: 40); or a CDR-H1 comprising the amino acid sequence: G F R F D D Y A (SEQ ID NO: 52); a CDR-H2 comprising the amino acid sequence: I N W N S G G K (SEQ ID NO: 54); and a CDR-H3 comprising the amino acid sequence: A K D R G I A A R L L S R D A F D M (SEQ ID NO: 56); or a CDR-H1 comprising the amino acid sequence: S F T F S S Y G (SEQ ID NO: 68); a CDR-H2 comprising the amino acid sequence: I S Y D G S N K (SEQ ID NO: 70); and a CDR-H3 comprising the amino acid sequence: A R E V R R Y Y Y Y G M D V (SEQ ID NO: 72); or a CDR-H1 comprising the amino acid sequence: G F T F D D Y A (SEQ ID NO: 84); a CDR-H2 comprising the amino acid sequence: I S W N S G D I (SEQ ID NO: 86); and a CDR-H3 comprising the amino acid sequence: A K D T L S G T G T T W Y Y F D Y (SEQ ID NO: 88); or a CDR-H1 comprising the amino acid sequence: G F T F S S Y G (SEQ ID NO: 100); a CDR-H2 comprising the amino acid sequence: I S Y D G S N K (SEQ ID NO: 102); and a CDR-H3 comprising the amino acid sequence: A Q D G S S A I Y Y F Y G M D V (SEQ ID NO: 104); or a CDR-H1 comprising the amino acid sequence: G F T F S S Y G (SEQ ID NO: 116); a CDR-H2 comprising the amino acid sequence: I W Y D G S N K (SEQ ID NO: 118); and a CDR-H3 comprising the amino acid sequence: A R G E H Y Y G S G P F D P (SEQ ID NO: 120); or a CDR-H1 comprising the amino acid sequence: G G S I S S F G Y Y (SEQ ID NO: 132); a CDR-H2 comprising the amino acid sequence: I Y Y S G S I (SEQ ID NO: 134); and a CDR-H3 comprising the amino acid sequence: A R E R D Y G D Y F D Y (SEQ ID NO: 136); or a CDR-H1 comprising the amino acid sequence: G F T F S S Y G (SEQ ID NO: 148); a CDR-H2 comprising the amino acid sequence: I W Y D G S N K (SEQ ID NO: 150); and a CDR-H3 comprising the amino acid sequence: A R D Q D Y Y G S G S S Y G M D V (SEQ ID NO: 152); or a CDR-H1 comprising the amino acid sequence: G F T F S T Y G (SEQ ID NO: 164); a CDR-H2 comprising the amino acid sequence: I W Y D G T N K (SEQ ID NO: 166); and a CDR-H3 comprising the amino acid sequence: A R D P S G G D H Y Y Y Y G M D V (SEQ ID NO: 168); or a CDR-H1 comprising the amino acid sequence: G F T F S S Y G (SEQ ID NO: 180); a CDR-H2 comprising the amino acid sequence: I S F D E R N K (SEQ ID NO: 182); and a CDR-H3 comprising the amino acid sequence: A S E V G Y S F G H D A F D I (SEQ ID NO: 184); or a CDR-H1 comprising the amino acid sequence: G F T F N N Y A (SEQ ID NO: 196); a CDR-H2 comprising the amino acid sequence: I S G S G D S T (SEQ ID NO: 198); and a CDR-H3 comprising the amino acid sequence: A K D Q G L Y Y Y G S G S F D Y (SEQ ID NO: 200); or a CDR-H1 comprising the amino acid sequence: G F A F S D S A (SEQ ID NO: 212); a CDR-H2 comprising the amino acid sequence: I R N K A N R F A T (SEQ ID NO: 214); and a CDR-H3 comprising the amino acid sequence: A R H G H D T L T E G Y G M D V (SEQ ID NO: 216); or a CDR-H1 comprising the amino acid sequence: G G T F S S Y T (SEQ ID NO: 228); a CDR-H2 comprising the amino acid sequence: I I P L Y G T A (SEQ ID NO: 230); and a CDR-H3 comprising the amino acid sequence: A S T L E L R A F D A F D I (SEQ ID NO: 232); or a CDR-H1 comprising the amino acid sequence: G G S I S S G G Y Y (SEQ ID NO: 236); a CDR-H2 comprising the amino acid sequence: I Y Y S G S T (SEQ ID NO: 238); and a CDR-H3 comprising the amino acid sequence: A R A P P Y N W F D Y (SEQ ID NO: 240); or a CDR-H1 comprising the amino acid sequence: G F T F S D Y Y (SEQ ID NO: 244); a CDR-H2 comprising the amino acid sequence: I S N S G N T Q (SEQ ID NO: 246); and a CDR-H3 comprising the amino acid sequence: T R E G L E Y S S S E P F D Y (SEQ ID NO: 248); or a CDR-H1 comprising the amino acid sequence: G Y T F T A Y Y (SEQ ID NO: 252); a CDR-H2 comprising the amino acid sequence: I N P N N G D T (SEQ ID NO: 254); and a CDR-H3 comprising the amino acid sequence: A R D D L A A A G I G W F D S (SEQ ID NO: 256); or a CDR-H1 comprising the amino acid sequence: G F T F D D Y A (SEQ ID NO: 260); a CDR-H2 comprising the amino acid sequence: I S W N S E S I (SEQ ID NO: 262); and a CDR-H3 comprising the amino acid sequence: A K A P Y S G T Y F E Y F R H (SEQ ID NO: 264); or a CDR-H1 comprising the amino acid sequence: G F T F S S Y G (SEQ ID NO: 268); a CDR-H2 comprising the amino acid sequence: I S Y D G S N K (SEQ ID NO: 270); and a CDR-H3 comprising the amino acid sequence: A K D D W N Y D A F D I (SEQ ID NO: 272); or a CDR-H1 comprising the amino acid sequence: G G S I S S S G Y Y (SEQ ID NO: 276); a CDR-H2 comprising the amino acid sequence: I Y Y S G S T (SEQ ID NO: 278); and a CDR-H3 comprising the amino acid sequence: A R V D Y G S G S S F D Y (SEQ ID NO: 280); or a CDR-H1 comprising the amino acid sequence: G Y T F T S Y G (SEQ ID NO: 284); a CDR-H2 comprising the amino acid sequence: I S G F N G R T (SEQ ID NO: 286); and a CDR-H3 comprising the amino acid sequence: A R D G L E K L G D Y (SEQ ID NO: 288); or a CDR-H1 comprising the amino acid sequence: G F T F S N S G (SEQ ID NO: 292); a CDR-H2 comprising the amino acid sequence: I W H D G S Y K (SEQ ID NO: 294); and a CDR-H3 comprising the amino acid sequence: A R D D Y Y A S G T S V D V (SEQ ID NO: 296); or a CDR-H1 comprising the amino acid sequence: G Y T F T G Y Y (SEQ ID NO: 300); a CDR-H2 comprising the amino acid sequence: I N P N S G G T (SEQ ID NO: 302); and a CDR-H3 comprising the amino acid sequence: A R E E V D D F W S G Y L D Y (SEQ ID NO: 304); or a CDR-H1 comprising the amino acid sequence: G F A V N G D Y (SEQ ID NO: 316); a CDR-H2 comprising the amino acid sequence: I Y S S G N T (SEQ ID NO: 318); and a CDR-H3 comprising the amino acid sequence: A R D F P P M S G A D Y (SEQ ID NO: 320); or a CDR-H1 comprising the amino acid sequence: G Y T L T E L S (SEQ ID NO: 324); a CDR-H2 comprising the amino acid sequence: F D P E H G K I (SEQ ID NO: 326); and a CDR-H3 comprising the amino acid sequence: A T F Y N W N S Y Y F G M D V (SEQ ID NO: 328); or a CDR-H1 comprising the amino acid sequence: G F T F S S Y A (SEQ ID NO: 332); a CDR-H2 comprising the amino acid sequence: VS G S A D I T (SEQ ID NO: 334); and a CDR-H3 comprising the amino acid sequence: A K D K V Y N W N Y G I Y Y G M D V (SEQ ID NO: 336); or a CDR-H1 comprising the amino acid sequence: G G S I S S S Y Y (SEQ ID NO: 340); a CDR-H2 comprising the amino acid sequence: I Y Y S G S T (SEQ ID NO: 342); and a CDR-H3 comprising the amino acid sequence: A R Q G R W E R E N F D Y (SEQ ID NO: 344); or a CDR-H1 comprising the amino acid sequence: D E S F S D Y Y (SEQ ID NO: 348); a CDR-H2 comprising the amino acid sequence: I T H S G S T (SEQ ID NO: 350); and a CDR-H3 comprising the amino acid sequence: A R G G D Y G G L L D Y (SEQ ID NO: 352); and/or a light chain immunoglobulin variable region that comprises a CDR-L1 comprising the amino acid sequence: Q S I R N Y (SEQ ID NO: 12); a CDR-L2 comprising the amino acid sequence: A A S (SEQ ID NO: 14); and a CDR-L3 comprising the amino acid sequence: Q Q S Y S T P F T (SEQ ID NO: 16); or a CDR-L1 comprising the amino acid sequence: Q D I N R D (SEQ ID NO: 28); a CDR-L2 comprising the amino acid sequence: D A S (SEQ ID NO: 30); and a CDR-L3 comprising the amino acid sequence: Q Q Y K N L P Y T (SEQ ID NO: 32); or a CDR-L1 comprising the amino acid sequence: Q R I G S S (SEQ ID NO: 44); a CDR-L2 comprising the amino acid sequence: Y A S (SEQ ID NO: 46); and a CDR-L3 comprising the amino acid sequence: H Q S S T L P T (SEQ ID NO: 48); or a CDR-L1 comprising the amino acid sequence: Q D V S S Y (SEQ ID NO: 60); a CDR-L2 comprising the amino acid sequence: A A S (SEQ ID NO: 62); and a CDR-L3 comprising the amino acid sequence: Q H L N T Y P Y T (SEQ ID NO: 64); or a CDR-L1 comprising the amino acid sequence: Q D I S N Y (SEQ ID NO: 76); a CDR-L2 comprising the amino acid sequence: D A S (SEQ ID NO: 78); and a CDR-L3 comprising the amino acid sequence: Q Q Y N N L P L T (SEQ ID NO: 80); or a CDR-L1 comprising the amino acid sequence: Q G I S S Y (SEQ ID NO: 92); a CDR-L2 comprising the amino acid sequence: A A S (SEQ ID NO: 94); and a CDR-L3 comprising the amino acid sequence: Q Q V N S Y P L T (SEQ ID NO: 96); or a CDR-L1 comprising the amino acid sequence: Q D I N N Y (SEQ ID NO: 108); a CDR-L2 comprising the amino acid sequence: A A S (SEQ ID NO: 110); and a CDR-L3 comprising the amino acid sequence: L Q Y N S Y H P T (SEQ ID NO: 112); or a CDR-L1 comprising the amino acid sequence: Q S I S N Y (SEQ ID NO: 124); a CDR-L2 comprising the amino acid sequence: A A S (SEQ ID NO: 126); and a CDR-L3 comprising the amino acid sequence: Q Q S Y S S P L T (SEQ ID NO: 128); or a CDR-L1 comprising the amino acid sequence: Q S V S S N (SEQ ID NO: 140); a CDR-L2 comprising the amino acid sequence: G A S (SEQ ID NO: 142); and a CDR-L3 comprising the amino acid sequence: Q Q Y N N WP L T (SEQ ID NO: 144); or a CDR-L1 comprising the amino acid sequence: Q S I S S Y (SEQ ID NO: 156); a CDR-L2 comprising the amino acid sequence: A A S (SEQ ID NO: 158); and a CDR-L3 comprising the amino acid sequence: Q Q S Y S T P L T (SEQ ID NO: 160); or a CDR-L1 comprising the amino acid sequence: Q D I S N Y (SEQ ID NO: 172); a CDR-L2 comprising the amino acid sequence: D A S (SEQ ID NO: 174); and a CDR-L3 comprising the amino acid sequence: Q Q Y D N I P I T (SEQ ID NO: 176); or a CDR-L1 comprising the amino acid sequence: Q D I S N Y (SEQ ID NO: 188); a CDR-L2 comprising the amino acid sequence: D A S (SEQ ID NO: 190); and a CDR-L3 comprising the amino acid sequence: Q Q Y D N F P L T (SEQ ID NO: 192); or a CDR-L1 comprising the amino acid sequence: Q S I S S Y (SEQ ID NO: 204); a CDR-L2 comprising the amino acid sequence: A A S (SEQ ID NO: 206); and a CDR-L3 comprising the amino acid sequence: Q Q S Y S T P F T (SEQ ID NO: 208); or a CDR-L1 comprising the amino acid sequence: Q S I S S Y (SEQ ID NO: 220); a CDR-L2 comprising the amino acid sequence: A A S (SEQ ID NO: 222); and a CDR-L3 comprising the amino acid sequence: Q Q S Y S T P P I T (SEQ ID NO: 224); or a CDR-L1 comprising the amino acid sequence: Q S V S S S Y (SEQ ID NO: 308); a CDR-L2 comprising the amino acid sequence: G A S (SEQ ID NO: 310); and a CDR-L3 comprising the amino acid sequence: Q Q Y G S S P W T (SEQ ID NO: 312). In an embodiment of the invention, the antigen-binding protein (e.g., antibody or antigen-binding fragment thereof) comprises (1) a heavy chain immunoglobulin variable region that comprises a CDR-H1 comprising the amino acid sequence: G Y S F T S Y W (SEQ ID NO: 4); a CDR-H2 comprising the amino acid sequence: I Y P G D S D T (SEQ ID NO: 6); and a CDR-H3 comprising the amino acid sequence: A R Q D I T G T T G F D Y (SEQ ID NO: 8); and a light chain immunoglobulin variable region that comprises a CDR-L1 comprising the amino acid sequence: Q S I R N Y (SEQ ID NO: 12); a CDR-L2 comprising the amino acid sequence: A A S (SEQ ID NO: 14); and a CDR-L3 comprising the amino acid sequence: Q Q S Y S T P F T (SEQ ID NO: 16); (2) a heavy chain immunoglobulin variable region that comprises: a CDR-H1 comprising the amino acid sequence: G F T F S S Y A (SEQ ID NO: 20); a CDR-H2 comprising the amino acid sequence: I S Y D G S N K (SEQ ID NO: 22); a CDR-H3 comprising the amino acid sequence: A K E R L F G V V S Y Y G M D V (SEQ ID NO: 24); and a light chain immunoglobulin variable region that comprises: a CDR-L1 comprising the amino acid sequence: Q D I N R D (SEQ ID NO: 28); a CDR-L2 comprising the amino acid sequence: D A S (SEQ ID NO: 30); and a CDR-L3 comprising the amino acid sequence: Q Q Y K N L P Y T (SEQ ID NO: 32); (3) a heavy chain immunoglobulin variable region that comprises: a CDR-H1 comprising the amino acid sequence: G G S I S S S S Y Y (SEQ ID NO: 36); a CDR-H2 comprising the amino acid sequence: I Y Y S G S T (SEQ ID NO: 38); and a CDR-H3 comprising the amino acid sequence: A R Q D R E A L F D Y (SEQ ID NO: 40); and a light chain immunoglobulin variable region that comprises: a CDR-L1 comprising the amino acid sequence: Q R I G S S (SEQ ID NO: 44); a CDR-L2 comprising the amino acid sequence: Y A S (SEQ ID NO: 46); and a CDR-L3 comprising the amino acid sequence: H Q S S T L P T (SEQ ID NO: 48); (4) a heavy chain immunoglobulin variable region that comprises: a CDR-H1 comprising the amino acid sequence: G F R F D D Y A (SEQ ID NO: 52); a CDR-H2 comprising the amino acid sequence: I N W N S G G K (SEQ ID NO: 54); and a CDR-H3 comprising the amino acid sequence: A K D R G I A A R L L S R D A F D M (SEQ ID NO: 56); and a light chain immunoglobulin variable region that comprises: a CDR-L1 comprising the amino acid sequence: Q D V S S Y (SEQ ID NO: 60); a CDR-L2 comprising the amino acid sequence: A A S (SEQ ID NO: 62); and a CDR-L3 comprising the amino acid sequence: Q H L N T Y P Y T (SEQ ID NO: 64); (5) a heavy chain immunoglobulin variable region that comprises: a CDR-H1 comprising the amino acid sequence: SF T F S S Y G (SEQ ID NO: 68); a CDR-H2 comprising the amino acid sequence: I S Y D G S N K (SEQ ID NO: 70); and a CDR-H3 comprising the amino acid sequence: A R E V R R Y Y Y Y G M D V (SEQ ID NO: 72); and a light chain immunoglobulin variable region that comprises: a CDR-L1 comprising the amino acid sequence: Q D I S N Y (SEQ ID NO: 76); a CDR-L2 comprising the amino acid sequence: D A S (SEQ ID NO: 78); and a CDR-L3 comprising the amino acid sequence: Q Q Y N N L P L T (SEQ ID NO: 80); (6) a heavy chain immunoglobulin variable region that comprises: a CDR-H1 comprising the amino acid sequence: G F T F D D Y A (SEQ ID NO: 84); a CDR-H2 comprising the amino acid sequence: I S W N S G D I (SEQ ID NO: 86); and a CDR-H3 comprising the amino acid sequence: A K D T L S G T G T T W Y Y F D Y (SEQ ID NO: 88); and a light chain immunoglobulin variable region that comprises: a CDR-L1 comprising the amino acid sequence: Q G I S S Y (SEQ ID NO: 92); a CDR-L2 comprising the amino acid sequence: A A S (SEQ ID NO: 94); and a CDR-L3 comprising the amino acid sequence: Q Q V N S Y P L T (SEQ ID NO: 96); (7) a heavy chain immunoglobulin variable region that comprises: a CDR-H1 comprising the amino acid sequence: G F T F S S Y G (SEQ ID NO: 100); a CDR-H2 comprising the amino acid sequence: I S Y D G S N K (SEQ ID NO: 102); and a CDR-H3 comprising the amino acid sequence: A Q D G S S A I Y Y F Y G M D V (SEQ ID NO: 104); and a light chain immunoglobulin variable region that comprises: a CDR-L1 comprising the amino acid sequence: Q D I N N Y (SEQ ID NO: 108); a CDR-L2 comprising the amino acid sequence: A A S (SEQ ID NO: 110); and a CDR-L3 comprising the amino acid sequence: L Q Y N S Y H P T (SEQ ID NO: 112); (8) a heavy chain immunoglobulin variable region that comprises: a CDR-H1 comprising the amino acid sequence: G F T F S S Y G (SEQ ID NO: 116); a CDR-H2 comprising the amino acid sequence: I W Y D G S N K (SEQ ID NO: 118); and a CDR-H3 comprising the amino acid sequence: A R G E H Y Y G S G P F D P (SEQ ID NO: 120); and a light chain immunoglobulin variable region that comprises: a CDR-L1 comprising the amino acid sequence: Q S I S N Y (SEQ ID NO: 124); a CDR-L2 comprising the amino acid sequence: A A S (SEQ ID NO: 126); and a CDR-L3 comprising the amino acid sequence: Q Q S Y S S P L T (SEQ ID NO: 128); (9) a heavy chain immunoglobulin variable region that comprises: a CDR-H1 comprising the amino acid sequence: G G S I S S F G Y Y (SEQ ID NO: 132); a CDR-H2 comprising the amino acid sequence: I Y Y S G S I (SEQ ID NO: 134); and a CDR-H3 comprising the amino acid sequence: A R E R D Y G D Y F D Y (SEQ ID NO: 136); and a light chain immunoglobulin variable region that comprises: a CDR-L1 comprising the amino acid sequence: Q S V S S N (SEQ ID NO: 140); a CDR-L2 comprising the amino acid sequence: G A S (SEQ ID NO: 142); and a CDR-L3 comprising the amino acid sequence: Q Q Y N N W P L T (SEQ ID NO: 144); (10) a heavy chain immunoglobulin variable region that comprises: a CDR-H1 comprising the amino acid sequence: G F T F S S Y G (SEQ ID NO: 148); a CDR-H2 comprising the amino acid sequence: I W Y D G S N K (SEQ ID NO: 150); and a CDR-H3 comprising the amino acid sequence: A R D Q D Y Y G S G S S Y G M D V (SEQ ID NO: 152); and a light chain immunoglobulin variable region that comprises: a CDR-L1 comprising the amino acid sequence: Q S I S S Y (SEQ ID NO: 156); a CDR-L2 comprising the amino acid sequence: A A S (SEQ ID NO: 158); and a CDR-L3 comprising the amino acid sequence: Q Q S Y S T P L T (SEQ ID NO: 160); (11) a heavy chain immunoglobulin variable region that comprises: a CDR-H1 comprising the amino acid sequence: G F T F S T Y G (SEQ ID NO: 164); a CDR-H2 comprising the amino acid sequence: I W Y D G T N K (SEQ ID NO: 166); and a CDR-H3 comprising the amino acid sequence: A R D P S G G D H Y Y Y Y G M D V (SEQ ID NO: 168); and a light chain immunoglobulin variable region that comprises: a CDR-L1 comprising the amino acid sequence: Q D I S N Y (SEQ ID NO: 172); a CDR-L2 comprising the amino acid sequence: D A S (SEQ ID NO: 174); and a CDR-L3 comprising the amino acid sequence: Q Q Y D N I P I T (SEQ ID NO: 176); (12) a heavy chain immunoglobulin variable region that comprises: a CDR-H1 comprising the amino acid sequence: G F T F S S Y G (SEQ ID NO: 180); a CDR-H2 comprising the amino acid sequence: I S F D E R N K (SEQ ID NO: 182); and a CDR-H3 comprising the amino acid sequence: A S E V G Y S F G H D A F D I (SEQ ID NO: 184); and a light chain immunoglobulin variable region that comprises: a CDR-L1 comprising the amino acid sequence: Q D I S N Y (SEQ ID NO: 188); a CDR-L2 comprising the amino acid sequence: D A S (SEQ ID NO: 190); and a CDR-L3 comprising the amino acid sequence: Q Q Y D N F P L T (SEQ ID NO: 192); (13) a heavy chain immunoglobulin variable region that comprises: a CDR-H1 comprising the amino acid sequence: G F T F N N Y A (SEQ ID NO: 196); a CDR-H2 comprising the amino acid sequence: I S G S G DST (SEQ ID NO: 198); and a CDR-H3 comprising the amino acid sequence: A K D Q G L Y Y Y G S G S F D Y (SEQ ID NO: 200); and a light chain immunoglobulin variable region that comprises: a CDR-L1 comprising the amino acid sequence: Q SISSY (SEQ ID NO: 204); a CDR-L2 comprising the amino acid sequence: A A S (SEQ ID NO: 206); and a CDR-L3 comprising the amino acid sequence: Q Q S Y S T P F T (SEQ ID NO: 208); (14) a heavy chain immunoglobulin variable region that comprises: a CDR-H1 comprising the amino acid sequence: G F A F S D S A (SEQ ID NO: 212); a CDR-H2 comprising the amino acid sequence: I R N K A N R F A T (SEQ ID NO: 214); and a CDR-H3 comprising the amino acid sequence: A R H G H D T L T E G Y G M D (SEQ ID NO: 216); and a light chain immunoglobulin variable region that comprises: a CDR-L1 comprising the amino acid sequence: Q S I S S Y (SEQ ID NO: 220); a CDR-L2 comprising the amino acid sequence: A A S (SEQ ID NO: 222); and a CDR-L3 comprising the amino acid sequence: Q Q S Y S T P P I T (SEQ ID NO: 224); (15) a heavy chain immunoglobulin variable region that comprises: a CDR-H1 comprising the amino acid sequence: G G T F S S Y T (SEQ ID NO: 228); a CDR-H2 comprising the amino acid sequence: I I P L Y G T A (SEQ ID NO: 230); and a CDR-H3 comprising the amino acid sequence: A S T L E L R A F D A F D I (SEQ ID NO: 232); and a light chain immunoglobulin variable region that comprises: a CDR-L1 comprising the amino acid sequence: Q S I S S Y (SEQ ID NO: 220); a CDR-L2 comprising the amino acid sequence: A A S (SEQ ID NO: 222); and a CDR-L3 comprising the amino acid sequence: Q Q S Y S T P P I T (SEQ ID NO: 224); (16) a heavy chain immunoglobulin variable region that comprises: a CDR-H1 comprising the amino acid sequence: G G S I S S G G Y Y (SEQ ID NO: 236); a CDR-H2 comprising the amino acid sequence: I Y Y S G S T (SEQ ID NO: 238); and a CDR-H3 comprising the amino acid sequence: A R A P P Y N W F D Y (SEQ ID NO: 240); and a light chain immunoglobulin variable region that comprises: a CDR-L1 comprising the amino acid sequence: Q SISSY (SEQ ID NO: 220); a CDR-L2 comprising the amino acid sequence: A A S (SEQ ID NO: 222); and a CDR-L3 comprising the amino acid sequence: Q Q S Y S T P P I T (SEQ ID NO: 224); (17) a heavy chain immunoglobulin variable region that comprises: a CDR-H1 comprising the amino acid sequence: G F T F S D Y Y (SEQ ID NO: 244); a CDR-H2 comprising the amino acid sequence: I S N S G N T Q (SEQ ID NO: 246); and a CDR-H3 comprising the amino acid sequence: T R E G L E Y S S S E P F D Y (SEQ ID NO: 248); and a light chain immunoglobulin variable region that comprises: a CDR-L1 comprising the amino acid sequence: Q S I S S Y (SEQ ID NO: 220); a CDR-L2 comprising the amino acid sequence: A A S (SEQ ID NO: 222); and a CDR-L3 comprising the amino acid sequence: Q Q S Y S T P P I T (SEQ ID NO: 224); (18) a heavy chain immunoglobulin variable region that comprises: a CDR-H1 comprising the amino acid sequence: G Y T F T A Y Y (SEQ ID NO: 252); a CDR-H2 comprising the amino acid sequence: I N P N N G D T (SEQ ID NO: 254); and a CDR-H3 comprising the amino acid sequence: A R D D L A A A G I G W F D S (SEQ ID NO: 256); and a light chain immunoglobulin variable region that comprises: a CDR-L1 comprising the amino acid sequence: Q S I S S Y (SEQ ID NO: 220); a CDR-L2 comprising the amino acid sequence: A A S (SEQ ID NO: 222); and a CDR-L3 comprising the amino acid sequence: Q Q S Y S T P P I T (SEQ ID NO: 224); (19) a heavy chain immunoglobulin variable region that comprises: a CDR-H1 comprising the amino acid sequence: G F T F D D Y A (SEQ ID NO: 260); a CDR-H2 comprising the amino acid sequence: I S W N S E S I (SEQ ID NO: 262); and a CDR-H3 comprising the amino acid sequence: A K A P Y S G T Y F E Y F R H (SEQ ID NO: 264); and a light chain immunoglobulin variable region that comprises: a CDR-L1 comprising the amino acid sequence: Q SISSY (SEQ ID NO: 220); a CDR-L2 comprising the amino acid sequence: A A S (SEQ ID NO: 222); and a CDR-L3 comprising the amino acid sequence: Q Q S Y S T P P I T (SEQ ID NO: 224); (20) a heavy chain immunoglobulin variable region that comprises: a CDR-H1 comprising the amino acid sequence: G F T F S S Y G (SEQ ID NO: 268); a CDR-H2 comprising the amino acid sequence: I S Y D G S N K (SEQ ID NO: 270); and a CDR-H3 comprising the amino acid sequence: A K D D W N Y D A F D I (SEQ ID NO: 272); and a light chain immunoglobulin variable region that comprises: a CDR-L1 comprising the amino acid sequence: Q S I S S Y (SEQ ID NO: 220); a CDR-L2 comprising the amino acid sequence: A A S (SEQ ID NO: 222); and a CDR-L3 comprising the amino acid sequence: Q Q S Y S T P P I T (SEQ ID NO: 224); (21) a heavy chain immunoglobulin variable region that comprises: a CDR-H1 comprising the amino acid sequence: G G S I S S S G Y Y (SEQ ID NO: 276); a CDR-H2 comprising the amino acid sequence: I Y Y S G S T (SEQ ID NO: 278); and a CDR-H3 comprising the amino acid sequence: A R V D Y G S G S S F D Y (SEQ ID NO: 280); and a light chain immunoglobulin variable region that comprises: a CDR-L1 comprising the amino acid sequence: Q S I S S Y (SEQ ID NO: 220); a CDR-L2 comprising the amino acid sequence: A A S (SEQ ID NO: 222); and a CDR-L3 comprising the amino acid sequence: Q Q S Y S T P P I T (SEQ ID NO: 224); (22) a heavy chain immunoglobulin variable region that comprises: a CDR-H1 comprising the amino acid sequence: G Y T F T S Y G (SEQ ID NO: 284); a CDR-H2 comprising the amino acid sequence: I S G F N G R T (SEQ ID NO: 286); and a CDR-H3 comprising the amino acid sequence: A R D G L E K L G D Y (SEQ ID NO: 288); and a light chain immunoglobulin variable region that comprises: a CDR-L1 comprising the amino acid sequence: Q S I S S Y (SEQ ID NO: 220); a CDR-L2 comprising the amino acid sequence: A A S (SEQ ID NO: 222); and a CDR-L3 comprising the amino acid sequence: Q Q S Y S T P P I T (SEQ ID NO: 224); (23) a heavy chain immunoglobulin variable region that comprises: a CDR-H1 comprising the amino acid sequence: G F T F S N S G (SEQ ID NO: 292); a CDR-H2 comprising the amino acid sequence: I W H D G S Y K (SEQ ID NO: 294); and a CDR-H3 comprising the amino acid sequence: A R D D Y Y A S G T S V D V (SEQ ID NO: 296); and a light chain immunoglobulin variable region that comprises: a CDR-L1 comprising the amino acid sequence: Q SISSY (SEQ ID NO: 220); a CDR-L2 comprising the amino acid sequence: A A S (SEQ ID NO: 222); and a CDR-L3 comprising the amino acid sequence: Q Q S Y S T P P I T (SEQ ID NO: 224); (24) a heavy chain immunoglobulin variable region that comprises: a CDR-H1 comprising the amino acid sequence: G Y T F T G Y Y (SEQ ID NO: 300); a CDR-H2 comprising the amino acid sequence: I N P N S G G T (SEQ ID NO: 302); and a CDR-H3 comprising the amino acid sequence: A R E E V D D F W S G Y L D Y (SEQ ID NO: 304); and a light chain immunoglobulin variable region that comprises: a CDR-L1 comprising the amino acid sequence: Q S V S S S Y (SEQ ID NO: 308); a CDR-L2 comprising the amino acid sequence: G A S (SEQ ID NO: 310); and a CDR-L3 comprising the amino acid sequence: Q Q Y G S S P W T (SEQ ID NO: 312); (25) a heavy chain immunoglobulin variable region that comprises: a CDR-H1 comprising the amino acid sequence: G F A V N G D Y (SEQ ID NO: 316); a CDR-H2 comprising the amino acid sequence: I Y S S G N T (SEQ ID NO: 318); and a CDR-H3 comprising the amino acid sequence: A R D F PPM S G A D Y (SEQ ID NO: 320); and a light chain immunoglobulin variable region that comprises: a CDR-L1 comprising the amino acid sequence: Q S V S S S Y (SEQ ID NO: 308); a CDR-L2 comprising the amino acid sequence: G A S (SEQ ID NO: 310); and a CDR-L3 comprising the amino acid sequence: Q Q Y G S S P W T (SEQ ID NO: 312); (26) a heavy chain immunoglobulin variable region that comprises: a CDR-H1 comprising the amino acid sequence: G Y T L T E L S (SEQ ID NO: 324); a CDR-H2 comprising the amino acid sequence: F D P E H G K I (SEQ ID NO: 326); and a CDR-H3 comprising the amino acid sequence: A T F Y N W N S Y Y F G M D V (SEQ ID NO: 328); and a light chain immunoglobulin variable region that comprises: a CDR-L1 comprising the amino acid sequence: Q S V S S S Y (SEQ ID NO: 308); a CDR-L2 comprising the amino acid sequence: G A S (SEQ ID NO: 310); and a CDR-L3 comprising the amino acid sequence: Q Q Y G S S P W T (SEQ ID NO: 312); (27) a heavy chain immunoglobulin variable region that comprises: a CDR-H1 comprising the amino acid sequence: G F T F S S Y A (SEQ ID NO: 332); a CDR-H2 comprising the amino acid sequence: VS G S A D I T (SEQ ID NO: 334); and a CDR-H3 comprising the amino acid sequence: A K D K V Y N W N Y G I Y Y G M D V (SEQ ID NO: 336); and a light chain immunoglobulin variable region that comprises: a CDR-L1 comprising the amino acid sequence: Q S V S S S Y (SEQ ID NO: 308); a CDR-L2 comprising the amino acid sequence: G A S (SEQ ID NO: 310); and a CDR-L3 comprising the amino acid sequence: Q Q Y G S S P W T (SEQ ID NO: 312); (28) a heavy chain immunoglobulin variable region that comprises: a CDR-H1 comprising the amino acid sequence: G G S I S S S S Y Y (SEQ ID NO: 340); a CDR-H2 comprising the amino acid sequence: I Y Y S G S T (SEQ ID NO: 342); and a CDR-H3 comprising the amino acid sequence: A R Q G R W E R E N F D Y (SEQ ID NO: 344); and a light chain immunoglobulin variable region that comprises: a CDR-L1 comprising the amino acid sequence: Q S V S S S Y (SEQ ID NO: 308); a CDR-L2 comprising the amino acid sequence: G A S (SEQ ID NO: 310); and a CDR-L3 comprising the amino acid sequence: Q Q Y G S S P W T (SEQ ID NO: 312); and/or (29) a heavy chain immunoglobulin variable region that comprises: a CDR-H1 comprising the amino acid sequence: D E S F S D Y Y (SEQ ID NO: 348); a CDR-H2 comprising the amino acid sequence: I T H S G S T (SEQ ID NO: 350); and a CDR-H3 comprising the amino acid sequence: A R G G D Y G G L L D Y (SEQ ID NO: 352); and a light chain immunoglobulin variable region that comprises: a CDR-L1 comprising the amino acid sequence: Q S V S S S Y (SEQ ID NO: 308); a CDR-L2 comprising the amino acid sequence: G A S (SEQ ID NO: 310); and a CDR-L3 comprising the amino acid sequence: Q Q Y G S S P W T (SEQ ID NO: 312). For example, in an embodiment of the invention, the antigen-binding protein (e.g., antibody or antigen-binding fragment thereof) comprises (a) a heavy chain immunoglobulin that comprises the amino acid sequence set forth in SEQ ID NO: 2, 18, 34, 50, 66, 82, 98, 114, 130, 146, 162, 178, 194, 210, 226, 234, 242, 250, 258, 266, 274, 282, 290, 298, 314, 322, 330, 338, 346 or 354; and/or (b) a light chain immunoglobulin that comprises the amino acid sequence set forth in SEQ ID NO: 10, 26, 42, 58, 74, 90, 106, 122, 138, 154, 170, 186, 202, 218 or 306. In an embodiment of the invention, the antigen-binding protein is multispecific (e.g., bispecific, multiparatopic or biparatopic).

In an embodiment of the invention, the antigen-binding protein (e.g., antibody or antigen-binding fragment thereof) comprises one or more of the following properties: Inhibits growth of *Plasmodium falciparum* in human red blood cells; Inhibits growth of *Plasmodium falciparum* strain D10, Dd2, 7G8, W2-mef, 3D7, HB3, FCR-1/FVO, Cam3.II or RF7 in human red blood cells; Blocks binding of PfRH5 polypeptide to basigin polypeptide; for example, at a concentration of about 6.67 micromolar, causes maximal growth inhibition (e.g., in vitro) of *Plasmodium falciparum* (e.g., strain FCR-1/FVO) in heat-inactivated human or *Aotus* monkey serum (e.g., as measured by parasite lactate dehydrogenase (LDH) activity) that at about 1-10% (e.g., 1, 2, 3, 4, 5, 6, 7, 8, 9 or 10%) (relative to uninfected erythrocytes) higher than that of non-heat-inactivated human or *Aotus* monkey serum, respectively; when exposed to said antigen-binding protein, does not induce mutation of PfRH5 in *Plasmodium falciparum* (e.g., strain 3D7), e.g., in vitro after about 45 days of gradually increasing antibody concentration, e.g., from about $1 \times EC_{50}$ to about $110 \times EC_{50}$; and/or binds to PfRH5 lacking the amino-terminal residues M1-Y139 and including residues K140-Q526 but lacking K247-L295 and having the mutations T216A and T299A, for example, wherein the antigen-binding protein comprises an amino acid sequence as set forth herein.

The present invention also includes a complex comprising an antigen-binding protein (e.g., antibody or antigen-binding fragment thereof) bound to a *Plasmodium Falciparum* reticulocyte binding protein homologue 5 (PfRH5) polypeptide. For example, the PfRH5 is on the surface of a cell such as *Plasmodium Falciparum* (e.g., merozoites of *Plasmodium Falciparum*), e.g., in the body of a subject (e.g., a human). In an embodiment of the invention, the PfRH5 is on the surface of a *Plasmodium Falciparum*, e.g., a merozoite in a red blood cell.

The present invention also provides a method for making an anti-PfRH5 antigen-binding protein (e.g., antibody or antigen-binding fragment thereof) set forth herein or immunoglobulin chain thereof comprising: (a) introducing one or more polynucleotides encoding an immunoglobulin chain of said antigen-binding protein into a host cell (e.g., a Chinese hamster ovary cell); (b) culturing the host cell under conditions favorable to expression of the polynucleotide; and (c) optionally, isolating the antigen-binding protein or immunoglobulin chain from the host cell and/or medium in which the host cell is grown. An antigen-binding protein or immunoglobulin chain which is a product of such a method also forms part of the present invention.

A lateral flow immuno-chromatographic antigen-detection test strip comprising an anti-PfRH5 antigen-binding protein set forth herein (e.g., antibody or antigen-binding fragment thereof) is part of the present invention. Methods for detecting *Plasmodium falciparum* in a blood sample from a subject and/or the body of a subject, using the test strip, are also part of the present invention.

A polypeptide comprising: (a) CDR-H1, CDR-H2, and CDR-H3 of an immunoglobulin heavy chain variable region of an immunoglobulin chain that comprises the amino acid sequence set forth in SEQ ID NO: 2, 18, 34, 50, 66, 82, 98, 114, 130, 146, 162, 178, 194, 210, 226, 234, 242, 250, 258, 266, 274, 282, 290, 298, 314, 322, 330, 338, 346 or 354; or (b) CDR-L1, CDR-L2, and CDR-L3 of immunoglobulin light chain variable region of an immunoglobulin chain that comprises the amino acid sequence set forth in SEQ ID NO: 10, 26, 42, 58, 74, 90, 106, 122, 138, 154, 170, 186, 202, 218 or 306 also forms part of the present invention. Polynucleotides (e.g., DNA or RNA) encoding such a polypeptide also form part of the present invention along with a vector that comprises the polynucleotide.

The present invention also provides a host cell (e.g., a Chinese hamster ovary cell) comprising the antigen-binding protein (e.g., antibody or antigen-binding fragment thereof) or an immunoglobulin chain or a polypeptide or polynucleotide or vector which is set forth herein.

The present invention also provides a composition or kit that comprises one or more (e.g., 1, 2, 3 or 4) of the anti-PfRH5 antigen-binding proteins (e.g., antibody or antigen-binding fragment thereof) set forth herein, optionally in association with a further therapeutic agent (e.g., an antiparasitic drug, chloroquine, atovaquone, proguanil, artemether, lumefantrine, mefloquine, quinine, quinidine, doxycycline (optionally in combination with quinine), clindamycin, a vaccine, an anti-malarial vaccine or RTS,S/AS01). The present invention also provides a pharmaceutical composition comprising an anti-PfRH5 antigen-binding protein set forth herein and pharmaceutically acceptable carrier and, optionally, a further therapeutic agent.

The present invention also provides a vessel or injection device (e.g., an autoinjector or pre-filled syringe) comprising an anti-PfRH5 antigen-binding protein (e.g., antibody or antigen-binding fragment thereof) or composition (e.g., a pharmaceutical composition) set forth herein.

The present invention provides a method for treating or preventing *Plasmodium falciparum* infection (e.g., malaria) in a subject (e.g., a human) in need thereof, comprising administering (e.g., parenterally) a therapeutically effective amount of an anti-PfFRH5 antigen-binding protein discussed herein optionally in association with a further therapeutic agent. In an embodiment of the invention, the subject is diagnosed as suffering from a *Plasmodium falciparum* infection (e.g., malaria) prior to initiation of treatment. For example, in an embodiment of the invention, the subject is diagnosed using a lateral flow test strip as set forth herein. In an embodiment of the invention, the subject is not infected with *Plasmodium falciparum*, but is administered a therapeutically effective amount of the anti-PfRH5 antigen-binding protein prophylactically, i.e., so as to prevent such an infection.

The present invention also provides a method for diagnosing *Plasmodium falciparum* infection in a subject comprising contacting an anti-PfRH5 antigen-binding protein of the present invention with a sample (e.g., blood) from said subject and, if a complex between the antigen-binding protein and PfRH5 polypeptide in the sample is detected, determining that the subject is infected with *Plasmodium falciparum*. For example, said complex can be formed on a lateral flow test strip as set forth herein comprising an anti-PfRH5 antigen-binding protein of the present invention and the PfRH5 polypeptide (from the subject's sample).

The present invention provides a method for administering an anti-PfRH5 antigen-binding protein (e.g., antibody or antigen-binding fragment thereof) set forth herein into the body of a subject (e.g., a human) comprising injecting the antigen-binding protein into the body of the subject, optionally in association with a further therapeutic agent, e.g., subcutaneously, intravenously or intramuscularly.

The present invention also encompasses any immunoglobulin polypeptide or polynucleotide set forth herein, e.g., comprising any amino acid sequence set forth in a member selected from the group consisting of SEQ ID NO: 2, 4, 6, 8, 10, 12, 14, 18, 20, 22, 24, 26, 28, 30, 34, 36, 38, 40, 42, 44, 46, 50, 52, 54, 56, 58, 60, 62, 66, 68, 70, 72, 74, 76, 78, 82, 84, 86, 88, 90, 92, 94, 98, 100, 102, 104, 106, 108, 110, 114, 116, 118, 120, 122, 124, 126, 130, 132, 134, 136, 138, 140, 142, 146, 148, 150, 152, 154, 156, 158, 162, 164, 166, 168, 170, 172, 174, 178, 180, 182, 184, 186, 188, 190, 194, 196, 198, 200, 202, 204, 206, 210, 212, 214, 216, 218, 220, 222, 226, 228, 230, 232, 234, 236, 238, 240, 242, 244, 246, 248, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 314, 316, 318, 320, 322, 324, 326, 328, 330, 332, 334, 336, 338, 340, 342, 344, 346, 348, 350, 352, 354, 356, 358 and 360; or a polynucleotide comprising any nucleotide sequence set forth in a member selected from the group consisting of SEQ ID NO: 1, 3, 5, 7, 9, 11, 13, 17, 19, 21, 23, 25, 27, 29, 33, 35, 37, 39, 41, 43, 45, 49, 51, 53, 55, 57, 59, 61, 65, 67, 69, 71, 73, 75, 77, 81, 83, 85, 87, 89, 91, 93, 97, 99, 101, 103, 105, 107, 109, 113, 115, 117, 119, 121, 123, 125, 129, 131, 133, 135, 137, 139, 141, 145, 147, 149, 151, 153, 155, 157, 161, 163, 165, 167, 169, 171, 173, 177, 179, 181, 183, 185, 187, 189, 193, 195, 197, 199, 201, 203, 205, 209, 211, 213, 215, 217, 219, 221, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 313, 315, 317, 319, 321, 323, 325, 327, 329, 331, 333, 335, 337, 339, 341, 343, 345, 347, 349, 351, 353, 355, 357 and 359.

BRIEF DESCRIPTION OF THE FIGURES

Figure 1:
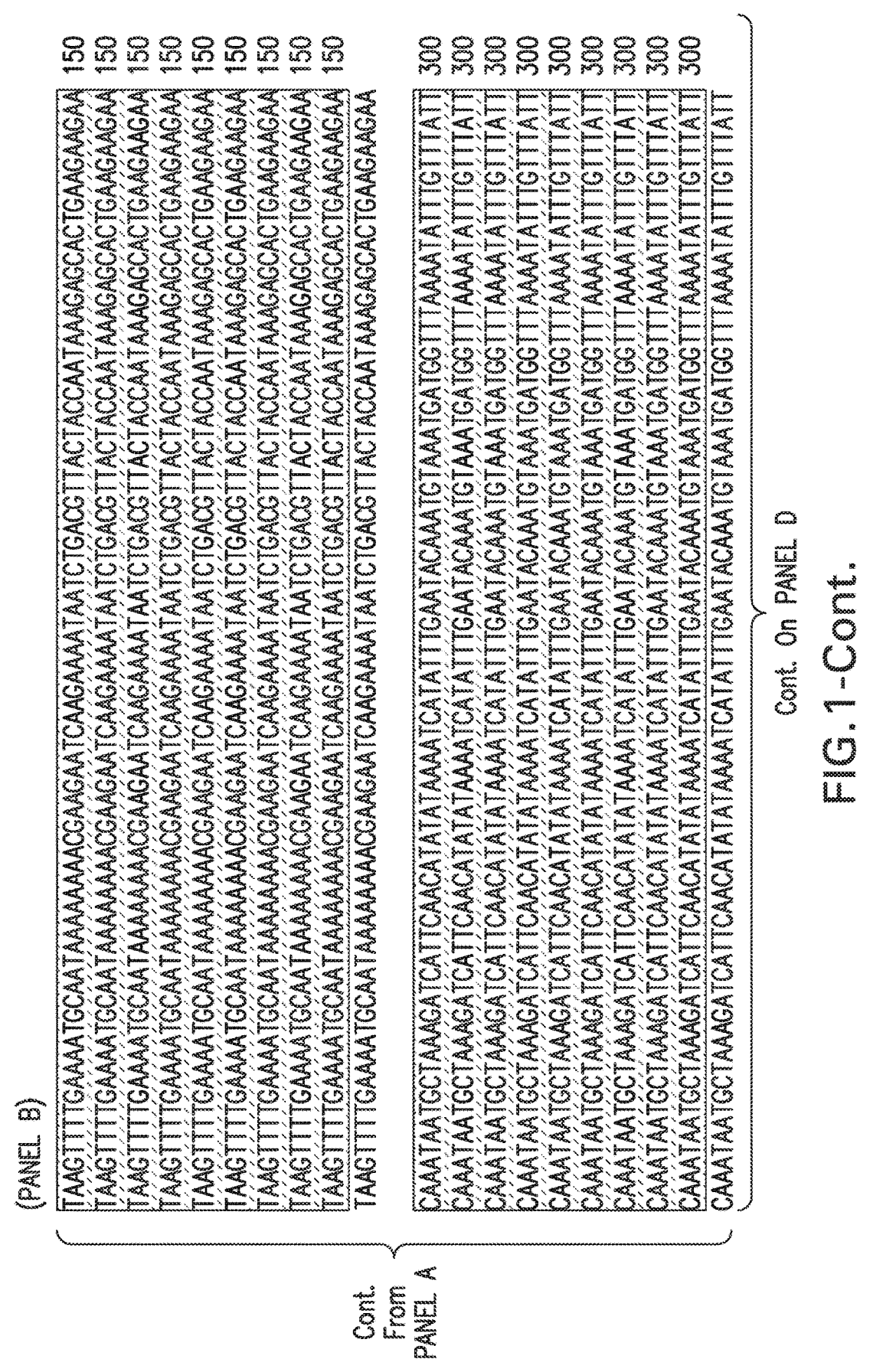
Figure 1:
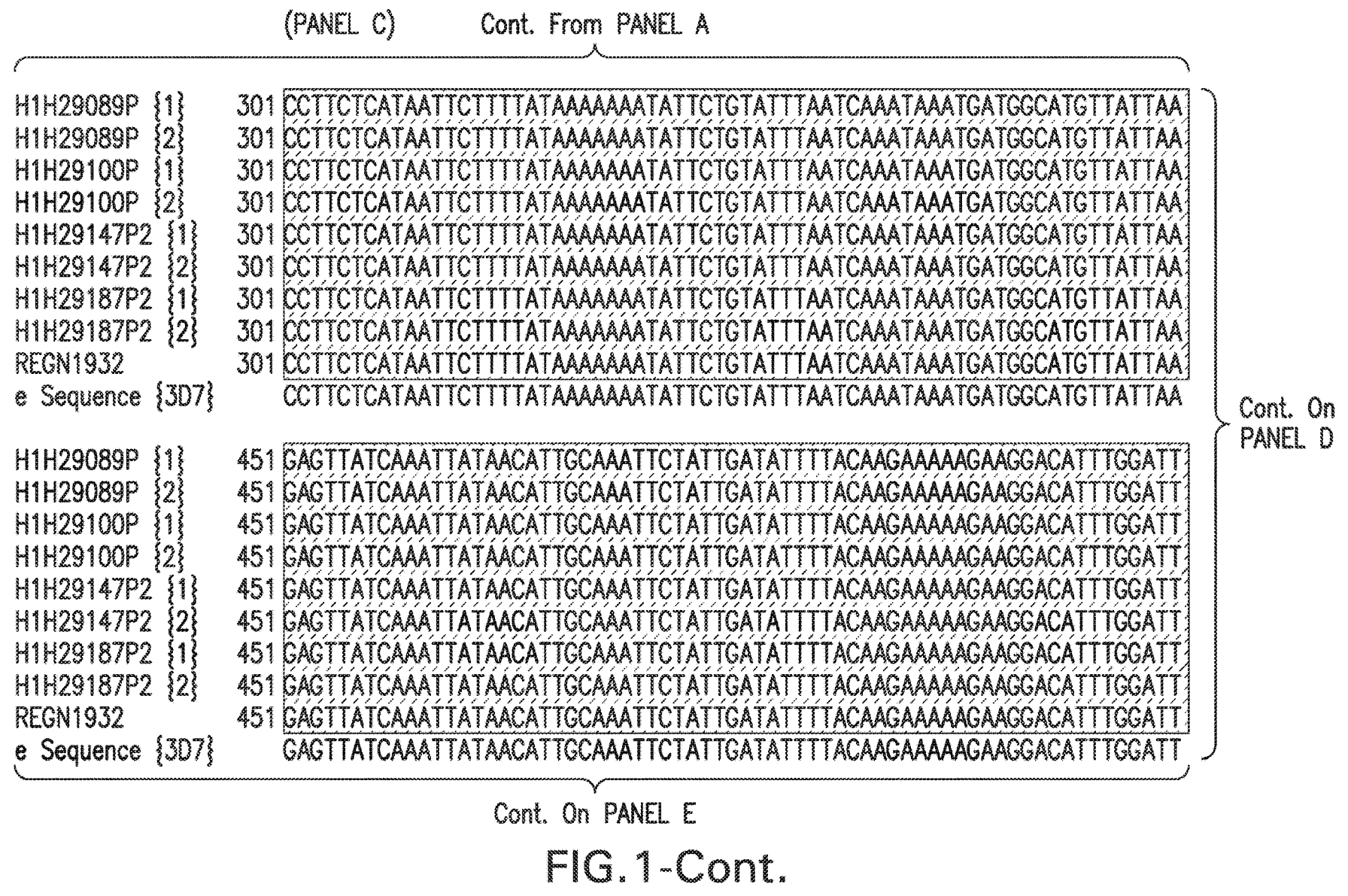
Figure 1:
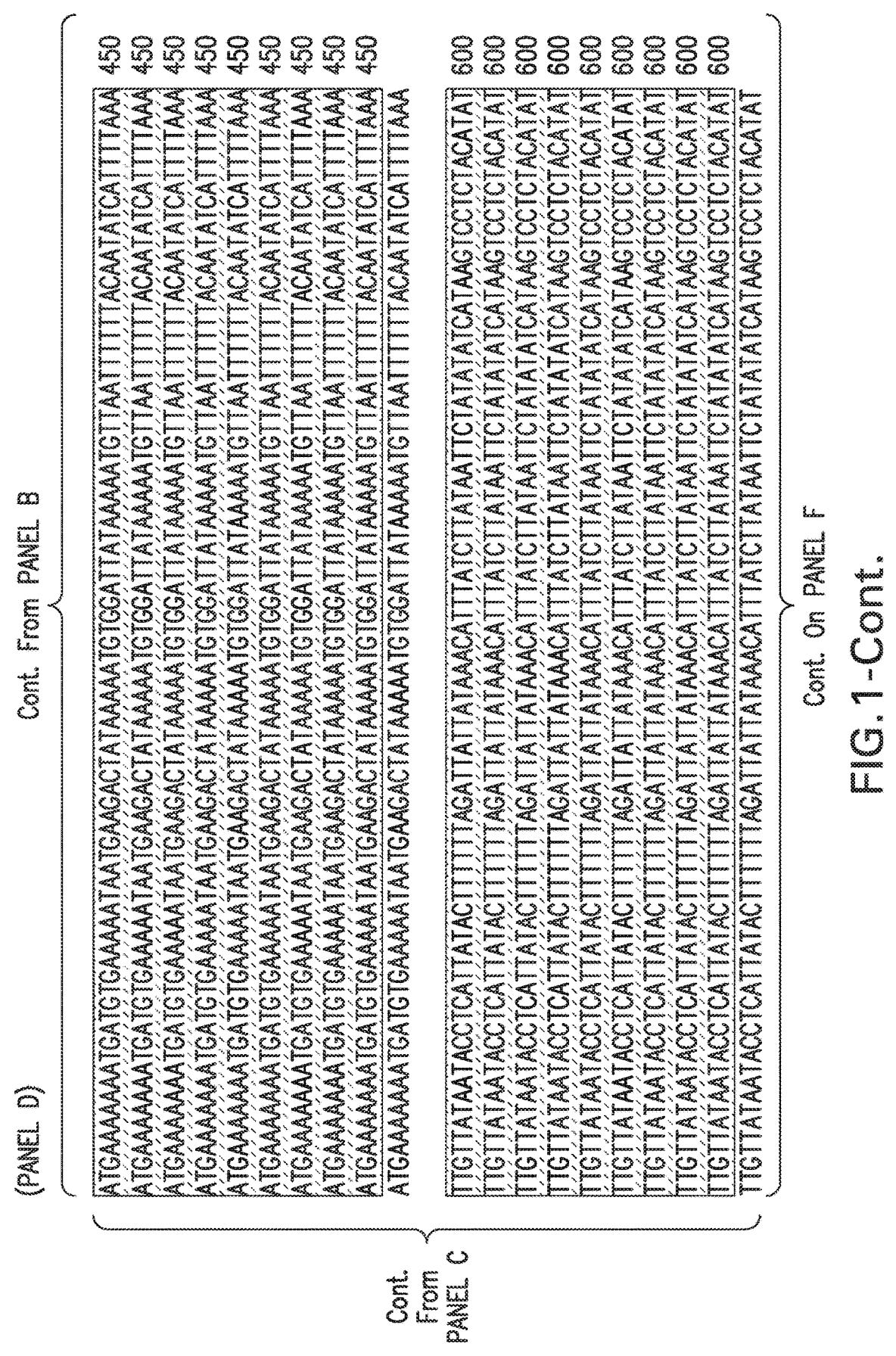
Figure 1:
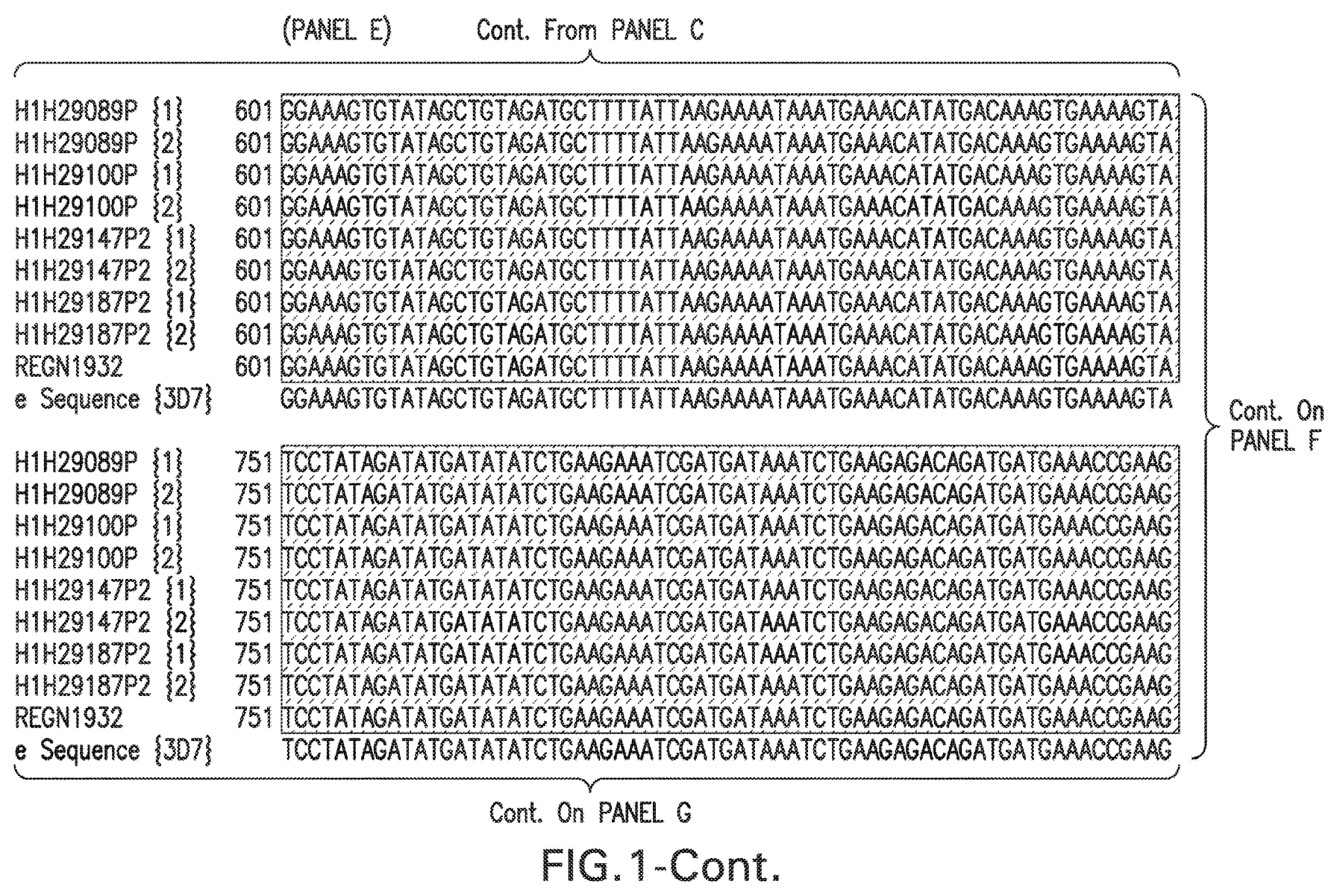
Figure 1:
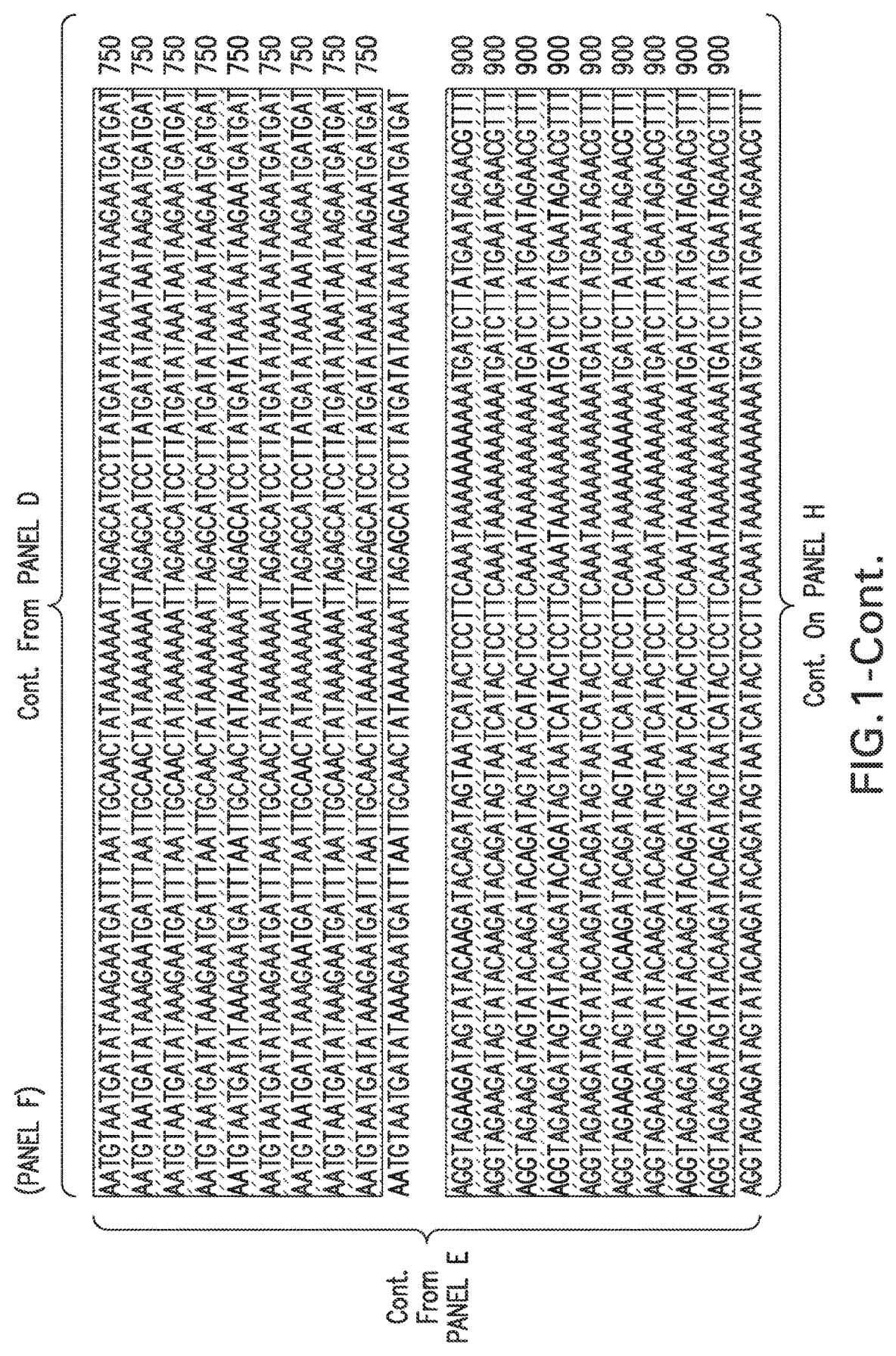
Figure 1:
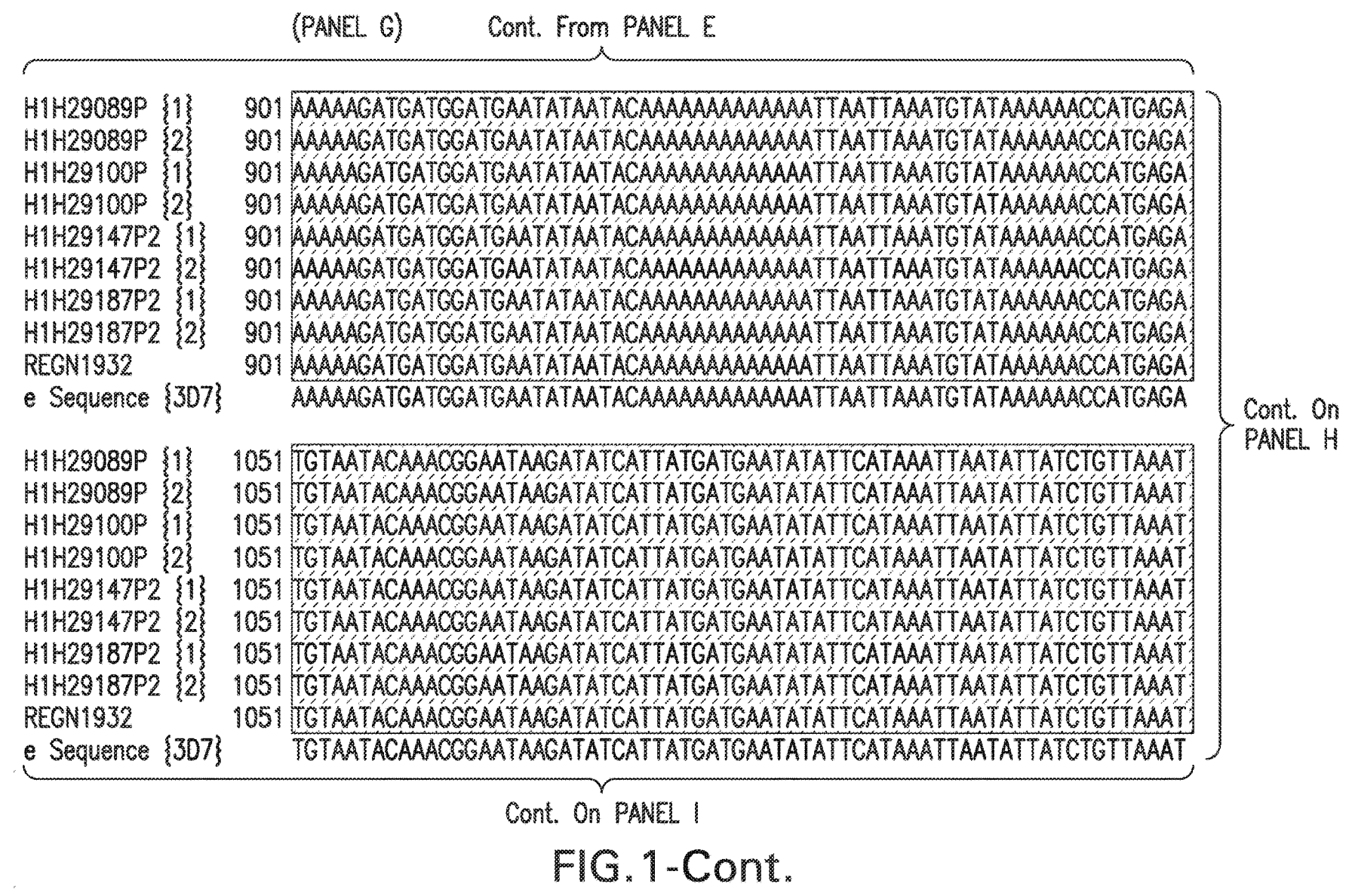
Figure 1:
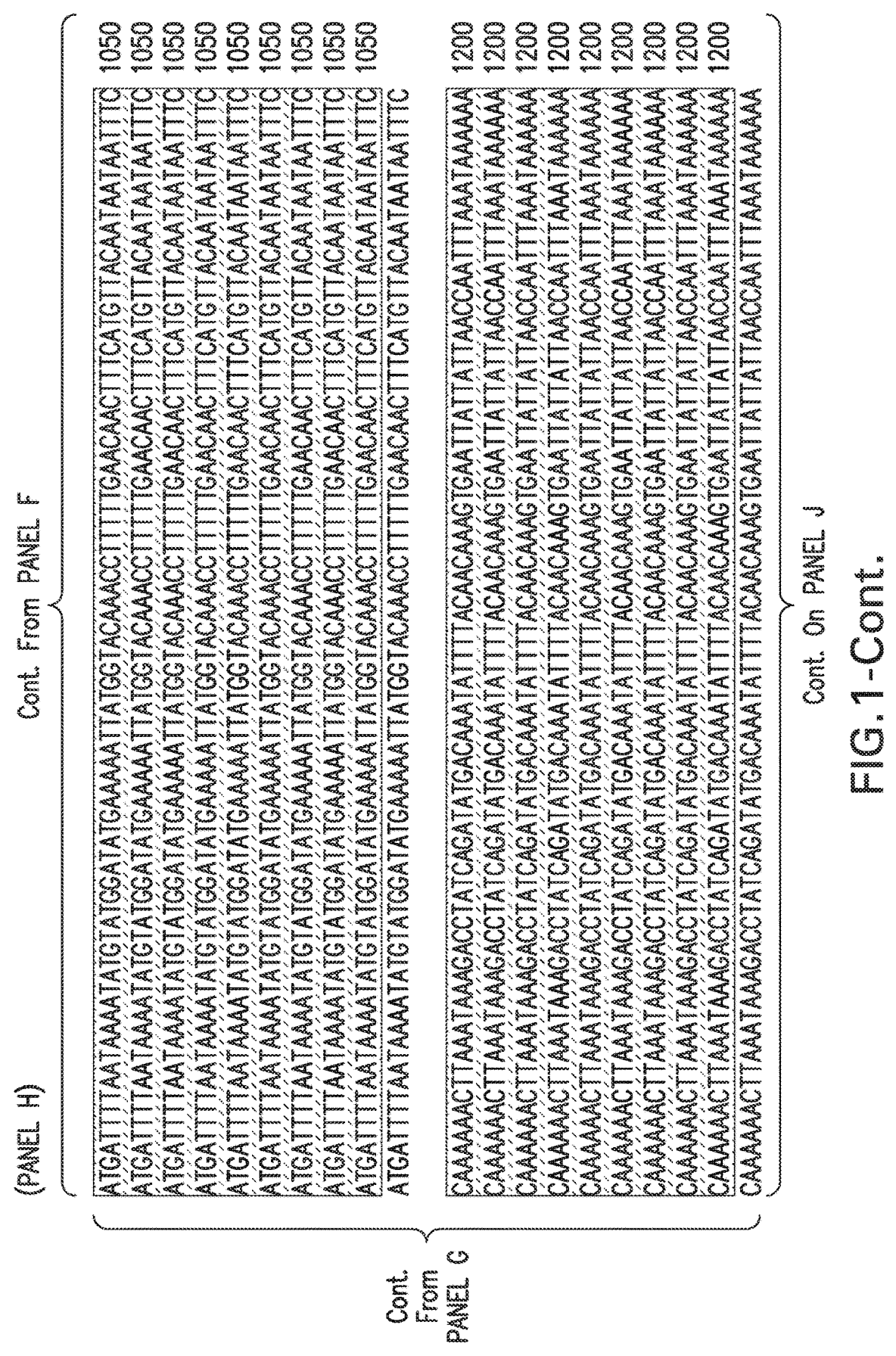
Figure 1:
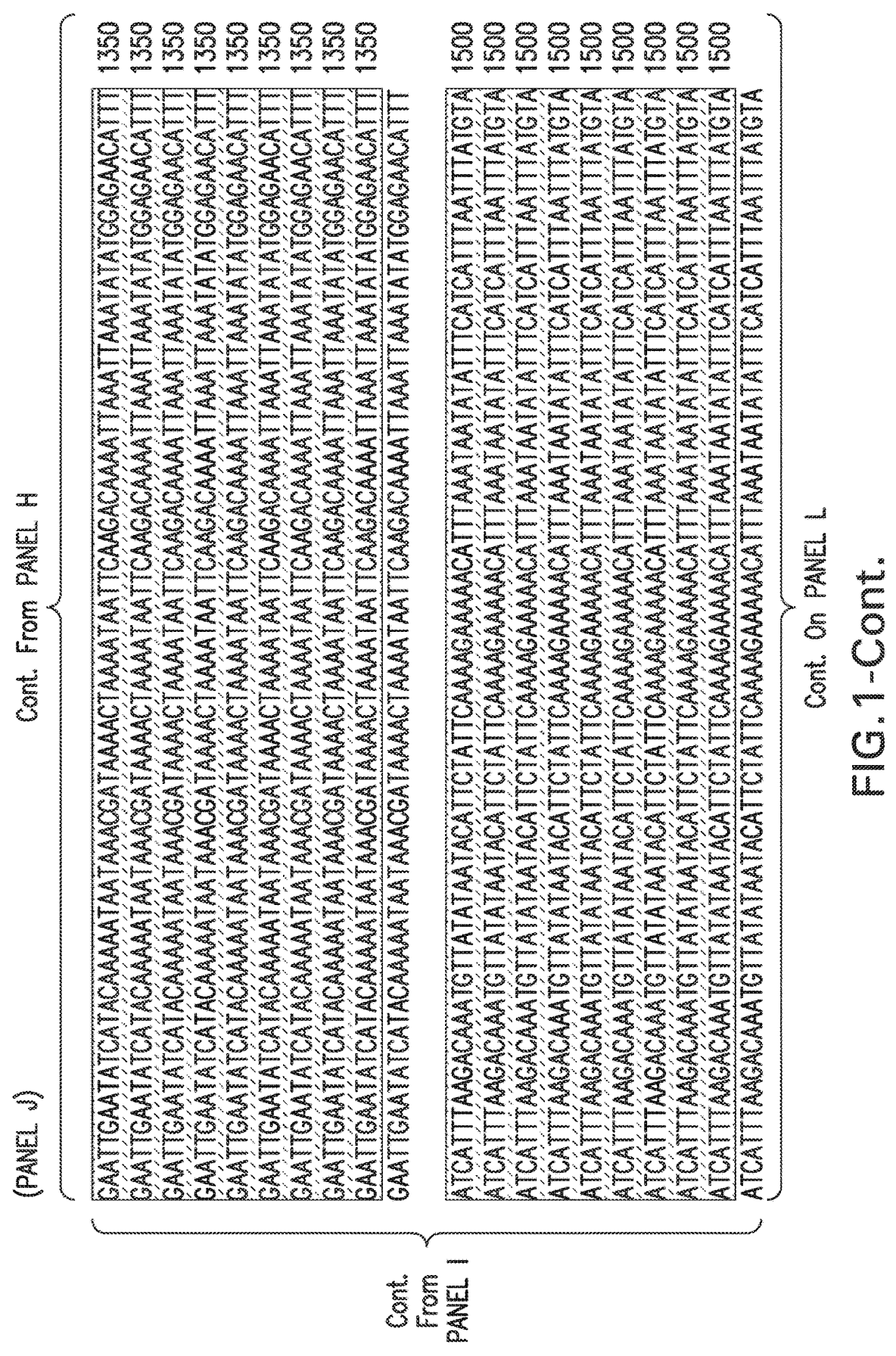

FIG. 1 shows sequence alignments of PfRH5 corresponding to each PfRH5-specific antibody after 45 days of gradual increases in antibody pressure ($1 \times EC_{50}$ to $110 \times EC_{50}$).

DETAILED DESCRIPTION OF THE INVENTION

*Plasmodium falciparum* is a protozoan parasite, one of the species of *Plasmodium* that cause malaria in humans which can be transmitted by the female *Anopheles* mosquito. Malaria caused by this species (which may be referred to as "*falciparum* malaria") is a highly dangerous form of malaria, with a high rate of complications and mortality. See e.g., Gardner et al., Genome sequence of the human malaria parasite *Plasmodium falciparum*, Nature 419(6906): 498-511 (2002). *Plasmodium falciparum* includes any strain thereof which exhibits sensitivity to an antigen-binding protein of the present invention, e.g., D10, Dd2, 7G8, W2-mef, 3D7, HB3, FCR-1/FVO, Cam3.II or RF7. "*Plasmodium falciparum* infection" refers to the invasion and multiplication of *Plasmodium falciparum* in the body of a subject. The present invention provides various antigen-binding proteins which are effective for treatment or prophylaxis of *Plasmodium falciparum* infection.

An anti-PfRH5 "antigen-binding protein" is a single polypeptide (e.g., an ScFv (single chain variable fragment)) or complex of more than one polypeptide (e.g., a tetrameric IgG antibody) that binds specifically to PfRH5 polypeptide, for example, an anti-PfRH5 antibody or antigen-binding fragment whether monospecific or multispecific (e.g., bispecific) or monovalent or multivalent (e.g., bivalent). A monovalent antigen-binding protein has a single antigen-binding domain whereas a bivalent antigen-binding protein has two antigen-binding domains.

Basigin (BSG, extracellular matrix metalloproteinase inducer, EMMPRIN, CD147) is a polypeptide which is a target on erythrocytes to which PfRH5 binds. In an embodiment of the invention, the amino acid sequence of basigin is set forth in Uniprot accession no. Q54A51. See e.g., Crosnier et al., Basigin is a receptor essential for erythrocyte invasion by *Plasmodium falciparum*, Nature. 2011 Nov. 9; 480(7378): 534-7. In an embodiment of the invention, an antigen-binding protein of the present invention blocks binding between PfRH5 an BSG.

*Plasmodium Falciparum* Reticulocyte-binding Protein Homologue 5 (PfRH5)

*Plasmodium falciparum* Reticulocyte Binding Protein Homologue 5 (PfRH5) is a member of the super family of erythrocyte ligands referred to as the Reticulocyte Binding-Like proteins (RBLs). Evidence suggests that PfRH5 is essential for blood-stage growth of a *Plasmodium falciparum* infection. PfRH5 binds erythrocytes and is implicated in the species tropism of erythrocyte invasion. See e.g., Bustamante et al., Vaccine. 2013 Jan. 2; 31(2): 373-379.

In an embodiment of the invention, PfRH5 comprises the amino acid sequence:

```
                                           (SEQ ID NO: 361)
MIRIKKKLIL TIIYIHLFIL NRLSFENAIK KTKNQENNLT

LLPIKSTEEE KDDIKNGKDI KKEIDNDKEN IKTNNAKDHS

TYIKSYLNTN VNDGLKYLFI PSHNSFIKKY SVFNQINDGM

LLNEKNDVKN NEDYKNVDYK NVNFLQYHFK ELSNYNIANS

IDILQEKEGH LDFVIIPHYT FLDYYKHLSY NSIYHKSSTY

GKCIAVDAFI KKINETYDKV KSKCNDIKND LIATIKKLEH

PYDINNKNDD SYRYDISEEI DDKSEETDDE TEEVEDSIQD

TDSNHTPSNK KKNDLMNRTF KKMMDEYNTK KKKLIKCIKN

HENDFNKICM DMKNYGTNLF EQLSCYNNNF CNTNGIRYHY

DEYIHKLILS VKSKNLNKDL SDMTNILQQS ELLLTNLNKK

MGSYIYIDTI KFIHKEMKHI FNRIEYHTKI INDKTKIIQD

KIKLNIWRTF QKDELLKRIL DMSNEYSLFI TSDHLRQMLY

NTFYSKEKHL NNIFHHLIYV LQMKFNDVPI KMEYFQTYKK

NKPLTQ
```

The polypeptide "PfRH5ΔNL.6his" (PfRH5 (K140-Q526; del M1-Y139; del K247-L295; T216A; T299A)) which lacks the N-terminal residues 1-139 and residues 247-295 and has mutations T216A and T299A as well as a C-terminal Hiss tag forms part of the present invention along with polynucleotides encoding the polypeptide. In an embodiment of the invention, the PfRH5ΔNL.6his polypeptide comprises the amino acid sequence set forth in SEQ ID NO: 362:

```
                                           (SEQ ID NO: 362)
KNVNFLQYHFKELSNYNIANSIDILQEKEGHLDFVIIPHYTFLDYYKHLS

YNSIYHKSSTYGKYIAVDAFIKKINEAYDKVKSKCNDIKNDLIATIKKLE

HPYDINNMNRAFKKMMDEYNTKKKKLIKCIKNHENDFNKICMDMKNYGTN

LFEQLSCYNNNFCNTNGIRYHYDEYIHKLILSVKSKNLNKDLSDMTNILQ

QSELLLTNLNKKMGSYIYIDTIKFIHKEMKHIFNRIEYHTKIINDKTKII
```

-continued

QDKIKLNIWRTFQKDELLKRILDMSNEYSLFITSDHLRQMLYNTFYSKEK

HLNNIFHHLIYVLQMKFNDVPIKMEYFQTYKKNKPLTQHHHHHH.

In an embodiment of the invention, the polypeptide is in a crystallized form or a non-crystallized form.

Antibodies and Antigen-Binding Fragments

The present invention provides antigen-binding proteins, such as antibodies and antigen-binding fragments thereof, that specifically bind to PfRH5 protein or an antigenic fragment thereof. Immunoglobulin chains of the present invention are described herein in Example 1 at Table 1-1.

The term "antibody", as used herein, refers to immunoglobulin molecules comprising four polypeptide chains, two heavy chains (HCs) and two light chains (LCs) inter-connected by disulfide bonds (i.e., "full antibody molecules"), as well as multimers thereof (e.g. IgM)—for example, H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2. Each heavy chain (HC) comprises a heavy chain variable region ("HCVR" or "$V_H$") (e.g., SEQ ID NO: 2, 18, 34, 50, 66, 82, 98, 114, 130, 146, 162, 178, 194, 210, 226, 234, 242, 250, 258, 266, 274, 282, 290, 298, 314, 322, 330, 338, 346 or 354) and a heavy chain constant region (comprised of domains CH1, CH2 and CH3). Each light chain (LC) is comprised of a light chain variable region ("LCVR or "$V_L$") (e.g., SEQ ID NO: 10, 26, 42, 58, 74, 90, 106, 122, 138, 154, 170, 186, 202, 218 or 306) and a light chain constant region (CL). The $V_H$ and $V_L$ regions can be further subdivided into regions of hypervariability, termed complementarity determining regions (CDR), interspersed with regions that are more conserved, termed framework regions (FR). Each $V_H$ and $V_L$ comprises three CDRs and four FRs, arranged from amino-terminus to carboxy-terminus in the following order: FR1, CDR1, FR2, CDR2, FR3, CDR3, FR4. In certain embodiments of the invention, the FRs of the antibody (or antigen binding fragment thereof) are identical to the human germline sequences, or are naturally or artificially modified.

Typically, the variable domains of both the heavy and light immunoglobulin chains comprise three hypervariable regions, also called complementarity determining regions (CDRs), located within relatively conserved framework regions (FR). In general, from N-terminal to C-terminal, both light and heavy chains variable domains comprise FR1, CDR1, FR2, CDR2, FR3, CDR3 and FR4. In an embodiment of the invention, the assignment of amino acids to each domain is in accordance with the definitions of Sequences of Proteins of Immunological Interest, Kabat, et al.; National Institutes of Health, Bethesda, Md.; 5$^{th}$ ed.; NIH Publ. No. 91-3242 (1991); Kabat (1978) Adv. Prot. Chem. 32:1-75; Kabat, et al., (1977) J. Biol. Chem. 252:6609-6616; Chothia, et al., (1987) J Mol. Biol. 196:901-917 or Chothia, et al., (1989) Nature 342:878-883.

The present invention includes monoclonal anti-PfRH5 antigen-binding proteins, e.g., antibodies and antigen-binding fragments thereof, as well as monoclonal compositions comprising a plurality of isolated monoclonal antigen-binding proteins. The term "monoclonal antibody", as used herein, refers to a population of substantially homogeneous antibodies, i.e., the antibody molecules comprising the population are identical in amino acid sequence except for possible naturally occurring mutations that may be present in minor amounts. A "plurality" of such monoclonal antibodies and fragments in a composition refers to a concentration of identical (i.e., as discussed above, in amino acid sequence except for possible naturally occurring mutations that may be present in minor amounts) antibodies and fragments which is above that which would normally occur in nature, e.g., in the blood of a host organism such as a mouse or a human.

In an embodiment of the invention, an anti-PfRH5 antigen-binding protein, e.g., antibody or antigen-binding fragment comprises a heavy chain constant domain, e.g., of the type IgA (e.g., IgA1 or IgA2), IgD, IgE, IgG (e.g., IgG1, IgG2, IgG3 and IgG4) or IgM. In an embodiment of the invention, an antigen-binding protein, e.g., antibody or antigen-binding fragment, comprises a light chain constant domain, e.g., of the type kappa or lambda.

The term "human" antigen-binding protein, such as an antibody or antigen-binding fragment, as used herein, includes antibodies and fragments having variable and constant regions derived from human germline immunoglobulin sequences whether in a human cell or grafted into a non-human cell, e.g., a mouse cell. See e.g., U.S. Pat. Nos. 8,502,018, 6,596,541 or 5,789,215. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse) have been grafted onto human FR sequences. The term includes antibodies recombinantly produced in a non-human mammal or in cells of a non-human mammal. The term is not intended to include antibodies isolated from or generated in a human subject.

The present invention includes anti-PfRH5 chimeric antigen-binding proteins, e.g., antibodies and antigen-binding fragments thereof, and methods of use thereof. As used herein, a "chimeric antibody" is an antibody having the variable domain from a first antibody and the constant domain from a second antibody, where the first and second antibodies are from different species. (see e.g., U.S. Pat. No. 4,816,567; and Morrison et al., (1984) Proc. Natl. Acad. Sci. USA 81: 6851-6855).

The term "recombinant" antigen-binding proteins, such as antibodies or antigen-binding fragments thereof, refers to such molecules created, expressed, isolated or obtained by technologies or methods known in the art as recombinant DNA technology which include, e.g., DNA splicing and transgenic expression. The term includes antibodies expressed in a non-human mammal (including transgenic non-human mammals, e.g., transgenic mice), or a cell (e.g., CHO cells) expression system or isolated from a recombinant combinatorial human antibody library.

Recombinant anti-PfRH5 antigen-binding proteins, e.g., antibodies and antigen-binding fragments, disclosed herein may also be produced in an E. coli/T7 expression system. In this embodiment, nucleic acids encoding the anti-PfRH5 antibody immunoglobulin molecules of the invention (e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2;

H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2, H1H29214P2; or H1H29215P2) may be inserted into a pET-based plasmid and expressed in the *E. coli*/T7 system. For example, the present invention includes methods for expressing an antibody or antigen-binding fragment thereof or immunoglobulin chain thereof in a host cell (e.g., bacterial host cell such as *E. coli* such as BL21 or BL21DE3) comprising expressing T7 RNA polymerase in the cell which also includes a polynucleotide encoding an immunoglobulin chain that is operably linked to a T7 promoter. For example, in an embodiment of the invention, a bacterial host cell, such as an *E. coli*, includes a polynucleotide encoding the T7 RNA polymerase gene operably linked to a lac promoter and expression of the polymerase and the chain is induced by incubation of the host cell with IPTG (isopropyl-beta-D-thiogalactopyranoside). See U.S. Pat. Nos. 4,952, 496 and 5,693,489 or Studier & Moffatt, Use of bacteriophage T7 RNA polymerase to direct selective high-level expression of cloned genes, J. Mol. Biol. 1986 May 5; 189(1): 113-30.

There are several methods by which to produce recombinant antibodies which are known in the art. One example of a method for recombinant production of antibodies is disclosed in U.S. Pat. No. 4,816,567.

Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, nucleic acid molecules may be introduced into mammalian cells by viral vectors. Methods of transforming cells are well known in the art. See, for example, U.S. Pat. Nos. 4,399,216; 4,912,040; 4,740,461 and 4,959,455.

Polynucleotides encoding the immunoglobulins set forth herein (e.g., comprising an nucleotide sequence set forth in SEQ ID NO: 1, 3, 5, 7, 9, 11, 13, 17, 19, 21, 23, 25, 27, 29, 33, 35, 37, 39, 41, 43, 45, 49, 51, 53, 55, 57, 59, 61, 65, 67, 69, 71, 73, 75, 77, 81, 83, 85, 87, 89, 91, 93, 97, 99, 101, 103, 105, 107, 109, 113, 115, 117, 119, 121, 123, 125, 129, 131, 133, 135, 137, 139, 141, 145, 147, 149, 151, 153, 155, 157, 161, 163, 165, 167, 169, 171, 173, 177, 179, 181, 183, 185, 187, 189, 193, 195, 197, 199, 201, 203, 205, 209, 211, 213, 215, 217, 219, 221, 225, 227, 229, 231, 233, 235, 237, 239, 241, 243, 245, 247, 249, 251, 253, 255, 257, 259, 261, 263, 265, 267, 269, 271, 273, 275, 277, 279, 281, 283, 285, 287, 289, 291, 293, 295, 297, 299, 301, 303, 305, 307, 309, 313, 315, 317, 319, 321, 323, 325, 327, 329, 331, 333, 335, 337, 339, 341, 343, 345, 347, 349, 351, 353, 355, 357 and 359) which are in a vector and/or operably linked to an expression control sequence such as a promoter form part of the present invention. A promoter may be, for example, a CMV promoter (e.g., a human cytomegalovirus (CMV) major immediate-early (MIE) promoter or a mouse CMV promoter) or an SV40 promoter (e.g., SV40 early promoter). A vector may be a plasmid (e.g., a circular plasmid or a linearized plasmid) or a viral vector which may be maintained ectopically in a host cell or integrated into a host chromosome. Such host cells form part of the present invention.

A polynucleotide is "operably linked" when it is placed into a functional relationship with another nucleic acid sequence. For example, a promoter or enhancer is operably linked to a coding sequence if it affects the transcription of the sequence. Generally, but not always, "operably linked" means that the DNA sequences being linked are contiguous, and, in the case of a secretory leader, contiguous and in reading phase. However, enhancers do not have to be contiguous.

Thus, the present invention includes recombinant methods for making an anti-PfRH5 antigen-binding protein, such as an antibody or antigen-binding fragment thereof of the present invention, or an immunoglobulin chain thereof, comprising (i) introducing one or more polynucleotides (e.g., including the nucleotide sequence in any one or more of SEQ ID NOs: 1, 9, 17, 25, 33, 41, 49, 57, 65, 73, 81, 89, 97, 105, 113, 121, 129, 137, 145, 153, 161, 169, 177, 185, 193, 201, 209, 217, 225, 233, 241, 249, 257, 265, 273, 281, 289, 297, 305, 313, 321, 329, 337, 345 and/or 353) encoding light and/or heavy immunoglobulin chains of the antigen-binding protein, e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2, H1H29214P2; or H1H29215P2, for example, wherein the polynucleotide is in a vector; and/or integrated into a host cell chromosome and/or is operably linked to a promoter; (ii) culturing the host cell (e.g., CHO or *Pichia* or *Pichia pastoris*) under conditions favorable to expression of the polynucleotide and, (iii) optionally, isolating the antigen-binding protein, (e.g., antibody or fragment) or chain from the host cell and/or medium in which the host cell is grown. When making an antigen-binding protein (e.g., antibody or antigen-binding fragment) comprising more than one immunoglobulin chain, e.g., an antibody that comprises two heavy immunoglobulin chains and two light immunoglobulin chains, co-expression of the chains in a single host cell leads to association of the chains, e.g., in the cell or on the cell surface or outside the cell if such chains are secreted, so as to form the antigen-binding protein (e.g., antibody or antigen-binding fragment). The methods of the present invention include those wherein only a heavy immunoglobulin chain or only a light immunoglobulin chain or both (e.g., any of those discussed herein including mature fragments and/or variable domains thereof) are expressed in a cell. Such single chains are useful, for example, as intermediates in the expression of an antibody or antigen-binding fragment that includes such a chain. For example, the present invention also includes anti-PfRH5 antigen-binding proteins, such as antibodies and antigen-binding fragments thereof, comprising a heavy chain immunoglobulin (or variable domain thereof or comprising the CDRs thereof) encoded by a polynucleotide comprising the nucleotide sequences set forth in SEQ ID NO: 1 17, 33, 49, 65, 81, 97, 113, 129, 145, 161, 177, 193, 209, 225, 233, 241, 249, 257, 265, 273, 281, 289, 297, 313, 321, 329, 337, 345 or 353 and a light chain immunoglobulin (or variable domain thereof or comprising the CDRs thereof) encoded by the nucleotide sequence set forth in SEQ ID NO: 9, 25, 41, 57, 73, 89, 105, 121, 137, 153, 169, 185, 201, 217 or 305, which are the product of such production methods, and, optionally, the purification methods set forth herein. For example, in an embodiment of the invention, the product of the method is an anti-PfRH5 antigen-binding protein which is an antibody or fragment comprising a $V_H$ comprising the amino acid sequence set forth in SEQ ID NO: 2, 18, 34, 50, 66, 82, 98, 114, 130, 146, 162, 178, 194, 210, 226, 234, 242, 250, 258, 266, 274, 282, 290, 298, 314, 322, 330, 338, 346 or 354 and a $V_L$ comprising the amino acid sequence set forth in SEQ ID NO: 10, 26, 42, 58, 74, 90, 106, 122, 138, 154, 170, 186, 202, 218 or 306.

In an embodiment of the invention, a method for making an anti-PfRH5 antigen-binding protein, e.g., antibody or antigen-binding fragment thereof, includes a method of purifying the antigen-binding protein, e.g., by column chromatography, precipitation, and/or filtration. The product of such a method also forms part of the present invention.

Eukaryotic and prokaryotic host cells, including mammalian cells, may be used as hosts for expression of an anti-PfRH5 antigen-binding protein (e.g., antibody or antigen-binding fragment thereof). Such host cells are well known in the art and many are available from the American Type Culture Collection (ATCC). These host cells include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Other cell lines that may be used are insect cell lines (e.g., *Spodoptera frugiperda* or *Trichoplusia ni*), amphibian cells, bacterial cells, plant cells and fungal cells. Fungal cells include yeast and filamentous fungus cells including, for example, *Pichia, Pichia pastoris, Pichia finlandica, Pichia trehalophila, Pichia koclamae, Pichia membranaefaciens, Pichia minuta (Ogataea minuta, Pichia lindnen), Pichia opuntiae, Pichia thermotolerans, Pichia salictaria, Pichia guercuum, Pichia pijperi, Pichia stiptis, Pichia methanolica, Pichia sp., Saccharomyces cerevisiae, Saccharomyces sp., Hansenula polymorpha, Kluyveromyces sp., Kluyveromyceslactis, Candida albicans, Aspergillus nidulans, Aspergillus niger, Aspergillus oryzae, Trichoderma reesei, Chrysosporiumlucknowense, Fusarium sp., Fusarium gramineum, Fusarium venenatum, Physcomitrella patens* and *Neurospora crassa*. The present invention includes an isolated host cell (e.g., a CHO cell) comprising an antigen-binding protein, such as H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2, H1H29214P2; or H1H29215P2; or one or more polynucleotides encoding an immunoglobulin chain or chains thereof.

The present invention also includes a *Plasmodium falciparum* cell which is expressing PfRH5 which is bound by an antigen-binding protein of the present invention e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2, H1H29214P2; or H1H29215P2, e.g., wherein the cell is in the body of a subject or is in vitro.

The term "specifically binds" refers to those antigen-binding proteins (e.g., mAbs) having a binding affinity to an antigen, such as PfRH5 protein (e.g., PfRH5ΔNL.6his), expressed as K D, of at least about $10^{-8}$ M (e.g., any K D set forth in Table 5-1 or 5-2 herein), as measured by real-time, label free bio-layer interferometry assay, for example, at 25° C. or 37° C., e.g., an Octet® HTX biosensor, or by surface plasmon resonance, e.g., BIACORE™, or by ELISA (enzyme linked immunosorbent assay). The present invention includes antigen-binding proteins that specifically bind to PfRH5 protein. In an embodiment of the invention, an antigen-binding protein comprises a $K_a$, $K_d$ and/or $t_{1/2}$ as set forth in Table 5-1 or 5-2 herein.

The terms "antigen-binding portion" or "antigen-binding fragment" of an antibody or antigen-binding protein, and the like, as used herein, include any naturally occurring, enzymatically obtainable, synthetic, or genetically engineered polypeptide or glycoprotein that specifically binds an antigen to form a complex. Non-limiting examples of antigen-binding fragments include: (i) Fab fragments; (ii) F(ab')$_2$ fragments; (iii) Fd fragments; (iv) Fv fragments; (v) single-chain Fv (scFv) molecules; (vi) dAb fragments and (vii) constrained FR3-CDR3-FR4 peptides (e.g., comprising a FR3, FR4 and CDR-H3 or CDR-L3 as set forth herein). Other engineered molecules, such as domain-specific antibodies, single domain antibodies, domain-deleted antibodies, chimeric antibodies, CDR-grafted antibodies, diabodies, triabodies, tetrabodies, minibodies and small modular immunopharmaceuticals (SMIPs) are also encompassed within the expression "antigen-binding fragment," as used herein. In an embodiment of the invention, the antigen-binding fragment comprises three or more CDRs of H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2, H1H29214P2; or H1H29215P2 (e.g., CDR-H1, CDR-H2 and CDR-H3; and/or CDR-L1, CDR-L2 and CDR-L3).

An antigen-binding fragment of an antibody will, in an embodiment of the invention, comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$—$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_H$1-$C_H$2; (V) $V_H$-$C_H$1-$C_H$2-$C_H$3; $V_H$-$C_H$2-$C_H$3; $V_H$-$C_L$; $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (Xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or heterodimer (or other multimer) of any of the variable and constant domain configurations listed above in non-covalent association with one another and/or with one or more monomeric $V_H$ or $V_L$ domain (e.g., by disulfide bond(s)).

Antigen-binding proteins (e.g., antibodies and antigen-binding fragments) may be monospecific or multi-specific (e.g., bispecific). Multispecific antigen-binding proteins are discussed further herein.

In an embodiment of the invention, antigen-binding proteins of the present invention (e.g., an antibody or antibody fragment) may be conjugated to a moiety such as a therapeutic moiety ("immunoconjugate"), such as an anti-malarial drug, a second anti-PfRH5 antibody, or any other therapeutic moiety useful for treating a Plasmodium falciparum infection. See e.g., below.

The present invention also provides a complex comprising an anti-PfRH5 antigen-binding protein, e.g., antibody or antigen-binding fragment, discussed herein complexed with PfRH5 polypeptide or an antigenic fragment thereof and/or with a secondary antibody or antigen-binding fragment thereof (e.g., detectably labeled secondary antibody) that binds specifically to the anti-PfRH5 antibody or fragment. In an embodiment of the invention, the complex is in vitro (e.g., is immobilized to a solid substrate) or is in the body of a subject. In an embodiment of the invention, the PfRH5 is immobilized to a solid substrate (e.g., a lateral flow test strip) or is on the surface of a cell such as Plasmodium falciparum. Immobilized anti-PfRH5 antibodies and antigen-binding fragments thereof which are covalently linked to an insoluble matrix material (e.g., glass or polysaccharide such as agarose or sepharose, e.g., a bead or other particle thereof) are also part of the present invention; optionally, wherein the immobilized antibody is complexed with PfRH5 or antigenic fragment thereof or a secondary antibody or fragment thereof.

"Isolated" antigen-binding proteins (e.g., antibodies or antigen-binding fragments thereof), polypeptides, polynucleotides and vectors, are at least partially free of other biological molecules from the cells or cell culture from which they are produced. Such biological molecules include nucleic acids, proteins, other antibodies or antigen-binding fragments, lipids, carbohydrates, or other material such as cellular debris and growth medium. An isolated antigen-binding protein may further be at least partially free of expression system components such as biological molecules from a host cell or of the growth medium thereof. Generally, the term "isolated" is not intended to refer to a complete absence of such biological molecules or to an absence of water, buffers, or salts or to components of a pharmaceutical formulation that includes the antigen-binding proteins (e.g., antibodies or antigen-binding fragments).

The present invention includes antigen-binding proteins, e.g., antibodies or antigen-binding fragments, that bind to the same epitope as an antigen-binding protein of the present invention (e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2, H1H29214P2; or H1H29215P2). For example, the present invention includes antigen-binding proteins that bind to a PfRH5 variant epitope (e.g., PfRH5ΔNL.6his) lacking amino acids M1-Y139 and including residues K140-Q526 but lacking K247-L295 and having the mutations T216A and T299A (optionally, including a His×6 tag).

The term "epitope" refers to an antigenic determinant (e.g., on PfRH5 polypeptide) that interacts with a specific antigen-binding site of an antigen-binding protein, e.g., a variable region of an antibody molecule, known as a paratope. A single antigen may have more than one epitope. Thus, different antibodies may bind to different areas on an antigen and may have different biological effects. The term "epitope" may also refer to a site on an antigen to which B and/or T cells respond and/or to a region of an antigen that is bound by an antibody. Epitopes may be defined as structural or functional. Functional epitopes are generally a subset of the structural epitopes and have those residues that directly contribute to the affinity of the interaction. Epitopes may be linear or conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

Methods for determining the epitope of an antigen-binding protein, e.g., antibody or fragment or polypeptide, include alanine scanning mutational analysis, peptide blot analysis (Reineke (2004) Methods Mol. Biol. 248: 443-63), peptide cleavage analysis, crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antigen-binding protein (e.g., antibody or fragment or polypeptide) interacts is hydrogen/deuterium exchange detected by mass spectrometry. See, e.g., Ehring (1999) Analytical Biochemistry 267: 252-259; Engen and Smith (2001) Anal. Chem. 73: 256A-265A.

The present invention includes antigen-binding proteins that compete for binding to PfRH5, e.g., a variant PfRH5 epitope as discussed herein, with an antigen-binding protein of the present invention, e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2, H1H29214P2; or H1H29215P2. The term "competes" as used herein, refers to an antigen-binding protein (e.g., antibody or antigen-binding fragment thereof) that binds to an antigen (e.g., PfRH5 or PfRH5ΔNL.6his) and inhibits or blocks the binding of another antigen-binding protein (e.g., antibody or antigen-binding fragment thereof) to the antigen. The term also includes competition between two antigen-binding proteins e.g., antibodies, in both orientations, i.e., a first antibody that binds and blocks binding of second antibody and vice versa. In certain embodiments, the first antigen-binding protein (e.g., antibody) and second antigen-binding protein (e.g., antibody) may bind to the same epitope. Alternatively, the first and second antigen-binding proteins (e.g., antibodies) may bind to different, but, for example, overlapping epitopes, wherein binding of one inhibits or blocks the binding of the second antibody, e.g., via steric hindrance. Competition between antigen-binding proteins (e.g., antibodies) may be measured by methods known in the art, for example, by a real-time, label-free bio-layer interferometry assay. In an embodiment of the invention, competition between a first and second anti-PfRH5 antigen-binding protein (e.g., antibody) is determined by measuring the ability of an immobilized first anti-PfRH5 antigen-binding protein (e.g., antibody) (not initially complexed with PfRH5 protein) to bind to PfRH5 protein or a fragment thereof complexed with a second anti-PfRH5 antigen-binding protein (e.g., antibody). A reduction in the ability of the first anti-PfRH5 antigen-binding protein (e.g., antibody) to bind to the complexed PfRH5 protein, relative to uncomplexed PfRH5 protein, indicates that the first and second anti-PfRH5 antigen-binding proteins (e.g., antibodies) compete. The degree of competition can be expressed as a percentage of the reduction in binding. Such competition can be measured using a real time, label-free bio-layer interferometry assay, e.g., on an Octet RED384 biosensor (Pall ForteBio Corp.), ELISA (enzyme-linked immunosorbent assays) or SPR (surface plasmon resonance).

Binding competition between anti-PfRH5 antigen-binding proteins (e.g., monoclonal antibodies (mAbs)) can be determined using a real time, label-free bio-layer interferometry assay on an Octet RED384 biosensor (Pall ForteBio Corp.). For example, to determine competition between two anti-PfRH5 monoclonal antibodies, the anti-PfRH5 mAb can be first captured onto anti-hFc antibody coated Octet biosensor tips (Pall ForteBio Corp., #18-5060) by submerging the tips into a solution of anti-PfRH5 mAb (subsequently referred to as "mAb1"). As a positive-control for blocking, the antibody captured biosensor tips can then be saturated with a known blocking isotype control mAb (subsequently referred to as "blocking mAb") by dipping into a solution of blocking mAb. To determine if mAb2 competes with mAb1, the biosensor tips can then be subsequently dipped into a complexed solution of PfRH5 polypeptide and a second anti-PfRH5 mAb (subsequently referred to as "mAb2"), that had been pre-incubated for a period of time and binding of mAb1 to the PfRH5 polypeptide can be determined. The biosensor tips can be washed in buffer in between every step of the experiment. The real-time binding response can be monitored during the course of the experiment and the binding response at the end of every step can be recorded.

In an embodiment of the invention, the competition assay is conducted on an biosensor platform (e.g., Octet HTX), wherein one antibody is bound/complexed to PfRH5 polypeptide which has been bound to a sensor tip and binding of a second antibody to the PfRH5 is then assessed. The ability of the second antibody to bind to the pre-complexed PfRH5 polypeptide can be assessed and, if reduced binding (e.g., relative to PfRH5 not complexed with a first antibody) or an absence of binding of the second antibody is detected, then the first and second antibodies are determined to compete for PfRH5 polypeptide binding. In an embodiment of the invention, the assay is conducted at 25° C. and pH about 7, e.g., 7.4, e.g., in the presence of buffer (e.g., HEPES), salt (e.g., NaCl), EDTA, surfactant (e.g., Tween-20) and/or a non-specific protein (e.g., bovine serum albumin). In an embodiment of the invention, binding to a PfRH5 variant (e.g., PfRH5ΔNL.6his) is assessed in the competition assay, e.g., wherein the variant is PfRH5 lacking amino acids M1-Y139 and including residues K140-Q526 but lacking K247-L295 and having the mutations T216A and T299A (optionally, including a His×6 tag). A His×6 or $His_6$ tag is a tag that includes HHHHHH (SEQ ID NO: 365).

Typically, an antibody or antigen-binding fragment of the invention which is modified in some way retains the ability to specifically bind to PfRH5, e.g., retains at least 10% of its PfRH5 binding activity (when compared to the parental antibody) when that activity is expressed on a molar basis. Preferably, an antibody or antigen-binding fragment of the invention retains at least 20%, 50%, 70%, 80%, 90%, 95% or 100% or more of the PfRH5 binding affinity as the parental antibody. It is also intended that an antibody or antigen-binding fragment of the invention may include conservative or non-conservative amino acid substitutions (referred to as "conservative variants" or "function conserved variants" of the antibody) that do not substantially alter its biologic activity.

Anti-PfRH5 antigen-binding proteins of the present invention may comprise variants of the immunoglobulin chains whose amino acid and nucleotide sequences are specifically set forth herein.

A "variant" of a polypeptide, such as an immunoglobulin chain (e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2 $V_H$, $V_L$, HC or LC), refers to a polypeptide comprising an amino acid sequence that is at least about 70-99.9% (e.g., 70, 72, 74, 75, 76, 79, 80, 81, 82, 83, 84, 85, 86, 87, 88, 89, 90, 91, 92, 93, 94, 95, 96, 97, 98, 99, 99.5, 99.9%) identical or similar to a referenced amino acid sequence that is set forth herein (e.g., SEQ ID NO: 2, 18, 34, 50, 66, 82, 98, 114, 130, 146, 162, 178, 194, 210, 226, 234, 242, 250, 258, 266, 274, 282, 290, 298, 314, 322, 330, 338, 346, 354, 10, 26, 42, 58, 74, 90, 106, 122, 138, 154, 170, 186, 202, 218 or 306); when the comparison is performed by a BLAST algorithm wherein the parameters of the algorithm are selected to give the largest match between the respective sequences over the entire length of the respective reference sequences (e.g., expect threshold: 10; word size: 3; max matches in a query range: 0; BLOSUM 62 matrix; gap costs: existence 11, extension 1; conditional compositional score matrix adjustment).

A "variant" of a polynucleotide refers to a polynucleotide comprising a nucleotide sequence that is at least about 70-99.9% (e.g., 70, 72, 74, 75, 76, 79, 80, 81, 82, 83, 84, 85, 86, 87, 88, 89, 90, 91, 92, 93, 94, 95, 96, 97, 98, 99, 99.5, 99.9%) identical to a referenced nucleotide sequence that is set forth herein (e.g., SEQ ID NO: 1, 17, 33, 49, 65, 81, 97, 113, 129, 145, 161, 177, 193, 209, 225, 233, 241, 249, 257, 265, 273, 281, 289, 297, 313, 321, 329, 337, 345, 353, 9, 25, 41, 57, 73, 89, 105, 121, 137, 153, 169, 185, 201, 217 or 305); when the comparison is performed by a BLAST algorithm wherein the parameters of the algorithm are selected to give the largest match between the respective sequences over the entire length of the respective reference sequences (e.g., expect threshold: 10; word size: 28; max matches in a query range: 0; match/mismatch scores: 1, −2; gap costs: linear).

Anti-PfRH5 antigen-binding proteins, e.g., antibodies and antigen-binding fragments thereof of the present invention, in an embodiment of the invention, include a heavy chain immunoglobulin variable region having at least 70% (e.g., 80%, 85%, 90%, 95%, 99%) amino acid sequence identity to that of an immunoglobulin heavy chain whose amino acid sequence is set forth herein, e.g., in SEQ ID NO: 2, 18, 34, 50, 66, 82, 98, 114, 130, 146, 162, 178, 194, 210, 226, 234, 242, 250, 258, 266, 274, 282, 290, 298, 314, 322, 330, 338, 346 or 354; and/or a light chain immunoglobulin variable region having at least 70% (e.g., 80%, 85%, 90%, 95%, 99%) amino acid sequence identity to an immunoglobulin light chain whose amino acid sequence is set forth herein, e.g., in SEQ ID NO: 10, 26, 42, 58, 74, 90, 106, 122, 138, 154, 170, 186, 202, 218 or 306.

In addition, an anti-PfRH5 antigen-binding protein of the present invention may include a variant immunoglobulin polypeptide comprising an amino acid sequence that is set forth herein except for one or more (e.g., 1, 2, 3, 4, 5, 6, 7, 8, 9 or 10) mutations such as, for example, missense mutations (e.g., conservative substitutions), non-sense mutations, deletions, or insertions. For example, the present invention includes antigen-binding proteins which include an immunoglobulin light chain variant comprising the amino acid sequence set forth in SEQ ID NO: 10, 26, 42, 58, 74, 90, 106, 122, 138, 154, 170, 186, 202, 218 or 306 but having one or more of such mutations and/or an immunoglobulin heavy chain variant comprising the amino acid sequence set forth in SEQ ID NO: 2, 18, 34, 50, 66, 82, 98, 114, 130, 146, 162, 178, 194, 210, 226, 234, 242, 250, 258, 266, 274, 282, 290, 298, 314, 322, 330, 338, 346 or 354 but having one or more of such mutations. In an embodiment of the invention, an anti-PfRH5 antigen-binding protein includes an immunoglobulin light chain variant comprising CDR-L1, CDR-L2 and CDR-L3 wherein one or more (e.g., 1 or 2 or 3) of such CDRs has one or more of such mutations (e.g., conservative substitutions) relative to a sequence which is specifically set forth herein and/or an immunoglobulin heavy chain variant comprising CDR-H1, CDR-H2 and CDR-H3 wherein one or more (e.g., 1 or 2 or 3) of such CDRs has one or more of such mutations (e.g., conservative substitutions) relative to a sequence which is specifically set forth herein.

The invention further provides variant anti-PfRH5 antigen-binding proteins, e.g., antibodies or antigen-binding fragments thereof, comprising one or more variant CDRs (e.g., any one or more of CDR-L1, CDR-L2, CDR-L3, CDR-H1, CDR-H2 and/or CDR-H3) that are set forth herein with at least 70%, 75%, 80%, 85%, 90%, 95%, 98%, 99% or 99.9% sequence identity or similarity thereto.

Embodiments of the present invention also include anti-PfRH5 antibodies and antigen-binding fragments thereof, that comprise variant immunoglobulin $V_H$s and $V_L$s; or HCs and LCs, which comprise an amino acid sequence having 70% or more (e.g., 80%, 85%, 90%, 95%, 97% or 99%) overall amino acid sequence identity or similarity to the amino acid sequences of the corresponding $V_H$s, $V_L$s, HCs or LCs specifically set forth herein, but wherein the CDR-L1, CDR-L2, CDR-L3, CDR-H1, CDR-H2 and CDR-H3 of such immunoglobulins are not variants and comprise the amino acid sequences set forth herein. Thus, in such embodiments, the CDRs within such antigen-binding proteins are not, themselves, variants.

A "conservatively modified variant" or a "conservative substitution" refers to a variant wherein there are one or more substitutions of amino acids in a polypeptide with other amino acids having similar characteristics (e.g. charge, side-chain size, hydrophobicity/hydrophilicity, backbone conformation and rigidity, etc.). Such changes can frequently be made without significantly disrupting the biological activity of the antibody or fragment. Those of skill in this art recognize that, in general, single amino acid substitutions in non-essential regions of a polypeptide do not substantially alter biological activity (see, e.g., Watson et al. (1987) Molecular Biology of the Gene, The Benjamin/Cummings Pub. Co., p. 224 (4th Ed.)). In addition, substitutions of structurally or functionally similar amino acids are less likely to significantly disrupt biological activity. Anti-PfRH5 antigen-binding proteins of the present invention may include immunoglobulin chains having an amino acid sequence set forth herein but having one or more conservatively modified variations.

Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45.

In an embodiment of the invention, an anti-PfRH5 antigen-binding protein of the present invention, e.g., comprising an immunoglobulin chain comprising a variant of an amino acid sequence set forth herein, exhibits one or more of the following functional properties:

Inhibits in vitro or in vivo growth of *Plasmodium falciparum* in human red blood cells, e.g., as measured by parasite lactate dehydrogenase (LDH) activity (e.g., at a rate of about 51 to about 69%, or up to 100% (e.g., when anti-PfRH5 antigen-binding protein is incubated with the cells for 96 hours) relative to uninfected red blood cells), for example, wherein the antigen-binding protein is H1H29100P, H1H29104P, H1H29127P, H1H29143P or any combination thereof of two of such proteins (see e.g., Table 2-1).

Inhibits growth of in vitro or in vivo *Plasmodium falciparum* strain 3D7 or 7G8 in human red blood cells, e.g., as measured by Parasite lactate dehydrogenase (LDH) activity, e.g., in the presence of chloroquine phosphate (CQ) (e.g., at a concentration of about 4.81 nM or 6.58 nM), for example, at a rate of about 34 to 61% in the absence of CQ, about 32 to 51% in the presence of 4.81 nM CQ or about 20% to 75% in the presence of 6.58 nM CQ.

Binds to PfRH5 polypeptide or an antigenic fragment thereof, e.g., PfRH5ΔNL.6his, with a $K_D$ of about 4.72 pM to about 1.67 nM at 25° C. and/or of about 1.10 pM to about 1.10 nM at 37° C., e.g., as set forth in Tables 5-1 and 5-2 herein.

Inhibits growth of in vitro or in vivo *Plasmodium falciparum* strain D10, Dd2, 7G8, W2-mef, 3D7, HB3, FCR-1/FVO, Cam3.11 or RF7 in human red blood cells, e.g., as measured by Parasite lactate dehydrogenase (LDH) activity, for example, at a concentration of about 666.67 nM at a rate as set forth in Table 4-2 relative to uninfected red blood cells.

Blocks binding of PfRH5 polypeptide (e.g., PfRH5ΔNL.6his, for example, at a concentration of about 0.5 nM or 2.0 nM) to basigin polypeptide (e.g., by about 1%, 10%, 20%, 30%, 40%, 50%, 60%, 70%, 80%, 90%, 95%, 99% or 100%), for example, binding of PfRH5 to basigin that is bound to a solid matrix (e.g., an ELISA plate) wherein the anti-PfRH5 antigen-binding protein is present at about 100 nM. For example, wherein basigin was amino acids Thr25-His205 thereof, e.g., expressed with a C-terminal linker, DIEGRMD (SEQ ID NO: 363), followed by a portion of the human IgG1 (Pro100-Lys330) and a 6× histidine tag.

Binds to the same epitope as H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2, for example, binds to PfRH5 lacking the amino-terminal residues M1-Y139 and including residues K140-Q526 but lacking K247-L295 and having the mutations T216A and T299A (PfRH5ΔNL.6his), e.g., further including C-terminal hexahistidine tag, for example, as measured by surface plasmon resonance.

Competes with H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2, H1H29214P2; or H1H29215P2 for binding to PfRH5 polypeptide, e.g., PfRH5ΔNL.6his.

The present invention includes a non-human primate (NHP) (e.g., monkey such as an *Aotus* monkey) whose body includes an anti-PfRH5 antigen-binding protein (e.g., antibody or antigen-binding fragment) such as H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2. For example, the non-human primate may have been injected with the antigen-binding protein or may be engineered to express the protein. In an embodiment of the invention, the non-human primate is *Aotus nancymaae*. In an embodiment of the invention, the non-human primate (e.g., monkey) is infected with *Plasmodium falciparum* (e.g., strain 3D7).

The present invention includes "neutralizing" or "antagonist" anti-PfRH5 antigen-binding proteins, e.g., antibody or antigen-binding fragment, which include molecules that inhibits an activity of PfRH5 to any detectable degree. For example, a neutralizing anti-PfRH5 antigen-binding protein may inhibit *Plasmodium falciparum* growth and/or block PfRH5/BSG binding.

"H1H29089P"; "H1H29094P"; "H1H29100P"; "H1H29104P"; "H1H29106P"; "H1H29109P"; "H1H29125P"; "H1H29127P"; "H1H29131P"; "H1H29134P"; "H1H29138P"; "H1H29141P"; "H1H29143P"; "H1H29146P2"; "H1H29147P2"; H1H29149P2"; "H1H29151P2"; "H1H29163P2"; "H1H29166P2"; "H1H29171P2"; "H1H29179P2"; "H1H29183P2"; "H1H29187P2"; "H1H29192P2"; "H1H29196P2"; "H1H29198P2"; "H1H29207P2"; "H1H29209P2"; "H1H29214P2"; or "H1H29215P2" refer to antigen-binding proteins, e.g., antibodies and antigen-binding fragments thereof (including multispecific antigen-binding proteins), comprising an immunoglobulin heavy chain variable region ($V_H$; or a variant thereof) and an immunoglobulin light chain variable region ($V_L$; or a variant thereof) which are set forth herein in Table 1-1; or that comprise a $V_H$ that comprises the CDRs thereof (CDR-H1 (or a variant thereof), CDR-H2 (or a variant thereof) and CDR-H3 (or a variant thereof)) and/or a $V_L$ that comprises the CDRs thereof (CDR-L1 (or a variant thereof), CDR-L2 (or a variant thereof) and CDR-L3 (or a variant thereof)), e.g., wherein the immunoglobulin chains, variable regions and/or CDRs comprise the specific amino acid sequences described below. In an embodiment of the invention, the $V_H$ is linked to a constant heavy immunoglobulin chain (e.g., an IgG such as IgG1 or IgG4) and/or the $V_L$ is linked to a constant light immunoglobulin chain (e.g., kappa or lambda).

Antibodies and antigen-binding fragments of the present invention comprise immunoglobulin chains including the amino acid sequences set forth herein as well as cellular and in vitro post-translational modifications to the antibody or fragment. For example, the present invention includes antibodies and antigen-binding fragments thereof that specifically bind to PfRH5 comprising heavy and/or light chain amino acid sequences set forth herein (e.g., CDR-H1, CDR-H2, CDR-H3, CDR-L1, CDR-L2 and/or CDR-L3) as well as antibodies and fragments wherein one or more amino acid residues is glycosylated, one or more Asn residues is deamidated, one or more residues (e.g., Met, Trp and/or His) is oxidized, the N-terminal Gln is pyroglutamate (pyroE) and/or the C-terminal Lysine is missing.

The present invention provides a vessel (e.g., a plastic or glass vial, e.g., with a cap or a chromatography column, hollow bore needle or a syringe cylinder) comprising an anti-PfRH5 antigen-binding protein of the present invention, e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2.

The present invention also provides an injection device comprising one or more antigen-binding proteins (e.g., antibody or antigen-binding fragment) that bind specifically to PfRH5, e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2, or a pharmaceutical composition thereof. The injection device may be packaged into a kit. An injection device is a device that introduces a substance into the body of a subject via a parenteral route, e.g., intramuscular, subcutaneous or intravenous. For example, an injection device may be a syringe (e.g., pre-filled with the pharmaceutical composition, such as an auto-injector) which, for example, includes a cylinder or barrel for holding fluid to be injected (e.g., comprising the antibody or fragment or a pharmaceutical composition thereof), a needle for piecing skin and/or blood vessels for injection of the fluid; and a plunger for pushing the fluid out of the cylinder and through the needle bore.

The present invention further provides methods for administering an anti-PfRH5 antigen-binding protein of the present invention, e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2, to a subject, comprising introducing the antigen-binding protein into the body of the subject (e.g., a human), for example, parenterally. For example, the method comprises piercing the body of the subject with a needle of a syringe and injecting the antigen-binding protein into the body of the subject, e.g., into the vein, artery, tumor, muscular tissue or subcutis of the subject.

Preparation of Human Antibodies

Methods for generating human antibodies in transgenic mice are known in the art. Any such known methods can be used in the context of the present invention to make human antibodies that specifically bind to PfRH5. An immunogen comprising any one of the following can be used to generate antibodies that specifically bind to PfRH5. In certain embodiments of the invention, the antibodies of the invention are obtained from mice immunized with a full length, native PfRH5, or with a live attenuated or inactivated virus, or with DNA encoding the protein or fragment thereof. Alternatively, the PfRH5 protein or a fragment thereof may be produced using standard biochemical techniques and modified and used as immunogen. In one embodiment of the invention, the immunogen is a recombinantly produced PfRH5 protein or fragment thereof. In certain embodiments of the invention, the immunogen may be a PfRH5 polypeptide vaccine. In certain embodiments, one or more booster injections may be administered. In certain embodiments, the immunogen may be a recombinant PfRH5 polypeptide expressed in *E. coli* or in any other eukaryotic or mammalian cells such as Chinese hamster ovary (CHO) cells.

Using VELOCIMMUNE® technology (see, for example, U.S. Pat. No. 6,596,541, Regeneron Pharmaceuticals, VELOCIMMUNE®), high affinity chimeric antibodies to PfRH5 can be initially isolated having human variable regions and mouse constant regions. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Antibodies of interest may also be isolated from mouse B-cells. Briefly, splenocytes are harvested from each mouse and B-cells are sorted (as described in US 2007/0280945A1, for example) by FACS using the antigen of interest as the sorting reagent that binds and identifies reactive antibodies (antigen-positive B cells). Various methods of identifying and sorting antigen-positive B cells, as well as constructing immunoglobulin gene expression cassettes by PCR for preparation of cells expressing recombinant antibodies, are well-known in the art. See e.g. WO20141460741, U.S. Pat. No. 7,884,054B2, and Liao, et al. June 2009. High-Throughput Isolation of Immunoglobulin Genes from Single Human B Cells and Expression as Monoclonal Antibodies. J Virol Methods 158(1-2):171-9.

Initially, high affinity chimeric antibodies are isolated having a human variable region and a mouse constant region. The antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

Anti-PfRH5 Antibodies Comprising Fc Variants

According to certain embodiments of the present invention, anti-PfRH5 antigen-binding proteins, e.g., antibodies or antigen-binding fragments, are provided comprising an Fc domain comprising one or more mutations, which, for example, enhance or diminish antibody binding to the FcRn receptor, e.g., at acidic pH as compared to neutral pH. For example, the present invention includes anti-PfRH5 antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, the present invention includes anti-PfRH5 antigen-binding proteins, e.g., antibodies or antigen-binding fragments, comprising an Fc domain comprising one or more pairs or groups of mutations selected from the group consisting of: 250Q and 248L (e.g., T250Q and M248L);

252Y, 254T and 256E (e.g., M252Y, S254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F).

Anti-PfRH5 antigen-binding proteins, e.g., antibodies and antigen-binding fragments thereof, that comprise a $V_H$ and/or $V_L$ as set forth herein comprising any possible combinations of the foregoing Fc domain mutations, are contemplated within the scope of the present invention.

The present invention also includes anti-PfRH5 antigen-binding proteins, antibodies or antigen-binding fragments, comprising a $V_H$ set forth herein and a chimeric heavy chain constant ($C_H$) region, wherein the chimeric $C_H$ region comprises segments derived from the $C_H$ regions of more than one immunoglobulin isotype. For example, the antibodies of the invention may comprise a chimeric $C_H$ region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antibodies of the invention comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., WO2014/022540).

Multispecific Antigen-Binding Proteins

The present invention includes anti-PfRH5 antigen-binding proteins, e.g., antibodies and antigen-binding fragments thereof, as well as methods of use thereof and methods of making such antigen-binding proteins. The term "anti-PfRH5" antigen-binding proteins, e.g., antibodies or antigen-binding fragments, includes multispecific (e.g., bispecific or biparatopic) molecules that include at least one first antigen-binding domain that specifically binds to PfRH5 (e.g., an antigen-binding domain from H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2) and at least one second antigen-binding domain that binds to a different antigen or to an epitope in PfRH5 which is different from that of the first antigen-binding domain (e.g., CD3, CD16, BSG (basigin), EXP1, MSP1, MSP2, MSPMSP3, MSP4, MSP5, MSP6, MSP7, MSP9, MSP10 GLURP, Sera, RAMA, SEA, AMA1, MTRAP, PTRAMP, ASP, RH1, RH2a, RH2b, RH4, RAP1, RAP2, RAP3, RhopH1, RhopH2, RhopH3, EMA175, EMA140 and/or EBA181). In an embodiment of the invention, the first and second epitopes overlap. In another embodiment of the invention, the first and second epitopes do not overlap.

In an embodiment of the invention, a multispecific antigen-binding protein binds to PfRH5 and to an antigen which causes activation of the immune cells such as cytotoxic T cells, N K cells, mononuclear phagocytes or neutrophils, e.g., CD3 or CD16.

"H1H29089P"; "H1H29094P"; "H1H29100P"; "H1H29104P"; "H1H29106P"; "H1H29109P"; "H1H29125P"; "H1H29127P"; "H1H29131P"; "H1H29134P"; "H1H29138P"; "H1H29141P"; "H1H29143P"; "H1H29146P2"; "H1H29147P2"; "H1H29149P2"; "H1H29151P2"; "H1H29163P2"; "H1H29166P2"; "H1H29171P2"; "H1H29179P2"; "H1H29183P2"; "H1H29187P2"; "H1H29192P2"; "H1H29196P2"; "H1H29198P2"; "H1H29207P2"; "H1H29214P2"; or "H1H29215P2" includes a multispecific molecules, e.g., antibodies or antigen-binding fragments, that include the HCDRs and LCDRs, $V_H$ and $V_L$, or HC and LC of H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2, respectively (including variants thereof as set forth herein) and one or more antigen-binding domains that bind to a different epitope.

In an embodiment of the invention, an antigen-binding domain that binds specifically to PfRH5, which may be included in a multispecific molecule, comprises:

(1)

(i) a heavy chain variable domain sequence that comprises CDR-H1, CDR-H2 and CDR-H3 from an immunoglobulin heavy chain selected from: H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; and H1H29215P2, and (ii) a light chain variable domain sequence that comprises CDR-L1, CDR-L2 and CDR-L3 from an immunoglobulin heavy chain selected from: H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; and H1H29215P2, respectively;

or, (2)

(i) a heavy chain variable domain ($V_H$) sequence selected from: H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2;

H1H29192P2; H1H29196P2; H1H29198P2; H1H29207P2; H1H29209P2; H1H29214P2; and H1H29215P2; and (ii) a light chain variable domain (V$_L$) sequence selected from: H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; and H1H29215P2, respectively;

and one or more antigen-binding domains that bind to a different epitope.

In an embodiment of the invention, the multispecific antibody or fragment includes more than two different binding specificities (e.g., a trispecific molecule), for example, one or more additional antigen-binding domains which are the same or different from the first and/or second antigen-binding domain.

In one embodiment of the invention, a bispecific antigen-binding fragment comprises a first scFv (e.g., comprising V$_H$ and V$_L$ of H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; and H1H29215P2) having binding specificity for a first epitope (e.g., PfRH5) and a second scFv having binding specificity for a second, different epitope. For example, in an embodiment of the invention, the first and second scFv are tethered with a linker, e.g., a peptide linker (e.g., a GS linker such as (GGGGS)$_n$ (SEQ ID NO: 364) wherein n is, for example, 1, 2, 3, 4, 5, 6, 7, 8, 9 or 10). Other bispecific antigen-binding fragments include an F(ab)$_2$ of a bispecific IgG antibody which comprises the heavy and light chain CDRs of H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2 H1H29209P2; H1H29214P2; and H1H29215P2 and of another antibody that binds to a different epitope.

Immunoconjugates

The invention encompasses anti-PfRH5 antigen-binding proteins, e.g., antibodies or antigen-binding fragments, conjugated to another moiety, e.g., a therapeutic moiety (an "immunoconjugate"), such as a toxoid (e.g., diptheria toxoid or tetanus toxoid) or an anti-parasitic drug to treat *Plasmodium falciparum* infection. In an embodiment of the invention, an anti-PfRH5 antibody or fragment is conjugated to any of the further therapeutic agents set forth herein. As used herein, the term "immunoconjugate" refers to an antigen-binding protein, e.g., an antibody or antigen-binding fragment, which is chemically or biologically linked to another molecule.

Therapeutic Methods

The present invention provides methods for treating or preventing *Plasmodium falciparum* infection (e.g., malaria) by administering a therapeutically effective amount of anti-PfRH5 antigen-binding protein, e.g., antibody or antigen-binding fragment, (e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2) to a subject (e.g., a human) in need of such treatment or prevention. "Malaria" is a disease, frequently transmitted by the bite of an infected female mosquito (e.g., *Anopheles* mosquitos), caused by infection of a host with the parasite *Plasmodium falciparum*. The term "*Plasmodium falciparum* infection" refers to invasion of the body of a subject with *Plasmodium falciparum* and encompasses malaria.

An effective or therapeutically effective dose of anti-PfRH5 antigen-binding protein, e.g., antibody or antigen-binding fragment (e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2), for treating or preventing a *Plasmodium falciparum* infection refers to the amount of the antibody or fragment sufficient to alleviate one or more signs and/or symptoms of the infection in the treated subject, whether by inducing the regression or elimination of such signs and/or symptoms or by inhibiting the progression of such signs and/or symptoms. The dose amount may vary depending upon the age and the size of a subject to be administered, target disease, conditions, route of administration, and the like. In an embodiment of the invention, an effective or therapeutically effective dose of anti-PfRH5 antigen-binding protein, e.g., antibody or antigen-binding fragment thereof, of the present invention, for treating or preventing *Plasmodium falciparum* infection, e.g., in an adult human subject, is about 1 mg/kg to 150 mg/kg. Depending on the severity of the infection, the frequency and the duration of the treatment can be adjusted. In certain embodiments, the antigen-binding protein of the present invention can be administered at an initial dose, followed by one or more secondary doses. In certain embodiments, the initial dose may be followed by administration of a second or a plurality of subsequent doses of antigen-binding protein in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

As used herein, the term "subject" refers to a mammal (e.g., rat, mouse, cat, dog, cow, sheep, horse, goat, rabbit), preferably a human, for example, in need of prevention and/or treatment of a *Plasmodium falciparum* infection. A subject may have a *Plasmodium falciparum* infection or be predisposed to developing a *Plasmodium falciparum* infection or be at elevated risk of developing such an infection. Subjects predisposed to developing a *Plasmodium falciparum* infection or subjects who may be at elevated risk for contracting a *Plasmodium falciparum* infection, include those subjects with compromised immune systems, e.g., because of autoimmune disease, those persons receiving immunosuppressive therapy, those persons afflicted with human immunodeficiency syndrome (HIV) or acquired immune deficiency syndrome (AIDS), certain forms of anemia that deplete or destroy white blood cells, those persons receiving radiation or chemotherapy, or those persons afflicted with an inflammatory disorder. Additionally, subjects of extreme young or old age may be predisposed. Any person who comes into contact with or close proximity to mosquitos, especially in the tropics, South America, Central America, Africa, South East Asia, and the Eastern Mediterranean Region, has an increased risk of developing *Plasmodium falciparum* infection.

"Treat" or "treating" means to administer an anti-PfRH5 antigen-binding protein, e.g., antibody or antigen-binding fragment of the present invention (e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2), to a subject having *Plasmodium falciparum* infection, such that one or more signs or symptoms of the infection in the subject are reduced or eliminated, e.g., wherein *Plasmodium falciparum* is reduced or substantially eliminated (e.g., completely eliminated) from the body of the subject.

Signs and symptoms of *Plasmodium falciparum* infection include:
Anemia;
Bloody stools;
Chills, fever, sweating;
Coma;
Convulsions;
Headache;
Jaundice;
Muscle pain;
Nausea and vomiting;
Enlarged spleen;
Jaundice;
Enlargement of the liver;
Increased respiratory rate;
*Plasmodium falciparum* in the blood stream, liver or erythrocytes;
Anemia;
Hemolysis;
Free hemoglobin in the blood stream;
Hemoglobinuria;
Acute kidney failure;
Acute respiratory distress syndrome (ARDS);
Low blood pressure;
Metabolic acidosis; and
Hypoglycemia.

The present invention also encompasses prophylactically administering an anti-PfRH5 antigen-binding protein, e.g., antibody or antigen-binding fragment thereof of the present invention (e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2), to a subject who is at risk (e.g., predisposed or at an elevated risk) of *Plasmodium falciparum* infection so as to prevent such infection. "Prevent" or "preventing" means to administer an anti-PfRH5 antigen-binding protein, e.g., antibody or antigen-binding fragment of the present invention, to a subject who is not infected with *Plasmodium falciparum* such that manifestation of the infection in the body of a subject is inhibited or decreased in likelihood or decreased in severity if infection does occur.

Combinations and Pharmaceutical Compositions

The present invention provides compositions that include anti-PfRH5 antigen-binding proteins and one or more ingredients; as well as methods of use thereof and methods of making such compositions.

To prepare pharmaceutical compositions of the anti-PfRH5 antigen-binding proteins, e.g., antibodies and antigen-binding fragments thereof (e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2), antigen-binding protein is admixed with a pharmaceutically acceptable carrier or excipient. See, e.g., Remington's Pharmaceutical Sciences and U.S. Pharmacopeia: National Formulary, Mack Publishing Company, Easton, Pa. (1984); Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, N Y; Lieberman, et al. (eds.) (1990) Pharmaceutical Dosage Forms: Tablets, Marcel Dekker, N Y; Lieberman, et al. (eds.) (1990) Pharmaceutical Dosage Forms: Disperse Systems, Marcel Dekker, N Y; Weiner and Kotkoskie (2000) Excipient Toxicity and Safety, Marcel Dekker, Inc., New York, N.Y. In an embodiment of the invention, the pharmaceutical composition is sterile. Such compositions are part of the present invention.

Pharmaceutical compositions of the present invention include pharmaceutically acceptable carriers, diluents, excipients and/or stabilizers, such as, for example, water, buffering agents, stabilizing agents, preservatives, isotonifiers, non-ionic detergents, antioxidants and/or other miscellaneous additives.

The scope of the present invention includes desiccated, e.g., freeze-dried, compositions comprising an anti-PfRH5 antigen-binding protein, e.g., antibody or antigen-binding fragment thereof (e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2), or a pharmaceutical composition thereof that includes a pharmaceutically acceptable carrier but substantially lacks water.

In a further embodiment of the invention, a further therapeutic agent that is administered to a subject in association with an anti-PfRH5 antigen-binding protein, e.g., antibody or antigen-binding fragment thereof (e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2), disclosed herein is administered to the subject in accordance with the Physicians' Desk Reference 2003 (Thomson Healthcare; 57th edition (Nov. 1, 2002)).

The mode of administration of an antigen-binding protein or composition thereof can vary. Routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal or intra-arterial.

The present invention provides methods for administering an anti-PfRH5 antigen-binding protein, e.g., antibody or antigen-binding fragment thereof (e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2) to a subject, comprising introducing the protein or a pharmaceutical composition or combination thereof into the body of the subject. For example, the method comprises piercing the body of the subject with a needle of a syringe and injecting the antigen-binding protein or a pharmaceutical composition or combination thereof into the body of the subject, e.g., into the vein, artery, tumor, muscular tissue or subcutis of the subject.

The present invention provides a vessel (e.g., a plastic or glass vial, e.g., with a cap or a chromatography column, hollow bore needle or a syringe cylinder) comprising any of the anti-PfRH5 antigen-binding proteins, e.g., antibodies or antigen-binding fragments thereof (e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2) or a pharmaceutical composition comprising a pharmaceutically acceptable carrier or combination thereof.

The present invention includes combinations including an anti-PfRH5 antigen-binding protein, e.g., antibody or antigen-binding fragment thereof of the present invention (e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2), in association with one or more further therapeutic agents. The anti-PfRH5 antigen-binding protein and the further therapeutic agent can be in a single composition or in separate compositions. For example, in an embodiment of the invention, the further therapeutic agent is an anti-parasitic or anti-malarial therapeutic agent. In an embodiment of the invention, the further therapeutic agent is chloroquine, atovaquone and/or proguanil, artemether and/or lumefantrine, mefloquine, quinine, quinidine, doxycycline (optionally in combination with quinine) and/or clindamycin (optionally in combination with quinine). In an embodiment of the invention, the further therapeutic agent is a vaccine such as an anti-malarial vaccine, e.g., RTS,S/AS01 (sold as Mosquirix). Methods for treating or preventing *Plasmodium falciparum* infection in a subject in need of said treatment or prevention by administering H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2 in association with a further therapeutic agent are part of the present invention.

The present invention includes a combination comprising two or more (e.g., 2, 3 or 4) of the antigen-binding proteins of the present invention (e.g., antibody or antigen-binding protein) in association with one another. For example, if H1H29089P is Ab1; if H1H29094P is Ab2; if H1H29100P is Ab3; if H1H29104P is Ab4; if H1H29106P is Ab5; if H1H29109P is Ab6; if H1H29125P is Ab7; if H1H29127P is Ab8; if H1H29131P is Ab9; if H1H29134P is Ab10; if H1H29138P is Ab11; if H1H29141P is Ab12; if H1H29143P is Ab13; if H1H29146P2 is Ab14; if H1H29147P2 is Ab15; if H1H29149P2 is Ab16; if H1H29151P2 is Ab17; if H1H29163P2 is Ab18; if H1H29166P2 is Ab19; if H1H29171P2 is Ab20; if H1H29179P2 is Ab21; if H1H29183P2 is Ab22; if H1H29187P2 is Ab23; if H1H29192P2 is Ab24; if H1H29196P2 is Ab25; if H1H29198P2 is Ab26; if H1H29207P2 is Ab27; if H1H29214P2 is Ab28; if H1H29215P2 is Ab29 and if H1H29209P is Ab30, then such compositions of the present invention include combinations including the following antigen-binding proteins of the present invention (e.g., antibodies and/or antigen-binding proteins) in association with one another:

| Ab1 & Ab2 | Ab1 & Ab18 | Ab2 & Ab7 | Ab2 & Ab23 | Ab3 & Ab13 | Ab3 & Ab29 | Ab4 & Ab20 | Ab5 & Ab12 | Ab5 & Ab28 | Ab6 & Ab21 |
|---|---|---|---|---|---|---|---|---|---|
| Ab1 & Ab3 | Ab1 & Ab19 | Ab2 & Ab8 | Ab2 & Ab24 | Ab3 & Ab14 | Ab4 & Ab5 | Ab4 & Ab21 | Ab5 & Ab13 | Ab5 & Ab29 | Ab6 & Ab22 |
| Ab1 & Ab4 | Ab1 & Ab20 | Ab2 & Ab9 | Ab2 & Ab25 | Ab3 & Ab15 | Ab4 & Ab6 | Ab4 & Ab22 | Ab5 & Ab14 | Ab6 & Ab7 | Ab6 & Ab23 |
| Ab1 & Ab5 | Ab1 & Ab21 | Ab2 & Ab10 | Ab2 & Ab26 | Ab3 & Ab16 | Ab4 & Ab7 | Ab4 & Ab23 | Ab5 & Ab15 | Ab6 & Ab8 | Ab6 & Ab24 |
| Ab1 & Ab6 | Ab1 & Ab22 | Ab2 & Ab11 | Ab2 & Ab27 | Ab3 & Ab17 | Ab4 & Ab8 | Ab4 & Ab24 | Ab5 & Ab16 | Ab6 & Ab9 | Ab6 & Ab25 |
| Ab1 & Ab7 | Ab1 & Ab23 | Ab2 & Ab12 | Ab2 & Ab28 | Ab3 & Ab18 | Ab4 & Ab9 | Ab4 & Ab25 | Ab5 & Ab17 | Ab6 & Ab10 | Ab6 & Ab26 |

-continued

| | | | | | | | | | |
|---|---|---|---|---|---|---|---|---|---|
| Ab1 & Ab8 | Ab1 & Ab24 | Ab2 & Ab13 | Ab2 & Ab29 | Ab3 & Ab19 | Ab4 & Ab10 | Ab4 & Ab26 | Ab5 & Ab18 | Ab6 & Ab11 | Ab6 & Ab27 |
| Ab1 & Ab9 | Ab1 & Ab25 | Ab2 & Ab14 | Ab3 & Ab4 | Ab3 & Ab20 | Ab4 & Ab11 | Ab4 & Ab27 | Ab5 & Ab19 | Ab6 & Ab12 | Ab6 & Ab28 |
| Ab1 & Ab10 | Ab1 & Ab26 | Ab2 & Ab15 | Ab3 & Ab5 | Ab3 & Ab21 | Ab4 & Ab12 | Ab4 & Ab28 | Ab5 & Ab20 | Ab6 & Ab13 | Ab6 & Ab29 |
| Ab1 & Ab11 | Ab1 & Ab27 | Ab2 & Ab16 | Ab3 & Ab6 | Ab3 & Ab22 | Ab4 & Ab13 | Ab4 & Ab29 | Ab5 & Ab21 | Ab6 & Ab14 | Ab7 & Ab8 |
| Ab1 & Ab12 | Ab1 & Ab28 | Ab2 & Ab17 | Ab3 & Ab7 | Ab3 & Ab23 | Ab4 & Ab14 | Ab5 & Ab6 | Ab5 & Ab22 | Ab6 & Ab15 | Ab7 & Ab9 |
| Ab1 & Ab13 | Ab1 & Ab29 | Ab2 & Ab18 | Ab3 & Ab8 | Ab3 & Ab24 | Ab4 & Ab15 | Ab5 & Ab7 | Ab5 & Ab23 | Ab6 & Ab16 | Ab7 & Ab10 |
| Ab1 & Ab14 | Ab2 & Ab3 | Ab2 & Ab19 | Ab3 & Ab9 | Ab3 & Ab25 | Ab4 & Ab16 | Ab5 & Ab8 | Ab5 & Ab24 | Ab6 & Ab17 | Ab7 & Ab11 |
| Ab1 & Ab15 | Ab2 & Ab4 | Ab2 & Ab20 | Ab3 & Ab10 | Ab3 & Ab26 | Ab4 & Ab17 | Ab5 & Ab9 | Ab5 & Ab25 | Ab6 & Ab18 | Ab7 & Ab12 |
| Ab1 & Ab16 | Ab2 & Ab5 | Ab2 & Ab21 | Ab3 & Ab11 | Ab3 & Ab27 | Ab4 & Ab18 | Ab5 & Ab10 | Ab5 & Ab26 | Ab6 & Ab19 | Ab7 & Ab13 |
| Ab1 & Ab17 | Ab2 & Ab6 | Ab2 & Ab22 | Ab3 & Ab12 | Ab3 & Ab28 | Ab4 & Ab19 | Ab5 & Ab11 | Ab5 & Ab27 | Ab6 & Ab20 | Ab7 & Ab14 |
| Ab7 & Ab15 | Ab8 & Ab10 | Ab8 & Ab26 | Ab9 & Ab22 | Ab10 & Ab17 | Ab10 & Ab29 | Ab11 & Ab23 | Ab12 & Ab18 | Ab13 & Ab14 | Ab13 & Ab26 |
| Ab7 & Ab16 | Ab8 & Ab11 | Ab8 & Ab27 | Ab9 & Ab23 | Ab10 & Ab18 | Ab11 & Ab12 | Ab11 & Ab24 | Ab12 & Ab19 | Ab13 & Ab15 | Ab13 & Ab27 |
| Ab7 & Ab17 | Ab8 & Ab12 | Ab8 & Ab28 | Ab9 & Ab24 | Ab10 & Ab19 | Ab11 & Ab13 | Ab11 & Ab25 | Ab12 & Ab20 | Ab13 & Ab16 | Ab13 & Ab28 |
| Ab7 & Ab18 | Ab8 & Ab13 | Ab8 & Ab29 | Ab9 & Ab25 | Ab10 & Ab20 | Ab11 & Ab14 | Ab11 & Ab26 | Ab12 & Ab21 | Ab13 & Ab17 | Ab13 & Ab29 |
| Ab7 & Ab19 | Ab8 & Ab14 | Ab9 & Ab10 | Ab9 & Ab26 | Ab10 & Ab21 | Ab11 & Ab15 | Ab11 & Ab27 | Ab12 & Ab22 | Ab13 & Ab18 | Ab14 & Ab15 |
| Ab7 & Ab20 | Ab8 & Ab15 | Ab9 & Ab11 | Ab9 & Ab27 | Ab10 & Ab22 | Ab11 & Ab16 | Ab11 & Ab28 | Ab12 & Ab23 | Ab13 & Ab19 | Ab14 & Ab16 |
| Ab7 & Ab21 | Ab8 & Ab16 | Ab9 & Ab12 | Ab9 & Ab28 | Ab10 & Ab23 | Ab11 & Ab17 | Ab11 & Ab29 | Ab12 & Ab24 | Ab13 & Ab20 | Ab14 & Ab17 |
| Ab7 & Ab22 | Ab8 & Ab17 | Ab9 & Ab13 | Ab9 & Ab29 | Ab10 & Ab24 | Ab11 & Ab18 | Ab12 & Ab13 | Ab12 & Ab25 | Ab13 & Ab21 | Ab14 & Ab18 |
| Ab7 & Ab23 | Ab8 & Ab18 | Ab9 & Ab14 | Ab10 & Ab11 | Ab10 & Ab25 | Ab11 & Ab19 | Ab12 & Ab14 | Ab12 & Ab26 | Ab13 & Ab22 | Ab14 & Ab19 |
| Ab7 & Ab24 | Ab8 & Ab19 | Ab9 & Ab15 | Ab10 & Ab12 | Ab10 & Ab26 | Ab11 & Ab20 | Ab12 & Ab15 | Ab12 & Ab27 | Ab13 & Ab23 | Ab14 & Ab20 |
| Ab7 & Ab25 | Ab8 & Ab20 | Ab9 & Ab16 | Ab10 & Ab13 | Ab10 & Ab27 | Ab11 & Ab21 | Ab12 & Ab16 | Ab12 & Ab28 | Ab13 & Ab24 | Ab14 & Ab21 |
| Ab7 & Ab26 | Ab8 & Ab21 | Ab9 & Ab17 | Ab10 & Ab14 | Ab10 & Ab28 | Ab11 & Ab22 | Ab12 & Ab17 | Ab12 & Ab29 | Ab13 & Ab25 | Ab14 & Ab22 |
| Ab7 & Ab27 | Ab8 & Ab22 | Ab9 & Ab18 | Ab10 & Ab15 | Ab10 & Ab18 | Ab11 & Ab19 | Ab20 & Ab23 | Ab22 & Ab23 | Ab23 & Ab29 | Ab26 & Ab29 |
| Ab7 & Ab28 | Ab8 & Ab23 | Ab9 & Ab19 | Ab10 & Ab16 | Ab10 & Ab22 | Ab11 & Ab24 | Ab20 & Ab27 | Ab22 & Ab24 | Ab24 & Ab25 | Ab27 & Ab28 |
| Ab7 & Ab29 | Ab8 & Ab24 | Ab9 & Ab20 | Ab10 & Ab17 | Ab10 & Ab18 | Ab19 & Ab25 | Ab20 & Ab28 | Ab22 & Ab25 | Ab24 & Ab26 | Ab27 & Ab29 |
| Ab8 & Ab9 | Ab8 & Ab25 | Ab9 & Ab21 | Ab10 & Ab21 | Ab10 & Ab24 | Ab19 & Ab26 | Ab20 & Ab29 | Ab22 & Ab26 | Ab24 & Ab27 | Ab28 & Ab29 |
| Ab14 & Ab23 | Ab15 & Ab21 | Ab16 & Ab20 | Ab17 & Ab22 | Ab18 & Ab25 | Ab19 & Ab27 | Ab21 & Ab22 | Ab22 & Ab27 | Ab24 & Ab28 | Ab1 & Ab30 |
| Ab14 & Ab24 | Ab15 & Ab22 | Ab16 & Ab21 | Ab17 & Ab23 | Ab18 & Ab26 | Ab19 & Ab28 | Ab21 & Ab22 | Ab22 & Ab24 | Ab24 & Ab29 | Ab2 & Ab30 |
| Ab14 & Ab25 | Ab15 & Ab23 | Ab16 & Ab22 | Ab17 & Ab24 | Ab18 & Ab27 | Ab18 & Ab29 | Ab21 & Ab24 | Ab22 & Ab29 | Ab25 & Ab26 | Ab3 & Ab30 |
| Ab14 & Ab26 | Ab15 & Ab24 | Ab16 & Ab23 | Ab17 & Ab25 | Ab18 & Ab28 | Ab20 & Ab21 | Ab21 & Ab25 | Ab23 & Ab25 | Ab25 & Ab27 | Ab4 & Ab30 |
| Ab14 & Ab27 | Ab15 & Ab25 | Ab16 & Ab24 | Ab17 & Ab26 | Ab18 & Ab29 | Ab20 & Ab22 | Ab21 & Ab26 | Ab23 & Ab25 | Ab25 & Ab28 | Ab5 & Ab30 |
| Ab14 & Ab28 | Ab15 & Ab26 | Ab16 & Ab25 | Ab17 & Ab27 | Ab19 & Ab20 | Ab20 & Ab23 | Ab21 & Ab27 | Ab23 & Ab26 | Ab25 & Ab29 | Ab6 & Ab30 |
| Ab14 & Ab29 | Ab15 & Ab27 | Ab16 & Ab26 | Ab17 & Ab28 | Ab19 & Ab20 | Ab20 & Ab24 | Ab21 & Ab28 | Ab23 & Ab26 | Ab26 & Ab27 | Ab7 & Ab30 |
| Ab15 & Ab16 | Ab15 & Ab28 | Ab16 & Ab27 | Ab17 & Ab29 | Ab19 & Ab22 | Ab20 & Ab25 | Ab21 & Ab29 | Ab23 & Ab28 | Ab26 & Ab28 | Ab8 & Ab30 |
| Ab15 & Ab17 | Ab15 & Ab29 | Ab16 & Ab28 | Ab18 & Ab19 | Ab19 & Ab30 | Ab21 & Ab30 | Ab23 & Ab30 | Ab25 & Ab30 | Ab27 & Ab30 | Ab9 & Ab30 |
| Ab15 & Ab18 | Ab16 & Ab17 | Ab16 & Ab29 | Ab18 & Ab20 | Ab20 & Ab30 | Ab22 & Ab30 | Ab24 & Ab30 | Ab26 & Ab30 | Ab28 & Ab30 | Ab10 & Ab30 |
| Ab15 & Ab19 | Ab16 & Ab18 | Ab17 & Ab18 | Ab17 & Ab30 | | | | | | Ab29 & Ab30 |
| Ab15 & Ab20 | Ab16 & Ab19 | Ab17 & Ab19 | Ab18 & Ab30 | | | | | | |

-continued

| | | |
|---|---|---|
| Ab11 & Ab30 | Ab13 & Ab30 | Ab15 & Ab30 |
| Ab12 & Ab30 | Ab14 & Ab30 | Ab16 & Ab30 |

In an embodiment of the invention, the composition comprises two or more non-competing antigen-binding proteins. Cross-competition between anti-PfRH5 antibodies of the present invention is summarized below in Table 6-1.

The term "in association with" indicates that components, an anti-PfRH5 antigen-binding protein, e.g., antibody or antigen-binding fragment thereof of the present invention, along with another agent such as chloroquine, can be formulated into a single composition, e.g., for simultaneous delivery, or formulated separately into two or more compositions (e.g., a kit including each component). Each component can be administered to a subject at a different time than when the other component is administered; for example, each administration may be given non-simultaneously (e.g., separately or sequentially) at intervals over a given period of time. Moreover, the separate components may be administered to a subject by the same or by a different route.

Testing and Diagnosis

Early diagnosis of malaria is helpful to obtaining a positive clinical outcome. The present invention provides methods for treating *Plasmodium falciparum* infection (e.g., malaria), in a subject, comprising diagnosing the infection in the subject and, if the subject is diagnosed as having the infection, administering a therapeutically effective amount of the anti-PfRH5 antigen-binding protein, e.g., antibody or antigen-binding fragment, to the subject. See e.g., Moody, Rapid Diagnostic Tests for Malaria Parasites, Clinical Microbiology Reviews 15(1): 66-78 (2002).

*Plasmodium falciparum* infection can be diagnosed microscopically (e.g., fluorescence microscopy). For example, *Plasmodium falciparum* can be identified by examining, under the microscope, a drop of a subject's blood, e.g., spread out as a "blood smear" on a microscope slide (e.g., thick blood film or thin blood film). Prior to examination, the specimen can be stained (e.g., with Giemsa stain). The present invention includes methods for treatment of *Plasmodium falciparum* infection (as discussed herein) wherein the infection is diagnosed microscopically.

In an embodiment of the invention, the presence of *Plasmodium falciparum* in a sample from the subject is detected by detecting *Plasmodium falciparum* lactate dehydrogenase. If LDH is detected in a test sample above that of a control sample of a known uninfected sample, then the test sample is determined to contain *Plasmodium falciparum*. See e.g., Miura, H. Zhou, A. Diouf, SE. Moretz, M P. Fay, L H. Miller, L B. Martin, M A. Pierce, R D. Ellis, G E D. Mullen, C A. Long. Anti-Apical-Membrane-Antigen-1 antibody is more effective than anti-42-kilodalton-Merozoite-Surface-Protein-1 antibody in inhibiting *Plasmodium falciparum* growth, as determined by the in vitro growth inhibition assay. Clin Vaccine Immunol. 16, 963-968 (2009). PMID: PMC2708396.

The presence of *Plasmodium falciparum* nucleic acids can also be detected, e.g., using polymerase chain reaction (PCR) to detect, for example, the small-subunit 18S rRNA and/or circumsporozoite (CS) genes.

*Plasmodium falciparum* infection can also be diagnosed by detection of the parasite's antigens in the body of a subject. For example, in an embodiment of the invention, the antigen is detected immunogenically, e.g., using a rapid diagnostic test. See e.g., Van der Palen et al. Test characteristics of two rapid antigen detection tests (SD FK50 and SD FK60) for the diagnosis of malaria in returned travelers, Malaria Journal 8:90 (2009); or U.S. Pat. No. 5,712,170.

The anti-PfRH5 antigen-binding proteins, e.g., antibodies or antigen-binding fragments thereof of the present invention (e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2), may be used to detect and/or measure PfRH5 (e.g., a *Plasmodium falciparum* cell which includes the PfRH5 protein) in a sample (e.g., a bodily fluid such as blood). Exemplary assays for PfRH5 may include, e.g., contacting the sample with an anti-PfRH5 antigen-binding protein of the invention, wherein, for example, the anti-PfRH5 antigen-binding protein is labeled with a detectable label or reporter molecule. If the anti-PfRH5 antigen-binding protein complexed with PfRH5 is detected, then this indicates the presence of PfRH5 in the sample and/or the presence of *Plasmodium falciparum* in the sample and in the body of the subject.

For example, the present invention includes methods for detecting PfRH5 polypeptide or a cell including such a polypeptide (e.g., *Plasmodium falciparum*) using a lateral flow 'immuno-chromatographic' antigen-detection test. Such lateral flow tests rely on the capture of detectably labeled antigen-binding proteins (e.g., antibodies and antigen-binding fragments thereof) to produce a visible band on a strip of substrate. With *Plasmodium falciparum* malaria diagnostic tests, the labeled antigen-binding protein first binds to the parasite antigen, PfRH5, and the resultant complex is captured on the strip by a band of bound antigen-binding protein, forming a visible line (test line). A control line gives information on the integrity of the antibody-label conjugate, but does not confirm the ability to detect parasite antigen.

The present invention provides a lateral flow test strip for detecting the presence of PfRH5 (e.g., a *Plasmodium falciparum* cell) in a sample comprising a substrate (e.g., nitrocellulose) which includes the following regions arranged laterally across the substrate:

(i) a spot for introduction of a sample (sample zone);

(ii) a conjugate pad which includes a first anti-PfRH5 antigen-binding protein (e.g., H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; or H1H29215P2) which is detectably labeled, e.g., with a dye, but not immobilized to the substrate;
(iii) a test line containing a second anti-PfRH5 antigen-binding protein which is not detectably labeled and does not significantly compete with the first anti-PfRH5 antigen-binding protein for binding to PfRH5, but is immobilized to the substrate; and
(iv) a control line containing a secondary antigen-binding protein, immobilized to the substrate, which binds to the first anti-PfRH5 antigen-binding protein (e.g., an antibody or antigen-binding fragment or protein-A).

In an embodiment of the invention:
(i) once a liquid-containing sample is placed on the sample pad, the sample (and any PfRH5 polypeptide contained therein) diffuses, by capillary action, across the substrate, onto the conjugation pad, then into the test line and then into the control line;
(ii) PfRH5 polypeptide which reaches the conjugate pad forms a complex with the detectably labeled first anti-PfRH5 antigen-binding protein, and the complex further diffuses into the test line wherein a further complex is formed with the second anti-PfRH5 antigen-binding protein (forming a triple complex wherein PfRH5 is bound by said first and second antigen-binding proteins and immobilized within the test line);
(iii) any excess first anti-PfRH5 antigen-binding protein which does not immobilize at the test line continues to diffuse into the control line and binds to the secondary antigen-binding protein, thereby becoming immobilized in the control line; and/or
(iv) a positive test, indicating the presence of PfRH5 in the sample, is indicated by the presence of the detectable label in the test line; a negative test, indicating the lack of detectable levels of PfRH5 in the sample, is indicated by the absence of the detectable label in the test line; and detectable label in the control line indicates that the test system is operating properly.

In an embodiment of the invention, the detectable label is a dye (e.g., indigo blue), an enzyme, a ferritin, a fluorescent or colored microparticle/bead or nanoparticle/bead or a colloid metal (e.g., gold, selenium dye (e.g., in a liposome) or silver, e.g., a colloidal particle thereof). In an embodiment of the invention, the detectable label is visually detectable.

In an embodiment of the invention, the substrate is an insoluble material capable of supporting fluid flow, e.g., glass fiber filter paper; natural polymeric materials, cellulose-based materials, filter paper, chromatographic paper, nitrocellulose, cellulose acetate, poly(vinyl chloride), polyacrylamide or crosslinked dextran.

The present invention also provides a method for determining if a sample (e.g., bodily fluid such as, for example, blood) contains PfRH5 (e.g., a cell containing PfRH5 such as *Plasmodium falciparum*) comprising contacting the sample zone of a lateral flow device, as set forth herein, with the sample, waiting for capillary flow to carry the sample across the substrate to the control line, optionally waiting for a period of time, and observing the test and control lines, wherein the presence of the detectable label in the test line indicates that the sample contained PfRH5 and the presence of the detectable label in the control line indicates that the lateral flow test strip is functioning correctly. The absence of detectable label in the test line, with the presence of detectable label in the control line indicates the absence of PfRH5 from the sample. In an embodiment of the invention, the method further comprises treating the subject, from whom the sample was taken, with a therapeutically effective amount of anti-PfRH5 antigen-binding protein (e.g., antibody or antigen-binding fragment) if the test indicates the presence of PfRH5 in the sample and the flow test strip is functioning correctly.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Example 1: Generation of Human Antibodies That Bind to PfRH5

Human antibodies to *P. falciparum* RH5 (PfRH5) were generated in a VELOCIMMUNE® mouse comprising DNA encoding human immunoglobulin heavy and kappa light chain variable regions. The mice were immunized with recombinant RH5 protein (PfRH5ΔNL). Some mice were immunized with recombinant PfRH5 protein (PfRH5ΔNL.6his) followed by a booster of *P. falciparum* merozoites isolated from strain 3D7. The antibody immune response was monitored by a PfRH5-specific immunoassay. When a desired immune response was achieved, splenocytes were harvested and antibodies isolated directly from antigen-positive mouse B cells without fusion to myeloma cells, as described in U.S. Pat. No. 7,582,298, herein specifically incorporated by reference in its entirety. Using this method, several fully human anti-PfRH5 antibodies (i.e., antibodies possessing human variable domains and human constant domains) were obtained; exemplary antibodies generated in this manner were designated as H1H29089P; H1H29094P; H1H29100P; H1H29104P; H1H29106P; H1H29109P; H1H29125P; H1H29127P; H1H29131P; H1H29134P; H1H29138P; H1H29141P; H1H29143P; H1H29146P2; H1H29147P2; H1H29149P2; H1H29151P2; H1H29163P2; H1H29166P2; H1H29171P2; H1H29179P2; H1H29183P2; H1H29187P2; H1H29192P2; H1H29196P2; H1H29198P2; H1H29207P2; H1H29209P2; H1H29214P2; and H1H29215P2.

The biological properties of the exemplary antibodies generated in accordance with the methods of this Example are described in detail in the Examples set forth below. Sequences of the antibody immunoglobulin chains are set forth below.

TABLE 1-1

Immunoglobulin chain sequences of the present invention*

| Antibody | | $V_H$ | | CDR-H1 | | CDR-H2 | | CDR-H3 | | $V_L$ | | CDR-L1 | | CDR-L2 | | CDR-L3 | |
|---|---|---|---|---|---|---|---|---|---|---|---|---|---|---|---|---|---|
| # | Name | DNA | PEP | DNA | PEP | DNA | PEP | DNA | PEP | DNA | PEP | DNA | PEP | DNA | PEP | DNA | PEP |
| 1 | H1H29089P | 1 | 2 | 3 | 4 | 5 | 6 | 7 | 8 | 9 | 10 | 11 | 12 | 13 | 14 | 15 | 16 |
| 2 | H1H29094P | 17 | 18 | 19 | 20 | 21 | 22 | 23 | 24 | 25 | 26 | 27 | 28 | 29 | 30 | 31 | 32 |
| 3 | H1H29100P | 33 | 34 | 35 | 36 | 37 | 38 | 39 | 40 | 41 | 42 | 43 | 44 | 45 | 46 | 47 | 48 |
| 4 | H1H29104P | 49 | 50 | 51 | 52 | 53 | 54 | 55 | 56 | 57 | 58 | 59 | 60 | 61 | 62 | 63 | 64 |
| 5 | H1H29106P | 65 | 66 | 67 | 68 | 69 | 70 | 71 | 72 | 73 | 74 | 75 | 76 | 77 | 78 | 79 | 80 |
| 6 | H1H29109P | 81 | 82 | 83 | 84 | 85 | 86 | 87 | 88 | 89 | 90 | 91 | 92 | 93 | 94 | 95 | 96 |
| 7 | H1H29125P | 97 | 98 | 99 | 100 | 101 | 102 | 103 | 104 | 105 | 106 | 107 | 108 | 109 | 110 | 111 | 112 |
| 8 | H1H29127P | 113 | 114 | 115 | 116 | 117 | 118 | 119 | 120 | 121 | 122 | 123 | 124 | 125 | 126 | 127 | 128 |
| 9 | H1H29131P | 129 | 130 | 131 | 132 | 133 | 134 | 135 | 136 | 137 | 138 | 139 | 140 | 141 | 142 | 143 | 144 |
| 10 | H1H29134P | 145 | 146 | 147 | 148 | 149 | 150 | 151 | 152 | 153 | 154 | 155 | 156 | 157 | 158 | 159 | 160 |
| 11 | H1H29138P | 161 | 162 | 163 | 164 | 165 | 166 | 167 | 168 | 169 | 170 | 171 | 172 | 173 | 174 | 175 | 176 |
| 12 | H1H29141P | 177 | 178 | 179 | 180 | 181 | 182 | 183 | 184 | 185 | 186 | 187 | 188 | 189 | 190 | 191 | 192 |
| 13 | H1H29143P | 193 | 194 | 195 | 196 | 197 | 198 | 199 | 200 | 201 | 202 | 203 | 204 | 205 | 206 | 207 | 208 |
| 14 | H1H29146P2 | 209 | 210 | 211 | 212 | 213 | 214 | 215 | 216 | 217 | 218 | 219 | 220 | 221 | 222 | 223 | 224 |
| 15 | H1H29147P2 | 225 | 226 | 227 | 228 | 229 | 230 | 231 | 232 | 217 | 218 | 219 | 220 | 221 | 222 | 223 | 224 |
| 16 | H1H29149P2 | 233 | 234 | 235 | 236 | 237 | 238 | 239 | 240 | 217 | 218 | 219 | 220 | 221 | 222 | 223 | 224 |
| 17 | H1H29151P2 | 241 | 242 | 243 | 244 | 245 | 246 | 247 | 248 | 217 | 218 | 219 | 220 | 221 | 222 | 223 | 224 |
| 18 | H1H29163P2 | 249 | 250 | 251 | 252 | 253 | 254 | 255 | 256 | 217 | 218 | 219 | 220 | 221 | 222 | 223 | 224 |
| 19 | H1H29166P2 | 257 | 258 | 259 | 260 | 261 | 262 | 263 | 264 | 217 | 218 | 219 | 220 | 221 | 222 | 223 | 224 |
| 20 | H1H29171P2 | 265 | 266 | 267 | 268 | 269 | 270 | 271 | 272 | 217 | 218 | 219 | 220 | 221 | 222 | 223 | 224 |
| 21 | H1H29179P2 | 273 | 274 | 275 | 276 | 277 | 278 | 279 | 280 | 217 | 218 | 219 | 220 | 221 | 222 | 223 | 224 |
| 22 | H1H29183P2 | 281 | 282 | 283 | 284 | 285 | 286 | 287 | 288 | 217 | 218 | 219 | 220 | 221 | 222 | 223 | 224 |
| 23 | H1H29187P2 | 289 | 290 | 291 | 292 | 293 | 294 | 295 | 296 | 217 | 218 | 219 | 220 | 221 | 222 | 223 | 224 |
| 24 | H1H29192P2 | 297 | 298 | 299 | 300 | 301 | 302 | 303 | 304 | 305 | 306 | 307 | 308 | 309 | 310 | 311 | 312 |
| 25 | H1H29196P2 | 313 | 314 | 315 | 316 | 317 | 318 | 319 | 320 | 305 | 306 | 307 | 308 | 309 | 310 | 311 | 312 |
| 26 | H1H29198P2 | 321 | 322 | 323 | 324 | 325 | 326 | 327 | 328 | 305 | 306 | 307 | 308 | 309 | 310 | 311 | 312 |
| 27 | H1H29207P2 | 329 | 330 | 331 | 332 | 333 | 334 | 335 | 336 | 305 | 306 | 307 | 308 | 309 | 310 | 311 | 312 |
| 28 | H1H29214P2 | 337 | 338 | 339 | 340 | 341 | 342 | 343 | 344 | 305 | 306 | 307 | 308 | 309 | 310 | 311 | 312 |
| 29 | H1H29215P2 | 345 | 346 | 347 | 348 | 349 | 350 | 351 | 352 | 305 | 306 | 307 | 308 | 309 | 310 | 311 | 312 |
| 30 | H1H29209P2 | 353 | 354 | 355 | 356 | 357 | 358 | 359 | 360 | 305 | 306 | 307 | 308 | 309 | 310 | 311 | 312 |

*Numbers corresponding to $V_H$, CDR-H1, CDR-H2, CDR-H3, $V_L$, CDR-L1, CDR-L2 and CDR-L3 refer to SEQ ID NOs set forth herein.
"PEP" refers to an amino acid sequence; "DNA" refers to a nucleotide sequence.

The immunoglobulin sequences and their corresponding SEQ ID NOs which are summarized in Table 1-1 are set forth below. The sequences below are also in a Sequence Listing which is incorporated herein by reference.

SEQ ID NO: 1
GAGGTGCAGCTGGTGCAGTCTGGAGCAGAGGTGAAAAAGCCCGGGGAGTCTCTGAAGATCTCCTGTAAGGGTTCTGGATA
CAGCTTTACCAGTTACTGGATCGTCTGGGTGCGCCAGATGCCCGGGAAAGGCCTGGAGTGGATGGGGATCATCTATCCTG
GTGACTCTGATACCAGATACAGCCCGTCCTTCCAAGGCCAGGTCACCATCTCAGCCGACAAGTCCATCAGCACCGCCTAC
CTGCAGTGGAGCAGCCTGAAGGCCTCGGACACCGCCATGTATTACTGTGCGAGACAAGATATAACTGGAACTACGGGGTT
TGACTACTGGGGCCAGGGAACCCTGGTCACCGTCTCCTCA;

SEQ ID NO: 2
EVQLVQSGAEVKKPGESLKISCKGSGYSFTSYWIVWVRQMPGKGLEWMGIIYPGDSDTRYSPSFQGQVTISADKSISTAY
LQWSSLKASDTAMYYCARQDITGTTGFDYWGQGTLVTVSS;

SEQ ID NO: 3
GGA TAC AGC TTT ACC AGT TAC TGG;

SEQ ID NO: 4
G Y S F T S Y W;

SEQ ID NO: 5
ATC TAT CCT GGT GAC TCT GAT ACC;

SEQ ID NO: 6
I Y P G D S D T;

SEQ ID NO: 7
GCG AGA CAA GAT ATA ACT GGA ACT ACG GGG TTT GAC TAC;

SEQ ID NO: 8
A R Q D I T G T T G F D Y;

-continued

SEQ ID NO: 9
GACATCCAGATGACCCAGTCTCCATCCTCCCTGTCTGCATCTGTAGGAGACAGAGTCACCATCACTTGCCGGGCAAGTCA
GAGCATTAGGAACTATTTGAATTGGTATCAGCAGAAACCAGGGAAAGCCCCTAAGCTCCTGATCTATGCTGCATCCAGTT
TGCAAAGTGGGGTCCCATCAAGGTTCAGTGGCAGTGGATCTGGGACAGATTTCACTCTCACCATCAGCAGTCTGCAACCT
GAAGATTTTGCAACTTATTTCTGTCAACAGAGTTACAGTACCCCATTCACTTTCGGCCCTGGGACCAAAGTGGATATCAAACGA;

SEQ ID NO: 10
DIQMTQSPSSLSASVGDRVTITCRASQSIRNYLNWYQQKPGKAPKLLIYAASSLQSGVPSRFSGSGSGTDFTLTISSLQP
EDFATYFCQQSYSTPFTFGPGTKVDIKR;

SEQ ID NO: 11
CAG AGC ATT AGG AAC TAT;

SEQ ID NO: 12
Q S I R N Y;

SEQ ID NO: 13
GCT GCA TCC;

SEQ ID NO: 14
A A S;

SEQ ID NO: 15
CAA CAG AGT TAC AGT ACC CCA TTC ACT;

SEQ ID NO: 16
Q Q S Y S T P F T;

SEQ ID NO: 17
CAGGTGCAGCTGGTGGAGTCTGGGGGAGACGTGGTCCAGCCTGGGAGGTCCCTGCGACTCTCCTGTTCAGGCACTGGATT
CACCTTCAGTAGCTATGCCATGCACTGGGTCCGCCAGGCTCCAGGCAAGGGACTGGAATGGGTGGCACTTATATCATATG
ATGGAAGTAATAAATATTATGGAGACTCCGTGAAGGGCCGATTCACCGTCTCCAGAGACAATTCCAAGAACACGCTGTCT
CTGCAAATGAACAGCCTGAAAACTGAGGACACGGCGATATATTACTGTGCGAAAGAGAGGCTTTTTGGAGTGGTCTCTTA
TTACGGTATGGACGTCTGGGGCCAAGGGACCACGGTCACCGTCTCCTCA;

SEQ ID NO: 18
QVQLVESGGDVVQPGRSLRLSCSGTGFTFSSYAMHWVRQAPGKGLEWVALISYDGSNKYYGDSVKGRFTVSRDNSKNTLS
LQMNSLKTEDTAIYYCAKERLFGVVSYYGMDVWGQGTTVTVSS;

SEQ ID NO: 19
GGA TTC ACC TTC AGT AGC TAT GCC;

SEQ ID NO: 20
G F T F S S Y A;

SEQ ID NO: 21
ATA TCA TAT GAT GGA AGT AAT AAA;

SEQ ID NO: 22
I S Y D G S N K;

SEQ ID NO: 23
GCG AAA GAG AGG CTT TTT GGA GTG GTC TCT TAT TAC GGT ATG GAC GTC;

SEQ ID NO: 24
A K E R L F G V V S Y Y G M D V;

SEQ ID NO: 25
GACATCCAGATGACCCAGTCTCCATCCTCCCTGTCTGCATCTGTAGGAGACAGAGTCACCATCACTTGCCAGGCGAGTCA
GGACATTAATAGGGATCTAAATTGGTATCAGCAGAAATCAGGGAAAGGCCCCAAACTCCTGATCTACGATGCATCCAATT
TGGAAACAGGGGTCCCATCAAGGTTCAGTGGAAATAGATTTGGGACAGATTTTACTTTCACCATCAGCAGACTGCAGCCT
GAAGATATTGCAACATATTTCTGTCAACAGTATAAAAATCTCCCGTACACTTTTGGCCAGGGGACCAAGCTGGAGATCAAACGA;

SEQ ID NO: 26
DIQMTQSPSSLSASVGDRVTITCQASQDINRDLNWYQQKSGKGPKLLIYDASNLETGVPSRFSGNRFGTDFTFTISRLQP
EDIATYFCQQYKNLPYTFGQGTKLEIKR;

```
                                                           SEQ ID NO: 27
CAG GAC ATT AAT AGG GAT;

SEQ ID NO: 28
Q D I N R D;

SEQ ID NO: 29
GAT GCA TCC;

SEQ ID NO: 30
D A S;

SEQ ID NO: 31
CAA CAG TAT AAA AAT CTC CCG TAC ACT;

SEQ ID NO: 32
Q Q Y K N L P Y T;

SEQ ID NO: 33
CAGCTGCAGCTGCAGGAGTCGGGCCCAGGACTGGTGAAGCCTTCGGAGACCCTGTCCCTCACCTGCACTGTCTCTGGTGG

CTCCATCAGCAGTAGTAGTTACTACTGGGGCTGGATCCGCCAGCCCCCAGGGAAGGGCCTGGAGTGGATTGGGATTATCT

ATTATAGTGGGAGCACCTACTACAACCCGTCCCTCAAGAGTCGAGTCACCATTTCCGTAGACACGTCCAAGAACCAGTTC

TCCCTGAAGCTGAGCTCTGTGACCGCCGCAGACACGGCTGTGTATTACTGTGCGAGACAGGACAGGGAGGCCCTCTTTGA

CTACTGGGGCCAGGGAACCCTGGTCACCGTCTCCTCA;

SEQ ID NO: 34
QLQLQESGPGLVKPSETLSLTCTVSGGSISSSSYYWGWIRQPPGKGLEWIGIIYYSGSTYYNPSLK

SRVTISVDTSKNQFSLKLSSVTAADTAVYYCARQDREALFDYWGQGTLVTVSS;

SEQ ID NO: 35
GGT GGC TCC ATC AGC AGT AGT AGT TAC TAC;

SEQ ID NO: 36
G G S I S S S S Y Y;

SEQ ID NO: 37
ATC TAT TAT AGT GGG AGC ACC;

SEQ ID NO: 38
I Y Y S G S T;

SEQ ID NO: 39
GCG AGA CAG GAC AGG GAG GCC CTC TTT GAC TAC;

SEQ ID NO: 40
A R Q D R E A L F D Y;

SEQ ID NO: 41
GAAATTGTGCTGACTCAGTCTCCAGACTTTCAGTCTGTGACTCCAAAGGAGAAAGTCACCATCACCTGCCGGGCCAGTCA

GCGCATTGGTAGTAGCTTACACTGGTACCAGCAGAAACCAGATCAGTCTCCAAAGCTCCTCATCAAGTATGCTTCCCAGT

CCTTCTCAGGGGTCCCCTCGAGGTTCAGTGGCAGTGGATCTGGGACAGATTTCACCCTCACCATCAATAGCCTGGAAGCT

GAAGATGCTGCAACGTATTACTGTCATCAGAGTAGTACTTTACCCACCTTCGGCCAAGGGACACGACTGGAGATTAAACGA;

SEQ ID NO: 42
EIVLTQSPDFQSVTPKEKVTITCRASQRIGSSLHWYQQKPDQSPKLLIKYASQSFSGVPSRFSGSGSGTDFTLTINSLEA

EDAATYYCHQSSTLPTFGQGTRLEIKR;

SEQ ID NO: 43
CAG CGC ATT GGT AGT AGC;

SEQ ID NO: 44
Q R I G S S;

SEQ ID NO: 45
TAT GCT TCC;

SEQ ID NO: 46
Y A S;
```

```
                                                                    SEQ ID NO: 47
CAT CAG AGT AGT ACT TTA CCC ACC;

SEQ ID NO: 48
H Q S S T L P T;

SEQ ID NO: 49
GAAGTGCAGCTGGTGGAGTCTGGGGGAGGCCTGGTACAGCCTGGCAGGTCCCTGAGACTCTCCTGTGCAGCCTCTGGATT

CAGGTTTGACGATTATGCCATGCACTGGGTCCGACAAGCTCCAGGGAAGGGCCTGGAATGGGTCTCAGGTATTAATTGGA

ATAGTGGTGGCAAAGGCTATGCGGACTCTGTGCAGGGCCGATTCACCATCTCCAGAGACAACGCCAAGAACTCCCTTTAT

CTGCAAATGAACAGTCTGAGAACTGAGGACACGGCCTTGTATTATTGTGCAAAAGATAGGGGTATAGCAGCTCGTCTTCT

CTCTCGTGATGCTTTTGATATGTGGGGCCAAGGGACAATGGTCACCGTCTCTTCA;

SEQ ID NO: 50
EVQLVESGGGLVQPGRSLRLSCAASGFRFDDYAMHWVRQAPGKGLEWVSGINWNSGGKGYADSVQGRFTISRDNAKNSLY

LQMNSLRTEDTALYYCAKDRGIAARLLSRDAFDMWGQGTMVTVSS;

SEQ ID NO: 51
GGA TTC AGG TTT GAC GAT TAT GCC;

SEQ ID NO: 52
G F R F D D Y A;

SEQ ID NO: 53
ATT AAT TGG AAT AGT GGT GGC AAA;

SEQ ID NO: 54
I N W N S G G K;

SEQ ID NO: 55
GCA AAA GAT AGG GGT ATA GCA GCT CGT CTT CTC TCT CGT GAT GCT TTT GAT ATG;

SEQ ID NO: 56
A K D R G I A A R L L S R D A F D M;

SEQ ID NO: 57
GACATCCAGTTGACCCAGTCTCCATCCTTCCTGTCTGCATCTGTAGGAGACAGAGTCACCATCACTTGCTGGGCCAGTCA

GGACGTTAGCAGTTATTTAGCCTGGTATCAGCAAAAACCAGGGAAATCCCCTAAGCTCCTAATCTTTGCTGCATCCACTT

TGCAAGGTGGGATCCCATCAAGGTTCAGCGGCAGTGGATCTGGGACAGAATTCACTCTCACAATCAGCAGCCTGCGGCCT

GAAGATTTTGCAACTTATTACTGTCAACACCTTAATACTTACCCGTACACTTTTGGCCAGGGGACCAAGCTGGAGATCAAACGA;

SEQ ID NO: 58
DIQLTQSPSFLSASVGDRVTITCWASQDVSSYLAWYQQKPGKSPKLLIFAASTLQGGIPSRFSGSGSGTEFTLTISSLRP

EDFATYYCQHLNTYPYTFGQGTKLEIKR;

SEQ ID NO: 59
CAG GAC GTT AGC AGT TAT;

SEQ ID NO: 60
Q D V S S Y;

SEQ ID NO: 61
GCT GCA TCC;

SEQ ID NO: 62
A A S;

SEQ ID NO: 63
CAA CAC CTT AAT ACT TAC CCG TAC ACT;

SEQ ID NO: 64
Q H L N T Y P Y T;

SEQ ID NO: 65
CAGGTGCAGCTGGTGGAGTCTGGGGGAGGCGTGGTCCAGTCTGGGAGGTCCCTGAGACTCTCCTGTGCAGCGTCTTCATT

CACCTTCAGTAGCTATGGCATGCACTGGGTCCGCCAGTCTCCAGGCAAGGGGCTGGAGTGGGTGGCAGTTATAAGTTATG

ATGGAAGTAATAAATACTATGGAGACTTCGTGAGGGGCCGATTCACCATCTCCAGAGACAATTCCAAGAACACGCTGTAT
```

-continued

CTGCAAATGAACAGCCTGAGAGCCGAGGACACGGCTATGTATTATTGTGCGAGAGAAGTTCGTCGCTACTATTATTACGG

TATGGACGTCTGGGGCCAAGGGACCACGGTCACCGTCTCCTCA;

SEQ ID NO: 66

QVQLVESGGGVVQSGRSLRLSCAASSFTFSSYGMHWVRQSPGKGLEWVAVISYDGSNKYYGDFVRGRFTISRDNSKNTLY

LQMNSLRAEDTAMYYCAREVRRYYYYGMDVWGQGTTVTVSS;

SEQ ID NO: 67

TCA TTC ACC TTC AGT AGC TAT GGC;

SEQ ID NO: 68

S F T F S S Y G;

SEQ ID NO: 69

ATA AGT TAT GAT GGA AGT AAT AAA;

SEQ ID NO: 70

I S Y D G S N K;

SEQ ID NO: 71

GCG AGA GAA GTT CGT CGC TAC TAT TAT TAC GGT ATG GAC GTC;

SEQ ID NO: 72

A R E V R R Y Y Y Y G M D V;

SEQ ID NO: 73

GACATCCAGATGACCCAGTCTCCATCCTCCCTGTCTGCATCTGTAGGAGACAGAGTCACCATCACTTGCCAGGCGAGTCA

GGACATTAGTAATTATTTAAATTGGTATCTGCAGAAACCAGGGAAAGCCCCTAAGCTCCTGATCTCCGATGCATCCAATT

TGGAAACAGGGGTCCCATCAAGGTTCAGTGGAAGTGGATCTGGGACAGATTTTACTTTCACCATCAGCAGCCTGCAGCCT

GAAGATATTGCAACATATTACTGTCAACAGTATAATAATCTCCCGCTCACTTTCGGCGGAGGGACCAAGGTGGAGATCAAACGA;

SEQ ID NO: 74

DIQMTQSPSSLSASVGDRVTITCQASQDISNYLNWYLQKPGKAPKLLISDASNLETGVPSRFSGSGSGTDFTFTISSLQP

EDIATYYCQQYNNLPLTFGGGTKVEIKR;

SEQ ID NO: 75

CAG GAC ATT AGT AAT TAT;

SEQ ID NO: 76

Q D I S N Y;

SEQ ID NO: 77

GAT GCA TCC;

SEQ ID NO: 78

D A S;

SEQ ID NO: 79

CAA CAG TAT AAT AAT CTC CCG CTC ACT;

SEQ ID NO: 80

Q Q Y N N L P L T;

SEQ ID NO: 81

GAAGTGCAGCTGGTGGAGTCTGGGGGAGGCTTGGTACAGCCTGGCAGGTCCCTGAGACTCTCCTGTGCAGTCTCTGGATT

CACCTTTGATGATTATGCCATGCACTGGGTCCGGCAAGCTCCAGGGAAGGGCCTGGAGTGGGTCTCAGGTATTAGTTGGA

ATAGTGGTGACATAGACTATGCGGACTCTGTGAAGGGCCGATTCACCATTTCCAGAGACAACGCCAAGAACTCCCTGTAT

CTGCAAATGAACAGTCTGAGAGCTGAGGACACGGCCTTGTATTACTGTGCAAAAGATACCCTCTCAGGGACTGGAACTAC

GTGGTACTATTTTGACTACTGGGGCCAGGGAACCCTGGTCACCGTCTCCTCA;

SEQ ID NO: 82

EVQLVESGGGLVQPGRSLRLSCAVSGFTFDDYAMHWVRQAPGKGLEWVSGISWNSGDIDYADSVKGRFTISRDNAKNSLY

LQMNSLRAEDTALYYCAKDTLSGTGTTWYYFDYWGQGTLVTVSS;

SEQ ID NO: 83

GGA TTC ACC TTT GAT GAT TAT GCC;

SEQ ID NO: 84

G F T F D D Y A;

```
                                                            SEQ ID NO: 85
ATT AGT TGG AAT AGT GGT GAC ATA;

SEQ ID NO: 86
I S W N S G D I;

SEQ ID NO: 87
GCA AAA GAT ACC CTC TCA GGG ACT GGA ACT ACG TGG TAC TAT TTT GAC TAC;

SEQ ID NO: 88
A K D T L S G T G T T W Y Y F D Y;

SEQ ID NO: 89
GACATCCAGTTGACCCAGTCTCCATCCTTCCTGTCTGCATCTGTAGGAGACAGAGTCACCATCACTTGCTGGGCCAGTCA
GGGTATTAGCAGTTATTTAATCTGGTATCAGCAAAAACCAGGGAAAGCCCCTAAGCTCCTGATCTATGCTGCATCCACTT
TGCAAAGTGGGGTCCCATCAAGGTTCAGCGGCAGTGGATCTGGGACAGAATTCACTCTCACAATCAGCAGCCTGCAGCCT
GAAGATTTTGCAACTTATTACTGTCAACAGGTGAATAGTTACCCTCTCACTTTCGGCGGAGGGACCAAGGTGGAGATCAAACGA;

SEQ ID NO: 90
DIQLTQSPSFLSASVGDRVTITCWASQGISSYLIWYQQKPGKAPKLLIYAASTLQSGVPSRFSGSGSGTEFTLTISSLQP
EDFATYYCQQVNSYPLTFGGGTKVEIKR;

SEQ ID NO: 91
CAG GGT ATT AGC AGT TAT;

SEQ ID NO: 92
Q G I S S Y;

SEQ ID NO: 93
GCT GCA TCC;

SEQ ID NO: 94
A A S;

SEQ ID NO: 95
CAA CAG GTG AAT AGT TAC CCT CTC ACT;

SEQ ID NO: 96
Q Q V N S Y P L T;

SEQ ID NO: 97
CAGGTGCAGCTGGTGGAGTCTGGGGGAGGCGTGGTCCAGCCTGGGAGGTCCCTGAGACTCTCCTGTGCAGCCTCTGGATT
CACCTTCAGTAGTTATGGCATGCACTGGGTCCGCCAGGCTCCAGGCAAGGGACTGGAGTGGATGGCAGTTATATCATATG
ATGGAAGTAATAAATATTATGCAGACTCCGTGAAGGGCCGATTCACCATCTCCAGAGACAATTCCAAGAACACGCTGTTT
CTGCAAATGAACAGCCTGAGACCTGAAGACACGGCTGTATATTACTGTGCGCAAGATGGCAGCTCGGCGATTTACTATTT
CTACGGTATGGACGTCTGGGGCCAAGGGACCACGGTCACCGTCTCCTCA;

SEQ ID NO: 98
QVQLVESGGGVVQPGRSLRLSCAASGFTFSSYGMHWVRQAPGKGLEWMAVISYDGSNKYYADSVKGRFTISRDNSKNTLF
LQMNSLRPEDTAVYYCAQDGSSAIYYFYGMDVWGQGTTVTVSS;

SEQ ID NO: 99
GGA TTC ACC TTC AGT AGT TAT GGC;

SEQ ID NO: 100
G F T F S S Y G;

SEQ ID NO: 101
ATA TCA TAT GAT GGA AGT AAT AAA;

SEQ ID NO: 102
I S Y D G S N K;

SEQ ID NO: 103
GCG CAA GAT GGC AGC TCG GCG ATT TAC TAT TTC TAC GGT ATG GAC GTC;

SEQ ID NO: 104
A Q D G S S A I Y Y F Y G M D V;
```

SEQ ID NO: 105
GACATCCAGATGACCCAGTCTCCATCCTCACTGTCTGCATCTATAGGAGACAGAGTCACCATCACTTGTCGGGCGAGTCAGGACATCAACAATTATTTAGCCTGGTTTCAGCAGAAACCAGGGAAAGCCCCTAAGTCCCTGATCTATGCTGCATCCAGTTTGCAAAGTGGGGTCCCATCAAAGTTCAGCGGCAGTGGATCTGGGACAGATTTCACTCTCACCATCAGCAGCCTGCAGCCTGAAGATTTTGCAACTTATTACTGCCTTCAGTATAATAGTTACCATCCCACTTTTGGCCAGGGGACCAAGCTGGAGATCAAACGA;

SEQ ID NO: 106
DIQMTQSPSSLSASIGDRVTITCRASQDINNYLAWFQQKPGKAPKSLIYAASSLQSGVPSKFSGSGSGTDFTLTISSLQPEDFATYYCLQYNSYHPTFGQGTKLEIKR;

SEQ ID NO: 107
CAG GAC ATC AAC AAT TAT;

SEQ ID NO: 108
Q D I N N Y;

SEQ ID NO: 109
GCT GCA TCC;

SEQ ID NO: 110
A A S;

SEQ ID NO: 111
CTT CAG TAT AAT AGT TAC CAT CCC ACT;

SEQ ID NO: 112
L Q Y N S Y H P T;

SEQ ID NO: 113
CAGGTGCAGCTGGTGGAGTCTGGGGGAGGCGTGGTCCAGCCTGGGAGGTCCCTGAGACTCTCCTGTGCAGCGTCGGATTCACCTTCAGTAGCTATGGCATGCACTGGGTCCGCCAGGCTCCAGGCAAGGGGCTGGAGTGGGTGGCAGCTATATGGTATGATGGAAGTAATAAATATTATGCAGACTCCGTGAAGGGCCGATTCACCATCTCCAGAGACAATTCCAAGAACACGCTGTATCTGCAAATGAACAGCCTGAGAGCCGAGGACACGGCTGTGTATTTCTGTGCGAGAGGGGAACATTACTATGGTTCGGGGCCGTTCGACCCCTGGGGCCAGGGAACCCTGGTCACCGTCTCCTCA;

SEQ ID NO: 114
QVQLVESGGGVVQPGRSLRLSCAASGFTFSSYGMHWVRQAPGKGLEWVAAIWYDGSNKYYADSVKGRFTISRDNSKNTLYLQMNSLRAEDTAVYFCARGEHYYGSGPFDPWGQGTLVTVSS;

SEQ ID NO: 115
GGA TTC ACC TTC AGT AGC TAT GGC;

SEQ ID NO: 116
G F T F S S Y G;

SEQ ID NO: 117
ATA TGG TAT GAT GGA AGT AAT AAA;

SEQ ID NO: 118
I W Y D G S N K;

SEQ ID NO: 119
GCG AGA GGG GAA CAT TAC TAT GGT TCG GGG CCG TTC GAC CCC;

SEQ ID NO: 120
A R G E H Y Y G S G P F D P;

SEQ ID NO: 121
GACATCCAGATGACCCAGTCTCCATCCTCCCTGTCTGCATCTGTAGGAGACAGAGTCACCATCACTTGCCGGGCAAGTCAGAGCATTAGCAACTATTTAAATTGGTATCAGCAGAAACCAGGGAAAGCCCCTAAGCTCCTGATCTTTGCTGCATCCAGTTTACAAAGTGGGGTCCCATCAAGGTTCAGTGGCAGTGGATCTGGGACAGATTTCACTCTCACCATCAGCAGTCTGCAACCTGAAGATTTTGCAACTTACTACTGTCAACAGAGTTACAGTTCCCCGCTCACTTTCGGCGGAGGGACCAAGGTGGAGATCAAACGA;

```
                                                                SEQ ID NO: 122
DIQMTQSPSSLSASVGDRVTITCRASQSISNYLNWYQQKPGKAPKLLIFAASSLQSGVPSRFSGSG

SGTDFTLTISSLQPEDFATYYCQQSYSSPLTFGGGTKVEIKR;

SEQ ID NO: 123
CAG AGC ATT AGC AAC TAT;

SEQ ID NO: 124
Q S I S N Y;

SEQ ID NO: 125
GCT GCA TCC;

SEQ ID NO: 126
A A S;

SEQ ID NO: 127
CAA CAG AGT TAC AGT TCC CCG CTC ACT;

SEQ ID NO: 128
Q Q S Y S S P L T;

SEQ ID NO: 129
CAGGTGCAGCTGCAGGAGTCGGGGCCAGGACTGGTGAAGCCTTCACAGACCCTGTCCCTCACCTGCACTGTCTCAGGTGG

CTCCATCAGCAGTTTTGGTTACTACTGGAGCTGGATCCGCCAGCACCCAGGGAAGGGCCTGGAGTGGATTGGGTACATCT

ATTACAGTGGGAGCATCGACTACAACCCGTCCCTCAAGAGTCGAATTACCATATCAGTCGACACGTCTAAGAACCAGTTC

TCCCTGAAGCTGAGCTCTGTGACTGCCGCGGACACGGCCGTGTATTACTGTGCGAGAGAAAGGGACTACGGTGACTACTT

TGACTACTGGGGCCAGGGAACCCTGGTCACCGTCTCCTCA;

SEQ ID NO: 130
QVQLQESGPGLVKPSQTLSLTCTVSGGSISSFGYYWSWIRQHPGKGLEWIGYIYYSGSIDYNPSL

KSRITISVDTSKNQFSLKLSSVTAADTAVYYCARERDYGDYFDYWGQGTLVTVSS;

SEQ ID NO: 131
GGT GGC TCC ATC AGC AGT TTT GGT TAC TAC;

SEQ ID NO: 132
G G S I S S F G Y Y;

SEQ ID NO: 133
ATC TAT TAC AGT GGG AGC ATC;

SEQ ID NO: 134
I Y Y S G S I;

SEQ ID NO: 135
GCG AGA GAA AGG GAC TAC GGT GAC TAC TTT GAC TAC;

SEQ ID NO: 136
A R E R D Y G D Y F D Y;

SEQ ID NO: 137
GAAATAGTGATGACGCAGTCTCCAGCCACCCTGTCTGTCTCTCCAGGGGAAAGAGCCACCCTCTCCTGCAGGGCCAGTCA

GAGTGTTAGCAGCAACTTAGCCTGGTACCAGCAGAAACCTGGCCAGGCTCCCAGGCTCCTCATCTATGGTGCATCCACCA

GGGCCACTGGTGTCCCAGCCAGGTTCAGTGGCAGTGGGTCTGGGACAGAGTTCACTCTCACCATCAGCAGTTTGCAGTCT

GAGGATTTTGCAGTTTATTCCTGTCAGCAGTATAATAACTGGCCTCTCACTTTCGGCGGAGGGACCAAGGTGGAGATCAA

ACGA;

SEQ ID NO: 138
EIVMTQSPATLSVSPGERATLSCRASQSVSSNLAWYQQKPGQAPRLLIYGASTRATGVPARFSGS

GSGTEFTLTISSLQSEDFAVYSCQQYNNWPLTFGGGTKVEIKR;

SEQ ID NO: 139
CAG AGT GTT AGC AGC AAO;

SEQ ID NO: 140
Q S V S S N;
```

```
                                                          SEQ ID NO: 141
GGT GCA TCC;

SEQ ID NO: 142
G A S;

SEQ ID NO: 143
CAG CAG TAT AAT AAC TGG CCT CTC ACT;

SEQ ID NO: 144
Q Q Y N N W P L T;

SEQ ID NO: 145
CAGGTGCAGCTGGTGGAGTCTGGGGGAGGCGTGGTCCAGCCTGGGAGGTCCCTGAGACTCTCCTGTGCAGCGTCTGGATT

CACCTTCAGTAGCTATGGCATACACTGGGTCCGCCAGGCTCCAGGCAAGGGGCTGGAGTGGGTGGCACTTATATGGTATG

ATGGAAGTAATAAATACTATGCAGACTCCGTGAAGGGCCGATTCACCATCTCCAGAGACAATTCCAAGAACACGCTGTAT

CTGCAAATGAACAGCCTGAGAGCCGAGGACACGGCTGTGTATTACTGTGCGAGAGATCAGGATTACTATGGTTCGGGGAG

TTCCTACGGTATGGACGTCTGGGGCCAAGGGACCACGGTCACCGTCTCCTCA;

SEQ ID NO: 146
QVQLVESGGGVVQPGRSLRLSCAASGFTFSSYGIHWVRQAPGKGLEWVALIWYDGSNKYYADSVKGRFTISRDNSKNTLY

LQMNSLRAEDTAVYYCARDQDYYGSGSSYGMDVWGQGTTVTVSS;

SEQ ID NO: 147
GGA TTC ACC TTC AGT AGC TAT GGC;

SEQ ID NO: 148
G F T F S S Y G;

SEQ ID NO: 149
ATA TGG TAT GAT GGA AGT AAT AAA;

SEQ ID NO: 150
I W Y D G S N K;

SEQ ID NO: 151
GCG AGA GAT CAG GAT TAC TAT GGT TCG GGG AGT TCC TAC GGT ATG GAC GTC;

SEQ ID NO: 152
A R D Q D Y Y G S G S S Y G M D V;

SEQ ID NO: 153
GACATCCAGATGACCCAGTCGCCAGCCTCCCTGTCTGCATCTGTAGGAGACAGAGTCACCATCACTTGCCGGGCAAGTCA

GAGCATTAGCAGCTATTTAAATTGGTATCAGCAGAAACCAGGGAAAGCCCCTAAGCGCCTGATCTATGCTGCATCCAGTT

TGCAAAGTGGGGTCCCATCAAGGTTCAGTGGCAGTGGATCTGGGACAGATTTCACTCTCACCATCAGCAGTCTGCAACCT

GAAGATTTTGCAACTTACTACTGTCAACAGAGTTACAGTACCCCTCTCACTTTTGGCCAGGGGACCAAGCTGGAGATCAA

ACGA;

SEQ ID NO: 154
DIQMTQSPASLSASVGDRVTITCRASQSISSYLNWYQQKPGKAPKRLIYAASSLQSGVPSRFSGS

GSGTDFTLTISSLQPEDFATYYCQQSYSTPLTFGQGTKLEIKR;

SEQ ID NO: 155
CAG AGC ATT AGC AGC TAT;

SEQ ID NO: 156
Q S I S S Y;

SEQ ID NO: 157
GCT GCA TCC;

SEQ ID NO: 158
A A S;

SEQ ID NO: 159
CAA CAG AGT TAC AGT ACC CCT CTC ACT;

SEQ ID NO: 160
Q Q S Y S T P L T;
```

SEQ ID NO: 161
CAGGTGCAGCTGGTGGAGTCTGGGGGAGGCGTGGTCCAGCCTGGGAGGTCCCTGAGACTCTCCTGTGCAGCGTCTGGATT

CACCTTCAGTACCTATGGCATGCACTGGGTCCGCCAGGCTCCAGGCAAGGGGCTGGAGTGGGTGGCAGTTATATGGTATG

ATGGAACTAATAAATACTATGCAGACTCCGTGAAGGGCCGATTCACCATCTCCAGAGACAATTCCAAGAACACGCTGTAT

CTGCAAATGATCAGCCTGAGAGCCGAGGACACGGCTGTGTATTACTGTGCGAGAGACCCCTCAGGTGGGGACCACTACTA

TTACTACGGTATGGACGTCTGGGGCCAAGGGACCACGGTCACCGTCTCCTCA;

SEQ ID NO: 162
QVQLVESGGGVVQPGRSLRLSCAASGFTFSTYGMHWVRQAPGKGLEWVAVIWYDGTNKYYADSVKGRFTISRDNSKNTLY

LQMISLRAEDTAVYYCARDPSGGDHYYYYGMDVWGQGTTVTVSS;

SEQ ID NO: 163
GGA TTC ACC TTC AGT ACC TAT GGC;

SEQ ID NO: 164
G F T F S T Y G;

SEQ ID NO: 165
ATA TGG TAT GAT GGA ACT AAT AAA;

SEQ ID NO: 166
I W Y D G T N K;

SEQ ID NO: 167
GCG AGA GAC CCC TCA GGT GGG GAC CAC TAC TAT TAC TAC GGT ATG GAC GTC;

SEQ ID NO: 168
A R D P S G G D H Y Y Y Y G M D V;

SEQ ID NO: 169
GACATCCAGATGACCCAGTCTCCATCCTCCCTGTCTGCATCTGTAGGAGACAGAATCACCATCACTTGCCAGGCGAGTCA

GGACATTAGCAACTATTTAAATTGGTATCAGCAGAAGCCAGGGAAAGCCCCTAACCTCCTGATCTCCGATGCATCCGATT

TGGAAACAGGGGTCCCATCAAGGTTCAGTGGAAGTGGATCTGGGACAGATTTTACTTTCACCATCAGCAGCCTGCAGCCT

GAAGATTTTGCAACATATTACTGTCAACAGTATGATAATATACCGATCACCTTCGGCCAAGGGACACGACTGGAGATTAA

ACGA;

SEQ ID NO: 170
DIQMTQSPSSLSASVGDRITITCQASQDISNYLNWYQQKPGKAPNLLISDASDLETGVPSRFSGSG

SGTDFTFTISSLQPEDFATYYCQQYDNIPITFGQGTRLEIKR;

SEQ ID NO: 171
CAG GAC ATT AGC AAC TAT;

SEQ ID NO: 172
Q D I S N Y;

SEQ ID NO: 173
GAT GCA TCC;

SEQ ID NO: 174
D A S;

SEQ ID NO: 175
CAA CAG TAT GAT AAT ATA CCG ATC ACC;

SEQ ID NO: 176
Q Q Y D N I P I T;

SEQ ID NO: 177
CAGGTGCAGCTGGTGGAGTCAGGGGGAGGCGTGGTCCAGCCTGGGAGGTCCCTGAGACTCTCCTGTGCAGCCTCTGGATT

CACCTTCAGTAGCTATGGCATGCACTGGGTCCGCCAGGCTCCAGGCAAGGGGCTGGAGTGGGTGACATTTATATCATTTG

ATGAAAGGAATAAATACTATGCAGACTCCGTTAAGGGCCGATTCACCATCTCCAGAGACAATTCCAAGAACACGCTGTAT

CTGCAAATGAACAGCCTGAGAGCTGAGGACACGGCTATGTATTACTGTGCGAGCGAAGTCGGGTACAGTTTTGGTCATGA

TGCTTTTGATATCTGGGGCCAAGGGACAATGGTCACCGTCTCTTCA;

SEQ ID NO: 178
QVQLVESGGGVVQPGRSLRLSCAASGFTFSSYGMHWVRQAPGKGLEWVTFISFDERNKYYADSVKGRFTISRDNSKNTLYLQMNSLRAEDTAMYYCASEVGYSFGHDAFDIWGQGTMVTVSS;

SEQ ID NO: 179
GGA TTC ACC TTC AGT AGC TAT GGC;

SEQ ID NO: 180
G F T F S S Y G;

SEQ ID NO: 181
ATA TCA TTT GAT GAA AGG AAT AAA;

SEQ ID NO: 182
I S F D E R N K;

SEQ ID NO: 183
GCG AGC GAA GTC GGG TAC AGT TTT GGT CAT GAT GCT TTT GAT ATC;

SEQ ID NO: 184
A S E V G Y S F G H D A F D I;

SEQ ID NO: 185
GACATCCAGATGACCCAGTCTCCATCCTCCCTGTCTGCATCTGTAGGAGACAGAGTCACCATCACTTGCCAGGCGAGTCAGGACATTAGCAACTATTTAAATTGGTATCAGAAGAAACCAGGGAAAGCCCCTAAACTCCTGATCTACGATGCATCCAATTTGGAAACAGGGGTCCCGTCAAGGTTCAGTGGAAGTGGATCTGGGACAGATTTTACTTTCACCATCAGCAGCCTGCAGCCTGAAGATATTGCAACATATTACTGTCAACAGTATGATAATTTCCCGCTCACTTTCGGCGGAGGGACCAAGGTGGAGATCAAACGA;

SEQ ID NO: 186
DIQMTQSPSSLSASVGDRVTITCQASQDISNYLNWYQKKPGKAPKLLIYDASNLETGVPSRFSGSGSGTDFTFTISSLQPEDIATYYCQQYDNFPLTFGGGTKVEIKR;

SEQ ID NO: 187
CAG GAC ATT AGC AAC TAT;

SEQ ID NO: 188
Q D I S N Y;

SEQ ID NO: 189
GAT GCA TCC;

SEQ ID NO: 190
D A S;

SEQ ID NO: 191
CAA CAG TAT GAT AAT TTC CCG CTC ACT;

SEQ ID NO: 192
Q Q Y D N F P L T;

SEQ ID NO: 193
GAGGTGCAGCTGGTGGAGTCTGGGGGAGGCTTGGTACAGCCTGGGGGGTCCCTGAGACTCTCCTGTGCAGCCTCTGGATTCACCTTTAACAACTATGCCATGAGCTGGGTCCGCCAGGCTCCAGGGAGGGGGCTGGAGTGGGTCTCAGCTATTAGTGGTAGTGGTGATAGCACATACTACTCAGACTCCGTGAAGGGCCGGTTCACCATCTCCAGAGACAATTCCAAGAACACGCTGTATCTGCAAATGAACAGCCTGAGAGCCGAGGACACGGCCGTATATTACTGTGCGAAAGATCAGGGCCTGTATTACTATGGTTCGGGGAGTTTTGACTACTGGGGCCAGGGAACCCTGGTCACCGTCTCCTCA;

SEQ ID NO: 194
EVQLVESGGGLVQPGGSLRLSCAASGFTFNNYAMSWVRQAPGRGLEWVSAISGSGDSTYYSDSVKGRFTISRDNSKNTLYLQMNSLRAEDTAVYYCAKDQGLYYYGSGSFDYWGQGTLVTVSS;

SEQ ID NO: 195
GGA TTC ACC TTT AAC AAC TAT GCC;

SEQ ID NO: 196
G F T F N N Y A;

-continued

```
                                                            SEQ ID NO: 197
ATT AGT GGT AGT GGT GAT AGC ACA;

SEQ ID NO: 198
I S G S G D S T;

SEQ ID NO: 199
GCG AAA GAT CAG GGC CTG TAT TAC TAT GGT TCG GGG AGT TTT GAC TAC;

SEQ ID NO: 200
A K D Q G L Y Y Y G S G S F D Y;

SEQ ID NO: 201
GACATCCAGATGACCCAGTCTCCATCCTCCCTGTCTGCATCTGTAGGAGACAGAGTCACCATCACTTGCCGGGCAAGTCA

GAGCATTAGCAGCTATTTAAATTGGTATCAGCAGAAACCAGGGAAAGCCCCTAAGCTCCTGATCCAAGCTGCATCCAGTT

TGCAAAGTGGGGTCCCATCAAGGTTCAGTGGCAGTGGATCTGGGACAGATATCACTCTCACCATCAGCAGTCTGCAACCC

GAAGATTTTGCAACTTACTACTGTCAACAGAGTTACAGTACCCCATTCACTTTCGGCCCTGGGACCAAAGTGGATATCAA

ACGA;

SEQ ID NO: 202
DIQMTQSPSSLSASVGDRVTITCRASQSISSYLNWYQQKPGKAPKLLIQAASSLQSGVPSRFSGSGSGTDITLTISSLQP

EDFATYYCQQSYSTPFTFGPGTKVDIKR;

SEQ ID NO: 203
CAG AGC ATT AGC AGC TAT;

SEQ ID NO: 204
Q S I S S Y;

SEQ ID NO: 205
GCT GCA TCC;

SEQ ID NO: 206
A A S;

SEQ ID NO: 207
CAA CAG AGT TAC AGT ACC CCA TTC ACT;

SEQ ID NO: 208
Q Q S Y S T P F T;

SEQ ID NO: 209
GAGGTGCAGCTGGTGGAGTCTGGGGGAGGCTTGGTCCAGCCTGGGGGGTCCCTGCAACTCTCCTGTGCAGCCTCTGGGTT

TGCCTTCAGCGACTCTGCTATATACTGGGTCCGCCAGGCTTCCGGGAAAGGGCTGGAGTGGGTTGGCCGCATTAGAAACA

AAGCTAATAGGTTCGCGACAGCATATGGTGCGTCGGTGAAAGGCAGGTTCAGCATACACAGAGATGATTCAAAGAACACG

GCGTATCTACAAATGAACAGCCTGAAAACCGAGGACACGGCCGTGTATTACTGTGCCAGACATGGACACGATACTTTGAC

TGAGGGCTACGGTATGGACGTCTGGGGCCAAGGGACCACGGTCACCGTCTCCTCA;

SEQ ID NO: 210
EVQLVESGGGLVQPGGSLQLSCAASGFAFSDSAIYWVRQASGKGLEWVGRIRNKANRFATAYGA

SVKGRFSIHRDDSKNTAYLQMNSLKTEDTAVYYCARHGHDTLTEGYGMDVWGQGTTVTVSS;

SEQ ID NO: 211
GGG TTT GCC TTC AGC GAC TCT GCT;

SEQ ID NO: 212
G F A F S D S A;

SEQ ID NO: 213
ATT AGA AAC AAA GCT AAT AGG TTC GCG ACA;

SEQ ID NO: 214
I R N K A N R F A T;

SEQ ID NO: 215
GCC AGA CAT GGA CAC GAT ACT TTG ACT GAG GGC TAC GGT ATG GAC GTC;

SEQ ID NO: 216
A R H G H D T L T E G Y G M D V;
```

Light chain #1
SEQ ID NO: 217
GACATCCAGATGACCCAGTCTCCATCCTCCCTGTCTGCATCTGTAGGAGACAGAGTCACCATCACTTGCCGGGCAAGTCA

GAGCATTAGCAGCTATTTAAATTGGTATCAGCAGAAACCAGGGAAAGCCCCTAAGCTCCTGATCTATGCTGCATCCAGTT

TGCAAAGTGGGGTCCCGTCAAGGTTCAGTGGCAGTGGATCTGGGACAGATTTCACTCTCACCATCAGCAGTCTGCAACCT

GAAGATTTTGCAACTTACTACTGTCAACAGAGTTACAGTACCCCTCCGATCACCTTCGGCCAAGGGACACGACTGGAGAT

TAAA;

Light chain #1
SEQ ID NO: 218
DIQMTQSPSSLSASVGDRVTITCRASQSISSYLNWYQQKPGKAPKLLIYAASSLQSGVPSRFSGSG

SGTDFTLTISSLQPEDFATYYCQQSYSTPPITFGQGTRLEIK;

SEQ ID NO: 219
CAG AGC ATT AGC AGC TAT;

SEQ ID NO: 220
Q S I S S Y;

SEQ ID NO: 221
GCT GCA TCC;

SEQ ID NO: 222
A A S;

SEQ ID NO: 223
CAA CAG AGT TAC AGT ACC CCT CCG ATC ACC;

SEQ ID NO: 224
Q Q S Y S T P P I T;

SEQ ID NO: 225
CAGGTGCAGCTGGTGCAGTCTGGGGCTGAGGTAAAGAACCCTGGGTCCTCGGTGAAGGTCTCCTGCAAGGCTTCTGGAGG

CACCTTCAGCAGTTATACTATCAACTGGGTGCGACAGGCCCCTGGACAAGGGCTTGAGTGGATGGGAGGGATCATCCCTC

TCTATGGAACAGCAAACTACGCACAGAAGTTCCAGGCCAGAGTCACGATTTCCACGGACGAATCCACGAACACAGCCTAC

ATGGAACTGAGCAACCTGAGATTTGAAGACACGGCCGTGTATTTCTGTGCGAGTACACTGGAACTACGGGCTTTTGATGC

CTTTGATATCTGGGGCCAAGGGACAATGGTCACCGTCTCTTCA;

SEQ ID NO: 226
QVQLVQSGAEVKNPGSSVKVSCKASGGTFSSYTINWVRQAPGQGLEWMGGIIPLYGTANYAQKF

QARVTISTDESTNTAYMELSNLRFEDTAVYFCASTLELRAFDAFDIWGQGTMVTVSS;

SEQ ID NO: 227
GGA GGC ACC TTC AGC AGT TAT ACT;

SEQ ID NO: 228
G G T F S S Y T;

SEQ ID NO: 229
ATC ATC CCT CTC TAT GGA ACA GCA;

SEQ ID NO: 230
I I P L Y G T A;

SEQ ID NO: 231
GCG AGT ACA CTG GAA CTA CGG GCT TTT GAT GCC TTT GAT ATC;

SEQ ID NO: 232
A S T L E L R A F D A F D I;

SEQ ID NO: 233
CAGGTGCAGCTGCAGGAGTCGGGCCCAGGACTGGTGAAGCCTTCACAGACCCTGTCCCTCACCTGCACTGTCTCTGGTGG

CTCCATCAGCAGTGGTGGTTACTACTGGAACTGGATCCGCCAGCACCCAGGGAAGGGCCTGGAGTGGATTGGGTACATCT

ATTACAGTGGAAGCACCTACTACAACCCGTCCCTCAAGAGTCGAGTTACCATATCAGTAGACACGTCTAAGAACCAGTTC

TCCCTGAAGCTGGGCTCTGTGACTGCCGCGGACACGGCCGTGTATTACTGTGCGCGAGCTCCTCCTTATAACTGGTTTGA

CTACTGGGGCCAGGGAACCCTGGTCACCGTCTCCTCA;

-continued

SEQ ID NO: 234
QVQLQESGPGLVKPSQTLSLTCTVSGGSISSGGYYWNWIRQHPGKGLEWIGYIYYSGSTYYNPSL
KSRVTISVDTSKNQFSLKLGSVTAADTAVYYCARAPPYNWFDYWGQGTLVTVSS;

SEQ ID NO: 235
GGT GGC TCC ATC AGC AGT GGT GGT TAC TAC;

SEQ ID NO: 236
G G S I S S G G Y Y;

SEQ ID NO: 237
ATC TAT TAC AGT GGA AGC ACC;

SEQ ID NO: 238
I Y Y S G S T;

SEQ ID NO: 239
GCG CGA GCT CCT CCT TAT AAC TGG TTT GAC TAC;

SEQ ID NO: 240
A R A P P Y N W F D Y;

SEQ ID NO: 241
CAGGTGCAGCTGGTGGAGTCTGGGGGAGGCTTGGTCAAGCCTGGAGGGTCCCTGAGACTCTCCTGTGCAGCCTCTGGATT
CACCTTCAGTGACTACTACATGAACTGGGTCCGCCAGGCTCCAGGGAAGGGGCTGGAATGGGTTTCATACATTAGTAATA
GTGGTAATACCCAATACTACGCAGACTCTGTGAAGGGCCGGTTCACCATCTCCAGGGACAATGCCAAGAACTCCCTGTTT
CTGCAAATGAACAGCCTGCGAGCCGAGGACACGGCCGTTTATTACTGTACGAGAGAGGGACTCGAATATAGCAGCTCGGA
GCCCTTTGACTACTGGGGCCAGGGAACCCTGGTCACCGTCTCCTCA;

SEQ ID NO: 242
QVQLVESGGGLVKPGGSLRLSCAASGFTFSDYYMNWVRQAPGKGLEWVSYISNSGNTQYYADS
VKGRFTISRDNAKNSLFLQMNSLRAEDTAVYYCTREGLEYSSSEPFDYWGQGTLVTVSS;

SEQ ID NO: 243
GGA TTC ACC TTC AGT GAC TAC TAC;

SEQ ID NO: 244
G F T F S D Y Y;

SEQ ID NO: 245
ATT AGT AAT AGT GGT AAT ACC CAA;

SEQ ID NO: 246
I S N S G N T Q;

SEQ ID NO: 247
ACG AGA GAG GGA CTC GAA TAT AGC AGC TCG GAG CCC TTT GAC TAC;

SEQ ID NO: 248
T R E G L E Y S S S E P F D Y;

SEQ ID NO: 249
CAGGTGCAGCTGGTGCAGTCTGGGGCTGAAGTGAAGAAGCCTGGGGCCTCAGTGAAGGTCTCCTGCAAGACTTCTGGATA
CACCTTCACCGCCTACTACATACACTGGGTGCGACAGGCCCCTGGACAAGGGCTTGAGTGGATGGGATGGATCAACCCTA
ACAATGGTGACACAAACTATGCACTGAGGTTTCAGGGCAGGGTCACCATGACCAGGGACATGTCCATCAACACAGCCTAC
ATGGAGCTGCGCGGGCTGAGATCTGACGACACGGCCGTGTATTATTGTGCGAGAGATGATCTAGCAGCAGCGGGTATCGG
CTGGTTCGACTCCTGGGGCCAGGGAACCCTGGTCACCGTCTCCTCA;

SEQ ID NO: 250
QVQLVQSGAEVKKPGASVKVSCKTSGYTFTAYYIHWVRQAPGQGLEWMGWINPNNGDTNYALRFQGRVTMTRDMSINTAY
MELRGLRSDDTAVYYCARDDLAAAGIGWFDSWGQGTLVTVSS;

SEQ ID NO: 251
GGA TAC ACC TTC ACC GCC TAC TAC;

SEQ ID NO: 252
G Y T F T A Y Y;

SEQ ID NO: 253
ATC AAC CCT AAC AAT GGT GAC ACA;

```
                                                                    SEQ ID NO: 254
I N P N N G D T;

SEQ ID NO: 255
GCG AGA GAT GAT CTA GCA GCA GCG GGT ATC GGC TGG TTC GAC TCC;

SEQ ID NO: 256
A R D D L A A A G I G W F D S;

SEQ ID NO: 257
GAAGTGCAGCTGGTGGAGTCTGGGGGAGGCTTGCTACAGCCTGGCAGGTCCCTGAGACTCTCCTGTGTAGCCTCTGGATT
CACCTTTGATGATTATGCCATGCACTGGGTCCGGCAAGCTCCAGGGAAGGGCCTGGAGTGGGTCTCAGGAATTAGTTGGA
ATAGTGAAAGTATAGGCTATGCGGACTCTGTGAGGGGCCGATTCACCATTTCCAGAGACAACGCCAAGAACTCCCTGTAT
CTCCAAATGAACAGTCTGAGAGCTGAGGACACGGCCTTGTATTACTGTGCAAAAGCCCCGTATAGTGGGACCTACTTCGA
ATACTTCCGCCACTGGGGCCAGGGCACCCTGGTCACCGTCTCCTCA;

SEQ ID NO: 258
EVQLVESGGGLLQPGRSLRLSCVASGFTFDDYAMHWVRQAPGKGLEWVSGISWNSESIGYADS
VRGRFTISRDNAKNSLYLQMNSLRAEDTALYYCAKAPYSGTYFEYFRHWGQGTLVTVSS;

SEQ ID NO: 259
GGA TTC ACC TTT GAT GAT TAT GCC;

SEQ ID NO: 260
G F T F D D Y A;

SEQ ID NO: 261
ATT AGT TGG AAT AGT GAA AGT ATA;

SEQ ID NO: 262
I S W N S E S I;

SEQ ID NO: 263
GCA AAA GCC CCG TAT AGT GGG ACC TAC TTC GAA TAC TTC CGC CAC;

SEQ ID NO: 264
A K A P Y S G T Y F E Y F R H;

SEQ ID NO: 265
CAGGTGCAGCTGGTGGAGTCTGGGGGAGGCGTGGTCCAGCCTGGGAGGTCCCTGAGACTCTCCTGTGCAGCCTCTGGATT
CACCTTCAGTAGCTATGGCATGCACTGGGTCCGCCAGGCTCCAGGCAAGGGGCTGGAGTGGGTGGCAGTTATATCATATG
ATGGAAGTAATAAATACTATGCAGACTCCGTGAAGGGCCGATTCACCATCTCCAGAGACAATTCCAAGAACACGCTGTAT
CTGCAAATGAACAGCCTGAGAGCTGAGGACACGGCTGTGTATTACTGTGCGAAAGATGACTGGAACTACGACGCCTTTGA
TATCTGGGGCCAAGGGACAATGGTCACCGTCTCTTCA;

SEQ ID NO: 266
QVQLVESGGGVVQPGRSLRLSCAASGFTFSSYGMHWVRQAPGKGLEWVAVISYDGSNKYYADS
VKGRFTISRDNSKNTLYLQMNSLRAEDTAVYYCAKDDWNYDAFDIWGQGTMVTVSS;

SEQ ID NO: 267
GGA TTC ACC TTC AGT AGC TAT GGC;

SEQ ID NO: 268
G F T F S S Y G;

SEQ ID NO: 269
ATA TCA TAT GAT GGA AGT AAT AAA;

SEQ ID NO: 270
I S Y D G S N K;

SEQ ID NO: 271
GCG AAA GAT GAC TGG AAO TAC GAC GCC TTT GAT ATC;

SEQ ID NO: 272
A K D D W N Y D A F D I;
```

SEQ ID NO: 273
CAGGTGCAGCTGCAGGAGTCGGGCCCAGGACTGGTGAAGCCTTCACAGACCCTGTCCCTCACCTGCACTGTCTCTGGTGG
CTCCATCAGCAGTAGTGGTTACTACTGGAGCTGGATCCGCCAGCACCCAGGGAGGGGCCTGGAGTGGATTGGATACATCT
ATTACAGTGGGAGCACCTACTACAACCCGTCCCTCAAGAGTCGAGTTACCATATCAGTAGACACGTCTAAGAACCAGTTC
TCCCTGAAGCTGAACTCTGTGACTGCCGCGGACACGGCCGTGTATTACTGTGCGAGAGTGGACTATGGTTCGGGGAGTTC
GTTTGACTACTGGGGCCAGGGAACCCTGGTCACCGTCTCCTCA;

SEQ ID NO: 274
QVQLQESGPGLVKPSQTLSLTCTVSGGSISSSGYYWSWIRQHPGRGLEWIGYIYYSGSTYYNPSL
KSRVTISVDTSKNQFSLKLNSVTAADTAVYYCARVDYGSGSSFDYWGQGTLVTVSS;

SEQ ID NO: 275
GGT GGC TCC ATC AGC AGT AGT GGT TAC TAC;

SEQ ID NO: 276
G G S I S S S G Y Y;

SEQ ID NO: 277
ATC TAT TAC AGT GGG AGC ACC;

SEQ ID NO: 278
I Y Y S G S T;

SEQ ID NO: 279
GCG AGA GTG GAC TAT GGT TCG GGG AGT TCG TTT GAC TAC;

SEQ ID NO: 280
A R V D Y G S G S S F D Y;

SEQ ID NO: 281
CAGGTTCAGCTGGTGCAGTCTGGACCTGAGGTGAAGAAGCCTGGGGCCTCAGTGAAGGTCTCCTGCAAGGCTTCTGGTTA
CACCTTTACCAGCTATGGCATCAGCTGGGTGCGACAGGCCCCTGGACAAGGGCTTGAGTGGCTGGGATGGATCAGCGGTT
TCAATGGTAGAACAGACTATACAGAGAAGCTCCAGGACAGAATCACCATGACCACAGACAGATCCTCGAGCACAGCCTAC
ATGGAACTGAGGAGCCTGAGATATGACGACACGGCCGTGTATTACTGTGCGAGAGATGGACTGGAAAAACTTGGTGACTA
CTGGGGCCAGGGAACCCTGGTCACCGTCTCCTCA;

SEQ ID NO: 282
QVQLVQSGPEVKKPGASVKVSCKASGYTFTSYGISWVRQAPGQGLEWLGWISGFNGRTDYTEK
LQDRITMTTDRSSSTAYMELRSLRYDDTAVYYCARDGLEKLGDYWGQGTLVTVSS;

SEQ ID NO: 283
GGT TAC ACC TTT ACC AGC TAT GGC;

SEQ ID NO: 284
G Y T F T S Y G;

SEQ ID NO: 285
ATC AGC GGT TTC AAT GGT AGA ACA;

SEQ ID NO: 286
I S G F N G R T;

SEQ ID NO: 287
GCG AGA GAT GGA CTG GAA AAA CTT GGT GAC TAC;

SEQ ID NO: 288
A R D G L E K L G D Y;

SEQ ID NO: 289
CAGGTGCAGCTGGTGGAGTCTGGGGGAGGCGTGGTCCAGCCGGGGAGGTTCCTGAGACTCTCCTGTGCAGCGTCTGGATT
CACCTTCAGTAACTCTGGCATGCACTGGGTCCGCCAGGCTCCAGGCAAGGGGCTGGAGTGGGTGGCAGGAATATGGCATG
ATGGAAGTTATAAATATTATGTAGACTCCGTGAAGGGCCGATTCACCATCTCCAGAGACAATTCTAAGAACACGCTGTTT
CTGCAAATGAACAGCCTGCGAGCCGAGGACACGGCTGTATATTATTGTGCGAGAGATGATTACTATGCTTCGGGGACCAG
CGTGGACGTATGGGGCCAAGGGACCACGGTCACCGTCTCCTCA;

-continued

SEQ ID NO: 290
QVQLVESGGGVVQPGRFLRLSCAASGFTFSNSGMHWVRQAPGKGLEWVAGIWHDGSYKYYVDSVKGRFTISRDNSKNTLF
LQMNSLRAEDTAVYYCARDDYYASGTSVDVWGQGTTVTVSS;

SEQ ID NO: 291
GGA TTC ACC TTC AGT AAC TCT GGC;

SEQ ID NO: 292
G F T F S N S G;

SEQ ID NO: 293
ATA TGG CAT GAT GGA AGT TAT AAA;

SEQ ID NO: 294
I W H D G S Y K;

SEQ ID NO: 295
GCG AGA GAT GAT TAC TAT GCT TCG GGG ACC AGC GTG GAC GTA;

SEQ ID NO: 296
A R D D Y Y A S G T S V D V;

SEQ ID NO: 297
CAGGTGCAGCTGGTGCAGTCTGGGGCTGAGGTGAAGAAGCCTGGGGCCTCAGTGAGGGTCTCCTGCATGGCCTCTGGATA
CACCTTCACCGGCTACTATATGCACTGGGTGCGACAGGCCCCTGGACAAGGGCTTGAGTGGATGGGATGGATCAACCCTA
ACAGTGGTGGCACAAAATATGCACAGAAGTTTCAGGGCAGGGTCACCATGACCAGGGACACGTCCATCAGCACAGCCTAC
ATGGAGCTGAGCAGACTGAGATCTGACGACACCGGCCGTATATTACTGTGCGAGAGAAGAAGTCGACGATTTTTGGAGTGG
TTACCTTGACTACTGGGGCCAGGGAACCCTGGTCACCGTCTCCTCA;

SEQ ID NO: 298
QVQLVQSGAEVKKPGASVRVSCMASGYTFTGYYMHWVRQAPGQGLEWMGWINPNSGGTKYA
QKFQGRVTMTRDTSISTAYMELSRLRSDDTAVYYCAREEVDDFWSGYLDYWGQGTLVTVSS;

SEQ ID NO: 299
GGA TAC ACC TTC ACC GGC TAC TAT;

SEQ ID NO: 300
G Y T F T G Y Y;

SEQ ID NO: 301
ATC AAC CCT AAC AGT GGT GGC ACA;

SEQ ID NO: 302
I N P N S G G T;

SEQ ID NO: 303
GCG AGA GAA GAA GTC GAC GAT TTT TGG AGT GGT TAC CTT GAC TAC;

SEQ ID NO: 304
A R E E V D D F W S G Y L D Y;

Light chain #2
SEQ ID NO: 305
GAAATTGTGTTGACGCAGTCTCCAGGCACCCTGTCTTTGTCTCCAGGGGAAAGAGCCACCCTCTCCTGCAGGGCCAGTCA
GAGTGTTAGCAGCAGCTACTTAGCCTGGTACCAGCAGAAACCTGGCCAGGCTCCCAGGCTCCTCATCTATGGTGCATCCA
GCAGGGCCACTGGCATCCCAGACAGGTTCAGTGGCAGTGGGTCTGGGACAGACTTCACTCTCACCATCAGCAGACTGGAG
CCTGAAGATTTTGCAGTGTATTACTGTCAGCAGTATGGTAGCTCACCTTGGACGTTCGGCCAAGGGACCAAGGTGGAAAT
CAAA;

Light chain #2
SEQ ID NO: 306
EIVLTQSPGTLSLSPGERATLSCRASQSVSSSYLAWYQQKPGQAPRLLIYGASSRATGIPDRFSGS
GSGTDFTLTISRLEPEDFAVYYCQQYGSSPWTFGQGTKVEIK;

SEQ ID NO: 307
CAG AGT GTT AGC AGC AGC TAC;

SEQ ID NO: 308
Q S V S S S Y;

```
                                                            SEQ ID NO: 309
GGT GCA TCC;

SEQ ID NO: 310
G A S;

SEQ ID NO: 311
CAG CAG TAT GGT AGC TCA CCT TGG ACG;

SEQ ID NO: 312
Q Q Y G S S P W T;

SEQ ID NO: 313
GAGGTGCAGCTGGTGGAGTCTGGAGGAGACTTGGTCCAGCCGGGGGGGTCCCTGAGACTCTCCTGTGCAGCCTCTGGGTT

CGCCGTCAATGGCGACTATTTTAGTTGGGTCCGCCAGGCTCCAGGGAAGGGGCTGGAGTGGATCTCAGTTATTTATAGCA

GTGGTAACACATACTACGCAGACTCCGTGAAGGGCCGATTCACCATCTCCAGACACAATTCCAAGAACACGCTGTATCTT

CAAATGAGCAGCCTAAGACCTGAGGACACGGCCGTGTATTACTGTGCGAGAGACTTCCCTCCAATGTCTGGTGCGGACTA

CTGGGGCCAGGGAACCCTGGTCACCGTCTCCTCA;

SEQ ID NO: 314
EVQLVESGGDLVQPGGSLRLSCAASGFAVNGDYFSWVRQAPGKGLEWISVIYSSGNTYYADSVK

GRFTISRHNSKNTLYLQMSSLRPEDTAVYYCARDFPPMSGADYWGQGTLVTVSS;

SEQ ID NO: 315
GGG TTC GCC GTC AAT GGC GAC TAT;

SEQ ID NO: 316
G F A V N G D Y;

SEQ ID NO: 317
ATT TAT AGC AGT GGT AAC ACA;

SEQ ID NO: 318
I Y S S G N T;

SEQ ID NO: 319
GCG AGA GAC TTC CCT CCA ATG TCT GGT GCG GAC TAC;

SEQ ID NO: 320
A R D F P P M S G A D Y;

SEQ ID NO: 321
CAGGTCCAGCTGGTGCAGTCTGGGGCTGAGGTGAAGAAGCCTGGGGCCTCAGTGAAGGTCTCCTGCAAGGTTTCCGGATA

CACCCTCACTGAATTGTCCATGCACTGGGTGCGACAGGCTCCTGGAAAAGGGCTTGAATGGATGGGAGGTTTTGATCCTG

AACATGGTAAAATAATCTACGCACAGAAATTCCAGGGCAGAGTCACCATGACCGAGGACACATCTACAGACACAGCCTAC

ATGGAACTGAGCAGCCTGAGATCTGAGGACACGGCCGTCTATTACTGTGCAACATTTTATAACTGGAACTCCTACTACTT

CGGTATGGACGTCTGGGGCCACGGGACCACGGTCACCGTCTCCTCA;

SEQ ID NO: 322
QVQLVQSGAEVKKPGASVKVSCKVSGYTLTELSMHWVRQAPGKGLEWMGGFDPEHGKIIYAQK

FQGRVTMTEDTSTDTAYMELSSLRSEDTAVYYCATFYNWNSYYFGMDVWGHGTTVTVSS;

SEQ ID NO: 323
GGA TAC ACC CTC ACT GAA TTG TCC;

SEQ ID NO: 324
G Y T L T E L S;

SEQ ID NO: 325
TTT GAT CCT GAA CAT GGT AAA ATA;

SEQ ID NO: 326
F D P E H G K I;

SEQ ID NO: 327
GCA ACA TTT TAT AAC TGG AAC TCC TAC TAC TTC GGT ATG GAC GTC;

SEQ ID NO: 328
A T F Y N W N S Y Y F G M D V;
```

SEQ ID NO: 329
GAGGTGCAGCTGGTGGAGTCGGGGGGAGGCTTGGTACAGCCTGGGGGGTCCCTGAGACTCTCCTGTGCAGCCTCTGGATT

CACCTTTAGCAGCTATGCCATGAACTGGGTCCGCCAGGCTCCAGGAAAGGGACTGGAGTGGGTCTCAGCTGTTAGTGGAA

GTGCTGATATCACAAACTACGCAGACTCCGTGAAGGGCCGGTTCACCATCTCCAGAGACAATTCCAAACACACGCTGTAT

CTGCAAATGAACAGCCTGAGAGCCGAGGACACGGCCGTATATTACTGTGCGAAGGATAAAGTGTATAACTGGAACTACGG

GATCTACTACGGTATGGACGTCTGGGGCCAAGGGACCACGGTCACCGTCTCCTCA;

SEQ ID NO: 330
EVQLVESGGGLVQPGGSLRLSCAASGFTFSSYAMNWVRQAPGKGLEWVSAVSGSADITNYADS

VKGRFTISRDNSKHTLYLQMNSLRAEDTAVYYCAKDKVYNWNYGIYYGMDVWGQGTTVTVSS;

SEQ ID NO: 331
GGA TTC ACC TTT AGC AGC TAT GCC;

SEQ ID NO: 332
G F T F S S Y A;

SEQ ID NO: 333
GTT AGT GGA AGT GCT GAT ATC ACA;

SEQ ID NO: 334
V S G S A D I T;

SEQ ID NO: 335
GCG AAG GAT AAA GTG TAT AAC TGG AAC TAC GGG ATC TAC TAC GGT ATG GAC GTC;

SEQ ID NO: 336
A K D K V Y N W N Y G I Y Y G M D V;

SEQ ID NO: 337
CAGCTGCAGCTGCAGGAGTCGGGCCCAGGACTGGTGAAGCCTTCGGAGACCCTGTCCCTCACCTGCACTGTCTCTGGTGG

CTCCATCAGCAGTAGTAGTTACTACTGGGGCTGGATCCGCCAGCCCCCAGGGAAGGGACTAGAGTGGATTGGGAGTATCT

ATTATAGTGGGAGCACCTACTACAATCCGTCCCTCAAGAGTCGAGTCACCATATCCGTAGACACGTCCAAGAACCAGTTC

TCCCTGAAGCTGAGCTCTGTGACCGCCGCAGACACGGCTGTGTATTACTGTGCGAGACAAGGGAGGTGGGAGCGAGAAAA

CTTTGACTACTGGGGCCAGGGAACCCTGGTCACCGTCTCCTCA;

SEQ ID NO: 338
QLQLQESGPGLVKPSETLSLTCTVSGGSISSSSYYWGWIRQPPGKGLEWIGSIYYSGSTYYNPSL

KSRVTISVDTSKNQFSLKLSSVTAADTAVYYCARQGRWERENFDYWGQGTLVTVSS;

SEQ ID NO: 339
GGT GGC TCC ATC AGC AGT AGT AGT TAC TAC;

SEQ ID NO: 340
G G S I S S S S Y Y;

SEQ ID NO: 341
ATC TAT TAT AGT GGG AGC ACC;

SEQ ID NO: 342
I Y Y S G S T;

SEQ ID NO: 343
GCG AGA CAA GGG AGG TGG GAG CGA GAA AAC TTT GAC TAC;

SEQ ID NO: 344
ARQGRWER EN F DY;

SEQ ID NO: 345
CAGGTGCAGCTACAGCAGTGGGGCGCAGGACTATTGAAGCCTTCGGAGACCCTGTCCCTCACCTGCGCTGTCTCTGATGA

GTCCTTCAGTGATTACTACTGGACCTGGATCCGCCAGCCCCCAGGGAAGGGGCTGGAGTGGATTGGGGAAATTACTCATA

GTGGAAGTACCCACTACAACCCGTCCCTCAAGAGCCGAGTCACCCTGTCAGTTGACACGTCCAAGAACCACTTCTCCCTG

AGCCTCAACTCTGTGACCGCCGCGGACACGGCTATTTATTACTGTGCGAGAGGCGGTGACTACGGTGGTTTACTTGACTA

CTGGGGCCAGGGAACCCTGGTCACCGTCTCCTCA;

SEQ ID NO: 346

QVQLQQWGAGLLKPSETLSLTCAVSDESFSDYYWTWIRQPPGKGLEWIGEITHSGSTHYNPSLK

SRVTLSVDTSKNHFSLSLNSVTAADTAIYYCARGGDYGGLLDYWGQGTLVTVSS;

SEQ ID NO: 347

GAT GAG TCC TTC AGT GAT TAC TAC;

SEQ ID NO: 348

DESFSDYY;

SEQ ID NO: 349

ATT ACT CAT AGT GGA AGT ACC;

SEQ ID NO: 350

I T H S G S T;

SEQ ID NO: 351

GCG AGA GGC GGT GAC TAC GGT GGT TTA CTT GAC TAC;

SEQ ID NO: 352

A R G G D Y G G L L D Y;

SEQ ID NO: 353

CAGCTGCAGCTGCAGGAGTCGGGCCCAGGACTGGTGAAGCCCTCGGAGACCCTGTCCCTCACCTGCACTGTCTCTGGTGG

CTCCATCAGCAGTAGGAGTCACTACTGGGGCTGGATCCGCCAGCCCCCAGGGAAGGGGCTGGAGTGGATTGGGAGTATCT

ATTATAGTGGGAGCACCTATTACAACCCGTCCCTCAAGAGTCGAGTCACCATATCCGTAGACACGTCCAAGAACCAGTTC

TCCCTGAAGCTGAGCTCTGTGACCGCCGCAGACACGGCTGTGTATTACTGTGCGAGACTTGGCTGGTACGCAGAGGAGGC

TTTTGAAATCTGGGGTCAAGGGACAATGGTCACCGTCTCTTCA;

SEQ ID NO: 354

QLQLQESGPGLVKPSETLSLTCTVSGGSISSRSHYWGWIRQPPGKGLEWIGSIYYSGSTYYNPSL

KSRVTISVDTSKNQFSLKLSSVTAADTAVYYCARLGWYAEEAFEIWGQGTMVTVSS;

SEQ ID NO: 355

GGT GGC TCC ATC AGC AGT AGG AGT CAC TAC;

SEQ ID NO: 356

G G S I S S R S H Y;

SEQ ID NO: 357

ATC TAT TAT AGT GGG AGC ACC;

SEQ ID NO: 358

I Y Y S G S T;

SEQ ID NO: 359

GCG AGA CTT GGC TGG TAC GCA GAG GAG GCT TTT GAA ATC;

SEQ ID NO: 360

A R L G W Y A E E A F E I

Example 2: Growth Inhibition Assay to Assess the Ability of Anti-PfRH5 Antibodies to Inhibit The In Vitro Invasion of Human Red Blood Cells and Growth of *P. falciparum* Parasites In this example, a set of four PfRH5-specific mAbs of the invention were tested alone and in combination in a standard growth inhibition assay with one strain of *Plasmodium falciparum* (Dd2).

Experimental Procedure

The *P. falciparum* strain, Dd2 (BEI Resources) was first synchronized with 5% D-sorbitol following standard protocols at 3-5% hematocrit and 1-2% parasitaemia 20-24 hours prior to the start of the assay. Infected human erythrocytes were prepared at a starting parasitaemia of 0.4-0.7% and 2% hematocrit. Infected erythrocytes were combined with PfRH5-specific or control antibodies, starting at a concentration of 666.67 nM with 1:5 serial dilution for each antibody or antibody combination. All antibodies used were human IgG1. The parasites were grown for 40-48 h until the schizont stage was reached (one complete life cycle). Parasite growth was stopped with three washes of cold PBS. Final parasitaemia was determined by measuring the parasite lactate dehydrogenase (LDH) activity (Miura, H. Zhou, A. Diouf, S E. Moretz, M P. Fay, L H. Miller, L B. Martin, M A. Pierce, R D. Ellis, G E D. Mullen, C A. Long. Anti-Apical-Membrane-Antigen-1 antibody is more effective than anti-42-kilodalton-Merozoite-Surface-Protein-1 antibody in inhibiting *Plasmodium falciparum* growth, as determined by the in vitro growth inhibition assay. Clin Vaccine Immunol. 16, 963-968 (2009). PMID: PMC2708396). Percent growth inhibition is expressed relative to uninfected erythrocytes.

Results Summary and Conclusions

PfRH5-specific antibodies were produced and tested in vitro in a growth inhibition assay in the laboratory-adapted strain as described above. Table 2-1 shows the maximum percent growth inhibition for a subset of PfRH5-specific antibodies and PfRH5-specific antibody combinations. The individual antibodies and antibody combinations displayed similar percent maximum growth inhibition, ranging from approximately 51-69%.

TABLE 2-1

Summary of maximum growth inhibition activity of antibodies against PfRH5 from *Plasmodium falciparum* strain Dd2.*

| mAb/combo mAbs | Maximum growth inhibition (%) Dd2 |
|---|---|
| H1H29127P + H1H29100P | 66.33 |
| H1H29127P + H1H29143P | 51.37 |
| H1H29127P + H1H29104P | 56.96 |
| H1H29100P + H1H29143P | 68.70 |
| H1H29100P + H1H29104P | 54.04 |
| H1H29143P + H1H29104P | 58.54 |
| H1H29100P | 65.73 |
| H1H29104P | 54.12 |
| H1H29127P | 56.87 |
| H1H29143P | 56.00 |
| human IgG1 negative control antibody specific for cat allergy antigen—Fel d 1 | −0.93 |

*Maximum growth inhibition of antibodies against PfRH5 relative to uninfected human red blood cells. The growth inhibition assay was performed on *P. falciparum* (mature trophozoite or early schizont) infected red blood cells at 0.4-0.7% parasitaemia. The antibodies were combined with the infected red blood cells. The parasites were grown for 40-48 hours (the timing is parasite strain-dependent) until the schizont stage was reached. Parasite growth was stopped with three washes of cold PBS. Parasite lactate dehydrogenase (LDH) activity was measured immediately after the washes. Percent growth inhibition was expressed relative to uninfected erythrocytes. The results of one representative assay of the growth inhibition assay are shown above.

Example 3: Growth Inhibition Assay to Assess the Ability of Anti-PfRH5 Antibodies to Inhibit the In Vitro Invasion of Human Red Blood Cells and Growth of *P. falciparum* Parasites in Combination with Chloroquine In this example, a subset of four PfRH5-specific mAbs of the invention were tested alone and in combination with chloroquine (CQ), a commonly-used antimalarial drug in a standard growth inhibition assay with two laboratory strains. One strain of the *Plasmodium falciparum* parasite, 3D7, is susceptible to chloroquine, while strain 7G8 is resistant to the drug.

Experimental Procedure

Each *P. falciparum* strain (BEI Resources) was first synchronized with 5% D-sorbitol following standard protocols at 3-5% hematocrit and 1-2% parasitaemia 20-24 hours prior to the start of the assay. Infected human erythrocytes were prepared at a starting parasitaemia of 0.4-0.7% and 2% hematocrit. Infected erythrocytes were combined with PfRH5-specific or control antibodies starting at a concentration of 666.67 nM with 1:5 serial dilution for each IgG1 antibody and chloroquine at one of two concentrations, 4.91 or 6.58 nM. The two concentrations were selected based on the 1025, 4.91 nM, and $IC_{50}$, 6.58 nM, of chloroquine with the susceptible 3D7 strain. The parasites were grown for 40-48 h until the schizont stage was reached (one complete life cycle). Parasite growth was stopped with three washes of cold PBS. Final parasitaemia was determined by measuring the parasite lactate dehydrogenase (LDH) activity. Percent growth inhibition was expressed relative to uninfected erythrocytes.

Results Summary and Conclusions

Table 3-1 shows the maximum percent growth inhibition for each antibody alone and antibody/chloroquine combination. Combining chloroquine with PfRH5-specific antibodies further increased the percent maximum growth inhibition obtained with the antibodies alone in the 3D7 strain. Maximum growth inhibition with antibody alone was approximately 34 to 61%, while the addition of 4.81 nM CQ to the mAb had similar maximum growth inhibition (32 to 51%). The addition of 6.58 nM of CQ to the mAb increased the range of growth inhibition at least 20% to 59 to 75%. On the other hand, the individual antibodies and antibody/drug combinations displayed similar percent maximum growth inhibition with the 7G8 strain (mAb alone: 47-51%; mAb+ 4.81 nM CQ: 44-53%; mAb+6.58 nM CQ: 30-52%).

TABLE 3-1

Summary of maximum growth inhibition activity of antibodies against PfRH5 from various *Plasmodium falciparum* strains.*

| Chloroquine Phosphate | mAb | Max growth inhibition (%) | |
|---|---|---|---|
| | | 3D7 | 7G8 |
| N/A | H1H29089P | 61.06 | 51.10 |
| | H1H29100P | 58.02 | 48.85 |
| | H1H29147P2 | 34.93 | 47.34 |
| | H1H29187P2 | 47.58 | 49.30 |
| 4.81 nM | H1H29089P | 51.32 | 48.69 |
| | H1H29100P | 46.64 | 53.76 |
| | H1H29147P2 | 31.45 | 44.22 |
| | H1H29187P2 | 44.53 | 48.70 |
| 6.58 nM | H1H29089P | 75.59 | 52.78 |
| | H1H29100P | 71.21 | 50.67 |
| | H1H29147P2 | 59.11 | 29.96 |
| | H1H29187P2 | 71.20 | 38.95 |

*Maximum growth inhibition of antibodies against PfRH5 relative to uninfected human red blood cells. The growth inhibition assay was performed on *P. falciparum*—(mature trophozoite or early schizont) infected red blood cells at 0.4-0.7% parasitaemia. The antibodies were combined with the infected red blood cells. The parasites were grown for 40-48 hours (parasite strain dependent) until the schizont stage was reached. Parasite growth was stopped with three washes of cold PBS. Parasite lactate dehydrogenase activity was measured immediately after the washes. Percent growth inhibition was expressed relative to uninfected erythrocytes. The results of one representative assay of the growth inhibition assay are shown above.

Example 4: Growth Inhibition Assay to Assess the Ability of Anti-PfRH5 Antibodies to Inhibit the In Vitro Invasion of Human Red Blood Cells and Growth of *P. falciparum* Parasites In this example, a set of 30 PfRH5-specific mAbs of the invention were tested in a standard growth inhibition assay against a number of common laboratory strains (both susceptible and resistant to various antimalarial drugs) and multidrug resistant clinical lines.

Experimental Procedure

Each *P. falciparum* strain (BEI Resources) was first synchronized with 5% D-sorbitol following standard protocols at 3-5% hematocrit and 1-2% parasitaemia 20-24 hours prior to the start of the assay. Infected human erythrocytes were prepared at a starting parasitaemia of 0.4-0.7% and 2% hematocrit. Infected erythrocytes were combined with PfRH5-specific or control IgG1 antibodies starting at a concentration of 666.67 nM with 1:5 serial dilution for each antibody. The parasites were grown for 40-48 h until the schizont stage was reached (one complete life cycle). Parasite growth was stopped with three washes of cold PBS. Final parasitaemia was determined by measuring the parasite lactate dehydrogenase (LDH) activity (Miura et al, Clin Vaccine Immunol. 16: 963-968 (2009). PMID: PMC2708396). Percent growth inhibition was expressed relative to uninfected erythrocytes.

Results Summary and Conclusions

Table 4-1 shows the maximum percent growth inhibition for each of the 30 PfRH5-specific mAbs tested at 666.67 nM. Application of several antibodies resulted in decreased growth in all tested laboratory-adapted and clinical *P. falciparum* strains.

Example 5: Biacore Binding Kinetics of Anti-PfRH5 Monoclonal Antibodies Binding to PfRH5ΔNL.his at 25° C. and 37° C.

The binding kinetics of the various anti-PfRH5 antibodies of the present invention were determined in this example.

Equilibrium dissociation constants ($K_D$) for different PfRH5 reagents binding to purified anti-PfRH5 monoclonal antibodies were determined using a real-time surface plasmon resonance based Biacore T200 biosensor. All binding studies were performed in 10 mM HEPES, 150 mM NaCl, 3 mM EDTA, and 0.05% v/v Surfactant Tween-20, pH 7.4 (HBS-ET) running buffer at 25° C. and 37° C. The Biacore CM4 sensor chip surface was first derivatized by amine coupling with the goat anti-human Fcγ specific polyclonal antibody (Jackson ImmunoResearch Laboratories, Cat #109-005-098) or rabbit anti-mouse Fc specific polyclonal antibody (GE Healthcare Cat #BR100838) to capture anti-PfRH5 IgG1 monoclonal antibodies. Binding studies were performed on recombinant PfRH5 removing the amino terminus M1-Y139 and including residues K140-Q526 but

TABLE 4-1

Summary of maximum growth inhibition activity of antibodies against PfRH5 from various *Plasmodium falciparum* strains.*

| | Max growth inhibition (%) | | | | | | | |
| --- | --- | --- | --- | --- | --- | --- | --- | --- |
| mAb | D10 | Dd2 | 7G8 | W2-mef | 3D7 | HB3 | FCR-1/FVO | Cam3.II | RF7 |
| H1H29089P | 82.32 | 71.29 | 70.09 | 66.39 | 67.59 | 59.15 | 65.98 | 56.16 | 28.95 |
| H1H29094P | 35.86 | 41.58 | 29.95 | 34.94 | 14.38 | 45.39 | 51.23 | 26.18 | 15.23 |
| H1H29100P | 81.73 | 64.60 | 66.40 | 67.29 | 61.80 | 62.61 | 66.89 | 52.44 | 17.02 |
| H1H29104P | 55.70 | 61.31 | 35.16 | 47.40 | 34.42 | 39.81 | 67.38 | 50.02 | 23.62 |
| H1H29106P | 74.86 | 53.97 | 55.49 | 48.93 | 57.97 | 48.36 | 54.28 | 51.68 | 27.41 |
| H1H29109P | 44.79 | 42.05 | 39.04 | 37.92 | 32.22 | 32.24 | 56.74 | 35.91 | 8.24 |
| H1H29125P | 75.39 | 51.39 | 46.96 | 64.57 | 51.14 | 52.09 | 67.62 | 42.69 | 20.99 |
| H1H29127P | 74.44 | 64.67 | 61.19 | 53.61 | 63.90 | 59.36 | 61.13 | 47.00 | 25.68 |
| H1H29131P | 63.00 | 68.75 | 50.30 | 63.16 | 50.61 | 59.45 | 71.77 | 50.18 | 26.66 |
| H1H29134P | 50.59 | 39.99 | 34.84 | 26.89 | 40.72 | 28.21 | 41.17 | 28.53 | 16.69 |
| H1H29138P | 57.06 | 74.44 | 57.36 | 66.44 | 58.45 | 51.38 | 84.07 | 48.69 | 51.37 |
| H1H29141P | 50.01 | 65.27 | 54.63 | 56.19 | 48.20 | 49.98 | 74.25 | 49.31 | 32.06 |
| H1H29143P | 79.41 | 62.70 | 61.87 | 58.27 | 60.27 | 60.87 | 67.19 | 53.25 | 28.21 |
| H1H29146P2 | 10.78 | 26.90 | 19.07 | 0.57 | 8.57 | 33.87 | 7.32 | 8.18 | 5.97 |
| H1H29147P2 | 81.44 | 65.31 | 65.20 | 64.71 | 60.27 | 64.85 | 70.32 | 51.93 | 31.44 |
| H1H29149P2 | 66.03 | 50.32 | 41.38 | 42.77 | 44.15 | 40.01 | 57.98 | 36.22 | 14.74 |
| H1H29151P2 | 38.66 | 57.97 | 47.52 | 53.90 | 35.49 | 31.74 | 53.70 | 26.34 | 18.26 |
| H1H29163P2 | 71.83 | 61.17 | 62.62 | 63.66 | 55.62 | 56.45 | 64.52 | 46.72 | 10.73 |
| H1H29166P2 | 70.94 | 60.02 | 54.60 | 61.87 | 53.11 | 54.93 | 69.69 | 55.90 | 19.41 |
| H1H29171P2 | 10.60 | 7.71 | 17.03 | 0.74 | 4.04 | 0.52 | 11.67 | 5.45 | −12.52 |
| H1H29179P2 | 62.50 | 13.49 | 34.11 | 22.88 | 24.24 | 40.86 | 49.01 | 33.41 | −2.99 |
| H1H29183P2 | 6.79 | 0.68 | 17.83 | −0.55 | 5.68 | 4.92 | 16.05 | 8.66 | −6.27 |
| H1H29187P2 | 79.61 | 66.02 | 71.80 | 67.28 | 70.71 | 63.91 | 72.16 | 49.22 | 32.73 |
| H1H29192P2 | 8.70 | −15.16 | 12.42 | 4.35 | −1.03 | 5.62 | 15.10 | −3.38 | −7.69 |
| H1H29196P2 | 14.33 | −1.65 | 23.44 | 17.00 | 6.72 | 26.76 | 21.94 | 6.09 | 3.78 |
| H1H29198P2 | 4.38 | 10.13 | 5.31 | −3.61 | −5.40 | 15.53 | 11.08 | 14.66 | 1.53 |
| H1H29207P2 | 73.90 | 61.30 | 58.68 | 65.21 | 61.84 | 49.30 | 69.23 | 45.30 | 31.06 |
| H1H29209P2 | 72.66 | 38.09 | 49.89 | 39.61 | 48.32 | 52.40 | 19.16 | 47.26 | 11.91 |
| H1H29214P2 | 76.52 | 47.21 | 56.74 | 52.72 | 52.09 | 59.09 | 13.05 | 46.67 | 11.18 |
| H1H29215P2 | 35.80 | 22.79 | 33.23 | 37.23 | 19.97 | 30.11 | 54.03 | 27.22 | 11.28 |
| Human IgG1 negative control antibody specific for cat allergy antigen-Fel d 1 | −1.42 | 11.02 | −11.68 | 6.66 | 13.18 | 27.50 | 4.04 | −0.41 | −6.62 |

*Maximum growth inhibition of antibodies against PfRH5 relative to uninfected human red blood cells. The growth inhibition assay was performed on *P. falciparum*- (mature trophozoite or early schizont) infected red blood cells at 0.4-0.7% parasitaemia. The antibodies were combined with the infected red blood cells. The parasites were grown for 40-48 hours (parasite strain dependent) until the schizont stage was reached. Parasite growth was stopped with three washes of cold PBS. Parasite lactate dehydrogenase(LDH) activity was measured immediately after the washes. Percent growth inhibition is expressed relative to uninfected erythrocytes. The results of one representative assay of the growth inhibition assay for each *P. falciparum* strain are shown above.

lacking K247-L295 and T216A and T299A expressed with a C-terminal hexahistidine tag (PfRH5ΔNL.6his). Different concentrations of PfRH5ΔNL.6his (3.125-50 nM; 2-fold serial dilution or 0.48-60 nM; 5-fold serial dilution) were first prepared in HBS-ET running buffer and were injected over anti-human Fcγ or anti-mouse Fc captured anti-PfRH5 monoclonal antibody surface for four minutes at a flow rate of 50 μL/minute, while the dissociation of monoclonal antibody bound PfRH5 reagent was monitored for ten minutes in HBS-ET running buffer. The association rate ($k_a$) and dissociation rate ($k_d$) constants were determined by fitting the real-time binding sensorgrams to a 1:1 binding model with mass transport limitation using Scrubber 2.0c curve-fitting software. Binding dissociation equilibrium constant ($K_D$) and dissociative half-life (t½) were calculated from the kinetic rates as:

$$K_D(M) = \frac{kd}{ka}, \text{ and } t1/2(\min) = \frac{\ln(2)}{60 * kd}$$

Kinetics parameters for PfRH5ΔNL.6his binding to different anti-PfRH5 monoclonal antibodies of the invention at 25° C. and 37° C. are shown in Tables 5-1 through 5-2, respectively.

At 25° C., all of the anti-PfRH5 monoclonal antibodies of the invention bound to PfRH5ΔNL.6his with $K_D$ values ranging from 4.72 pM to 1.67 nM, as shown in Table 5-1. At 37° C., all of the anti-PfRH5 monoclonal antibodies of the invention bound to PfRH5ΔNL.6his with $K_D$ values ranging from 1.10 pM to 1.10 nM, as shown in Table 5-2.

TABLE 5-1

Binding kinetics parameters of PfRH5ΔNL.6his binding to anti-PfRH5 monoclonal antibodies at 25° C.

| Antibody | mAb Capture Level (RU) | 100 nM Ag Bound (RU) | $k_a$ (1/Ms) | $k_d$ (1/s) | $K_D$ (M) | t½ (min) |
|---|---|---|---|---|---|---|
| H1H29141P | 62.8 ± 4.0 | 29.9 | 2.75E+06 | 1.30E−05 | 4.72E−12 | 888 |
| H1H29209P2 | 152.6 ± 0.6 | 79.5 | 1.54E+06 | 1.37E−05 | 9.09E−12 | 843 |
| H1H29125P | 175.4 ± 1.3 | 88.3 | 8.10E+05 | 1.00E−05* | 1.23E−11 | 1155 |
| H1H29138P | 118.1 ± 0.4 | 61.2 | 1.98E+07 | 4.04E−04 | 2.04E−11 | 28.6 |
| H1H29106P | 109.4 ± 4.0 | 49.3 | 6.31E+06 | 9.93E−04 | 1.57E−10 | 11.6 |
| H1H29134P | 147.7 ± 0.6 | 68.3 | 7.98E+05 | 1.00E−05* | 1.25E−11 | 1155 |
| H1H29109P | 70.4 ± 4.4 | 36.7 | 2.17E+06 | 1.01E−03 | 4.68E−10 | 11.4 |
| H1H29100P | 163.2 ± 1.1 | 83.3 | 2.49E+06 | 1.96E−04 | 7.87E−11 | 59.1 |
| H1H29127P | 177.5 ± 0.3 | 88.1 | 1.91E+06 | 9.12E−04 | 4.76E−10 | 12.7 |
| H1H29089P | 180.4 ± 0.9 | 96 | 1.46E+06 | 3.99E−04 | 2.73E−10 | 29 |
| H1H29094P | 186.1 ± 0.9 | 87.2 | 1.07E+06 | 5.30E−04 | 4.98E−10 | 21.8 |
| H1H29179P2 | 171.7 ± 1.0 | 66.3 | 1.83E+06 | 4.88E−03 | 2.66E−09 | 2.4 |
| H1H29214P2 | 115.5 ± 2.9 | 59.9 | 1.71E+06 | 2.17E−04 | 1.27E−10 | 53.3 |
| H1H29131P | 103.8 ± 5.1 | 52.4 | 3.14E+06 | 2.23E−03 | 7.11E−10 | 5.2 |
| H1H29215P2 | 74.5 ± 0.4 | 34.6 | 1.56E+06 | 1.52E−03 | 9.74E−10 | 7.6 |
| H1H29147P2 | 91.5 ± 4.5 | 43.2 | 3.29E+06 | 1.67E−03 | 5.07E−10 | 6.9 |
| H1H29163P2 | 93.6 ± 0.2 | 38 | 3.02E+06 | 2.00E−03 | 6.63E−10 | 5.8 |
| H1H29187P2 | 108.1 ± 1.3 | 53.2 | 2.18E+06 | 2.19E−04 | 1.01E−10 | 52.8 |
| H1H29149P2 | 195.6 ± 1.6 | 82.9 | 1.51E+06 | 4.14E−04 | 2.74E−10 | 27.9 |
| H1H29207P2 | 204.0 ± 2.0 | 104.9 | 1.68E+06 | 1.72E−03 | 1.03E−09 | 6.7 |
| H1H29104P | 139.4 ± 2.6 | 58.4 | 1.24E+06 | 1.30E−03 | 1.05E−09 | 8.9 |
| H1H29196P2 | 138.3 ± 0.9 | 61 | 1.22E+06 | 2.21E−03 | 1.80E−09 | 5.2 |
| H1H29183P2 | 156.6 ± 1.0 | 23 | 1.59E+05 | 1.00E−05* | 6.28E−11 | 1155 |
| H1H29143P | 110.8 ± 0.3 | 53.4 | 3.41E+06 | 2.77E−03 | 8.13E−10 | 4.2 |
| H1H29166P2 | 102.5 ± 6.6 | 28 | 4.27E+06 | 3.56E−03 | 8.34E−10 | 3.2 |
| H1H29151P2 | 122.4 ± 0.2 | 26 | 1.48E+07 | 2.47E−02 | 1.67E−09 | 0.5 |
| H1H29192P2 | 148.3 ± 0.6 | −0.4 | NB$ | NB$ | NB$ | NB$ |
| H1H29198P2 | 121.7 ± 0.3 | −0.8 | NB$ | NB$ | NB$ | NB$ |
| H1H29146P2 | 143.2 ± 0.4 | −1.5 | NB$ | NB$ | NB$ | NB$ |
| H1H29171P2 | 144.2 ± 0.4 | 0.4 | NB$ | NB$ | NB$ | NB$ |
| IgG1 Isotype Control | 165.3 ± 0.9 | −1.3 | NB$ | NB$ | NB$ | NB$ |

*indicates that no dissociation of PfRH5ΔNL.6his was observed under the current experimental conditions and the $k_d$ value was manually fixed at 1.00E−05 while fitting the data.
$indicates that no binding was observed under the current experimental conditions.
NB means no binding

TABLE 5-2

Binding kinetics parameters of PfRH5ΔNL.6his binding to anti-PfRH5 monoclonal antibodies at 37° C.

| Antibody | mAb Capture Level (RU) | 100 nM Ag Bound (RU) | $k_a$ (1/Ms) | $k_d$ (1/s) | $K_D$ (M) | t½ (min) |
|---|---|---|---|---|---|---|
| H1H29141P | 38.8 ± 1.3 | 18.8 | 9.11E+06 | 1.00E−05* | 1.10E−12 | 1155 |
| H1H29209P2 | 66.7 ± 0.8 | 28.6 | 2.11E+06 | 1.00E−05* | 4.74E−12 | 1155 |
| H1H29125P | 65.8 ± 2.6 | 19.9 | 1.58E+06 | 1.00E−05* | 6.34E−12 | 1155 |

TABLE 5-2-continued

Binding kinetics parameters of PfRH5ΔNL.6his binding to anti-PfRH5 monoclonal antibodies at 37° C.

| Antibody | mAb Capture Level (RU) | 100 nM Ag Bound (RU) | $k_a$ (1/Ms) | $k_d$ (1/s) | $K_D$ (M) | $t^½$ (min) |
|---|---|---|---|---|---|---|
| H1H29138P | 40.3 ± 0.2 | 18.7 | 4.26E+07 | 6.87E−04 | 1.61E−11 | 16.8 |
| H1H29106P | 58.6 ± 6.5 | 17.3 | 1.60E+07 | 6.36E−04 | 3.97E−11 | 18.2 |
| H1H29134P | 58.9 ± 0.6 | 19.8 | 2.71E+07 | 1.18E−03 | 4.37E−11 | 9.8 |
| H1H29109P | 40.5 ± 8.0 | 19.7 | 1.20E+07 | 5.51E−04 | 4.58E−11 | 21 |
| H1H29100P | 72.4 ± 1.1 | 33.2 | 4.03E+06 | 2.10E−04 | 5.21E−11 | 55 |
| H1H29127P | 67.3 ± 0.6 | 27.3 | 1.29E+07 | 7.02E−04 | 5.46E−11 | 16.4 |
| H1H29089P | 76.0 ± 1.9 | 32.7 | 4.04E+06 | 2.33E−04 | 5.77E−11 | 49.5 |
| H1H29094P | 72.1 ± 2.1 | 21.2 | 2.05E+06 | 1.19E−04 | 5.79E−11 | 97.2 |
| H1H29179P2 | 79.6 ± 1.1 | 15.3 | 2.14E+07 | 1.26E−03 | 5.88E−11 | 9.2 |
| H1H29214P2 | 59.0 ± 0.7 | 22.9 | 2.70E+06 | 1.63E−04 | 6.04E−11 | 70.9 |
| H1H29131P | 64.8 ± 0.4 | 26.6 | 1.31E+07 | 8.66E−04 | 6.61E−11 | 13.3 |
| H1H29215P2 | 41.9 ± 3.3 | 9.9 | 1.40E+07 | 1.21E−03 | 8.64E−11 | 9.5 |
| H1H29147P2 | 54.6 ± 1.5 | 24.9 | 1.24E+07 | 1.12E−03 | 9.01E−11 | 10.3 |
| H1H29163P2 | 32.7 ± 0.2 | 13 | 1.54E+07 | 1.68E−03 | 1.09E−10 | 6.9 |
| H1H29187P2 | 76.4 ± 8.6 | 29 | 3.19E+06 | 6.87E−04 | 2.16E−10 | 16.8 |
| H1H29149P2 | 117.5 ± 4.1 | 33.9 | 1.49E+06 | 6.47E−04 | 4.36E−10 | 17.9 |
| H1H29207P2 | 111.6 ± 3.9 | 40.8 | 2.61E+06 | 1.23E−03 | 4.72E−10 | 9.4 |
| H1H29104P | 110.3 ± 11.5 | 23 | 1.91E+06 | 9.38E−04 | 4.92E−10 | 12.3 |
| H1H29196P2 | 73.6 ± 1.6 | 14.1 | 2.50E+06 | 2.74E−03 | 1.10E−09 | 4.2 |
| H1H29183P2 | 78.4 ± 1.7 | 3.5 | IC# | IC# | IC# | IC# |
| H1H29143P | 41.5 ± 0.2 | 12.3 | IC# | IC# | IC# | IC# |
| H1H29166P2 | 59.0 ± 1.0 | 23.5 | IC# | IC# | IC# | IC# |
| H1H29151P2 | 45.0 ± 0.2 | 2.7 | NB$ | NB$ | NB$ | NB$ |
| H1H29192P2 | 60.3 ± 0.8 | −1.2 | NB$ | NB$ | NB$ | NB$ |
| H1H29198P2 | 46.4 ± 1.6 | −3.2 | NB$ | NB$ | NB$ | NB$ |
| H1H29146P2 | 52.6 ± 0.4 | −2.6 | NB$ | NB$ | NB$ | NB$ |
| H1H29171P2 | 52.0 ± 0.3 | −5.6 | NB$ | NB$ | NB$ | NB$ |
| IgG1 Isotype Control | 74.3 ± 1.0 | −1.2 | NB$ | NB$ | NB$ | NB$ |

*indicates that no dissociation of PfRH5ΔNL.6his was observed under the current experimental conditions and the $k_d$ value was manually fixed at 1.00E−05 while fitting the data.
$indicates that no binding was observed under the current experimental conditions.
indicates that binding was observed under the current experimental conditions, but kinetic values is unfit table.
IC means inconclusive
NB means no binding Example 6: Octet Cross-Competition Between Different Anti-PfRH5 Monoclonal Antibodies Binding competition between a panel of anti-PfRH5 monoclonal antibodies was determined using a real time, label-free bio-layer interferometry assay on the Octet HTX biosensor platform (Pall ForteBio Corp.).

The experiment was performed at 25° C. in 10 mM HEPES, 150 mM NaCl, 3 mM EDTA, 0.05% v/v Surfactant Tween-20, and 1 mg/mL BSA, pH7.4 (HBS-EBT) buffer with the plate shaking at the speed of 1000 rpm. To assess whether two antibodies are able to compete with one another for binding to their respective epitopes on the recombinant PfRH5 removing the amino terminus M1-Y139 and including residues K140-Q526 but lacking K247-L295 and T216A and T299A expressed with a C-terminal hexahistidine tag (PfRH5ΔNL.6his; SEQ ID: 362), around 1.4-2.0 nm of PfRH5ΔNL.6his was first captured onto anti-Penta-His antibody coated Octet biosensor tips (Fortebio Inc, #18-5122) by submerging the biosensor tips for 60 seconds in wells containing 20 μg/mL solution of PfRH5ΔNL.6his. The antigen captured biosensor tips were then saturated with a first anti-PfRH5 monoclonal antibody (subsequently referred to as mAb-1) by dipping into wells containing 50 μg/mL solution of mAb-1 for 3 minutes. Antibodies used were IgG1. The biosensor tips were then subsequently dipped into wells containing 50 pg/mL solution of second anti-PfRH5 monoclonal antibody (subsequently referred to as mAb-2) for 3 minutes. The biosensor tips were washed in HBS-ETB buffer in between every step of the experiment. The real-time binding response was monitored during the entire course of the experiment and the binding response at the end of every step was recorded. The response of mAb-2 binding to PfRH5ΔNL.6his pre-complexed with mAb-1 was compared and competitive/non-competitive behavior of different anti-PfRH5 monoclonal antibodies was determined as shown in Table 6-1.

TABLE 6-1

Cross-competition between anti-PfRH5 monoclonal antibodies.

| mAb-1 | mAb-2 that competes with mAb-1 |
|---|---|
| H1H29127P | H1H29106P |
|  | H1H29134P |
| H1H29106P | H1H29127P |
|  | H1H29134P |
| H1H29134P | H1H29106P |
|  | H1H29127P |
| H1H29143P | H1H29187P2 |
| H1H29187P2 | H1H29143P |
|  | H1H29151P2 |
| H1H29183P2 | No mAb |
| H1H29104P | No mAb |
| H1H29207P2 | H1H29109P |
|  | H1H29147P2 |
|  | H1H29166P2 |
|  | H1H29171P2 |
|  | H1H29163P2 |

TABLE 6-1-continued

Cross-competition between anti-PfRH5 monoclonal antibodies.

| mAb-1 | mAb-2 that competes with mAb-1 |
|---|---|
| H1H29109P | H1H29207P2 |
|  | H1H29147P2 |
|  | H1H29166P2 |
|  | H1H29171P2 |
|  | H1H29163P2 |
| H1H29147P2 | H1H29207P2 |
|  | H1H29109P |
|  | H1H29166P2 |
|  | H1H29171P2 |
|  | H1H29163P2 |
|  | H1H29131P |
| H1H29166P2 | H1H29207P2 |
|  | H1H29109P |
|  | H1H29147P2 |
|  | H1H29171P2 |
|  | H1H29163P2 |
|  | H1H29131P |
| H1H29171P2 | H1H29207P2 |
|  | H1H29109P |
|  | H1H29147P2 |
|  | H1H29166P2 |
|  | H1H29163P2 |
|  | H1H29131P |
|  | H1H29094P |
| H1H29163P2 | H1H29207P2 |
|  | H1H29109P |
|  | H1H29147P2 |
|  | H1H29166P2 |
|  | H1H29171P2 |
|  | H1H29131P |
|  | H1H29094P |
|  | H1H29215P2 |
| H1H29131P | H1H29147P2 |
|  | H1H29166P2 |
|  | H1H29171P2 |
|  | H1H29163P2 |
|  | H1H29094P |
|  | H1H29215P2 |
| H1H29094P | H1H29171P2 |
|  | H1H29163P2 |
|  | H1H29131P |
|  | H1H29215P2 |
|  | H1H29151P2 |
|  | H1H29138P |
| H1H29215P2 | H1H29163P2 |
|  | H1H29131P |
|  | H1H29094P |
|  | H1H29151P2 |
|  | H1H29125P |
| H1H29151P2 | H1H29187P2 |
|  | H1H29094P |
|  | H1H29215P2 |
|  | H1H29198P2 |
| H1H29125P | H1H29215P2 |
| H1H29149P2 | H1H29100P |
|  | H1H29209P2 |
|  | H1H29179P2 |
|  | H1H29214P2 |
|  | H1H29089P |
| H1H29100P | H1H29149P2 |
|  | H1H29209P2 |
|  | H1H29179P2 |
|  | H1H29214P2 |
|  | H1H29089P |
| H1H29209P2 | H1H29149P2 |
|  | H1H29100P |
|  | H1H29179P2 |
|  | H1H29214P2 |
|  | H1H29089P |
| H1H29179P2 | H1H29149P2 |
|  | H1H29100P |
|  | H1H29209P2 |
|  | H1H29214P2 |
|  | H1H29089P |
| H1H29214P2 | H1H29149P2 |
|  | H1H29100P |
|  | H1H29209P2 |
|  | H1H29179P2 |
|  | H1H29089P |
| H1H29089P | H1H29149P2 |
|  | H1H29100P |
|  | H1H29209P2 |
|  | H1H29179P2 |
|  | H1H29214P2 |
| H1H29138P | H1H29094P |
| H1H29141P | No mAb |
| H1H29196P2 | No mAb |
| H1H29198P2 | H1H29151P2 |
| H1H29146P2 | No mAb |

Example 7: Multicycle Growth Inhibition Assay to Assess the Resultant Parasites after Anti-PfRH5 Antibody Pressure

*Plasmodium falciparum* RH5 specific antibodies inhibit invasion of human red blood cells assay over multiple replication cycles and do not induce mutations in the PfRH5 gene. Invasion of host erythrocytes is an essential step of the *Plasmodium falciparum* (*P. falciparum*) life cycle and of malaria pathology. Multiple antimalarial drugs target the asexual blood stages however, their efficacy is threatened by the appearance of drug resistant strains (Arrow et al., Saving Lives, Buying Time: Economics of Malaria Drugs in an Age of Resistance. National Acamies Press (US). 254-266 (2004); Blasco et al., Antimalarial drug resistance: linking *Plasmodium falciparum* parasite biology to the clinic. Nature Medicine. 23, 917-928 (2017)). Furthermore, antimalarial drugs display different pharmacokinetic properties. Some antimalarial drugs, such as artemisinin and quinine, are rapidly cleared within one parasite life cycle. On the other hand, hydrophobic and lipophilic antimalarial drugs are eliminated slowly, but they are characterized by different absorption rates depending on the amount of dietary fat consumed (Arrow et al., Saving Lives, Buying Time: Economics of Malaria Drugs in an Age of Resistance. National Acamies Press (US). 254-266 (2004)).

Targeting the reticulocyte-binding protein homolog 5 (RH5) protein with polyclonal (pAb) and monoclonal antibodies (mAb) efficiently blocks parasite invasion of several *P. falciparum* strains into human erythrocytes in vitro (Wright et al., Structure of malaria invasion protein RH5 with erythrocyte basigin and blocking antibodies. Nature. 515, 427-430 (2014); Galaway et al., P113 is a merozoite surface protein that binds the N-terminus of *Plasmodium falciparum* RH5. Nature Communications. 8, 14333 (2017)). Targeting the RH5 protein with a single antibody or an antibody cocktail may be necessary to generate opposing selection pressures on the same target. In addition, antibodies could compensate for the short half-life of common antimalarial drugs.

Lastly, the *Plasmodium* parasite has developed ways to escape the host immune response that tries to block the parasite development such as gene polymorphisms. This genetic diversity is often the result of immune pressure (Renia & Goh, Malaria Parasites: The Great Escape. Front Immunol. 7, 463 (2016). PMC5098170). Whole genome sequencing of more than 300 *P. falciparum* clinical isolates or laboratory strains identified only 15 non-synonymous PfRH5 SNPs within the possible mAb epitopes, demonstrating the conserved nature and the importance of the protein. Immune pressure on conserved regions of a protein may limit the ability of the parasite to develop escape mechanisms (Bustamante et al., A full-length recombinant *Plasmodium falciparum* PfRH5 protein induces inhibitory antibodies that are effective across common PfRH5 genetic variants, Vaccine, 31, 373-9 (2013)).

homolog 5 (PfRH5) protein would efficiently block parasite invasion of human erythrocytes in vitro with *P. falciparum*. Gradually increasing the PfRH5-specific antibody pressure on the *P. falciparum* 3D7 parasites did not result in PfRH5 polymorphisms compared to the isotype control antibody pressure. Table 7-1 shows the percent PfRH5 sequence identity scores of each sample relative to all other sequenced samples after 45 days of gradual increases in antibody pressure ($1 \times EC_{50}$ to $110 \times EC_{50}$). All sequences are 100% identical throughout. FIG. 1 shows the sequence alignments of PfRH5 corresponding to each PfRH5-specific antibody after 45 days of gradual increases in antibody pressure ($1 \times EC_{50}$ to $110 \times EC_{50}$) showing no differences in sequences at the nucleotide level.

TABLE 7-1

Percent PfRH5 sequence identity scores of each sample relative to all other sequenced samples after 45 days of gradual increases in antibody pressure ($1 \times EC_{50}$ to $110 \times EC_{50}$).

| | Percent Identity Scores (PfRH5 sequence) | | | | | |
|---|---|---|---|---|---|---|
| | H1H29089P | H1H29100P | H1H29147P2 | H1H29187P2 | REGN1932 | Reference sequence (3D7) |
| H1H29089P | 100 | 100 | 100 | 100 | 100 | 100 |
| H1H29100P | 100 | 100 | 100 | 100 | 100 | 100 |
| H1H29147P2 | 100 | 100 | 100 | 100 | 100 | 100 |
| H1H29187P2 | 100 | 100 | 100 | 100 | 100 | 100 |
| REGN1932 | 100 | 100 | 100 | 100 | 100 | 100 |
| Reference sequence (3D7) | 100 | 100 | 100 | 100 | 100 | 100 |

In this example, a set of four (4) RH5-specific mAbs, each with hIgG1, of the invention were tested alone in an escape mutant assay with one strain of *Plasmodium falciparum* (3D7).

Monoclonal antibodies used were H1H29089P, H1H29100P, H1H29147P2, H1H29187P2 and REGN1932.

Experimental Procedure (include description of relevant cell lines, proteins, reagents, and instrument type and model): The *P. falciparum* strain, 3D7 (BEI Resources) was grown following standard protocols at 4% hematocrit and 0.5% parasitaemia. Infected erythrocytes were combined with PfRH5-specific or control antibodies at a concentration corresponding to their respective $IC_{50}$ value on the *P. falciparum* strain described above. Antibody concentration was gradually increased every 7-14 days, up to a final concentration corresponding to 110× their respective $IC_{50}$ values. Growth medium containing the antibody was refreshed every 48 hours and fresh blood was added to the culture weekly.

Every week, parasite RNA was extracted by Trizol lysis of infected red blood cells and purified by Qiagen RNeasy kit. Reverse transcription was completed with the High-Capacity cDNA Reverse Transcription Kit (Applied Biosystems). Amplification of the RH5 gene was performed using PfRH5-specific primers. PCR products were analyzed on 1.5% agarose gel and cloned into TOPO TA cloning vector (Life Technologies). Sequencing of RH5 was achieved with M13 forward and reverse sequencing primers.

Results summary and conclusions. Several groups have reported that targeting the reticulocyte-binding protein Example 8: Growth Inhibition Assay to Assess the Ability of Anti-PfRH5 Antibodies to Inhibit the In Vitro Invasion of Human Red Blood Cells and Growth of *P. falciparum* Parasites in the Presence of Serum

*Plasmodium falciparum* RH5 Specific Antibodies Inhibit Invasion of Human Red Blood Cells in a pLDH Based Growth Inhibition Assay in the Presence of Serum.

One group suggested that complement activation on the merozoite surface enhances the parasite's ability to invade red blood cells (Biryukov et al., Complement and Antibody-mediated Enhancement of Red Blood Cell Invasion and Growth of Malaria Parasites. EBioMedicine. 9, 207-216 (2016)). However, other studies indicate that the presence of complement active serum results in reduced or comparable parasite growth compared to complement inactive serum (Boyle et al, Human antibodies fix complement to inhibit *Plasmodium falciparum* invasion of erythrocytes and are associated with protection against malaria. Immunity. 42, 580-90 (2015); Chulay et al., Inhibition of in vitro growth of *Plasmodium falciparum* by immune serum from monkeys. J Infect Dis. 144, 270-278). Also, in all cases of vaccination of merozoite antigens in humans (or any malaria antigens), there are no documented cases of antibody-dependent increases in parasitemia.

In this example, a set of four (4) RH5-specific mAbs (each with hIgG1 (designated with a H1H prefix) or hIgG4 (designated with a H4H prefix)) of the invention were tested alone and in combination with *Aotus* monkey normal serum (ANS), *Aotus* heat-inactivated serum (AHIS), human normal serum (HNS) or human heat-inactivated serum (HHIS) in a standard growth inhibition assay with one strain of *Plasmodium falciparum* (FCR-1/FVO).

Monoclonal antibodies used were H1H29089P, H1H29100P, H1H29147P2, H1H29187P2, H4H29089P, H4H29100P, H4H29147P2, H4H29187P2, REGN1932 (anti-Fel d1 (human IgG1)) and REGN1945 (anti-Fel d1 (human IgG4)).

Experimental Procedure (include description of relevant cell lines, proteins, reagents, and instrument type and model). The *P. falciparum* strain, FCR-1/FVO (BEI Resources) was first synchronized with 5% D-sortibol following standard protocols at 3-5% hematocrit and 1-2% parasitaemia 20-24 hours prior to the start of the assay.

Infected human erythrocytes were prepared at a starting parasitaemia of 0.4-0.7% and 2% hematocrit. Infected erythrocytes were combined with RH5-specific or control antibodies, at a concentration of 6.67 µM in the presence of 10% *Aotus* normal serum, *Aotus* heat-inactivated serum, human normal serum or human heat-inactivated serum. The parasites were grown for 40-48 hours until the schizont stage was reached (one complete life cycle). Parasite growth was stopped with three washes of cold PBS. Final parasitaemia was determined by measuring the parasite lactate dehydrogenase (LDH) activity (Miura et al., Anti-Apical-Membrane-Antigen-1 antibody is more effective than anti-42-kilodalton-Merozoite-Surface-Protein-1 antibody in inhibiting *Plasmodium falciparum* growth, as determined by the in vitro growth inhibition assay. Clin Vaccine Immunol. 16, 963-968 (2009)). Percent growth inhibition is expressed relative to uninfected erythrocytes.

Results summary and conclusions. Targeting the reticulocyte-binding protein homolog 5 (RH5) protein efficiently blocks parasite invasion of human erythrocytes in vitro with *P. falciparum*. Conflicting findings have been published about the role of complement in merozoite invasion of red blood cells. RH5-specific antibodies were produced and tested in presence of *Aotus* or human sera in vitro in a growth inhibition assay in a *P. falciparum* strain as described above. Table 8-1 shows the maximum percent growth inhibition for each RH5-specific antibody (both hIgG1 and hIgG4 formats) with active or inactive serum complement. The individual antibodies and active or inactive serum combinations displayed similar percent maximum growth inhibition, ranging from approximately 67-86%.

TABLE 8-1

Summary of maximum growth inhibition activity of anti-PfRH5 antibodies, in the presence of 10% *Aotus* or human serum.

| | Percent Maximum Growth Inhibition | | | | |
|---|---|---|---|---|---|
| mAb | mAb (6.67 µM) + ANS (10%) | mAb (6.67 µM) + AHIS (10%) | mAb (6.67 µM) + HNS (10%) | mAb (6.67 µM) + HHIS (10%) | mAb (6.67 µM) + No serum |
| H1H29089P | 75.7 | 84.3 | 85.0 | 85.2 | 85.3 |
| H1H29100P | 73.2 | 82.5 | 82.4 | 81.9 | 83.9 |
| H1H29147P2 | 80.3 | 86.2 | 85.6 | 83.4 | 84.1 |
| H1H29187P2 | 80.1 | 89.4 | 85.9 | 85.4 | 85.3 |
| H4H29089p | 75.7 | 82.4 | 85.3 | 86.2 | 84.8 |
| H4H29100p | 67.7 | 79.8 | 75.5 | 79.6 | 83.9 |
| H4H29147P2 | 67.0 | 76.8 | 73.0 | 75.5 | 82.4 |
| H4H29187P2 | 69.9 | 82.9 | 77.0 | 77.8 | 84.0 |
| REGN1932 | 0 | 0 | 0 | 0 | 0 |
| REGN1945 | 0 | 0 | 0 | 0 | 0 |

Maximum growth inhibition of antibodies against PfRH5 relative to uninfected human red blood cells. The growth inhibition assay was performed on *P. falciparum* (mature trophozoite or early schizont) infected red blood cells at 0.4-0.7% parasitaemia. The antibodies and sera were combined with the infected red blood cells. The parasites were grown for 40-48 hours (the timing is parasite strain-dependent) until the schizont stage was reached. Parasite growth was stopped with three washes of cold PBS. Parasite lactate dehydrogenase (LDH) activity was measured immediately after the washes. Percent growth inhibition is expressed relative to uninfected erythrocytes. The results of one representative assay of the growth inhibition assay is shown above.

ANS: *Aotus* monkey normal serum,

AHIS: *Aotus* heat-inactivated serum,

HNS: Normal human serum,

HHIS: Human heat-inactivated serum.

All references cited herein are incorporated by reference to the same extent as if each individual publication, database entry (e.g., Genbank sequences or GeneID entries), patent application, or patent, was specifically and individually indicated to be incorporated by reference. This statement of incorporation by reference is intended by Applicants, to relate to each and every individual publication, database entry (e.g., Genbank sequences or GeneID entries), patent application, or patent even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

I claim:

1. An antigen-binding protein that specifically binds to *Plasmodium Falciparum* reticulocyte binding protein homologue 5 (PfRH5) polypeptide, wherein the antigen binding protein comprises a heavy chain variable region (HCVR) comprising complementarity determining regions (CDRs) HCDR1, HCDR2 and HCDR3 comprising the amino acid sequences of SEQ ID NOs: 4, 6 and 8, respectively, and a light chain variable region (LCVR) comprising CDRs LCDR1, LCDR2 and LCDR3 comprising the amino acid sequences of SEQ ID NOs: 12, 14 and 16, respectively.

2. The antigen-binding protein of claim 1, wherein the HCVR comprises the amino acid sequence of SEQ ID NO: 2 and the LCVR comprises the amino acid sequence of SEQ ID NO: 10.

3. The antigen-binding protein of claim 1, which is an antibody or antigen-binding fragment thereof.

4. The antigen-binding protein of claim 1, which is multispecific.

5. The antigen-binding protein of claim 1, which comprises one or more of the following properties:
   Inhibits growth of *Plasmodium falciparum* in human red blood cells;
   Inhibits growth of *Plasmodium falciparum* strain D10, Dd2, 7G8, W2-mef, 3D7, HB3, FCR-1/FVO, Cam3.II or RF7 in human red blood cells;
   Binds to PfRH5 polypeptide or an antigenic fragment thereof with a $K_D$ of about 4.72 pM to about 1.67 nM at 25° C. and/or of about 1.10 pM to about 1.10 nM at 37° C. when measured by surface plasmon resonance;
   Blocks binding of PfRH5 polypeptide to basigin polypeptide;
   Binds to PfRH5 lacking the amino-terminal residues M1-Y139 and including residues K140-Q526 but lacking K247-L295 and having the mutations T216A and T299A; and/or
   Causes maximal growth inhibition of *Plasmodium falciparum* in heat inactivated human or *Aotus* monkey serum that is about 1-10% higher than that of non-heat-inactivated human or *Aotus* monkey serum, respectively;
   When exposed to said antigen-binding protein, does not induce mutation of PfRH5 in *Plasmodium falciparum*.

6. A complex comprising an antigen-binding protein of claim 1 bound to a *Plasmodium falciparum* reticulocyte binding protein homologue 5 (PfRH5) polypeptide.

7. A composition or kit comprising the antigen-binding protein of claim 1.

8. A pharmaceutical composition comprising the antigen-binding protein of claim 1 and pharmaceutically acceptable carrier.

9. The composition or kit of claim 7 in association with a further therapeutic agent which is an anti-parasitic drug or a vaccine.

10. The composition or kit of claim 9, wherein the further therapeutic agent is selected from the group consisting of: chloroquine, atovaquone, proguanil, artemether, lumefantrine, mefloquine, quinine, quinidine, doxycycline, clindamycin, a vaccine, an anti-malarial vaccine and RTS,S/AS01.

11. A vessel or injection device comprising the antigen-binding protein of claim 1.

* * * * *

SEQUENCE LISTING

<160> NUMBER OF SEQ ID NOS: 365

<210> SEQ ID NO 1
<211> LENGTH: 360
<212> TYPE: DNA
<213> ORGANISM: Homo sapiens

<400> SEQUENCE: 1
gaggtgcagc tggtgcagtc tggagcagag gtgaaaaagc ccggggagtc tctgaagatc        60
tcctgtaagg gttctggata cagctttacc agttactgga tcgtctgggt gcgccagatg       120
cccgggaaag gcctggagtg gatggggatc atctatcctg gtgactctga taccagatac       180
agcccgtcct tccaaggcca ggtcaccatc tcagccgaca agtccatcag caccgcctac       240
ctgcagtgga gcagcctgaa ggcctcggac accgccatgt attactgtgc gagacaagat       300
ataactggaa ctacggggtt tgactactgg ggccagggaa ccctggtcac cgtctcctca       360

<210> SEQ ID NO 2
<211> LENGTH: 120
<212> TYPE: PRT
<213> ORGANISM: Homo Sapiens

<400> SEQUENCE: 2

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Val Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Asp Ile Thr Gly Thr Thr Gly Phe Asp Tyr Trp Gly Gln
            100                 105                 110

Gly Thr Leu Val Thr Val Ser Ser
        115                 120

<210> SEQ ID NO 3
<211> LENGTH: 24
<212> TYPE: DNA
<213> ORGANISM: Homo sapiens

<400> SEQUENCE: 3
ggatacagct ttaccagtta ctgg        24

<210> SEQ ID NO 4
<211> LENGTH: 8
<212> TYPE: PRT
<213> ORGANISM: Homo Sapiens

<400> SEQUENCE: 4

Gly Tyr Ser Phe Thr Ser Tyr Trp
1               5

<210> SEQ ID NO 5
<211> LENGTH: 24
<212> TYPE: DNA

<213> ORGANISM: Homo sapiens

<400> SEQUENCE: 5
atctatcctg gtgactctga tacc                                            24

<210> SEQ ID NO 6
<211> LENGTH: 8
<212> TYPE: PRT
<213> ORGANISM: Homo Sapiens

<400> SEQUENCE: 6

Ile Tyr Pro Gly Asp Ser Asp Thr
1               5

<210> SEQ ID NO 7
<211> LENGTH: 39
<212> TYPE: DNA
<213> ORGANISM: Homo sapiens

<400> SEQUENCE: 7
gcgagacaag atataactgg aactacgggg tttgactac                             39

<210> SEQ ID NO 8
<211> LENGTH: 13
<212> TYPE: PRT
<213> ORGANISM: Homo Sapiens

<400> SEQUENCE: 8

Ala Arg Gln Asp Ile Thr Gly Thr Thr Gly Phe Asp Tyr
1               5                   10

<210> SEQ ID NO 9
<211> LENGTH: 324
<212> TYPE: DNA
<213> ORGANISM: Homo sapiens

<400> SEQUENCE: 9
gacatccaga tgacccagtc tccatcctcc ctgtctgcat ctgtaggaga cagagtcacc     60
atcacttgcc gggcaagtca gagcattagg aactatttga attggtatca gcagaaacca    120
gggaaagccc ctaagctcct gatctatgct gcatccagtt tgcaaagtgg ggtcccatca    180
aggttcagtg gcagtggatc tgggacagat tcactctcac ccatcagcag tctgcaacct    240
gaagattttg caacttattt ctgtcaacag agttacagta ccccattcac tttcggccct    300
gggaccaaag tggatatcaa acga                                           324

<210> SEQ ID NO 10
<211> LENGTH: 108
<212> TYPE: PRT
<213> ORGANISM: Homo Sapiens

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro

```
                65                  70                  75                  80
Glu Asp Phe Ala Thr Tyr Phe Cys Gln Gln Ser Tyr Ser Thr Pro Phe
                    85                  90                  95

Thr Phe Gly Pro Gly Thr Lys Val Asp Ile Lys Arg
            100                 105
```

<210> SEQ ID NO 11
<211> LENGTH: 18
<212> TYPE: DNA
<213> ORGANISM: Homo sapiens

<400> SEQUENCE: 11
cagagcatta ggaactat                                                       18

<210> SEQ ID NO 12
<211> LENGTH: 6
<212> TYPE: PRT
<213> ORGANISM: Homo Sapiens

<400> SEQUENCE: 12

```
Gln Ser Ile Arg Asn Tyr
1               5
```

<210> SEQ ID NO 13
<211> LENGTH: 9
<212> TYPE: DNA
<213> ORGANISM: Homo sapiens

<400> SEQUENCE: 13 gctgcatcc                                                                  9

<210> SEQ ID NO 14
<211> LENGTH: 3
<212> TYPE: PRT
<213> ORGANISM: Homo Sapiens

<400> SEQUENCE: 14

```
Ala Ala Ser
1
```

<210> SEQ ID NO 15
<211> LENGTH: 27
<212> TYPE: DNA
<213> ORGANISM: Homo sapiens

<400> SEQUENCE: 15
caacagagtt acagtacccc attcact                                             27

<210> SEQ ID NO 16
<211> LENGTH: 9
<212> TYPE: PRT
<213> ORGANISM: Homo Sapiens

<400> SEQUENCE: 16

```
Gln Gln Ser Tyr Ser Thr Pro Phe Thr
1               5
```

<210> SEQ ID NO 17
<211> LENGTH: 369
<212> TYPE: DNA
<213> ORGANISM: Homo sapiens

<400> SEQUENCE: 17

```
caggtgcagc tggtggagtc tgggggagac gtggtccagc ctggggaggtc cctgcgactc      60 tcctgttcag gcactggatt caccttcagt agctatgcca tgcactgggt ccgccaggct     120
ccaggcaagg gactggaatg ggtggcactt atatcatatg atggaagtaa taaatattat     180
ggagactccg tgaagggccg attcaccgtc tccagagaca attccaagaa cacgctgtct     240
ctgcaaatga acagcctgaa aactgaggac acggcgatat attactgtgc gaaagagagg     300 cttttttggag tggtctctta ttacggtatg gacgtctggg gccaagggac cacggtcacc     360
gtctcctca                                                             369
```

<210> SEQ ID NO 18
<211> LENGTH: 123
<212> TYPE: PRT
<213> ORGANISM: Homo Sapiens

<400> SEQUENCE: 18

Gln Val Gln Leu Val Glu Ser Gly Gly Asp Val Val Gln Pro Gly Arg
1               5                   10                  15

Ser Leu Arg Leu Ser Cys Ser Gly Thr Gly Phe Thr Phe Ser Ser Tyr
            20                  25                  30

Ala Met His Trp Val Arg Gln Ala Pro Gly Lys Gly Leu Glu Trp Val
        35                  40                  45

Ala Leu Ile Ser Tyr Asp Gly Ser Asn Lys Tyr Tyr Gly Asp Ser Val
    50                  55                  60

Lys Gly Arg Phe Thr Val Ser Arg Asp Asn Ser Lys Asn Thr Leu Ser
65                  70                  75                  80

Leu Gln Met Asn Ser Leu Lys Thr Glu Asp Thr Ala Ile Tyr Tyr Cys
                85                  90                  95

Ala Lys Glu Arg Leu Phe Gly Val Val Ser Tyr Tyr Gly Met Asp Val
            100                 105                 110

Trp Gly Gln Gly Thr Thr Val Thr Val Ser Ser
        115                 120

<210> SEQ ID NO 19
<211> LENGTH: 24
<212> TYPE: DNA
<213> ORGANISM: Homo sapiens

<400> SEQUENCE: 19
ggattcacct tcagtagcta tgcc                                             24

<210> SEQ ID NO 20
<211> LENGTH: 8
<212> TYPE: PRT
<213> ORGANISM: Homo Sapiens

<400> SEQUENCE: 20

Gly Phe Thr Phe Ser Ser Tyr Ala
1               5

<210> SEQ ID NO 21
<211> LENGTH: 24
<212> TYPE: DNA
<213> ORGANISM: Homo sapiens

<400> SEQUENCE: 21
atatcatatg atggaagtaa taaa                                             24

<210> SEQ ID NO 22

```
<211> LENGTH: 8
<212> TYPE: PRT
<213> ORGANISM: Homo Sapiens

<400> SEQUENCE: 22

Ile Ser Tyr Asp Gly Ser Asn Lys
1               5

<210> SEQ ID NO 23
<211> LENGTH: 48
<212> TYPE: DNA
<213> ORGANISM: Homo sapiens

<400> SEQUENCE: 23
gcgaaagaga ggcttttggg agtggtctct tattacggta tggacgtc            48

<210> SEQ ID NO 24
<211> LENGTH: 16
<212> TYPE: PRT
<213> ORGANISM: Homo Sapiens

<400> SEQUENCE: 24

Ala Lys Glu Arg Leu Phe Gly Val Val Ser Tyr Tyr Gly Met Asp Val
1               5                   10                  15

<210> SEQ ID NO 25
<211> LENGTH: 324
<212> TYPE: DNA
<213> ORGANISM: Homo sapiens

<400> SEQUENCE: 25
gacatccaga tgacccagtc tccatcctcc ctgtctgcat ctgtaggaga cagagtcacc     60
atcacttgcc aggcgagtca ggacattaat agggatctaa attggtatca gcagaaatca    120
gggaaaggcc ccaaactcct gatctacgat gcatccaatt tggaaacagg ggtcccatca    180
aggttcagtg gaaatagatt tgggacagat tttactttca ccatcagcag actgcagcct    240
gaagatattg caacatattt ctgtcaacag tataaaaatc tcccgtacac ttttggccag    300
gggaccaagc tggagatcaa acga                                            324

<210> SEQ ID NO 26
<211> LENGTH: 108
<212> TYPE: PRT
<213> ORGANISM: Homo sapiens

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Asn Arg Asp
                20                  25                  30

Leu Asn Trp Tyr Gln Gln Lys Ser Gly Lys Gly Pro Lys Leu Leu Ile
            35                  40                  45

Tyr Asp Ala Ser Asn Leu Glu Thr Gly Val Pro Ser Arg Phe Ser Gly
        50                  55                  60

Asn Arg Phe Gly Thr Asp Phe Thr Phe Thr Ile Ser Arg Leu Gln Pro
65                  70                  75                  80

Glu Asp Ile Ala Thr Tyr Phe Cys Gln Gln Tyr Lys Asn Leu Pro Tyr
                85                  90                  95

Thr Phe Gly Gln Gly Thr Lys Leu Glu Ile Lys Arg
            100                 105
```

<210> SEQ ID NO 27
<211> LENGTH: 18
<212> TYPE: DNA
<213> ORGANISM: Homo sapiens

<400> SEQUENCE: 27
caggacatta atagggat                                                       18

<210> SEQ ID NO 28
<211> LENGTH: 6
<212> TYPE: PRT
<213> ORGANISM: Homo Sapiens

<400> SEQUENCE: 28

Gln Asp Ile Asn Arg Asp
1               5

<210> SEQ ID NO 29
<211> LENGTH: 9
<212> TYPE: DNA
<213> ORGANISM: Homo sapiens

<400> SEQUENCE: 29 gatgcatcc                                                                  9

<210> SEQ ID NO 30
<211> LENGTH: 3
<212> TYPE: PRT
<213> ORGANISM: Homo Sapiens

<400> SEQUENCE: 30

Asp Ala Ser
1

<210> SEQ ID NO 31
<211> LENGTH: 27
<212> TYPE: DNA
<213> ORGANISM: Homo sapiens

<400> SEQUENCE: 31
caacagtata aaaatctccc gtacact                                             27

<210> SEQ ID NO 32
<211> LENGTH: 9
<212> TYPE: PRT
<213> ORGANISM: Homo Sapiens

<400> SEQUENCE: 32

Gln Gln Tyr Lys Asn Leu Pro Tyr Thr
1               5

<210> SEQ ID NO 33
<211> LENGTH: 357
<212> TYPE: DNA
<213> ORGANISM: Homo sapiens

<400> SEQUENCE: 33
cagctgcagc tgcaggagtc gggcccagga ctggtgaagc cttcggagac cctgtccctc         60
acctgcactg tctctggtgg ctccatcagc agtagtagtt actactgggg ctggatccgc        120
cagcccccag ggaagggcct ggagtggatt gggattatct attatagtgg gagcacctac        180
tacaacccgt ccctcaagag tcgagtcacc atttccgtag acacgtccaa gaaccagttc        240

```
tccctgaagc tgagctctgt gaccgccgca gacacggctg tgtattactg tgcgagacag    300
gacagggagg ccctctttga ctactggggc cagggaaccc tggtcaccgt ctcctca      357
```

<210> SEQ ID NO 34
<211> LENGTH: 119
<212> TYPE: PRT
<213> ORGANISM: Homo Sapiens

<400> SEQUENCE: 34

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ile Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gln Asp Arg Glu Ala Leu Phe Asp Tyr Trp Gly Gln Gly
            100                 105                 110

Thr Leu Val Thr Val Ser Ser
        115
```

<210> SEQ ID NO 35
<211> LENGTH: 30
<212> TYPE: DNA
<213> ORGANISM: Homo sapiens

<400> SEQUENCE: 35

```
ggtggctcca tcagcagtag tagttactac                                      30
```

<210> SEQ ID NO 36
<211> LENGTH: 10
<212> TYPE: PRT
<213> ORGANISM: Homo Sapiens

<400> SEQUENCE: 36

```
Gly Gly Ser Ile Ser Ser Ser Ser Tyr Tyr
1               5                   10
```

<210> SEQ ID NO 37
<211> LENGTH: 21
<212> TYPE: DNA
<213> ORGANISM: Homo sapiens

<400> SEQUENCE: 37

```
atctattata gtgggagcac c                                               21
```

<210> SEQ ID NO 38
<211> LENGTH: 7
<212> TYPE: PRT
<213> ORGANISM: Homo Sapiens

<400> SEQUENCE: 38

```
Ile Tyr Tyr Ser Gly Ser Thr
1               5
```

```
<210> SEQ ID NO 39
<211> LENGTH: 33
<212> TYPE: DNA
<213> ORGANISM: Homo sapiens

<400> SEQUENCE: 39
gcgagacagg acagggaggc cctctttgac tac                          33

<210> SEQ ID NO 40
<211> LENGTH: 11
<212> TYPE: PRT
<213> ORGANISM: Homo Sapiens

<400> SEQUENCE: 40

Ala Arg Gln Asp Arg Glu Ala Leu Phe Asp Tyr
1               5                   10

<210> SEQ ID NO 41
<211> LENGTH: 321
<212> TYPE: DNA
<213> ORGANISM: Homo sapiens

<400> SEQUENCE: 41
gaaattgtgc tgactcagtc tccagacttt cagtctgtga ctccaaagga gaaagtcacc    60
atcacctgcc gggccagtca gcgcattggt agtagcttac actggtacca gcagaaacca   120
gatcagtctc caaagctcct catcaagtat gcttcccagt ccttctcagg ggtcccctcg   180
aggttcagtg gcagtggatc tgggacagat ttcaccctca ccatcaatag cctggaagct   240
gaagatgctg caacgtatta ctgtcatcag agtagtactt tacccacctt cggccaaggg   300
acacgactgg agattaaacg a                                             321

<210> SEQ ID NO 42
<211> LENGTH: 107
<212> TYPE: PRT
<213> ORGANISM: Homo Sapiens

<400> SEQUENCE: 42

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Arg Ile Gly Ser Ser
                20                  25                  30

Leu His Trp Tyr Gln Gln Lys Pro Asp Gln Ser Pro Lys Leu Leu Ile
            35                  40                  45

Lys Tyr Ala Ser Gln Ser Phe Ser Gly Val Pro Ser Arg Phe Ser Gly
        50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Thr Leu Pro Thr
                85                  90                  95

Phe Gly Gln Gly Thr Arg Leu Glu Ile Lys Arg
            100                 105

<210> SEQ ID NO 43
<211> LENGTH: 18
<212> TYPE: DNA
<213> ORGANISM: Homo sapiens

<400> SEQUENCE: 43
cagcgcattg gtagtagc                                                   18
```

```
<210> SEQ ID NO 44
<211> LENGTH: 6
<212> TYPE: PRT
<213> ORGANISM: Homo Sapiens

<400> SEQUENCE: 44

Gln Arg Ile Gly Ser Ser
1               5

<210> SEQ ID NO 45
<211> LENGTH: 9
<212> TYPE: DNA
<213> ORGANISM: Homo sapiens

<400> SEQUENCE: 45 tatgcttcc                                                                  9

<210> SEQ ID NO 46
<211> LENGTH: 3
<212> TYPE: PRT
<213> ORGANISM: Homo Sapiens

<400> SEQUENCE: 46

Tyr Ala Ser
1

<210> SEQ ID NO 47
<211> LENGTH: 24
<212> TYPE: DNA
<213> ORGANISM: Homo sapiens

<400> SEQUENCE: 47
catcagagta gtactttacc cacc                                                24

<210> SEQ ID NO 48
<211> LENGTH: 8
<212> TYPE: PRT
<213> ORGANISM: Homo Sapiens

<400> SEQUENCE: 48

His Gln Ser Ser Thr Leu Pro Thr
1               5

<210> SEQ ID NO 49
<211> LENGTH: 375
<212> TYPE: DNA
<213> ORGANISM: Homo sapiens

<400> SEQUENCE: 49
gaagtgcagc tggtggagtc tgggggaggc ctggtacagc ctggcaggtc cctgagactc         60
tcctgtgcag cctctggatt caggtttgac gattatgcca tgcactgggt ccgacaagct        120
ccagggaagg gcctggaatg ggtctcaggt attaattgga atagtggtgg caaaggctat        180
gcggactctg tgcagggccg attcaccatc tccagagaca cgccaagaa ctccctttat         240 ctgcaaatga acagtctgag aactgaggac acggccttgt attattgtgc aaaagatagg        300
ggtatagcag ctcgtcttct ctctcgtgat gcttttgata tgtggggcca agggacaatg        360
gtcaccgtct cttca                                                         375

<210> SEQ ID NO 50
<211> LENGTH: 125
<212> TYPE: PRT
```

<213> ORGANISM: Homo Sapiens

<400> SEQUENCE: 50

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Arg Phe Asp Asp Tyr
            20                  25                  30

Ala Met His Trp Val Arg Gln Ala Pro Gly Lys Gly Leu Glu Trp Val
        35                  40                  45

Ser Gly Ile Asn Trp Asn Ser Gly Lys Gly Tyr Ala Asp Ser Val
    50                  55                  60

Gln Gly Arg Phe Thr Ile Ser Arg Asp Asn Ala Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Lys Asp Arg Gly Ile Ala Ala Arg Leu Leu Ser Arg Asp Ala Phe
            100                 105                 110

Asp Met Trp Gly Gln Gly Thr Met Val Thr Val Ser Ser
            115                 120                 125

<210> SEQ ID NO 51
<211> LENGTH: 24
<212> TYPE: DNA
<213> ORGANISM: Homo sapiens

<400> SEQUENCE: 51
ggattcaggt ttgacgatta tgcc                                          24

<210> SEQ ID NO 52
<211> LENGTH: 8
<212> TYPE: PRT
<213> ORGANISM: Homo Sapiens

<400> SEQUENCE: 52

Gly Phe Arg Phe Asp Asp Tyr Ala
1               5

<210> SEQ ID NO 53
<211> LENGTH: 24
<212> TYPE: DNA
<213> ORGANISM: Homo sapiens

<400> SEQUENCE: 53
attaattgga atagtggtgg caaa                                          24

<210> SEQ ID NO 54
<211> LENGTH: 8
<212> TYPE: PRT
<213> ORGANISM: Homo Sapiens

<400> SEQUENCE: 54

Ile Asn Trp Asn Ser Gly Gly Lys
1               5

<210> SEQ ID NO 55
<211> LENGTH: 54
<212> TYPE: DNA
<213> ORGANISM: Homo sapiens

<400> SEQUENCE: 55
gcaaaagata ggggtatagc agctcgtctt ctctctcgtg atgcttttga tatg          54

<210> SEQ ID NO 56
<211> LENGTH: 18
<212> TYPE: PRT
<213> ORGANISM: Homo Sapiens

<400> SEQUENCE: 56

Ala Lys Asp Arg Gly Ile Ala Ala Arg Leu Leu Ser Arg Asp Ala Phe
1               5                   10                  15

Asp Met

<210> SEQ ID NO 57
<211> LENGTH: 324
<212> TYPE: DNA
<213> ORGANISM: Homo sapiens

<400> SEQUENCE: 57
gacatccagt tgacccagtc tccatccttc ctgtctgcat ctgtaggaga cagagtcacc    60
atcacttgct gggccagtca ggacgttagc agttatttag cctggtatca gcaaaaacca   120
gggaaatccc ctaagctcct aatctttgct gcatccactt tgcaaggtgg gatcccatca   180
aggttcagcg gcagtggatc tgggacagaa ttcactctca caatcagcag cctgcggcct   240
gaagattttg caacttatta ctgtcaacac cttaatactt acccgtacac ttttggccag   300
gggaccaagc tggagatcaa acga                                          324

<210> SEQ ID NO 58
<211> LENGTH: 108
<212> TYPE: PRT
<213> ORGANISM: Homo Sapiens

<400> SEQUENCE: 58

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Asp Val Ser Ser Tyr
            20                  25                  30

Leu Ala Trp Tyr Gln Gln Lys Pro Gly Lys Ser Pro Lys Leu Leu Ile
        35                  40                  45

Phe Ala Ala Ser Thr Leu Gln Gly Gly Ile Pro Ser Arg Phe Ser Gly
    50                  55                  60

Ser Gly Ser Gly Thr Glu Phe Thr Leu Thr Ile Ser Ser Leu Arg Pro
65                  70                  75                  80

Glu Asp Phe Ala Thr Tyr Tyr Cys Gln His Leu Asn Thr Tyr Pro Tyr
                85                  90                  95

Thr Phe Gly Gln Gly Thr Lys Leu Glu Ile Lys Arg
            100                 105

<210> SEQ ID NO 59
<211> LENGTH: 18
<212> TYPE: DNA
<213> ORGANISM: Homo sapiens

<400> SEQUENCE: 59
caggacgtta gcagttat                                                  18

<210> SEQ ID NO 60
<211> LENGTH: 6
<212> TYPE: PRT
<213> ORGANISM: Homo Sapiens

```
<400> SEQUENCE: 60

Gln Asp Val Ser Ser Tyr
1               5

<210> SEQ ID NO 61
<211> LENGTH: 9
<212> TYPE: DNA
<213> ORGANISM: Homo sapiens

<400> SEQUENCE: 61 gctgcatcc                                                                  9

<210> SEQ ID NO 62
<211> LENGTH: 3
<212> TYPE: PRT
<213> ORGANISM: Homo Sapiens

<400> SEQUENCE: 62

Ala Ala Ser
1

<210> SEQ ID NO 63
<211> LENGTH: 27
<212> TYPE: DNA
<213> ORGANISM: Homo sapiens

<400> SEQUENCE: 63
caacacctta atacttaccc gtacact                                             27

<210> SEQ ID NO 64
<211> LENGTH: 9
<212> TYPE: PRT
<213> ORGANISM: Homo Sapiens

<400> SEQUENCE: 64

Gln His Leu Asn Thr Tyr Pro Tyr Thr
1               5

<210> SEQ ID NO 65
<211> LENGTH: 363
<212> TYPE: DNA
<213> ORGANISM: Homo sapiens

<400> SEQUENCE: 65
caggtgcagc tggtggagtc tgggggaggc gtggtccagt ctggggaggt cctgagactc         60
tcctgtgcag cgtcttcatt caccttcagt agctatggca tgcactgggt ccgccagtct        120
ccaggcaagg ggctggagtg ggtggcagtt ataagttatg atggaagtaa taaatactat        180
ggagacttcg tgaggggccg attcaccatc tccagagaca attccaagaa cacgctgtat        240
ctgcaaatga acagcctgag agccgaggac acggctatgt attattgtgc gagagaagtt        300
cgtcgctact attattacgg tatggacgtc tggggccaag gaccacggt caccgtctcc        360 tca                                                                      363

<210> SEQ ID NO 66
<211> LENGTH: 121
<212> TYPE: PRT
<213> ORGANISM: Homo sapiens

<400> SEQUENCE: 66

Gln Val Gln Leu Val Glu Ser Gly Gly Gly Val Val Gln Ser Gly Arg
1               5                   10                  15
```

```
Ser Leu Arg Leu Ser Cys Ala Ala Ser Ser Phe Thr Phe Ser Ser Tyr
         20                  25                  30

Gly Met His Trp Val Arg Gln Ser Pro Gly Lys Gly Leu Glu Trp Val
         35                  40                  45

Ala Val Ile Ser Tyr Asp Gly Ser Asn Lys Tyr Tyr Gly Asp Phe Val
 50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Met Tyr Tyr Cys
                 85                  90                  95

Ala Arg Glu Val Arg Arg Tyr Tyr Tyr Gly Met Asp Val Trp Gly
            100                 105                 110

Gln Gly Thr Thr Val Thr Val Ser Ser
        115                 120

<210> SEQ ID NO 67
<211> LENGTH: 24
<212> TYPE: DNA
<213> ORGANISM: Homo sapiens

<400> SEQUENCE: 67
tcattcacct tcagtagcta tggc                                          24

<210> SEQ ID NO 68
<211> LENGTH: 8
<212> TYPE: PRT
<213> ORGANISM: Homo Sapiens

<400> SEQUENCE: 68

Ser Phe Thr Phe Ser Ser Tyr Gly
 1               5

<210> SEQ ID NO 69
<211> LENGTH: 24
<212> TYPE: DNA
<213> ORGANISM: Homo sapiens

<400> SEQUENCE: 69
ataagttatg atggaagtaa taaa                                          24

<210> SEQ ID NO 70
<211> LENGTH: 8
<212> TYPE: PRT
<213> ORGANISM: Homo Sapiens

<400> SEQUENCE: 70

Ile Ser Tyr Asp Gly Ser Asn Lys
 1               5

<210> SEQ ID NO 71
<211> LENGTH: 42
<212> TYPE: DNA
<213> ORGANISM: Homo sapiens

<400> SEQUENCE: 71
gcgagagaag ttcgtcgcta ctattattac ggtatggacg tc                      42

<210> SEQ ID NO 72
<211> LENGTH: 14
<212> TYPE: PRT
<213> ORGANISM: Homo Sapiens
```

<400> SEQUENCE: 72

Ala Arg Glu Val Arg Arg Tyr Tyr Tyr Gly Met Asp Val
1               5                   10

<210> SEQ ID NO 73
<211> LENGTH: 324
<212> TYPE: DNA
<213> ORGANISM: Homo sapiens

<400> SEQUENCE: 73

```
gacatccaga tgacccagtc tccatcctcc ctgtctgcat ctgtaggaga cagagtcacc    60
atcacttgcc aggcgagtca ggacattagt aattatttaa attggtatct gcagaaacca   120
gggaaagccc ctaagctcct gatctccgat gcatccaatt tggaaacagg ggtcccatca   180
aggttcagtg aagtggatc tgggacagat tttactttca ccatcagcag cctgcagcct   240
gaagatattg caacatatta ctgtcaacag tataataatc tcccgctcac tttcggcgga   300
gggaccaagg tggagatcaa acga                                          324
```

<210> SEQ ID NO 74
<211> LENGTH: 108
<212> TYPE: PRT
<213> ORGANISM: Homo Sapiens

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Leu Gln Lys Pro Gly Lys Ala Pro Lys Leu Leu Ile
        35                  40                  45

Ser Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asn Asn Leu Pro Leu
                85                  90                  95

Thr Phe Gly Gly Gly Thr Lys Val Glu Ile Lys Arg
            100                 105

<210> SEQ ID NO 75
<211> LENGTH: 18
<212> TYPE: DNA
<213> ORGANISM: Homo sapiens

<400> SEQUENCE: 75
caggacatta gtaattat                                                  18

<210> SEQ ID NO 76
<211> LENGTH: 6
<212> TYPE: PRT
<213> ORGANISM: Homo Sapiens

<400> SEQUENCE: 76

Gln Asp Ile Ser Asn Tyr
1               5

<210> SEQ ID NO 77
<211> LENGTH: 9

```
<212> TYPE: DNA
<213> ORGANISM: Homo sapiens

<400> SEQUENCE: 77 gatgcatcc                                                                    9

<210> SEQ ID NO 78
<211> LENGTH: 3
<212> TYPE: PRT
<213> ORGANISM: Homo Sapiens

<400> SEQUENCE: 78

Asp Ala Ser
1

<210> SEQ ID NO 79
<211> LENGTH: 27
<212> TYPE: DNA
<213> ORGANISM: Homo sapiens

<400> SEQUENCE: 79
caacagtata ataatctccc gctcact                                               27

<210> SEQ ID NO 80
<211> LENGTH: 9
<212> TYPE: PRT
<213> ORGANISM: Homo Sapiens

<400> SEQUENCE: 80

Gln Gln Tyr Asn Asn Leu Pro Leu Thr
1               5

<210> SEQ ID NO 81
<211> LENGTH: 372
<212> TYPE: DNA
<213> ORGANISM: Homo sapiens

<400> SEQUENCE: 81
gaagtgcagc tggtggagtc tgggggaggc ttggtacagc ctggcaggtc cctgagactc           60
tcctgtgcag tctctggatt cacctttgat gattatgcca tgcactgggt ccggcaagct          120
ccagggaagg gcctggagtg ggtctcaggt attagttgga atagtggtga catagactat          180
gcggactctg tgaagggccg attcaccatt tccagagaca cgccaagaa ctccctgtat           240
ctgcaaatga acagtctgag agctgaggac acggccttgt attactgtgc aaaagatacc          300
ctctcaggga ctggaactac gtggtactat tttgactact ggggccaggg aaccctggtc          360
accgtctcct ca                                                              372

<210> SEQ ID NO 82
<211> LENGTH: 124
<212> TYPE: PRT
<213> ORGANISM: Homo Sapiens

<400> SEQUENCE: 82

Glu Val Gln Leu Val Glu Ser Gly Gly Gly Leu Val Gln Pro Gly Arg
1               5                   10                  15

Ser Leu Arg Leu Ser Cys Ala Val Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Asp Ile Asp Tyr Ala Asp Ser Val
```

```
            50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Asp Thr Leu Ser Gly Thr Gly Thr Thr Trp Tyr Tyr Phe Asp
            100                 105                 110

Tyr Trp Gly Gln Gly Thr Leu Val Thr Val Ser Ser
        115                 120
```

<210> SEQ ID NO 83
<211> LENGTH: 24
<212> TYPE: DNA
<213> ORGANISM: Homo sapiens

<400> SEQUENCE: 83
ggattcacct ttgatgatta tgcc                                             24

<210> SEQ ID NO 84
<211> LENGTH: 8
<212> TYPE: PRT
<213> ORGANISM: Homo Sapiens

<400> SEQUENCE: 84

```
Gly Phe Thr Phe Asp Asp Tyr Ala
 1               5
```

<210> SEQ ID NO 85
<211> LENGTH: 24
<212> TYPE: DNA
<213> ORGANISM: Homo sapiens

<400> SEQUENCE: 85
attagttgga atagtggtga cata                                             24

<210> SEQ ID NO 86
<211> LENGTH: 8
<212> TYPE: PRT
<213> ORGANISM: Homo Sapiens

<400> SEQUENCE: 86

```
Ile Ser Trp Asn Ser Gly Asp Ile
 1               5
```

<210> SEQ ID NO 87
<211> LENGTH: 51
<212> TYPE: DNA
<213> ORGANISM: Homo sapiens

<400> SEQUENCE: 87
gcaaaagata ccctctcagg gactggaact acgtggtact attttgacta c               51

<210> SEQ ID NO 88
<211> LENGTH: 17
<212> TYPE: PRT
<213> ORGANISM: Homo Sapiens

<400> SEQUENCE: 88

```
Ala Lys Asp Thr Leu Ser Gly Thr Gly Thr Thr Trp Tyr Tyr Phe Asp
 1               5                  10                  15

Tyr
```

<210> SEQ ID NO 89
<211> LENGTH: 324
<212> TYPE: DNA
<213> ORGANISM: Homo sapiens

<400> SEQUENCE: 89
gacatccagt tgacccagtc tccatccttc ctgtctgcat ctgtaggaga cagagtcacc     60
atcacttgct gggccagtca gggtattagc agttatttaa tctggtatca gcaaaaacca    120
gggaaagccc ctaagctcct gatctatgct gcatccactt tgcaaagtgg ggtcccatca    180
aggttcagcg gcagtggatc tgggacagaa ttcactctca caatcagcag cctgcagcct    240
gaagattttg caacttatta ctgtcaacag gtgaatagtt accctctcac tttcggcgga    300
gggaccaagg tggagatcaa acga                                           324

<210> SEQ ID NO 90
<211> LENGTH: 108
<212> TYPE: PRT
<213> ORGANISM: Homo Sapiens

<400> SEQUENCE: 90

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ile Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Val Asn Ser Tyr Pro Leu
                85                  90                  95

Thr Phe Gly Gly Gly Thr Lys Val Glu Ile Lys Arg
            100                 105

<210> SEQ ID NO 91
<211> LENGTH: 18
<212> TYPE: DNA
<213> ORGANISM: Homo sapiens

<400> SEQUENCE: 91
cagggtatta gcagttat                                                   18

<210> SEQ ID NO 92
<211> LENGTH: 6
<212> TYPE: PRT
<213> ORGANISM: Homo Sapiens

<400> SEQUENCE: 92

Gln Gly Ile Ser Ser Tyr
1               5

<210> SEQ ID NO 93
<211> LENGTH: 9
<212> TYPE: DNA
<213> ORGANISM: Homo sapiens

<400> SEQUENCE: 93 gctgcatcc                                                              9

<210> SEQ ID NO 94
<211> LENGTH: 3
<212> TYPE: PRT
<213> ORGANISM: Homo Sapiens

<400> SEQUENCE: 94

Ala Ala Ser
1

<210> SEQ ID NO 95
<211> LENGTH: 27
<212> TYPE: DNA
<213> ORGANISM: Homo sapiens

<400> SEQUENCE: 95
caacaggtga atagttaccc tctcact        27

<210> SEQ ID NO 96
<211> LENGTH: 9
<212> TYPE: PRT
<213> ORGANISM: Homo Sapiens

<400> SEQUENCE: 96

Gln Gln Val Asn Ser Tyr Pro Leu Thr
1               5

<210> SEQ ID NO 97
<211> LENGTH: 369
<212> TYPE: DNA
<213> ORGANISM: Homo sapiens

<400> SEQUENCE: 97
caggtgcagc tggtggagtc tgggggaggc gtggtccagc ctggagggtc cctgagactc        60
tcctgtgcag cctctggatt caccttcagt agttatggca tgcactgggt ccgccaggct       120
ccaggcaagg gactggagtg gatggcagtt atatcatatg atggaagtaa taaatattat       180
gcagactccg tgaagggccg attcaccatc tccagagaca attccaagaa cacgctgttt       240
ctgcaaatga acagcctgag acctgaagac acggctgtat attactgtgc gcaagatggc       300
agctcggcga tttactattt ctacggtatg gacgtctggg gccaagggac cacggtcacc       360
gtctcctca                                                              369

<210> SEQ ID NO 98
<211> LENGTH: 123
<212> TYPE: PRT
<213> ORGANISM: Homo Sapiens

<400> SEQUENCE: 98

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Met
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met Asn Ser Leu Arg Pro Glu Asp Thr Ala Val Tyr Tyr Cys

```
                    85                  90                  95

Ala Gln Asp Gly Ser Ser Ala Ile Tyr Tyr Phe Tyr Gly Met Asp Val
            100                 105                 110

Trp Gly Gln Gly Thr Thr Val Thr Val Ser Ser
        115                 120

<210> SEQ ID NO 99
<211> LENGTH: 24
<212> TYPE: DNA
<213> ORGANISM: Homo sapiens

<400> SEQUENCE: 99
ggattcacct tcagtagtta tggc                                          24

<210> SEQ ID NO 100
<211> LENGTH: 8
<212> TYPE: PRT
<213> ORGANISM: Homo Sapiens

<400> SEQUENCE: 100

Gly Phe Thr Phe Ser Ser Tyr Gly
1               5

<210> SEQ ID NO 101
<211> LENGTH: 24
<212> TYPE: DNA
<213> ORGANISM: Homo sapiens

<400> SEQUENCE: 101
atatcatatg atggaagtaa taaa                                          24

<210> SEQ ID NO 102
<211> LENGTH: 8
<212> TYPE: PRT
<213> ORGANISM: Homo Sapiens

<400> SEQUENCE: 102

Ile Ser Tyr Asp Gly Ser Asn Lys
1               5

<210> SEQ ID NO 103
<211> LENGTH: 48
<212> TYPE: DNA
<213> ORGANISM: Homo sapiens

<400> SEQUENCE: 103
gcgcaagatg gcagctcggc gatttactat ttctacggta tggacgtc                48

<210> SEQ ID NO 104
<211> LENGTH: 16
<212> TYPE: PRT
<213> ORGANISM: Homo Sapiens

<400> SEQUENCE: 104

Ala Gln Asp Gly Ser Ser Ala Ile Tyr Tyr Phe Tyr Gly Met Asp Val
1               5                   10                  15

<210> SEQ ID NO 105
<211> LENGTH: 324
<212> TYPE: DNA
<213> ORGANISM: Homo sapiens

<400> SEQUENCE: 105
```

```
gacatccaga tgacccagtc tccatcctca ctgtctgcat ctataggaga cagagtcacc    60
atcacttgtc gggcgagtca ggacatcaac aattatttag cctggtttca gcagaaacca   120
gggaaagccc ctaagtccct gatctatgct gcatccagtt tgcaaagtgg ggtcccatca   180
aagttcagcg gcagtggatc tgggacagat ttcactctca ccatcagcag cctgcagcct   240
gaagattttg caacttatta ctgccttcag tataatagtt accatcccac ttttggccag   300
gggaccaagc tggagatcaa acga                                          324
```

```
<210> SEQ ID NO 106
<211> LENGTH: 108
<212> TYPE: PRT
<213> ORGANISM: Homo Sapiens

<400> SEQUENCE: 106

Asp Ile Gln Met Thr Gln Ser Pro Ser Ser Leu Ser Ala Ser Ile Gly
1               5                   10                  15

Asp Arg Val Thr Ile Thr Cys Arg Ala Ser Gln Asp Ile Asn Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Tyr Asn Ser Tyr His Pro
                85                  90                  95

Thr Phe Gly Gln Gly Thr Lys Leu Glu Ile Lys Arg
            100                 105
```

```
<210> SEQ ID NO 107
<211> LENGTH: 18
<212> TYPE: DNA
<213> ORGANISM: Homo sapiens

<400> SEQUENCE: 107
caggacatca acaattat                                                  18
```

```
<210> SEQ ID NO 108
<211> LENGTH: 6
<212> TYPE: PRT
<213> ORGANISM: Homo Sapiens

<400> SEQUENCE: 108

Gln Asp Ile Asn Asn Tyr
1               5
```

```
<210> SEQ ID NO 109
<211> LENGTH: 9
<212> TYPE: DNA
<213> ORGANISM: Homo sapiens

<400> SEQUENCE: 109 gctgcatcc                                                             9
```

```
<210> SEQ ID NO 110
<211> LENGTH: 3
<212> TYPE: PRT
<213> ORGANISM: Homo Sapiens

<400> SEQUENCE: 110
```

Ala Ala Ser
1

<210> SEQ ID NO 111
<211> LENGTH: 27
<212> TYPE: DNA
<213> ORGANISM: Homo sapiens

<400> SEQUENCE: 111
cttcagtata atagttacca tcccact                                          27

<210> SEQ ID NO 112
<211> LENGTH: 9
<212> TYPE: PRT
<213> ORGANISM: Homo Sapiens

<400> SEQUENCE: 112

Leu Gln Tyr Asn Ser Tyr His Pro Thr
1               5

<210> SEQ ID NO 113
<211> LENGTH: 363
<212> TYPE: DNA
<213> ORGANISM: Homo sapiens

<400> SEQUENCE: 113
caggtgcagc tggtggagtc tgggggaggc gtggtccagc ctggggaggtc cctgagactc      60 tcctgtgcag cgtctggatt caccttcagt agctatggca tgcactgggt ccgccaggct     120
ccaggcaagg ggctggagtg ggtggcagct atatggtatg atggaagtaa taaatattat     180
gcagactccg tgaagggccg attcaccatc tccagagaca attccaagaa cacgctgtat     240
ctgcaaatga acagcctgag agccgaggac acggctgtgt atttctgtgc gagaggggaa     300
cattactatg gttcggggcc gttcgacccc tggggccagg gaaccctggt caccgtctcc     360
tca                                                                  363

<210> SEQ ID NO 114
<211> LENGTH: 121
<212> TYPE: PRT
<213> ORGANISM: Homo Sapiens

<400> SEQUENCE: 114

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Gly Glu His Tyr Tyr Gly Ser Gly Pro Phe Asp Pro Trp Gly
            100                 105                 110

Gln Gly Thr Leu Val Thr Val Ser Ser
        115                 120

```
<210> SEQ ID NO 115
<211> LENGTH: 24
<212> TYPE: DNA
<213> ORGANISM: Homo sapiens

<400> SEQUENCE: 115
ggattcacct tcagtagcta tggc                                            24

<210> SEQ ID NO 116
<211> LENGTH: 8
<212> TYPE: PRT
<213> ORGANISM: Homo Sapiens

<400> SEQUENCE: 116

Gly Phe Thr Phe Ser Ser Tyr Gly
1               5

<210> SEQ ID NO 117
<211> LENGTH: 24
<212> TYPE: DNA
<213> ORGANISM: Homo sapiens

<400> SEQUENCE: 117
atatggtatg atggaagtaa taaa                                            24

<210> SEQ ID NO 118
<211> LENGTH: 8
<212> TYPE: PRT
<213> ORGANISM: Homo Sapiens

<400> SEQUENCE: 118

Ile Trp Tyr Asp Gly Ser Asn Lys
1               5

<210> SEQ ID NO 119
<211> LENGTH: 42
<212> TYPE: DNA
<213> ORGANISM: Homo sapiens

<400> SEQUENCE: 119
gcgagagggg aacattacta tggttcgggg ccgttcgacc cc                        42

<210> SEQ ID NO 120
<211> LENGTH: 14
<212> TYPE: PRT
<213> ORGANISM: Homo Sapiens

<400> SEQUENCE: 120

Ala Arg Gly Glu His Tyr Tyr Gly Ser Gly Pro Phe Asp Pro
1               5                   10

<210> SEQ ID NO 121
<211> LENGTH: 324
<212> TYPE: DNA
<213> ORGANISM: Homo sapiens

<400> SEQUENCE: 121
gacatccaga tgacccagtc tccatcctcc ctgtctgcat ctgtaggaga cagagtcacc     60
atcacttgcc gggcaagtca gagcattagc aactatttaa attggtatca gcagaaacca   120
gggaaagccc ctaagctcct gatctttgct gcatccagtt tacaaagtgg ggtcccatca   180
aggttcagtg gcagtggatc tgggacagat ttcactctca ccatcagcag tctgcaacct   240
```

-continued

```
gaagattttg caacttacta ctgtcaacag agttacagtt ccccgctcac tttcggcgga        300
gggaccaagg tggagatcaa acga                                              324
```

<210> SEQ ID NO 122
<211> LENGTH: 108
<212> TYPE: PRT
<213> ORGANISM: Homo Sapiens

<400> SEQUENCE: 122

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Phe Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser Pro Leu
                85                  90                  95

Thr Phe Gly Gly Gly Thr Lys Val Glu Ile Lys Arg
           100                 105
```

<210> SEQ ID NO 123
<211> LENGTH: 18
<212> TYPE: DNA
<213> ORGANISM: Homo sapiens

<400> SEQUENCE: 123

```
cagagcatta gcaactat                                                      18
```

<210> SEQ ID NO 124
<211> LENGTH: 6
<212> TYPE: PRT
<213> ORGANISM: Homo Sapiens

<400> SEQUENCE: 124

```
Gln Ser Ile Ser Asn Tyr
 1               5
```

<210> SEQ ID NO 125
<211> LENGTH: 9
<212> TYPE: DNA
<213> ORGANISM: Homo sapiens

<400> SEQUENCE: 125

```
gctgcatcc                                                                 9
```

<210> SEQ ID NO 126
<211> LENGTH: 3
<212> TYPE: PRT
<213> ORGANISM: Homo Sapiens

<400> SEQUENCE: 126

```
Ala Ala Ser
 1
```

<210> SEQ ID NO 127
<211> LENGTH: 27
<212> TYPE: DNA

<213> ORGANISM: Homo sapiens

<400> SEQUENCE: 127
caacagagtt acagttcccc gctcact                                                27

<210> SEQ ID NO 128
<211> LENGTH: 9
<212> TYPE: PRT
<213> ORGANISM: Homo Sapiens

<400> SEQUENCE: 128

Gln Gln Ser Tyr Ser Ser Pro Leu Thr
1               5

<210> SEQ ID NO 129
<211> LENGTH: 360
<212> TYPE: DNA
<213> ORGANISM: Homo sapiens

<400> SEQUENCE: 129
caggtgcagc tgcaggagtc ggggccagga ctggtgaagc cttcacagac cctgtccctc     60
acctgcactg tctcaggtgg ctccatcagc agttttggtt actactggag ctggatccgc    120
cagcacccag ggaagggcct ggagtggatt gggtacatct attacagtgg gagcatcgac    180
tacaacccgt ccctcaagag tcgaattacc atatcagtcg acacgtctaa gaaccagttc    240
tccctgaagc tgagctctgt gactgccgcg gacacggccg tgtattactg tgcgagagaa    300
agggactacg gtgactactt tgactactgg ggccagggaa ccctggtcac cgtctcctca    360

<210> SEQ ID NO 130
<211> LENGTH: 120
<212> TYPE: PRT
<213> ORGANISM: Homo Sapiens

<400> SEQUENCE: 130

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Phe
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Ile Asp Tyr Asn Pro Ser
    50                  55                  60

Leu Lys Ser Arg Ile Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Arg Asp Tyr Gly Asp Tyr Phe Asp Tyr Trp Gly Gln
            100                 105                 110

Gly Thr Leu Val Thr Val Ser Ser
        115                 120

<210> SEQ ID NO 131
<211> LENGTH: 30
<212> TYPE: DNA
<213> ORGANISM: Homo sapiens

<400> SEQUENCE: 131
ggtggctcca tcagcagttt tggttactac                                     30

<210> SEQ ID NO 132
<211> LENGTH: 10
<212> TYPE: PRT
<213> ORGANISM: Homo Sapiens

<400> SEQUENCE: 132

Gly Gly Ser Ile Ser Ser Phe Gly Tyr Tyr
1               5                   10

<210> SEQ ID NO 133
<211> LENGTH: 21
<212> TYPE: DNA
<213> ORGANISM: Homo sapiens

<400> SEQUENCE: 133
atctattaca gtgggagcat c                                         21

<210> SEQ ID NO 134
<211> LENGTH: 7
<212> TYPE: PRT
<213> ORGANISM: Homo Sapiens

<400> SEQUENCE: 134

Ile Tyr Tyr Ser Gly Ser Ile
1               5

<210> SEQ ID NO 135
<211> LENGTH: 36
<212> TYPE: DNA
<213> ORGANISM: Homo sapiens

<400> SEQUENCE: 135
gcgagagaaa gggactacgg tgactacttt gactac                         36

<210> SEQ ID NO 136
<211> LENGTH: 12
<212> TYPE: PRT
<213> ORGANISM: Homo Sapiens

<400> SEQUENCE: 136

Ala Arg Glu Arg Asp Tyr Gly Asp Tyr Phe Asp Tyr
1               5                   10

<210> SEQ ID NO 137
<211> LENGTH: 324
<212> TYPE: DNA
<213> ORGANISM: Homo sapiens

<400> SEQUENCE: 137
gaaatagtga tgacgcagtc tccagccacc ctgtctgtct ctccagggga aagagccacc    60
ctctcctgca gggccagtca gagtgttagc agcaacttag cctggtacca gcagaaacct   120
ggccaggctc ccaggctcct catctatggt gcatccacca gggccactgg tgtcccagcc   180
aggttcagtg gcagtgggtc tgggacagag ttcactctca ccatcagcag tttgcagtct   240
gaggattttg cagtttattc ctgtcagcag tataataact ggcctctcac tttcggcgga   300
gggaccaagg tggagatcaa acga                                         324

<210> SEQ ID NO 138
<211> LENGTH: 108
<212> TYPE: PRT
<213> ORGANISM: Homo Sapiens -continued

<400> SEQUENCE: 138

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Val Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Ser Cys Gln Gln Tyr Asn Asn Trp Pro Leu
                85                  90                  95

Thr Phe Gly Gly Gly Thr Lys Val Glu Ile Lys Arg
            100                 105

<210> SEQ ID NO 139
<211> LENGTH: 18
<212> TYPE: DNA
<213> ORGANISM: Homo sapiens

<400> SEQUENCE: 139
cagagtgtta gcagcaac                                                 18

<210> SEQ ID NO 140
<211> LENGTH: 6
<212> TYPE: PRT
<213> ORGANISM: Homo Sapiens

<400> SEQUENCE: 140

Gln Ser Val Ser Ser Asn
1               5

<210> SEQ ID NO 141
<211> LENGTH: 9
<212> TYPE: DNA
<213> ORGANISM: Homo sapiens

<400> SEQUENCE: 141 ggtgcatcc                                                            9

<210> SEQ ID NO 142
<211> LENGTH: 3
<212> TYPE: PRT
<213> ORGANISM: Homo Sapiens

<400> SEQUENCE: 142

Gly Ala Ser
1

<210> SEQ ID NO 143
<211> LENGTH: 27
<212> TYPE: DNA
<213> ORGANISM: Homo sapiens

<400> SEQUENCE: 143
cagcagtata ataactggcc tctcact                                       27

<210> SEQ ID NO 144
<211> LENGTH: 9
<212> TYPE: PRT

<210> ORGANISM: Homo Sapiens

<400> SEQUENCE: 144

Gln Gln Tyr Asn Asn Trp Pro Leu Thr
1               5

<210> SEQ ID NO 145
<211> LENGTH: 372
<212> TYPE: DNA
<213> ORGANISM: Homo sapiens

<400> SEQUENCE: 145

```
caggtgcagc tggtggagtc tgggggaggc gtggtccagc ctgggaggtc cctgagactc    60
tcctgtgcag cgtctggatt caccttcagt agctatggca tacactgggt ccgccaggct   120
ccaggcaagg gctggagtg gtggcactt atatggtatg atggaagtaa taaatactat    180
gcagactccg tgaagggccg attcaccatc tccagagaca attccaagaa cacgctgtat   240
ctgcaaatga acagcctgag agccgaggac acggctgtgt attactgtgc gagagatcag   300
gattactatg gttcggggag ttcctacggt atggacgtct ggggccaagg gaccacggtc   360
accgtctcct ca                                                       372
```

<210> SEQ ID NO 146
<211> LENGTH: 124
<212> TYPE: PRT
<213> ORGANISM: Homo Sapiens

<400> SEQUENCE: 146

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Ile His Trp Val Arg Gln Ala Pro Gly Lys Gly Leu Glu Trp Val
        35                  40                  45

Ala Leu Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Asp Tyr Tyr Gly Ser Gly Ser Ser Tyr Gly Met Asp
            100                 105                 110

Val Trp Gly Gln Gly Thr Thr Val Thr Val Ser Ser
        115                 120

<210> SEQ ID NO 147
<211> LENGTH: 24
<212> TYPE: DNA
<213> ORGANISM: Homo sapiens

<400> SEQUENCE: 147

```
ggattcacct tcagtagcta tggc                                           24
```

<210> SEQ ID NO 148
<211> LENGTH: 8
<212> TYPE: PRT
<213> ORGANISM: Homo Sapiens

<400> SEQUENCE: 148

```
Gly Phe Thr Phe Ser Ser Tyr Gly
1               5
```

<210> SEQ ID NO 149
<211> LENGTH: 24
<212> TYPE: DNA
<213> ORGANISM: Homo sapiens

<400> SEQUENCE: 149

```
atatggtatg atggaagtaa taaa                                              24
```

<210> SEQ ID NO 150
<211> LENGTH: 8
<212> TYPE: PRT
<213> ORGANISM: Homo Sapiens

<400> SEQUENCE: 150

```
Ile Trp Tyr Asp Gly Ser Asn Lys
1               5
```

<210> SEQ ID NO 151
<211> LENGTH: 51
<212> TYPE: DNA
<213> ORGANISM: Homo sapiens

<400> SEQUENCE: 151

```
gcgagagatc aggattacta tggttcgggg agttcctacg gtatggacgt c                51
```

<210> SEQ ID NO 152
<211> LENGTH: 17
<212> TYPE: PRT
<213> ORGANISM: Homo Sapiens

<400> SEQUENCE: 152

```
Ala Arg Asp Gln Asp Tyr Tyr Gly Ser Gly Ser Ser Tyr Gly Met Asp
1               5                   10                  15

Val
```

<210> SEQ ID NO 153
<211> LENGTH: 324
<212> TYPE: DNA
<213> ORGANISM: Homo sapiens

<400> SEQUENCE: 153

```
gacatccaga tgacccagtc gccagcctcc ctgtctgcat ctgtaggaga cagagtcacc        60
atcacttgcc gggcaagtca gagcattagc agctatttaa attggtatca gcagaaacca       120
gggaaagccc ctaagcgcct gatctatgct gcatccagtt tgcaaagtgg ggtcccatca       180
aggttcagtg gcagtggatc tgggacagat ttcactctca ccatcagcag tctgcaacct       240
gaagattttg caacttacta ctgtcaacag agttacagta cccctctcac ttttggccag       300
gggaccaagc tggagatcaa acga                                              324
```

<210> SEQ ID NO 154
<211> LENGTH: 108
<212> TYPE: PRT
<213> ORGANISM: Homo Sapiens

<400> SEQUENCE: 154

```
Asp Ile Gln Met Thr Gln Ser Pro Ala Ser Leu Ser Ala Ser Val Gly
1               5                   10                  15

Asp Arg Val Thr Ile Thr Cys Arg Ala Ser Gln Ser Ile Ser Ser Tyr
```

```
            20                  25                  30
Leu Asn Trp Tyr Gln Gln Lys Pro Gly Lys Ala Pro Lys Arg Leu Ile
         35                  40                  45
Tyr Ala Ala Ser Ser Leu Gln Ser Gly Val Pro Ser Arg Phe Ser Gly
     50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ser Tyr Ser Thr Pro Leu
                 85                  90                  95
Thr Phe Gly Gln Gly Thr Lys Leu Glu Ile Lys Arg
             100                 105
```

<210> SEQ ID NO 155
<211> LENGTH: 18
<212> TYPE: DNA
<213> ORGANISM: Homo sapiens

<400> SEQUENCE: 155
cagagcatta gcagctat                                              18

<210> SEQ ID NO 156
<211> LENGTH: 6
<212> TYPE: PRT
<213> ORGANISM: Homo Sapiens

<400> SEQUENCE: 156

Gln Ser Ile Ser Ser Tyr
1               5

<210> SEQ ID NO 157
<211> LENGTH: 9
<212> TYPE: DNA
<213> ORGANISM: Homo sapiens

<400> SEQUENCE: 157 gctgcatcc                                                         9

<210> SEQ ID NO 158
<211> LENGTH: 3
<212> TYPE: PRT
<213> ORGANISM: Homo Sapiens

<400> SEQUENCE: 158

Ala Ala Ser
1

<210> SEQ ID NO 159
<211> LENGTH: 27
<212> TYPE: DNA
<213> ORGANISM: Homo sapiens

<400> SEQUENCE: 159
caacagagtt acagtacccc tctcact                                    27

<210> SEQ ID NO 160
<211> LENGTH: 9
<212> TYPE: PRT
<213> ORGANISM: Homo Sapiens

<400> SEQUENCE: 160

Gln Gln Ser Tyr Ser Thr Pro Leu Thr
1               5

<210> SEQ ID NO 161
<211> LENGTH: 372
<212> TYPE: DNA
<213> ORGANISM: Homo sapiens

<400> SEQUENCE: 161

```
caggtgcagc tggtggagtc tgggggaggc gtggtccagc ctgggaggtc cctgagactc      60
tcctgtgcag cgtctggatt caccttcagt acctatggca tgcactgggt ccgccaggct     120
ccaggcaagg ggctggagtg ggtggcagtt atatggtatg atggaactaa taaatactat     180
gcagactccg tgaagggccg attcaccatc tccagagaca attccaagaa cacgctgtat     240
ctgcaaatga tcagcctgag agccgaggac acggctgtgt attactgtgc gagagacccc     300
tcaggtgggg accactacta ttactacggt atggacgtct ggggccaagg gaccacggtc     360
accgtctcct ca                                                          372
```

<210> SEQ ID NO 162
<211> LENGTH: 124
<212> TYPE: PRT
<213> ORGANISM: Homo Sapiens

<400> SEQUENCE: 162

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ala Val Ile Trp Tyr Asp Gly Thr Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ile Ser Leu Arg Ala Glu Asp Thr Ala Val Tyr Tyr Cys
                85                  90                  95

Ala Arg Asp Pro Ser Gly Gly Asp His Tyr Tyr Tyr Gly Met Asp
            100                 105                 110

Val Trp Gly Gln Gly Thr Thr Val Thr Val Ser Ser
        115                 120

<210> SEQ ID NO 163
<211> LENGTH: 24
<212> TYPE: DNA
<213> ORGANISM: Homo sapiens

<400> SEQUENCE: 163

```
ggattcacct tcagtaccta tggc                                              24
```

<210> SEQ ID NO 164
<211> LENGTH: 8
<212> TYPE: PRT
<213> ORGANISM: Homo Sapiens

<400> SEQUENCE: 164

Gly Phe Thr Phe Ser Thr Tyr Gly
1               5

<210> SEQ ID NO 165
<211> LENGTH: 24

<212> TYPE: DNA
<213> ORGANISM: Homo sapiens

<400> SEQUENCE: 165
atatggtatg atggaactaa taaa                                            24

<210> SEQ ID NO 166
<211> LENGTH: 8
<212> TYPE: PRT
<213> ORGANISM: Homo Sapiens

<400> SEQUENCE: 166

Ile Trp Tyr Asp Gly Thr Asn Lys
1               5

<210> SEQ ID NO 167
<211> LENGTH: 51
<212> TYPE: DNA
<213> ORGANISM: Homo sapiens

<400> SEQUENCE: 167
gcgagagacc cctcaggtgg ggaccactac tattactacg gtatggacgt c              51

<210> SEQ ID NO 168
<211> LENGTH: 17
<212> TYPE: PRT
<213> ORGANISM: Homo Sapiens

<400> SEQUENCE: 168

Ala Arg Asp Pro Ser Gly Gly Asp His Tyr Tyr Tyr Tyr Gly Met Asp
1               5                   10                  15

Val

<210> SEQ ID NO 169
<211> LENGTH: 324
<212> TYPE: DNA
<213> ORGANISM: Homo sapiens

<400> SEQUENCE: 169
gacatccaga tgacccagtc tccatcctcc ctgtctgcat ctgtaggaga cagaatcacc      60
atcacttgcc aggcgagtca ggacattagc aactatttaa attggtatca gcagaagcca     120
gggaaagccc ctaacctcct gatctccgat gcatccgatt tggaaacagg ggtcccatca     180
aggttcagtg gaagtggatc tgggacagat tttactttca ccatcagcag cctgcagcct     240
gaagattttg caacatatta ctgtcaacag tatgataata taccgatcac cttcggccaa     300
gggacacgac tggagattaa acga                                           324

<210> SEQ ID NO 170
<211> LENGTH: 108
<212> TYPE: PRT
<213> ORGANISM: Homo Sapiens

<400> SEQUENCE: 170

Asp Ile Gln Met Thr Gln Ser Pro Ser Ser Leu Ser Ala Ser Val Gly
1               5                   10                  15

Asp Arg Ile Thr Ile Thr Cys Gln Ala Ser Gln Asp Ile Ser Asn Tyr
            20                  25                  30

Leu Asn Trp Tyr Gln Gln Lys Pro Gly Lys Ala Pro Asn Leu Leu Ile
        35                  40                  45

Ser Asp Ala Ser Asp Leu Glu Thr Gly Val Pro Ser Arg Phe Ser Gly

```
                50                  55                  60
Ser Gly Ser Gly Thr Asp Phe Thr Phe Thr Ile Ser Ser Leu Gln Pro
 65                  70                  75                  80

Glu Asp Phe Ala Thr Tyr Tyr Cys Gln Gln Tyr Asp Asn Ile Pro Ile
                 85                  90                  95

Thr Phe Gly Gln Gly Thr Arg Leu Glu Ile Lys Arg
            100                 105
```

<210> SEQ ID NO 171
<211> LENGTH: 18
<212> TYPE: DNA
<213> ORGANISM: Homo sapiens

<400> SEQUENCE: 171
caggacatta gcaactat                                                18

<210> SEQ ID NO 172
<211> LENGTH: 6
<212> TYPE: PRT
<213> ORGANISM: Homo Sapiens

<400> SEQUENCE: 172

```
Gln Asp Ile Ser Asn Tyr
 1               5
```

<210> SEQ ID NO 173
<211> LENGTH: 9
<212> TYPE: DNA
<213> ORGANISM: Homo sapiens

<400> SEQUENCE: 173 gatgcatcc                                                           9

<210> SEQ ID NO 174
<211> LENGTH: 3
<212> TYPE: PRT
<213> ORGANISM: Homo Sapiens

<400> SEQUENCE: 174

```
Asp Ala Ser
 1
```

<210> SEQ ID NO 175
<211> LENGTH: 27
<212> TYPE: DNA
<213> ORGANISM: Homo sapiens

<400> SEQUENCE: 175
caacagtatg ataatatacc gatcacc                                       27

<210> SEQ ID NO 176
<211> LENGTH: 9
<212> TYPE: PRT
<213> ORGANISM: Homo Sapiens

<400> SEQUENCE: 176

```
Gln Gln Tyr Asp Asn Ile Pro Ile Thr
 1               5
```

<210> SEQ ID NO 177
<211> LENGTH: 366
<212> TYPE: DNA
<213> ORGANISM: Homo sapiens

<400> SEQUENCE: 177

```
caggtgcagc tggtggagtc agggggaggc gtggtccagc ctgggaggtc cctgagactc    60
tcctgtgcag cctctggatt caccttcagt agctatggca tgcactgggt ccgccaggct   120
ccaggcaagg ggctggagtg ggtgacattt atatcatttg atgaaaggaa taaatactat   180
gcagactccg ttaagggccg attcaccatc tccagagaca attccaagaa cacgctgtat   240
ctgcaaatga acagcctgag agctgaggac acggctatgt attactgtgc gagcgaagtc   300
gggtacagtt ttggtcatga tgcttttgat atctggggcc aagggacaat ggtcaccgtc   360
tcttca                                                              366
```

<210> SEQ ID NO 178
<211> LENGTH: 122
<212> TYPE: PRT
<213> ORGANISM: Homo Sapiens

<400> SEQUENCE: 178

```
Gln Val Gln Leu Val Glu Ser Gly Gly Gly Val Val Gln Pro Gly Arg
 1               5                  10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Thr Phe Ile Ser Phe Asp Glu Arg Asn Lys Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Met Tyr Tyr Cys
                85                  90                  95
Ala Ser Glu Val Gly Tyr Ser Phe Gly His Asp Ala Phe Asp Ile Trp
            100                 105                 110
Gly Gln Gly Thr Met Val Thr Val Ser Ser
        115                 120
```

<210> SEQ ID NO 179
<211> LENGTH: 24
<212> TYPE: DNA
<213> ORGANISM: Homo sapiens

<400> SEQUENCE: 179

```
ggattcacct tcagtagcta tggc                                           24
```

<210> SEQ ID NO 180
<211> LENGTH: 8
<212> TYPE: PRT
<213> ORGANISM: Homo Sapiens

<400> SEQUENCE: 180

```
Gly Phe Thr Phe Ser Ser Tyr Gly
 1               5
```

<210> SEQ ID NO 181
<211> LENGTH: 24
<212> TYPE: DNA
<213> ORGANISM: Homo sapiens

<400> SEQUENCE: 181

```
atatcatttg atgaaaggaa taaa                                           24
```

<210> SEQ ID NO 182
<211> LENGTH: 8
<212> TYPE: PRT
<213> ORGANISM: Homo Sapiens

<400> SEQUENCE: 182

Ile Ser Phe Asp Glu Arg Asn Lys
1               5

<210> SEQ ID NO 183
<211> LENGTH: 45
<212> TYPE: DNA
<213> ORGANISM: Homo sapiens

<400> SEQUENCE: 183
gcgagcgaag tcgggtacag ttttggtcat gatgcttttg atatc            45

<210> SEQ ID NO 184
<211> LENGTH: 15
<212> TYPE: PRT
<213> ORGANISM: Homo Sapiens

<400> SEQUENCE: 184

Ala Ser Glu Val Gly Tyr Ser Phe Gly His Asp Ala Phe Asp Ile
1               5                   10                  15

<210> SEQ ID NO 185
<211> LENGTH: 324
<212> TYPE: DNA
<213> ORGANISM: Homo sapiens

<400> SEQUENCE: 185
gacatccaga tgacccagtc tccatcctcc ctgtctgcat ctgtaggaga cagagtcacc      60
atcacttgcc aggcgagtca ggacattagc aactatttaa attggtatca agaaaaacca    120
gggaaagccc ctaaactcct gatctacgat gcatccaatt tggaaacagg ggtcccgtca    180
aggttcagtg gaagtggatc tgggacagat tttactttca ccatcagcag cctgcagcct    240
gaagatattg caacatatta ctgtcaacag tatgataatt tcccgctcac tttcggcgga    300
gggaccaagg tggagatcaa acga                                            324

<210> SEQ ID NO 186
<211> LENGTH: 108
<212> TYPE: PRT
<213> ORGANISM: Homo Sapiens

<400> SEQUENCE: 186

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Lys Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Phe Pro Leu
                85                  90                  95

```
Thr Phe Gly Gly Gly Thr Lys Val Glu Ile Lys Arg
            100                 105
```

<210> SEQ ID NO 187
<211> LENGTH: 18
<212> TYPE: DNA
<213> ORGANISM: Homo sapiens

<400> SEQUENCE: 187
caggacatta gcaactat                                                   18

<210> SEQ ID NO 188
<211> LENGTH: 6
<212> TYPE: PRT
<213> ORGANISM: Homo Sapiens

<400> SEQUENCE: 188

```
Gln Asp Ile Ser Asn Tyr
1               5
```

<210> SEQ ID NO 189
<211> LENGTH: 9
<212> TYPE: DNA
<213> ORGANISM: Homo sapiens

<400> SEQUENCE: 189 gatgcatcc                                                              9

<210> SEQ ID NO 190
<211> LENGTH: 3
<212> TYPE: PRT
<213> ORGANISM: Homo Sapiens

<400> SEQUENCE: 190

```
Asp Ala Ser
1
```

<210> SEQ ID NO 191
<211> LENGTH: 27
<212> TYPE: DNA
<213> ORGANISM: Homo sapiens

<400> SEQUENCE: 191
caacagtatg ataatttccc gctcact                                          27

<210> SEQ ID NO 192
<211> LENGTH: 9
<212> TYPE: PRT
<213> ORGANISM: Homo Sapiens

<400> SEQUENCE: 192

```
Gln Gln Tyr Asp Asn Phe Pro Leu Thr
1               5
```

<210> SEQ ID NO 193
<211> LENGTH: 369
<212> TYPE: DNA
<213> ORGANISM: Homo sapiens

<400> SEQUENCE: 193
gaggtgcagc tggtggagtc tgggggaggc ttggtacagc ctggggggtc cctgagactc      60
tcctgtgcag cctctggatt cacctttaac aactatgcca tgagctgggt ccgccaggct     120
ccagggaggg ggctggagtg ggtctcagct attagtggta gtggtgatag cacatactac     180

```
tcagactccg tgaagggccg gttcaccatc tccagagaca attccaagaa cacgctgtat    240
ctgcaaatga acagcctgag agccgaggac acggccgtat attactgtgc gaaagatcag    300
ggcctgtatt actatggttc ggggagtttt gactactggg ccagggaac cctggtcacc    360 gtctcctca                                                             369
```

```
<210> SEQ ID NO 194
<211> LENGTH: 123
<212> TYPE: PRT
<213> ORGANISM: Homo Sapiens

<400> SEQUENCE: 194
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Ala Met Ser Trp Val Arg Gln Ala Pro Gly Arg Gly Leu Glu Trp Val
        35                  40                  45

Ser Ala Ile Ser Gly Ser Gly Asp Ser Thr Tyr Tyr Ser Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gln Gly Leu Tyr Tyr Gly Ser Gly Ser Phe Asp Tyr
            100                 105                 110

Trp Gly Gln Gly Thr Leu Val Thr Val Ser Ser
        115                 120

```
<210> SEQ ID NO 195
<211> LENGTH: 24
<212> TYPE: DNA
<213> ORGANISM: Homo sapiens

<400> SEQUENCE: 195
ggattcacct ttaacaacta tgcc                                             24

<210> SEQ ID NO 196
<211> LENGTH: 8
<212> TYPE: PRT
<213> ORGANISM: Homo Sapiens

<400> SEQUENCE: 196
```

Gly Phe Thr Phe Asn Asn Tyr Ala
1               5

```
<210> SEQ ID NO 197
<211> LENGTH: 24
<212> TYPE: DNA
<213> ORGANISM: Homo sapiens

<400> SEQUENCE: 197
attagtggta gtggtgatag caca                                             24

<210> SEQ ID NO 198
<211> LENGTH: 8
<212> TYPE: PRT
<213> ORGANISM: Homo Sapiens

<400> SEQUENCE: 198
```

Ile Ser Gly Ser Gly Asp Ser Thr
1               5

<210> SEQ ID NO 199
<211> LENGTH: 48
<212> TYPE: DNA
<213> ORGANISM: Homo sapiens

<400> SEQUENCE: 199
gcgaaagatc agggcctgta ttactatggt tcggggagtt ttgactac           48

<210> SEQ ID NO 200
<211> LENGTH: 16
<212> TYPE: PRT
<213> ORGANISM: Homo Sapiens

<400> SEQUENCE: 200

Ala Lys Asp Gln Gly Leu Tyr Tyr Tyr Gly Ser Gly Ser Phe Asp Tyr
1               5                   10                  15

<210> SEQ ID NO 201
<211> LENGTH: 324
<212> TYPE: DNA
<213> ORGANISM: Homo sapiens

<400> SEQUENCE: 201
gacatccaga tgacccagtc tccatcctcc ctgtctgcat ctgtaggaga cagagtcacc      60
atcacttgcc gggcaagtca gagcattagc agctatttaa attggtatca gcagaaacca    120
gggaaagccc ctaagctcct gatccaagct gcatccagtt tgcaaagtgg ggtcccatca    180
aggttcagtg gcagtggatc tgggacagat atcactctca ccatcagcag tctgcaaccc    240
gaagattttg caacttacta ctgtcaacag agttacagta cccccattca ctttcggccct    300 gggaccaaag tggatatcaa acga                                          324

<210> SEQ ID NO 202
<211> LENGTH: 108
<212> TYPE: PRT
<213> ORGANISM: Homo Sapiens

<400> SEQUENCE: 202

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Gln Ala Ala Ser Ser Leu Gln Ser Gly Val Pro Ser Arg Phe Ser Gly
    50                  55                  60

Ser Gly Ser Gly Thr Asp Ile Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Pro Gly Thr Lys Val Asp Ile Lys Arg
            100                 105

<210> SEQ ID NO 203
<211> LENGTH: 18
<212> TYPE: DNA
<213> ORGANISM: Homo sapiens

<400> SEQUENCE: 203
cagagcatta gcagctat                                                          18

<210> SEQ ID NO 204
<211> LENGTH: 6
<212> TYPE: PRT
<213> ORGANISM: Homo Sapiens

<400> SEQUENCE: 204

Gln Ser Ile Ser Ser Tyr
1               5

<210> SEQ ID NO 205
<211> LENGTH: 9
<212> TYPE: DNA
<213> ORGANISM: Homo sapiens

<400> SEQUENCE: 205 gctgcatcc                                                                     9

<210> SEQ ID NO 206
<211> LENGTH: 3
<212> TYPE: PRT
<213> ORGANISM: Homo Sapiens

<400> SEQUENCE: 206

Ala Ala Ser
1

<210> SEQ ID NO 207
<211> LENGTH: 27
<212> TYPE: DNA
<213> ORGANISM: Homo sapiens

<400> SEQUENCE: 207
caacagagtt acagtacccc attcact                                                27

<210> SEQ ID NO 208
<211> LENGTH: 9
<212> TYPE: PRT
<213> ORGANISM: Homo Sapiens

<400> SEQUENCE: 208

Gln Gln Ser Tyr Ser Thr Pro Phe Thr
1               5

<210> SEQ ID NO 209
<211> LENGTH: 375
<212> TYPE: DNA
<213> ORGANISM: Homo sapiens

<400> SEQUENCE: 209
gaggtgcagc tggtggagtc tgggggaggc ttggtccagc ctgggggtc cctgcaactc      60 tcctgtgcag cctctgggtt tgccttcagc gactctgcta tatactgggt ccgccaggct    120
tccgggaaag gctggagtg gttggccgc attagaaaca aagctaatag gttcgcgaca     180
gcatatggtg cgtcggtgaa aggcaggttc agcatacaca gagatgattc aaagaacacg    240
gcgtatctac aaatgaacag cctgaaaacc gaggacacgg ccgtgtatta ctgtgccaga    300
catggacacg atactttgac tgagggctac ggtatggacg tctggggcca agggaccacg    360
gtcaccgtct cctca                                                             375

<210> SEQ ID NO 210
<211> LENGTH: 125
<212> TYPE: PRT
<213> ORGANISM: Homo Sapiens

<400> SEQUENCE: 210

Glu Val Gln Leu Val Glu Ser Gly Gly Gly Leu Val Gln Pro Gly Gly
1               5                   10                  15

Ser Leu Gln Leu Ser Cys Ala Ala Ser Gly Phe Ala Phe Ser Asp Ser
            20                  25                  30

Ala Ile Tyr Trp Val Arg Gln Ala Ser Gly Lys Gly Leu Glu Trp Val
        35                  40                  45

Gly Arg Ile Arg Asn Lys Ala Asn Arg Phe Ala Thr Ala Tyr Gly Ala
    50                  55                  60

Ser Val Lys Gly Arg Phe Ser Ile His Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Ala Arg His Gly His Asp Thr Leu Thr Glu Gly Tyr Gly Met
            100                 105                 110

Asp Val Trp Gly Gln Gly Thr Thr Val Thr Val Ser Ser
        115                 120                 125

<210> SEQ ID NO 211
<211> LENGTH: 24
<212> TYPE: DNA
<213> ORGANISM: Homo sapiens

<400> SEQUENCE: 211
gggtttgcct tcagcgactc tgct                                          24

<210> SEQ ID NO 212
<211> LENGTH: 8
<212> TYPE: PRT
<213> ORGANISM: Homo Sapiens

<400> SEQUENCE: 212

Gly Phe Ala Phe Ser Asp Ser Ala
1               5

<210> SEQ ID NO 213
<211> LENGTH: 30
<212> TYPE: DNA
<213> ORGANISM: Homo sapiens

<400> SEQUENCE: 213
attagaaaca aagctaatag gttcgcgaca                                    30

<210> SEQ ID NO 214
<211> LENGTH: 10
<212> TYPE: PRT
<213> ORGANISM: Homo Sapiens

<400> SEQUENCE: 214

Ile Arg Asn Lys Ala Asn Arg Phe Ala Thr
1               5                   10

<210> SEQ ID NO 215
<211> LENGTH: 48
<212> TYPE: DNA

```
<213> ORGANISM: Homo sapiens

<400> SEQUENCE: 215
gccagacatg gacacgatac tttgactgag ggctacggta tggacgtc          48

<210> SEQ ID NO 216
<211> LENGTH: 16
<212> TYPE: PRT
<213> ORGANISM: Homo Sapiens

<400> SEQUENCE: 216

Ala Arg His Gly His Asp Thr Leu Thr Glu Gly Tyr Gly Met Asp Val
1               5                   10                  15

<210> SEQ ID NO 217
<211> LENGTH: 324
<212> TYPE: DNA
<213> ORGANISM: Homo sapiens

<400> SEQUENCE: 217
gacatccaga tgacccagtc tccatcctcc ctgtctgcat ctgtaggaga cagagtcacc      60
atcacttgcc gggcaagtca gagcattagc agctatttaa attggtatca gcagaaacca    120
gggaaagccc ctaagctcct gatctatgct gcatccagtt tgcaaagtgg ggtcccgtca    180
aggttcagtg gcagtggatc tgggacagat ttcactctca ccatcagcag tctgcaacct    240
gaagattttg caacttacta ctgtcaacag agttacagta cccctccgat caccttcggc    300
caagggacac gactggagat taaa                                            324

<210> SEQ ID NO 218
<211> LENGTH: 108
<212> TYPE: PRT
<213> ORGANISM: Homo Sapiens

<400> SEQUENCE: 218

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 219
<211> LENGTH: 18
<212> TYPE: DNA
<213> ORGANISM: Homo sapiens

<400> SEQUENCE: 219
cagagcatta gcagctat                                                    18

<210> SEQ ID NO 220
<211> LENGTH: 6
```

<212> TYPE: PRT
<213> ORGANISM: Homo Sapiens

<400> SEQUENCE: 220

Gln Ser Ile Ser Ser Tyr
1               5

<210> SEQ ID NO 221
<211> LENGTH: 9
<212> TYPE: DNA
<213> ORGANISM: Homo sapiens

<400> SEQUENCE: 221 gctgcatcc                                                              9

<210> SEQ ID NO 222
<211> LENGTH: 3
<212> TYPE: PRT
<213> ORGANISM: Homo Sapiens

<400> SEQUENCE: 222

Ala Ala Ser
1

<210> SEQ ID NO 223
<211> LENGTH: 30
<212> TYPE: DNA
<213> ORGANISM: Homo sapiens

<400> SEQUENCE: 223
caacagagtt acagtacccc tccgatcacc                                      30

<210> SEQ ID NO 224
<211> LENGTH: 10
<212> TYPE: PRT
<213> ORGANISM: Homo Sapiens

<400> SEQUENCE: 224

Gln Gln Ser Tyr Ser Thr Pro Pro Ile Thr
1               5                   10

<210> SEQ ID NO 225
<211> LENGTH: 363
<212> TYPE: DNA
<213> ORGANISM: Homo sapiens

<400> SEQUENCE: 225
caggtgcagc tggtgcagtc tggggctgag gtaaagaacc ctgggtcctc ggtgaaggtc      60
tcctgcaagg cttctggagg caccttcagc agttatacta tcaactgggt gcgacaggcc    120
cctggacaag ggcttgagtg gatgggaggg atcatccctc tctatggaac agcaaactac    180
gcacagaagt tccaggccag agtcacgatt tccgacg aatccacgaa cacagcctac       240
atggaactga gcaacctgag atttgaagac acggccgtgt atttctgtgc gagtacactg    300
gaactacggg cttttgatgc ctttgatatc tggggccaag ggacaatggt caccgtctct    360
tca                                                                  363

<210> SEQ ID NO 226
<211> LENGTH: 121
<212> TYPE: PRT
<213> ORGANISM: Homo Sapiens

<400> SEQUENCE: 226

Gln Val Gln Leu Val Gln Ser Gly Ala Glu Val Lys Asn Pro Gly Ser
1               5                   10                  15

Ser Val Lys Val Ser Cys Lys Ala Ser Gly Gly Thr Phe Ser Ser Tyr
                20                  25                  30

Thr Ile Asn Trp Val Arg Gln Ala Pro Gly Gln Gly Leu Glu Trp Met
            35                  40                  45

Gly Gly Ile Ile Pro Leu Tyr Gly Thr Ala Asn Tyr Ala Gln Lys Phe
        50                  55                  60

Gln Ala Arg Val Thr Ile Ser Thr Asp Glu Ser Thr Asn Thr Ala Tyr
65                  70                  75                  80

Met Glu Leu Ser Asn Leu Arg Phe Glu Asp Thr Ala Val Tyr Phe Cys
                85                  90                  95

Ala Ser Thr Leu Glu Leu Arg Ala Phe Asp Ala Phe Asp Ile Trp Gly
                100                 105                 110

Gln Gly Thr Met Val Thr Val Ser Ser
            115                 120

<210> SEQ ID NO 227
<211> LENGTH: 24
<212> TYPE: DNA
<213> ORGANISM: Homo sapiens

<400> SEQUENCE: 227
ggaggcacct tcagcagtta tact                                      24

<210> SEQ ID NO 228
<211> LENGTH: 8
<212> TYPE: PRT
<213> ORGANISM: Homo Sapiens

<400> SEQUENCE: 228

Gly Gly Thr Phe Ser Ser Tyr Thr
1               5

<210> SEQ ID NO 229
<211> LENGTH: 24
<212> TYPE: DNA
<213> ORGANISM: Homo sapiens

<400> SEQUENCE: 229
atcatccctc tctatggaac agca                                      24

<210> SEQ ID NO 230
<211> LENGTH: 8
<212> TYPE: PRT
<213> ORGANISM: Homo Sapiens

<400> SEQUENCE: 230

Ile Ile Pro Leu Tyr Gly Thr Ala
1               5

<210> SEQ ID NO 231
<211> LENGTH: 42
<212> TYPE: DNA
<213> ORGANISM: Homo sapiens

<400> SEQUENCE: 231
gcgagtacac tggaactacg ggcttttgat gcctttgata tc                  42

<210> SEQ ID NO 232

```
<211> LENGTH: 14
<212> TYPE: PRT
<213> ORGANISM: Homo Sapiens

<400> SEQUENCE: 232

Ala Ser Thr Leu Glu Leu Arg Ala Phe Asp Ala Phe Asp Ile
1               5                   10

<210> SEQ ID NO 233
<211> LENGTH: 357
<212> TYPE: DNA
<213> ORGANISM: Homo sapiens

<400> SEQUENCE: 233
caggtgcagc tgcaggagtc gggcccagga ctggtgaagc cttcacagac cctgtccctc      60
acctgcactg tctctggtgg ctccatcagc agtggtggtt actactggaa ctggatccgc     120
cagcacccag ggaagggcct ggagtggatt gggtacatct attacagtgg aagcacctac     180
tacaacccgt ccctcaagag tcgagttacc atatcagtag acacgtctaa gaaccagttc     240
tccctgaagc tgggctctgt gactgccgcg gacacggccg tgtattactg cgcgagct      300 cctccttata actggtttga ctactggggc cagggaaccc tggtcaccgt ctcctca       357

<210> SEQ ID NO 234
<211> LENGTH: 119
<212> TYPE: PRT
<213> ORGANISM: Homo Sapiens

<400> SEQUENCE: 234

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Asn Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Gly Ser Val Thr Ala Ala Asp Thr Ala Val Tyr Tyr
                85                  90                  95

Cys Ala Arg Ala Pro Pro Tyr Asn Trp Phe Asp Tyr Trp Gly Gln Gly
            100                 105                 110

Thr Leu Val Thr Val Ser Ser
        115

<210> SEQ ID NO 235
<211> LENGTH: 30
<212> TYPE: DNA
<213> ORGANISM: Homo sapiens

<400> SEQUENCE: 235
ggtggctcca tcagcagtgg tggttactac                                        30

<210> SEQ ID NO 236
<211> LENGTH: 10
<212> TYPE: PRT
<213> ORGANISM: Homo Sapiens

<400> SEQUENCE: 236
```

```
<210> SEQ ID NO 237
<211> LENGTH: 21
<212> TYPE: DNA
<213> ORGANISM: Homo sapiens

<400> SEQUENCE: 237
atctattaca gtggaagcac c                                             21

<210> SEQ ID NO 238
<211> LENGTH: 7
<212> TYPE: PRT
<213> ORGANISM: Homo Sapiens

<400> SEQUENCE: 238
```

Ile Tyr Tyr Ser Gly Ser Thr
1               5

```
<210> SEQ ID NO 239
<211> LENGTH: 33
<212> TYPE: DNA
<213> ORGANISM: Homo sapiens

<400> SEQUENCE: 239
gcgcgagctc ctccttataa ctggtttgac tac                                33

<210> SEQ ID NO 240
<211> LENGTH: 11
<212> TYPE: PRT
<213> ORGANISM: Homo Sapiens

<400> SEQUENCE: 240
```

Ala Arg Ala Pro Pro Tyr Asn Trp Phe Asp Tyr
1               5               10

```
<210> SEQ ID NO 241
<211> LENGTH: 366
<212> TYPE: DNA
<213> ORGANISM: Homo sapiens

<400> SEQUENCE: 241
caggtgcagc tggtggagtc tgggggaggc ttggtcaagc ctggagggtc cctgagactc    60
tcctgtgcag cctctggatt caccttcagt gactactaca tgaactgggt ccgccaggct   120
ccagggaagg ggctggaatg ggtttcatac attagtaata gtggtaatac ccaatactac   180
gcagactctg tgaagggccg gttcaccatc tccagggaca atgccaagaa ctccctgttt   240
ctgcaaatga acagcctgcg agccgaggac acggccgttt attactgtac gagagaggga   300
ctcgaatata gcagctcgga gccctttgac tactggggcc agggaaccct ggtcaccgtc   360
tcctca                                                              366

<210> SEQ ID NO 242
<211> LENGTH: 122
<212> TYPE: PRT
<213> ORGANISM: Homo Sapiens

<400> SEQUENCE: 242
```

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr

```
            20                  25                  30
Tyr Met Asn Trp Val Arg Gln Ala Pro Gly Lys Gly Leu Glu Trp Val
        35                  40                  45

Ser Tyr Ile Ser Asn Ser Gly Asn Thr Gln Tyr Tyr Ala Asp Ser Val
    50                  55                  60

Lys Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Thr Arg Glu Gly Leu Glu Tyr Ser Ser Ser Gly Pro Phe Asp Tyr Trp
            100                 105                 110

Gly Gln Gly Thr Leu Val Thr Val Ser Ser
            115                 120
```

<210> SEQ ID NO 243
<211> LENGTH: 24
<212> TYPE: DNA
<213> ORGANISM: Homo sapiens

<400> SEQUENCE: 243
ggattcacct tcagtgacta ctac                                       24

<210> SEQ ID NO 244
<211> LENGTH: 8
<212> TYPE: PRT
<213> ORGANISM: Homo Sapiens

<400> SEQUENCE: 244

Gly Phe Thr Phe Ser Asp Tyr Tyr
1               5

<210> SEQ ID NO 245
<211> LENGTH: 24
<212> TYPE: DNA
<213> ORGANISM: Homo sapiens

<400> SEQUENCE: 245
attagtaata gtggtaatac ccaa                                       24

<210> SEQ ID NO 246
<211> LENGTH: 8
<212> TYPE: PRT
<213> ORGANISM: Homo Sapiens

<400> SEQUENCE: 246

Ile Ser Asn Ser Gly Asn Thr Gln
1               5

<210> SEQ ID NO 247
<211> LENGTH: 45
<212> TYPE: DNA
<213> ORGANISM: Homo sapiens

<400> SEQUENCE: 247
acgagagagg gactcgaata tagcagctcg gagccctttg actac                45

<210> SEQ ID NO 248
<211> LENGTH: 15
<212> TYPE: PRT
<213> ORGANISM: Homo Sapiens

<400> SEQUENCE: 248

```
Thr Arg Glu Gly Leu Glu Tyr Ser Ser Glu Pro Phe Asp Tyr
1               5                   10                  15
```

<210> SEQ ID NO 249
<211> LENGTH: 366
<212> TYPE: DNA
<213> ORGANISM: Homo sapiens

<400> SEQUENCE: 249

```
caggtgcagc tggtgcagtc tggggctgaa gtgaagaagc ctggggcctc agtgaaggtc     60
tcctgcaaga cttctggata caccttcacc gcctactaca tacactgggt gcgacaggcc    120
cctggacaag gcttgagtg gatgggatgg atcaaccta acaatggtga cacaaactat      180
```
gcactgaggt ttcagggcag ggtcaccatg accagggaca tgtccatcaa cacagcctac    240
atggagctgc gcgggctgag atctgacgac acggccgtgt attattgtgc gagagatgat    300
ctagcagcag cgggtatcgg ctggttcgac tcctggggcc agggaaccct ggtcaccgtc    360
tcctca                                                               366

<210> SEQ ID NO 250
<211> LENGTH: 122
<212> TYPE: PRT
<213> ORGANISM: Homo Sapiens

<400> SEQUENCE: 250

```
Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Ala Tyr
            20                  25                  30

Tyr Ile His Trp Val Arg Gln Ala Pro Gly Gln Gly Leu Glu Trp Met
        35                  40                  45

Gly Trp Ile Asn Pro Asn Asn Gly Asp Thr Asn Tyr Ala Leu Arg Phe
    50                  55                  60

Gln Gly Arg Val Thr Met Thr Arg Asp Met Ser Ile Asn Thr Ala Tyr
65                  70                  75                  80

Met Glu Leu Arg Gly Leu Arg Ser Asp Asp Thr Ala Val Tyr Tyr Cys
                85                  90                  95

Ala Arg Asp Asp Leu Ala Ala Ala Gly Ile Gly Trp Phe Asp Ser Trp
            100                 105                 110

Gly Gln Gly Thr Leu Val Thr Val Ser Ser
        115                 120
```

<210> SEQ ID NO 251
<211> LENGTH: 24
<212> TYPE: DNA
<213> ORGANISM: Homo sapiens

<400> SEQUENCE: 251

```
ggatacacct tcaccgccta ctac                                            24
```

<210> SEQ ID NO 252
<211> LENGTH: 8
<212> TYPE: PRT
<213> ORGANISM: Homo Sapiens

<400> SEQUENCE: 252

```
Gly Tyr Thr Phe Thr Ala Tyr Tyr
1               5
```

<210> SEQ ID NO 253
<211> LENGTH: 24
<212> TYPE: DNA
<213> ORGANISM: Homo sapiens

<400> SEQUENCE: 253 atcaaccctaacaatggtgacaca                                              24

<210> SEQ ID NO 254
<211> LENGTH: 8
<212> TYPE: PRT
<213> ORGANISM: Homo Sapiens

<400> SEQUENCE: 254

Ile Asn Pro Asn Asn Gly Asp Thr
1               5

<210> SEQ ID NO 255
<211> LENGTH: 45
<212> TYPE: DNA
<213> ORGANISM: Homo sapiens

<400> SEQUENCE: 255
gcgagagatg atctagcagc agcgggtatc ggctggttcg actcc                     45

<210> SEQ ID NO 256
<211> LENGTH: 15
<212> TYPE: PRT
<213> ORGANISM: Homo Sapiens

<400> SEQUENCE: 256

Ala Arg Asp Asp Leu Ala Ala Ala Gly Ile Gly Trp Phe Asp Ser
1               5                   10                  15

<210> SEQ ID NO 257
<211> LENGTH: 366
<212> TYPE: DNA
<213> ORGANISM: Homo sapiens

<400> SEQUENCE: 257
gaagtgcagc tggtggagtc tgggggaggc ttgctacagc ctggcaggtc cctgagactc      60
tcctgtgtag cctctggatt cacctttgat gattatgcca tgcactgggt ccggcaagct     120
ccagggaagg gcctggagtg ggtctcagga attagttgga atagtgaaag tataggctat     180
gcggactctg tgaggggccg attcaccatt tccagagaca cgccaagaa ctccctgtat      240 ctccaaatga acagtctgag agctgaggac acggccttgt attactgtgc aaaagccccg     300
tatagtggga cctacttcga atacttccgc cactggggcc agggcaccct ggtcaccgtc     360
tcctca                                                                366

<210> SEQ ID NO 258
<211> LENGTH: 122
<212> TYPE: PRT
<213> ORGANISM: Homo Sapiens

<400> SEQUENCE: 258

Glu Val Gln Leu Val Glu Ser Gly Gly Gly Leu Leu Gln Pro Gly Arg
1               5                   10                  15

Ser Leu Arg Leu Ser Cys Val Ala Ser Gly Phe Thr Phe Asp Asp Tyr
            20                  25                  30

Ala Met His Trp Val Arg Gln Ala Pro Gly Lys Gly Leu Glu Trp Val

-continued

```
                35                  40                  45
Ser Gly Ile Ser Trp Asn Ser Glu Ser Ile Gly Tyr Ala Asp Ser Val
    50                  55                  60

Arg Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Ala Pro Tyr Ser Gly Thr Tyr Phe Glu Tyr Phe Arg His Trp
            100                 105                 110

Gly Gln Gly Thr Leu Val Thr Val Ser Ser
        115                 120

<210> SEQ ID NO 259
<211> LENGTH: 24
<212> TYPE: DNA
<213> ORGANISM: Homo sapiens

<400> SEQUENCE: 259
ggattcacct ttgatgatta tgcc                                          24

<210> SEQ ID NO 260
<211> LENGTH: 8
<212> TYPE: PRT
<213> ORGANISM: Homo Sapiens

<400> SEQUENCE: 260

Gly Phe Thr Phe Asp Asp Tyr Ala
1               5

<210> SEQ ID NO 261
<211> LENGTH: 24
<212> TYPE: DNA
<213> ORGANISM: Homo sapiens

<400> SEQUENCE: 261
attagttgga atagtgaaag tata                                          24

<210> SEQ ID NO 262
<211> LENGTH: 8
<212> TYPE: PRT
<213> ORGANISM: Homo Sapiens

<400> SEQUENCE: 262

Ile Ser Trp Asn Ser Glu Ser Ile
1               5

<210> SEQ ID NO 263
<211> LENGTH: 45
<212> TYPE: DNA
<213> ORGANISM: Homo sapiens

<400> SEQUENCE: 263
gcaaaagccc cgtatagtgg gacctacttc gaatacttcc gccac                   45

<210> SEQ ID NO 264
<211> LENGTH: 15
<212> TYPE: PRT
<213> ORGANISM: Homo Sapiens

<400> SEQUENCE: 264

Ala Lys Ala Pro Tyr Ser Gly Thr Tyr Phe Glu Tyr Phe Arg His
1               5                   10                  15
```

<210> SEQ ID NO 265
<211> LENGTH: 357
<212> TYPE: DNA
<213> ORGANISM: Homo sapiens

<400> SEQUENCE: 265
caggtgcagc tggtggagtc tgggggaggc gtggtccagc ctgggaggtc cctgagactc        60
tcctgtgcag cctctggatt caccttcagt agctatggca tgcactgggt ccgccaggct       120
ccaggcaagg ggctggagtg ggtggcagtt atatcatatg atggaagtaa taaatactat       180
gcagactccg tgaagggccg attcaccatc tccagagaca attccaagaa cacgctgtat       240
ctgcaaatga acagcctgag agctgaggac acggctgtgt attactgtgc gaaagatgac       300
tggaactacg acgcctttga tatctggggc caagggacaa tggtcaccgt ctcttca         357

<210> SEQ ID NO 266
<211> LENGTH: 119
<212> TYPE: PRT
<213> ORGANISM: Homo Sapiens

<400> SEQUENCE: 266

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asp Trp Asn Tyr Asp Ala Phe Asp Ile Trp Gly Gln Gly
            100                 105                 110

Thr Met Val Thr Val Ser Ser
        115

<210> SEQ ID NO 267
<211> LENGTH: 24
<212> TYPE: DNA
<213> ORGANISM: Homo sapiens

<400> SEQUENCE: 267
ggattcacct tcagtagcta tggc                                              24

<210> SEQ ID NO 268
<211> LENGTH: 8
<212> TYPE: PRT
<213> ORGANISM: Homo Sapiens

<400> SEQUENCE: 268

Gly Phe Thr Phe Ser Ser Tyr Gly
1               5

<210> SEQ ID NO 269
<211> LENGTH: 24
<212> TYPE: DNA
<213> ORGANISM: Homo sapiens

<400> SEQUENCE: 269
atatcatatg atggaagtaa taaa                                          24

<210> SEQ ID NO 270
<211> LENGTH: 8
<212> TYPE: PRT
<213> ORGANISM: Homo Sapiens

<400> SEQUENCE: 270

Ile Ser Tyr Asp Gly Ser Asn Lys
1               5

<210> SEQ ID NO 271
<211> LENGTH: 36
<212> TYPE: DNA
<213> ORGANISM: Homo sapiens

<400> SEQUENCE: 271
gcgaaagatg actggaacta cgacgccttt gatatc                             36

<210> SEQ ID NO 272
<211> LENGTH: 12
<212> TYPE: PRT
<213> ORGANISM: Homo Sapiens

<400> SEQUENCE: 272

Ala Lys Asp Asp Trp Asn Tyr Asp Ala Phe Asp Ile
1               5                   10

<210> SEQ ID NO 273
<211> LENGTH: 363
<212> TYPE: DNA
<213> ORGANISM: Homo sapiens

<400> SEQUENCE: 273
caggtgcagc tgcaggagtc gggcccagga ctggtgaagc cttcacagac cctgtccctc      60
acctgcactg tctctggtgg ctccatcagc agtagtggtt actactggag ctggatccgc     120
cagcacccag ggaggggcct ggagtggatt ggatacatct attacagtgg gagcacctac     180
tacaacccgt ccctcaagag tcgagttacc atatcagtag acacgtctaa gaaccagttc     240
tccctgaagc tgaactctgt gactgccgcg gacacggccg tgtattactg tgcgagagtg     300
gactatggtt cggggagttc gtttgactac tggggccagg gaaccctggt caccgtctcc     360
tca                                                                  363

<210> SEQ ID NO 274
<211> LENGTH: 121
<212> TYPE: PRT
<213> ORGANISM: Homo Sapiens

<400> SEQUENCE: 274

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Ser
            20                  25                  30

Gly Tyr Tyr Trp Ser Trp Ile Arg Gln His Pro Gly Arg Gly Leu Glu
        35                  40                  45

Trp Ile Gly Tyr Ile Tyr Tyr Ser Gly Ser Thr Tyr Tyr Asn Pro Ser
    50                  55                  60

```
Leu Lys Ser Arg Val Thr Ile Ser Val Asp Thr Ser Lys Asn Gln Phe
 65                  70                  75                  80

Ser Leu Lys Leu Asn Ser Val Thr Ala Ala Asp Thr Ala Val Tyr Tyr
                 85                  90                  95

Cys Ala Arg Val Asp Tyr Gly Ser Gly Ser Ser Phe Asp Tyr Trp Gly
            100                 105                 110

Gln Gly Thr Leu Val Thr Val Ser Ser
        115                 120
```

<210> SEQ ID NO 275
<211> LENGTH: 30
<212> TYPE: DNA
<213> ORGANISM: Homo sapiens

<400> SEQUENCE: 275
ggtggctcca tcagcagtag tggttactac                                30

<210> SEQ ID NO 276
<211> LENGTH: 10
<212> TYPE: PRT
<213> ORGANISM: Homo Sapiens

<400> SEQUENCE: 276

```
Gly Gly Ser Ile Ser Ser Ser Gly Tyr Tyr
 1               5                   10
```

<210> SEQ ID NO 277
<211> LENGTH: 21
<212> TYPE: DNA
<213> ORGANISM: Homo sapiens

<400> SEQUENCE: 277
atctattaca gtgggagcac c                                         21

<210> SEQ ID NO 278
<211> LENGTH: 7
<212> TYPE: PRT
<213> ORGANISM: Homo Sapiens

<400> SEQUENCE: 278

```
Ile Tyr Tyr Ser Gly Ser Thr
 1               5
```

<210> SEQ ID NO 279
<211> LENGTH: 39
<212> TYPE: DNA
<213> ORGANISM: Homo sapiens

<400> SEQUENCE: 279
gcgagagtgg actatggttc ggggagttcg tttgactac                      39

<210> SEQ ID NO 280
<211> LENGTH: 13
<212> TYPE: PRT
<213> ORGANISM: Homo Sapiens

<400> SEQUENCE: 280

```
Ala Arg Val Asp Tyr Gly Ser Gly Ser Ser Phe Asp Tyr
 1               5                   10
```

<210> SEQ ID NO 281
<211> LENGTH: 354
<212> TYPE: DNA

<213> ORGANISM: Homo sapiens

<400> SEQUENCE: 281

```
caggttcagc tggtgcagtc tggacctgag gtgaagaagc ctggggcctc agtgaaggtc    60
tcctgcaagg cttctggtta cacctttacc agctatggca tcagctgggt gcgacaggcc   120
cctggacaag ggcttgagtg gctgggatgg atcagcggtt tcaatggtag aacagactat   180
acagagaagc tccaggacag aatcaccatg accacagaca atcctcgag cacagcctac   240
atggaactga ggagcctgag atatgacgac acggccgtgt attactgtgc gagagatgga   300
ctggaaaaac ttggtgacta ctggggccag ggaaccctgg tcaccgtctc ctca          354
```

<210> SEQ ID NO 282
<211> LENGTH: 118
<212> TYPE: PRT
<213> ORGANISM: Homo Sapiens

<400> SEQUENCE: 282

Gln Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Leu
        35                  40                  45

Gly Trp Ile Ser Gly Phe Asn Gly Arg Thr Asp Tyr Thr Glu Lys Leu
    50                  55                  60

Gln Asp Arg Ile Thr Met Thr Thr Asp Arg Ser Ser Ser Thr Ala Tyr
65                  70                  75                  80

Met Glu Leu Arg Ser Leu Arg Tyr Asp Asp Thr Ala Val Tyr Tyr Cys
                85                  90                  95

Ala Arg Asp Gly Leu Glu Lys Leu Gly Asp Tyr Trp Gly Gln Gly Thr
            100                 105                 110

Leu Val Thr Val Ser Ser
        115

<210> SEQ ID NO 283
<211> LENGTH: 24
<212> TYPE: DNA
<213> ORGANISM: Homo sapiens

<400> SEQUENCE: 283

```
ggttacacct ttaccagcta tggc                                            24
```

<210> SEQ ID NO 284
<211> LENGTH: 8
<212> TYPE: PRT
<213> ORGANISM: Homo Sapiens

<400> SEQUENCE: 284

Gly Tyr Thr Phe Thr Ser Tyr Gly
1               5

<210> SEQ ID NO 285
<211> LENGTH: 24
<212> TYPE: DNA
<213> ORGANISM: Homo sapiens

<400> SEQUENCE: 285

```
atcagcggtt tcaatggtag aaca                                            24
```

<210> SEQ ID NO 286
<211> LENGTH: 8
<212> TYPE: PRT
<213> ORGANISM: Homo Sapiens

<400> SEQUENCE: 286

Ile Ser Gly Phe Asn Gly Arg Thr
1               5

<210> SEQ ID NO 287
<211> LENGTH: 33
<212> TYPE: DNA
<213> ORGANISM: Homo sapiens

<400> SEQUENCE: 287
gcgagagatg gactggaaaa acttggtgac tac                               33

<210> SEQ ID NO 288
<211> LENGTH: 11
<212> TYPE: PRT
<213> ORGANISM: Homo Sapiens

<400> SEQUENCE: 288

Ala Arg Asp Gly Leu Glu Lys Leu Gly Asp Tyr
1               5                   10

<210> SEQ ID NO 289
<211> LENGTH: 363
<212> TYPE: DNA
<213> ORGANISM: Homo sapiens

<400> SEQUENCE: 289
caggtgcagc tggtggagtc tgggggaggc gtggtccagc cggggaggtt cctgagactc    60
tcctgtgcag cgtctggatt caccttcagt aactctggca tgcactgggt ccgccaggct   120
ccaggcaagg ggctggagtg ggtggcagga atatggcatg atggaagtta taaatattat   180
gtagactccg tgaagggccg attcaccatc tccagagaca attctaagaa cacgctgttt   240
ctgcaaatga acagcctgcg agccgaggac acggctgtat attattgtgc gagagatgat   300
tactatgctt cggggaccag cgtggacgta tggggccaag ggaccacggt caccgtctcc   360
tca                                                                363

<210> SEQ ID NO 290
<211> LENGTH: 121
<212> TYPE: PRT
<213> ORGANISM: Homo Sapiens

<400> SEQUENCE: 290

Gln Val Gln Leu Val Glu Ser Gly Gly Gly Val Val Gln Pro Gly Arg
1               5                   10                  15

Phe Leu Arg Leu Ser Cys Ala Ala Ser Gly Phe Thr Phe Ser Asn Ser
            20                  25                  30

Gly Met His Trp Val Arg Gln Ala Pro Gly Lys Gly Leu Glu Trp Val
        35                  40                  45

Ala Gly Ile Trp His Asp Gly Ser Tyr Lys Tyr Tyr Val Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Asp Asp Tyr Tyr Ala Ser Gly Thr Ser Val Asp Val Trp Gly
            100                 105                 110
Gln Gly Thr Thr Val Thr Val Ser Ser
        115                 120

<210> SEQ ID NO 291
<211> LENGTH: 24
<212> TYPE: DNA
<213> ORGANISM: Homo sapiens

<400> SEQUENCE: 291
ggattcacct tcagtaactc tggc                                          24

<210> SEQ ID NO 292
<211> LENGTH: 8
<212> TYPE: PRT
<213> ORGANISM: Homo Sapiens

<400> SEQUENCE: 292

Gly Phe Thr Phe Ser Asn Ser Gly
1               5

<210> SEQ ID NO 293
<211> LENGTH: 24
<212> TYPE: DNA
<213> ORGANISM: Homo sapiens

<400> SEQUENCE: 293
atatggcatg atggaagtta taaa                                          24

<210> SEQ ID NO 294
<211> LENGTH: 8
<212> TYPE: PRT
<213> ORGANISM: Homo Sapiens

<400> SEQUENCE: 294

Ile Trp His Asp Gly Ser Tyr Lys
1               5

<210> SEQ ID NO 295
<211> LENGTH: 42
<212> TYPE: DNA
<213> ORGANISM: Homo sapiens

<400> SEQUENCE: 295
gcgagagatg attactatgc ttcggggacc agcgtggacg ta                      42

<210> SEQ ID NO 296
<211> LENGTH: 14
<212> TYPE: PRT
<213> ORGANISM: Homo Sapiens

<400> SEQUENCE: 296

Ala Arg Asp Asp Tyr Tyr Ala Ser Gly Thr Ser Val Asp Val
1               5                   10

<210> SEQ ID NO 297
<211> LENGTH: 366
<212> TYPE: DNA
<213> ORGANISM: Homo sapiens

<400> SEQUENCE: 297
caggtgcagc tggtgcagtc tggggctgag gtgaagaagc ctggggcctc agtgagggtc   60

```
tcctgcatgg cctctggata caccttcacc ggctactata tgcactgggt gcgacaggcc    120
cctggacaag ggcttgagtg gatgggatgg atcaaccccta acagtggtgg cacaaaatat    180
gcacagaagt tcagggcag ggtcaccatg accagggaca cgtccatcag cacagcctac    240
atggagctga gcagactgag atctgacgac acggccgtat attactgtgc gagagaagaa    300
gtcgacgatt tttggagtgg ttaccttgac tactggggcc agggaaccct ggtcaccgtc    360
tcctca                                                               366
```

<210> SEQ ID NO 298
<211> LENGTH: 122
<212> TYPE: PRT
<213> ORGANISM: Homo Sapiens

<400> SEQUENCE: 298

```
Gln Val Gln Leu Val Gln Ser Gly Ala Glu Val Lys Lys Pro Gly Ala
1               5                   10                  15

Ser Val Arg Val Ser Cys Met Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Lys Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Glu Val Asp Asp Phe Trp Ser Gly Tyr Leu Asp Tyr Trp
            100                 105                 110

Gly Gln Gly Thr Leu Val Thr Val Ser Ser
        115                 120
```

<210> SEQ ID NO 299
<211> LENGTH: 24
<212> TYPE: DNA
<213> ORGANISM: Homo sapiens

<400> SEQUENCE: 299

```
ggatacacct tcaccggcta ctat                                            24
```

<210> SEQ ID NO 300
<211> LENGTH: 8
<212> TYPE: PRT
<213> ORGANISM: Homo Sapiens

<400> SEQUENCE: 300

```
Gly Tyr Thr Phe Thr Gly Tyr Tyr
1               5
```

<210> SEQ ID NO 301
<211> LENGTH: 24
<212> TYPE: DNA
<213> ORGANISM: Homo sapiens

<400> SEQUENCE: 301

```
atcaacccta acagtggtgg caca                                            24
```

<210> SEQ ID NO 302
<211> LENGTH: 8

<212> TYPE: PRT
<213> ORGANISM: Homo Sapiens

<400> SEQUENCE: 302

Ile Asn Pro Asn Ser Gly Gly Thr
1               5

<210> SEQ ID NO 303
<211> LENGTH: 45
<212> TYPE: DNA
<213> ORGANISM: Homo sapiens

<400> SEQUENCE: 303
gcgagagaag aagtcgacga tttttggagt ggttaccttg actac          45

<210> SEQ ID NO 304
<211> LENGTH: 15
<212> TYPE: PRT
<213> ORGANISM: Homo Sapiens

<400> SEQUENCE: 304

Ala Arg Glu Glu Val Asp Asp Phe Trp Ser Gly Tyr Leu Asp Tyr
1               5                   10                  15

<210> SEQ ID NO 305
<211> LENGTH: 324
<212> TYPE: DNA
<213> ORGANISM: Homo sapiens

<400> SEQUENCE: 305
gaaattgtgt tgacgcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctcaccttg gacgttcggc    300
caagggacca aggtggaaat caaa                                           324

<210> SEQ ID NO 306
<211> LENGTH: 108
<212> TYPE: PRT
<213> ORGANISM: Homo Sapiens

<400> SEQUENCE: 306

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

```
<210> SEQ ID NO 307
<211> LENGTH: 21
<212> TYPE: DNA
<213> ORGANISM: Homo sapiens

<400> SEQUENCE: 307
cagagtgtta gcagcagcta c                                              21

<210> SEQ ID NO 308
<211> LENGTH: 7
<212> TYPE: PRT
<213> ORGANISM: Homo Sapiens

<400> SEQUENCE: 308

Gln Ser Val Ser Ser Ser Tyr
1               5

<210> SEQ ID NO 309
<211> LENGTH: 9
<212> TYPE: DNA
<213> ORGANISM: Homo sapiens

<400> SEQUENCE: 309 ggtgcatcc                                                            9

<210> SEQ ID NO 310
<211> LENGTH: 3
<212> TYPE: PRT
<213> ORGANISM: Homo Sapiens

<400> SEQUENCE: 310

Gly Ala Ser
1

<210> SEQ ID NO 311
<211> LENGTH: 27
<212> TYPE: DNA
<213> ORGANISM: Homo sapiens

<400> SEQUENCE: 311
cagcagtatg gtagctcacc ttggacg                                        27

<210> SEQ ID NO 312
<211> LENGTH: 9
<212> TYPE: PRT
<213> ORGANISM: Homo Sapiens

<400> SEQUENCE: 312

Gln Gln Tyr Gly Ser Ser Pro Trp Thr
1               5

<210> SEQ ID NO 313
<211> LENGTH: 354
<212> TYPE: DNA
<213> ORGANISM: Homo sapiens

<400> SEQUENCE: 313
gaggtgcagc tggtggagtc tggaggagac ttggtccagc cggggggtc cctgagactc     60 tcctgtgcag cctctgggtt cgccgtcaat ggcgactatt ttagttgggt ccgccaggct    120
ccagggaagg ggctggagtg gatctcagtt atttatagca gtggtaacac atactacgca    180
gactccgtga agggccgatt caccatctcc agacacaatt ccaagaacac gctgtatctt    240
caaatgagca gcctaagacc tgaggacacg gccgtgtatt actgtgcgag agacttccct    300
```

```
ccaatgtctg gtgcggacta ctggggccag ggaaccctgg tcaccgtctc ctca    354
```

<210> SEQ ID NO 314
<211> LENGTH: 118
<212> TYPE: PRT
<213> ORGANISM: Homo Sapiens

<400> SEQUENCE: 314

```
Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Ala Val Asn Gly Asp
            20                  25                  30

Tyr Phe Ser Trp Val Arg Gln Ala Pro Gly Lys Gly Leu Glu Trp Ile
        35                  40                  45

Ser Val Ile Tyr Ser Ser Gly Asn Thr Tyr Tyr Ala Asp Ser Val Lys
    50                  55                  60

Gly Arg Phe Thr Ile Ser Arg His Asn Ser Lys Asn Thr Leu Tyr Leu
65                  70                  75                  80

Gln Met Ser Ser Leu Arg Pro Glu Asp Thr Ala Val Tyr Tyr Cys Ala
                85                  90                  95

Arg Asp Phe Pro Pro Met Ser Gly Ala Asp Tyr Trp Gly Gln Gly Thr
            100                 105                 110

Leu Val Thr Val Ser Ser
        115
```

<210> SEQ ID NO 315
<211> LENGTH: 24
<212> TYPE: DNA
<213> ORGANISM: Homo sapiens

<400> SEQUENCE: 315

```
gggttcgccg tcaatggcga ctat                                       24
```

<210> SEQ ID NO 316
<211> LENGTH: 8
<212> TYPE: PRT
<213> ORGANISM: Homo Sapiens

<400> SEQUENCE: 316

```
Gly Phe Ala Val Asn Gly Asp Tyr
1               5
```

<210> SEQ ID NO 317
<211> LENGTH: 21
<212> TYPE: DNA
<213> ORGANISM: Homo sapiens

<400> SEQUENCE: 317

```
atttatagca gtggtaacac a                                          21
```

<210> SEQ ID NO 318
<211> LENGTH: 7
<212> TYPE: PRT
<213> ORGANISM: Homo Sapiens

<400> SEQUENCE: 318

```
Ile Tyr Ser Ser Gly Asn Thr
1               5
```

<210> SEQ ID NO 319

```
<211> LENGTH: 36
<212> TYPE: DNA
<213> ORGANISM: Homo sapiens

<400> SEQUENCE: 319
gcgagagact tccctccaat gtctggtgcg gactac                                      36

<210> SEQ ID NO 320
<211> LENGTH: 12
<212> TYPE: PRT
<213> ORGANISM: Homo Sapiens

<400> SEQUENCE: 320

Ala Arg Asp Phe Pro Pro Met Ser Gly Ala Asp Tyr
1               5                   10

<210> SEQ ID NO 321
<211> LENGTH: 366
<212> TYPE: DNA
<213> ORGANISM: Homo sapiens

<400> SEQUENCE: 321
caggtccagc tggtgcagtc tggggctgag gtgaagaagc ctggggcctc agtgaaggtc            60
tcctgcaagg tttccggata caccctcact gaattgtcca tgcactgggt gcgacaggct          120
cctggaaaag ggcttgaatg gatgggaggt tttgatcctg aacatggtaa aataatctac          180
gcacagaaat tccagggcag agtcaccatg accgaggaca catctacaga cacagcctac          240
atggaactga gcagcctgag atctgaggac acggccgtct attactgtgc aacattttat          300
aactggaact cctactactt cggtatggac gtctggggcc acgggaccac ggtcaccgtc          360
tcctca                                                                    366

<210> SEQ ID NO 322
<211> LENGTH: 122
<212> TYPE: PRT
<213> ORGANISM: Homo Sapiens

<400> SEQUENCE: 322

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu His Gly Lys Ile Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Phe Tyr Asn Trp Asn Ser Tyr Tyr Phe Gly Met Asp Val Trp
            100                 105                 110

Gly His Gly Thr Thr Val Thr Val Ser Ser
        115                 120

<210> SEQ ID NO 323
<211> LENGTH: 24
<212> TYPE: DNA
<213> ORGANISM: Homo sapiens
```

<400> SEQUENCE: 323
ggatacaccc tcactgaatt gtcc                                          24

<210> SEQ ID NO 324
<211> LENGTH: 8
<212> TYPE: PRT
<213> ORGANISM: Homo Sapiens

<400> SEQUENCE: 324

Gly Tyr Thr Leu Thr Glu Leu Ser
1               5

<210> SEQ ID NO 325
<211> LENGTH: 24
<212> TYPE: DNA
<213> ORGANISM: Homo sapiens

<400> SEQUENCE: 325
tttgatcctg aacatggtaa aata                                          24

<210> SEQ ID NO 326
<211> LENGTH: 8
<212> TYPE: PRT
<213> ORGANISM: Homo Sapiens

<400> SEQUENCE: 326

Phe Asp Pro Glu His Gly Lys Ile
1               5

<210> SEQ ID NO 327
<211> LENGTH: 45
<212> TYPE: DNA
<213> ORGANISM: Homo sapiens

<400> SEQUENCE: 327
gcaacatttt ataactggaa ctcctactac ttcggtatgg acgtc                   45

<210> SEQ ID NO 328
<211> LENGTH: 15
<212> TYPE: PRT
<213> ORGANISM: Homo Sapiens

<400> SEQUENCE: 328

Ala Thr Phe Tyr Asn Trp Asn Ser Tyr Tyr Phe Gly Met Asp Val
1               5                   10                  15

<210> SEQ ID NO 329
<211> LENGTH: 375
<212> TYPE: DNA
<213> ORGANISM: Homo sapiens

<400> SEQUENCE: 329
gaggtgcagc tggtggagtc ggggggaggc ttggtacagc ctggggggtc cctgagactc    60
tcctgtgcag cctctggatt cacctttagc agctatgcca tgaactgggt ccgccaggct   120
ccaggaaagg gactggagtg ggtctcagct gttagtggaa gtgctgatat cacaaactac   180
gcagactccg tgaagggccg gttcaccatc tccagagaca attccaaaca cacgctgtat   240
ctgcaaatga acagcctgag agccgaggac acggccgtat attactgtgc aaggataaaa   300
gtgtataact ggaactacgg gatctactac ggtatggacg tctggggcca agggaccacg   360
gtcaccgtct cctca                                                    375

<210> SEQ ID NO 330
<211> LENGTH: 125
<212> TYPE: PRT
<213> ORGANISM: Homo Sapiens

<400> SEQUENCE: 330

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Val Ser Gly Ser Ala Asp Ile Thr Asn Tyr Ala Asp Ser Val
    50                  55                  60

Lys Gly Arg Phe Thr Ile Ser Arg Asp Asn Ser Lys His Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Lys Val Tyr Asn Trp Asn Tyr Gly Ile Tyr Tyr Gly Met
            100                 105                 110

Asp Val Trp Gly Gln Gly Thr Thr Val Thr Val Ser Ser
        115                 120                 125

<210> SEQ ID NO 331
<211> LENGTH: 24
<212> TYPE: DNA
<213> ORGANISM: Homo sapiens

<400> SEQUENCE: 331
ggattcacct ttagcagcta tgcc                                          24

<210> SEQ ID NO 332
<211> LENGTH: 8
<212> TYPE: PRT
<213> ORGANISM: Homo Sapiens

<400> SEQUENCE: 332

Gly Phe Thr Phe Ser Ser Tyr Ala
1               5

<210> SEQ ID NO 333
<211> LENGTH: 24
<212> TYPE: DNA
<213> ORGANISM: Homo sapiens

<400> SEQUENCE: 333
gttagtggaa gtgctgatat caca                                          24

<210> SEQ ID NO 334
<211> LENGTH: 8
<212> TYPE: PRT
<213> ORGANISM: Homo Sapiens

<400> SEQUENCE: 334

Val Ser Gly Ser Ala Asp Ile Thr
1               5

<210> SEQ ID NO 335
<211> LENGTH: 54
<212> TYPE: DNA
<213> ORGANISM: Homo sapiens

<400> SEQUENCE: 335
gcgaaggata aagtgtataa ctggaactac gggatctact acggtatgga cgtc            54

<210> SEQ ID NO 336
<211> LENGTH: 18
<212> TYPE: PRT
<213> ORGANISM: Homo Sapiens

<400> SEQUENCE: 336

Ala Lys Asp Lys Val Tyr Asn Trp Asn Tyr Gly Ile Tyr Tyr Gly Met
1               5                   10                  15

Asp Val

<210> SEQ ID NO 337
<211> LENGTH: 363
<212> TYPE: DNA
<213> ORGANISM: Homo sapiens

<400> SEQUENCE: 337
cagctgcagc tgcaggagtc gggcccagga ctggtgaagc cttcggagac cctgtccctc      60
acctgcactg tctctggtgg ctccatcagc agtagtagtt actactgggg ctggatccgc     120
cagcccccag ggaagggact agagtggatt gggagtatct attatagtgg gagcacctac     180
tacaatccgt ccctcaagag tcgagtcacc atatccgtag acacgtccaa gaaccagttc     240
tccctgaagc tgagctctgt gaccgccgca gacacggctg tgtattactg tgcgagacaa     300
gggaggtggg agcgagaaaa ctttgactac tggggccagg gaaccctggt caccgtctcc     360
tca                                                                   363

<210> SEQ ID NO 338
<211> LENGTH: 121
<212> TYPE: PRT
<213> ORGANISM: Homo Sapiens

<400> SEQUENCE: 338

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Ser Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gln Gly Arg Trp Glu Arg Glu Asn Phe Asp Tyr Trp Gly
            100                 105                 110

Gln Gly Thr Leu Val Thr Val Ser Ser
        115                 120

<210> SEQ ID NO 339
<211> LENGTH: 30
<212> TYPE: DNA
<213> ORGANISM: Homo sapiens

<400> SEQUENCE: 339

```
ggtggctcca tcagcagtag tagttactac                                        30

<210> SEQ ID NO 340
<211> LENGTH: 10
<212> TYPE: PRT
<213> ORGANISM: Homo Sapiens

<400> SEQUENCE: 340

Gly Gly Ser Ile Ser Ser Ser Ser Tyr Tyr
1               5                   10

<210> SEQ ID NO 341
<211> LENGTH: 21
<212> TYPE: DNA
<213> ORGANISM: Homo sapiens

<400> SEQUENCE: 341
atctattata gtgggagcac c                                                 21

<210> SEQ ID NO 342
<211> LENGTH: 7
<212> TYPE: PRT
<213> ORGANISM: Homo Sapiens

<400> SEQUENCE: 342

Ile Tyr Tyr Ser Gly Ser Thr
1               5

<210> SEQ ID NO 343
<211> LENGTH: 39
<212> TYPE: DNA
<213> ORGANISM: Homo sapiens

<400> SEQUENCE: 343
gcgagacaag ggaggtggga gcgagaaaac tttgactac                              39

<210> SEQ ID NO 344
<211> LENGTH: 13
<212> TYPE: PRT
<213> ORGANISM: Homo Sapiens

<400> SEQUENCE: 344

Ala Arg Gln Gly Arg Trp Glu Arg Glu Asn Phe Asp Tyr
1               5                   10

<210> SEQ ID NO 345
<211> LENGTH: 354
<212> TYPE: DNA
<213> ORGANISM: Homo sapiens

<400> SEQUENCE: 345
caggtgcagc tacagcagtg gggcgcagga ctattgaagc cttcggagac cctgtccctc       60
acctgcgctg tctctgatga gtccttcagt gattactact ggacctggat ccgccagccc      120
ccagggaagg ggctggagtg gattggggaa attactcata gtggaagtac ccactacaac      180
ccgtccctca agagccgagt caccctgtca gttgacacgt ccaagaacca cttctccctg      240
agcctcaact ctgtgaccgc cgcggacacg gctatttatt actgtgcgag aggcggtgac      300
tacggtggtt tacttgacta ctgggggccag ggaaccctgg tcaccgtctc ctca           354

<210> SEQ ID NO 346
<211> LENGTH: 118
```

-continued

<212> TYPE: PRT
<213> ORGANISM: Homo Sapiens

<400> SEQUENCE: 346

Gln Val Gln Leu Gln Gln Trp Gly Ala Gly Leu Leu Lys Pro Ser Glu
1               5                   10                  15

Thr Leu Ser Leu Thr Cys Ala Val Ser Asp Glu Ser Phe Ser Asp Tyr
            20                  25                  30

Tyr Trp Thr Trp Ile Arg Gln Pro Pro Gly Lys Gly Leu Glu Trp Ile
        35                  40                  45

Gly Glu Ile Thr His Ser Gly Ser Thr His Tyr Asn Pro Ser Leu Lys
    50                  55                  60

Ser Arg Val Thr Leu Ser Val Asp Thr Ser Lys Asn His Phe Ser Leu
65                  70                  75                  80

Ser Leu Asn Ser Val Thr Ala Ala Asp Thr Ala Ile Tyr Tyr Cys Ala
                85                  90                  95

Arg Gly Gly Asp Tyr Gly Gly Leu Leu Asp Tyr Trp Gly Gln Gly Thr
            100                 105                 110

Leu Val Thr Val Ser Ser
        115

<210> SEQ ID NO 347
<211> LENGTH: 24
<212> TYPE: DNA
<213> ORGANISM: Homo sapiens

<400> SEQUENCE: 347
gatgagtcct tcagtgatta ctac                                          24

<210> SEQ ID NO 348
<211> LENGTH: 8
<212> TYPE: PRT
<213> ORGANISM: Homo Sapiens

<400> SEQUENCE: 348

Asp Glu Ser Phe Ser Asp Tyr Tyr
1               5

<210> SEQ ID NO 349
<211> LENGTH: 21
<212> TYPE: DNA
<213> ORGANISM: Homo sapiens

<400> SEQUENCE: 349
attactcata gtggaagtac c                                             21

<210> SEQ ID NO 350
<211> LENGTH: 7
<212> TYPE: PRT
<213> ORGANISM: Homo Sapiens

<400> SEQUENCE: 350

Ile Thr His Ser Gly Ser Thr
1               5

<210> SEQ ID NO 351
<211> LENGTH: 36
<212> TYPE: DNA
<213> ORGANISM: Homo sapiens

<400> SEQUENCE: 351
gcgagaggcg gtgactacgg tggtttactt gactac                                36

<210> SEQ ID NO 352
<211> LENGTH: 12
<212> TYPE: PRT
<213> ORGANISM: Homo Sapiens

<400> SEQUENCE: 352

Ala Arg Gly Gly Asp Tyr Gly Gly Leu Leu Asp Tyr
1               5                   10

<210> SEQ ID NO 353
<211> LENGTH: 363
<212> TYPE: DNA
<213> ORGANISM: Homo sapiens

<400> SEQUENCE: 353
cagctgcagc tgcaggagtc gggcccagga ctggtgaagc cctcggagac cctgtccctc    60
acctgcactg tctctggtgg ctccatcagc agtaggagtc actactgggg ctggatccgc   120
cagcccccag ggaaggggct ggagtggatt gggagtatct attatagtgg gagcacctat   180
tacaacccgt ccctcaagag tcgagtcacc atatccgtag acacgtccaa gaaccagttc   240
tccctgaagc tgagctctgt gaccgccgca gacacggctg tgtattactg tgcgagactt   300
ggctggtacg cagaggaggc ttttgaaatc tggggtcaag ggacaatggt caccgtctct   360
tca                                                                 363

<210> SEQ ID NO 354
<211> LENGTH: 121
<212> TYPE: PRT
<213> ORGANISM: Homo sapiens

<400> SEQUENCE: 354

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Arg
            20                  25                  30

Ser His Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Leu Gly Trp Tyr Ala Glu Glu Ala Phe Glu Ile Trp Gly
            100                 105                 110

Gln Gly Thr Met Val Thr Val Ser Ser
        115                 120

<210> SEQ ID NO 355
<211> LENGTH: 30
<212> TYPE: DNA
<213> ORGANISM: Homo sapiens

<400> SEQUENCE: 355
ggtggctcca tcagcagtag gagtcactac                                    30

<210> SEQ ID NO 356

```
<211> LENGTH: 10
<212> TYPE: PRT
<213> ORGANISM: Homo sapiens

<400> SEQUENCE: 356

Gly Gly Ser Ile Ser Ser Arg Ser His Tyr
1               5                   10

<210> SEQ ID NO 357
<211> LENGTH: 21
<212> TYPE: DNA
<213> ORGANISM: Homo sapiens

<400> SEQUENCE: 357
atctattata gtgggagcac c                                                  21

<210> SEQ ID NO 358
<211> LENGTH: 7
<212> TYPE: PRT
<213> ORGANISM: Homo sapiens

<400> SEQUENCE: 358

Ile Tyr Tyr Ser Gly Ser Thr
1               5

<210> SEQ ID NO 359
<211> LENGTH: 39
<212> TYPE: DNA
<213> ORGANISM: Homo sapiens

<400> SEQUENCE: 359
gcgagacttg gctggtacgc agaggaggct tttgaaatc                               39

<210> SEQ ID NO 360
<211> LENGTH: 13
<212> TYPE: PRT
<213> ORGANISM: Homo sapiens

<400> SEQUENCE: 360

Ala Arg Leu Gly Trp Tyr Ala Glu Glu Ala Phe Glu Ile
1               5                   10

<210> SEQ ID NO 361
<211> LENGTH: 526
<212> TYPE: PRT
<213> ORGANISM: Plasmodium falciparum

<400> SEQUENCE: 361

Met Ile Arg Ile Lys Lys Lys Leu Ile Leu Thr Ile Ile Tyr Ile His
1               5                   10                  15

Leu Phe Ile Leu Asn Arg Leu Ser Phe Glu Asn Ala Ile Lys Lys Thr
                20                  25                  30

Lys Asn Gln Glu Asn Asn Leu Thr Leu Leu Pro Ile Lys Ser Thr Glu
            35                  40                  45

Glu Glu Lys Asp Asp Ile Lys Asn Gly Lys Asp Ile Lys Lys Glu Ile
        50                  55                  60

Asp Asn Asp Lys Glu Asn Ile Lys Thr Asn Asn Ala Lys Asp His Ser
65                  70                  75                  80

Thr Tyr Ile Lys Ser Tyr Leu Asn Thr Asn Val Asn Asp Gly Leu Lys
                85                  90                  95

Tyr Leu Phe Ile Pro Ser His Asn Ser Phe Ile Lys Lys Tyr Ser Val
                100                 105                 110
```

-continued

Phe Asn Gln Ile Asn Asp Gly Met Leu Leu Asn Glu Lys Asn Asp Val
        115                 120                 125

Lys Asn Asn Glu Asp Tyr Lys Asn Val Asp Tyr Lys Asn Val Asn Phe
130                 135                 140

Leu Gln Tyr His Phe Lys Glu Leu Ser Asn Tyr Asn Ile Ala Asn Ser
145                 150                 155                 160

Ile Asp Ile Leu Gln Glu Lys Glu Gly His Leu Asp Phe Val Ile Ile
            165                 170                 175

Pro His Tyr Thr Phe Leu Asp Tyr Tyr Lys His Leu Ser Tyr Asn Ser
            180                 185                 190

Ile Tyr His Lys Ser Ser Thr Tyr Gly Lys Cys Ile Ala Val Asp Ala
            195                 200                 205

Phe Ile Lys Lys Ile Asn Glu Thr Tyr Asp Lys Val Lys Ser Lys Cys
            210                 215                 220

Asn Asp Ile Lys Asn Asp Leu Ile Ala Thr Ile Lys Lys Leu Glu His
225                 230                 235                 240

Pro Tyr Asp Ile Asn Asn Lys Asn Asp Ser Tyr Arg Tyr Asp Ile
                245                 250                 255

Ser Glu Glu Ile Asp Asp Lys Ser Glu Glu Thr Asp Asp Glu Thr Glu
            260                 265                 270

Glu Val Glu Asp Ser Ile Gln Asp Thr Asp Ser Asn His Thr Pro Ser
        275                 280                 285

Asn Lys Lys Lys Asn Asp Leu Met Asn Arg Thr Phe Lys Lys Met Met
        290                 295                 300

Asp Glu Tyr Asn Thr Lys Lys Lys Leu Ile Lys Cys Ile Lys Asn
305                 310                 315                 320

His Glu Asn Asp Phe Asn Lys Ile Cys Met Asp Met Lys Asn Tyr Gly
                325                 330                 335

Thr Asn Leu Phe Glu Gln Leu Ser Cys Tyr Asn Asn Asn Phe Cys Asn
            340                 345                 350

Thr Asn Gly Ile Arg Tyr His Tyr Asp Glu Tyr Ile His Lys Leu Ile
        355                 360                 365

Leu Ser Val Lys Ser Lys Asn Leu Asn Lys Asp Leu Ser Asp Met Thr
370                 375                 380

Asn Ile Leu Gln Gln Ser Glu Leu Leu Leu Thr Asn Leu Asn Lys Lys
385                 390                 395                 400

Met Gly Ser Tyr Ile Tyr Ile Asp Thr Ile Lys Phe Ile His Lys Glu
            405                 410                 415

Met Lys His Ile Phe Asn Arg Ile Glu Tyr His Thr Lys Ile Ile Asn
            420                 425                 430

Asp Lys Thr Lys Ile Ile Gln Asp Lys Ile Lys Leu Asn Ile Trp Arg
            435                 440                 445

Thr Phe Gln Lys Asp Glu Leu Leu Lys Arg Ile Leu Asp Met Ser Asn
450                 455                 460

Glu Tyr Ser Leu Phe Ile Thr Ser Asp His Leu Arg Gln Met Leu Tyr
465                 470                 475                 480

Asn Thr Phe Tyr Ser Lys Glu Lys His Leu Asn Asn Ile Phe His His
            485                 490                 495

Leu Ile Tyr Val Leu Gln Met Lys Phe Asn Asp Val Pro Ile Lys Met
            500                 505                 510

Glu Tyr Phe Gln Thr Tyr Lys Lys Asn Lys Pro Leu Thr Gln
            515                 520                 525

<210> SEQ ID NO 362
<211> LENGTH: 344
<212> TYPE: PRT
<213> ORGANISM: Plasmodium falciparum

<400> SEQUENCE: 362

Lys Asn Val Asn Phe Leu Gln Tyr His Phe Lys Glu Leu Ser Asn Tyr
1               5                   10                  15

Asn Ile Ala Asn Ser Ile Asp Ile Leu Gln Glu Lys Glu Gly His Leu
            20                  25                  30

Asp Phe Val Ile Ile Pro His Tyr Thr Phe Leu Asp Tyr Tyr Lys His
        35                  40                  45

Leu Ser Tyr Asn Ser Ile Tyr His Lys Ser Ser Thr Tyr Gly Lys Tyr
    50                  55                  60

Ile Ala Val Asp Ala Phe Ile Lys Lys Ile Asn Glu Ala Tyr Asp Lys
65                  70                  75                  80

Val Lys Ser Lys Cys Asn Asp Ile Lys Asn Asp Leu Ile Ala Thr Ile
                85                  90                  95

Lys Lys Leu Glu His Pro Tyr Asp Ile Asn Asn Met Asn Arg Ala Phe
            100                 105                 110

Lys Lys Met Met Asp Glu Tyr Asn Thr Lys Lys Lys Leu Ile Lys
        115                 120                 125

Cys Ile Lys Asn His Glu Asn Asp Phe Asn Lys Ile Cys Met Asp Met
130                 135                 140

Lys Asn Tyr Gly Thr Asn Leu Phe Glu Gln Leu Ser Cys Tyr Asn Asn
145                 150                 155                 160

Asn Phe Cys Asn Thr Asn Gly Ile Arg Tyr His Tyr Asp Glu Tyr Ile
                165                 170                 175

His Lys Leu Ile Leu Ser Val Lys Ser Lys Asn Leu Asn Lys Asp Leu
            180                 185                 190

Ser Asp Met Thr Asn Ile Leu Gln Gln Ser Glu Leu Leu Leu Thr Asn
        195                 200                 205

Leu Asn Lys Lys Met Gly Ser Tyr Ile Tyr Ile Asp Thr Ile Lys Phe
210                 215                 220

Ile His Lys Glu Met Lys His Ile Phe Asn Arg Ile Glu Tyr His Thr
225                 230                 235                 240

Lys Ile Ile Asn Asp Lys Thr Lys Ile Ile Gln Asp Lys Ile Lys Leu
                245                 250                 255

Asn Ile Trp Arg Thr Phe Gln Lys Asp Glu Leu Leu Lys Arg Ile Leu
            260                 265                 270

Asp Met Ser Asn Glu Tyr Ser Leu Phe Ile Thr Ser Asp His Leu Arg
        275                 280                 285

Gln Met Leu Tyr Asn Thr Phe Tyr Ser Lys Glu Lys His Leu Asn Asn
    290                 295                 300

Ile Phe His His Leu Ile Tyr Val Leu Gln Met Lys Phe Asn Asp Val
305                 310                 315                 320

Pro Ile Lys Met Glu Tyr Phe Gln Thr Tyr Lys Lys Asn Lys Pro Leu
                325                 330                 335

Thr Gln His His His His His His
            340

<210> SEQ ID NO 363
<211> LENGTH: 7
<212> TYPE: PRT
<213> ORGANISM: Artificial Sequence

```
<220> FEATURE:
<223> OTHER INFORMATION: Linker sequence

<400> SEQUENCE: 363

Asp Ile Glu Gly Arg Met Asp
1               5

<210> SEQ ID NO 364
<211> LENGTH: 5
<212> TYPE: PRT
<213> ORGANISM: Artificial Sequence
<220> FEATURE:
<223> OTHER INFORMATION: Linker sequence

<400> SEQUENCE: 364

Gly Gly Gly Gly Ser
1               5

<210> SEQ ID NO 365
<211> LENGTH: 6
<212> TYPE: PRT
<213> ORGANISM: Artificial Sequence
<220> FEATURE:
<223> OTHER INFORMATION: HisX6 tag

<400> SEQUENCE: 365

His His His His His His
1               5
```